United States Patent
Baryza et al.

(10) Patent No.: US 10,729,775 B2
(45) Date of Patent: Aug. 4, 2020

(54) LIPIDS AND LIPID COMPOSITIONS FOR THE DELIVERY OF ACTIVE AGENTS

(71) Applicant: Novartis AG, Basel (CH)

(72) Inventors: Jeremy Lee Baryza, Quincy, MA (US); Rohan Eric John Beckwith, Maynard, MA (US); Keith Bowman, Harleysville, PA (US); Crystal Byers, Allston, MA (US); Tanzina Fazal, Burlington, MA (US); Gabriel Grant Gamber, Marlborough, MA (US); Cameron Chuck-munn Lee, Cambridge, MA (US); Ritesh Bhanudasji Tichkule, Cambridge, MA (US); Chandra Vargeese, Schwenksville, PA (US); Shuangxi Wang, Carona, CA (US); Laura Ellen West, Weymouth, MA (US); Thomas Zabawa, Boston, MA (US); Junping Zhao, Waltham, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/021,193

(22) Filed: Jun. 28, 2018

(65) Prior Publication Data

US 2018/0296677 A1    Oct. 18, 2018

Related U.S. Application Data

(60) Division of application No. 15/277,402, filed on Sep. 27, 2016, which is a continuation of application No. 14/200,359, filed on Mar. 7, 2014, now Pat. No. 9,504,747.

(60) Provisional application No. 61/774,759, filed on Mar. 8, 2013.

(51) Int. Cl.
| | | |
|---|---|---|
| A61K 47/18 | (2017.01) | |
| C12N 15/113 | (2010.01) | |
| A61K 47/22 | (2006.01) | |
| C07D 213/79 | (2006.01) | |
| C07D 317/24 | (2006.01) | |
| C07D 317/28 | (2006.01) | |
| C07D 205/04 | (2006.01) | |
| C07D 295/096 | (2006.01) | |
| C07D 213/69 | (2006.01) | |
| A61K 9/127 | (2006.01) | |
| C07C 217/58 | (2006.01) | |
| C07C 217/60 | (2006.01) | |
| C07C 217/62 | (2006.01) | |
| C07C 219/22 | (2006.01) | |
| C07C 219/28 | (2006.01) | |
| C07C 229/12 | (2006.01) | |

(Continued)

(52) U.S. Cl.
CPC ............ *A61K 47/18* (2013.01); *A61K 9/1271* (2013.01); *A61K 9/1272* (2013.01); *A61K 47/183* (2013.01); *A61K 47/22* (2013.01); *C07C 217/58* (2013.01); *C07C 217/60* (2013.01); *C07C 217/62* (2013.01); *C07C 219/22* (2013.01); *C07C 219/28* (2013.01); *C07C 229/12* (2013.01); *C07C 235/46* (2013.01); *C07C 237/08* (2013.01); *C07D 205/04* (2013.01); *C07D 213/69* (2013.01); *C07D 213/79* (2013.01); *C07D 295/096* (2013.01); *C07D 317/24* (2013.01); *C07D 317/28* (2013.01); *C12N 15/1137* (2013.01); *C12N 2310/14* (2013.01); *C12N 2320/32* (2013.01)

(58) Field of Classification Search
USPC .......................................................... 514/44
See application file for complete search history.

(56) References Cited

U.S. PATENT DOCUMENTS

| | | |
|---|---|---|
| 4,438,131 A | 3/1984 | Ehrmann |
| 4,723,039 A | 2/1988 | Seitz |

(Continued)

FOREIGN PATENT DOCUMENTS

| | | |
|---|---|---|
| EP | 0064158 A1 | 11/1982 |
| EP | 0225543 A1 | 6/1987 |
| WO | WO 2007/122847 A1 | 11/2007 |

(Continued)

OTHER PUBLICATIONS

Erdelen, C.; Haussling, L.; Naumann, R.; Ringsdorf, H.; Wolf, H.; Yang, J. "Self-Assembled Disulfide-Functionalized Amphiphilic Copoloymers on Gold," Langmuir, 1994, 10, 1246-1250.

(Continued)

*Primary Examiner* — Ana Z Muresan
(74) *Attorney, Agent, or Firm* — Brinks Gilson & Lione; Yuezhong Feng

(57) ABSTRACT

This invention provides for a compound of formula (I):

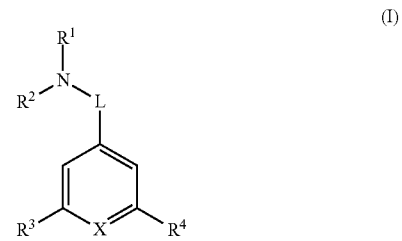

(I)

or a pharmaceutically acceptable salt thereof, wherein $R^1$-$R^4$, L and X are defined herein. The compounds of (Continued)

formula (I) and pharmaceutically acceptable salts thereof are cationic lipids useful in the delivery of biologically active agents to cells and tissues.

21 Claims, No Drawings

Specification includes a Sequence Listing.

(51) Int. Cl.
*C07C 235/46* (2006.01)
*C07C 237/08* (2006.01)

(56) References Cited

U.S. PATENT DOCUMENTS

| | | |
|---|---|---|
| 2004/0006061 A1 | 1/2004 | Haap |
| 2011/0224447 A1 | 9/2011 | Bowman et al. |

FOREIGN PATENT DOCUMENTS

| | | |
|---|---|---|
| WO | 2008103276 A2 | 8/2008 |
| WO | 2008147438 A2 | 12/2008 |
| WO | WO11150347 A2 | 12/2011 |

OTHER PUBLICATIONS

Fujii, S.; Nishimura, T.; Sakurai, K. "Thermodynamics of Lipoplex Formation: Relationship Between the Lipid Alkyl Tail Length and Thermodynamic Functions," Chem. Lett., 2012, 41, 501-503.
Hussein, I.A.; Ali, S.K.A.; Suleiman, M.A.; Umar, Y. "Rheological Behavior of Associating Ionic Polymers Based on Diallylammonium Salts Containing Single-, Twin-, and Triple-Tailed Hydrophobes," European Polymer Journal, 2010, 46, 1063-1073.
Mochizuki, S.; Kamikawa, Y.; Nishina, K.; Fujii, S.; Hamada, E.; Kusuki, S.; Matsuo, T.; Sakurai, K. "Relationship Between DNA-Transfection Efficiency and Chemical Structures of Aromatic Cationic Lipids," Bull. Chem. Soc. Jpn., 2012, 85, 354-359.
Pettit, G.R.; Bionda D.S.; Harrington, E.C. "Antineoplastic Agents IX. N-Benzyl-N-Bis(2-Haloethyl)Amines," Canadian Journal of Chemistry, 1963, 41, 2962-2968.
Ren, T.; Liu D. "Synthesis of Targetable Cationic Amphiphiles," Tetrahedron Letters, 1999, 40, 7621-7625.
Ren, T.; "Synthesis and Characterization of Aromatic Ring-Based Cationic Lipids for Gene Delivery In Vitro and In Vivo," Journal of Drug Targeting, 1999, 7, 4, 285-292.
Zhu, L.; "Lipid and Polymeric Carrier-Mediated Nucleic Acid Delivery," Expert Opin Drug De/iv., 2010, 7, 10, 1209-1226.
Ohta et al., "N-Heterocyclic Carbene Ligands Bearing Hydrophilic and/or hydrophobic Chains: Rh(I) and Pd(II) Complexes and Their Catalytic Activity," Dalton Transactions, 2008, (3), 379-385.
Extended European Search Report (13 pages) dated Jan. 14, 2020 from corresponding European Application No. EP 19183987.7.
Search Report issued for corresponding Brazilian patent application No. BR112015021791-5 dated Feb. 21, 2020, 5 pages.
Yoshio, M. et al., One-Dimensional Ion-Conductive Polymer Films: Alignment and Fixation of Ionic Channels Formed by Self-Organization of Polymerizable Columnar Liquid Crystals, Journal of the American Chemical Society, 2006.
Imam, M.R. et al., "Dendronized supramolecular polymers self-asembled from dendritic ionic liquids", Journal of Polymer Science, Part A: Polymer Chemistry, 2009 47(16), 4165-4193.
Ichikawa, T. et al, "Co-organization of ionic liquids with amphiphilic diethanolamines: construction of 3D continuous ionic nanochannels through the induction of liquid-crystalline bicontinuous cubic phases," Chemical Science, 2012; D)1: 10.1039/c2sc0098a1.

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-methyl-nucleotide
<220> FEATURE:
<221> NAME/KEY: modified_base
<222> LOCATION: (13)..(13)
<223> OTHER INFORMATION: 2'-O-methyl-nucleotide
<220> FEATURE:
<221> NAME/KEY: modified_base
<222> LOCATION: (18)..(18)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotides

<400> SEQUENCE: 1
uuuaauugaa accaagacau u                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl-nucleotide
<220> FEATURE:
<221> NAME/KEY: modified_base
<222> LOCATION: (3)..(6)
<223> OTHER INFORMATION: 2'-O-methyl-nucleotides
<220> FEATURE:
<221> NAME/KEY: modified_base
<222> LOCATION: (9)..(12)
<223> OTHER INFORMATION: 2'-O-methyl-nucleotides
<220> FEATURE:
<221> NAME/KEY: modified_base
<222> LOCATION: (15)..(16)
<223> OTHER INFORMATION: 2'-O-methyl-nucleotides
<220> FEATURE:
<221> NAME/KEY: modified_base
<222> LOCATION: (20)..(21)
<223> OTHER INFORMATION: 2'-O-methyl-nucleotides

<400> SEQUENCE: 2
ugucuugguu ucaauuaaau u                                              21

<210> SEQ ID NO 3
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-O-methyl-nucleotide
<220> FEATURE:
<221> NAME/KEY: modified_base
<222> LOCATION: (17)..(17)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotides

<400> SEQUENCE: 3
uauuuaagga gggugaucuu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(7)
<223> OTHER INFORMATION: 2'-O-methyl-nucleotides
<220> FEATURE:
<221> NAME/KEY: modified_base
<222> LOCATION: (11)..(14)
<223> OTHER INFORMATION: 2'-O-methyl-nucleotides
<220> FEATURE:
<221> NAME/KEY: modified_base
<222> LOCATION: (19)..(21)
<223> OTHER INFORMATION: 2'-O-methyl-nucleotides

<400> SEQUENCE: 4
agaucacccu ccuuaaauau u                                              21
```

LIPIDS AND LIPID COMPOSITIONS FOR THE DELIVERY OF ACTIVE AGENTS

RELATED APPLICATIONS

This application is a divisional of U.S. application Ser. No. 15/277,402, filed Sep. 27, 2016, which is a continuation of U.S. application Ser. No. 14/200,359, filed Mar. 7, 2014 (now U.S. Pat. No. 9,504,747), which claims priority to and the benefit of U.S. Provisional Application No. 61/774,759, filed Mar. 8, 2013. The entire contents of these patent applications are hereby incorporated herein by reference.

SEQUENCE LISTING

The instant application contains a Sequence Listing which has been submitted electronically in ASCII format and is hereby incorporated by reference in its entirety. Said ASCII copy, created on Sep. 23, 2015, is named PAT055439-US-NP-SEQ ID 1-4.txt and is 2,725 bytes in size.

FIELD OF THE INVENTION

This invention relates to cationic lipid compounds and to compositions comprising such compounds. This invention also relates to processes for making such compounds and compositions, and to methods and uses of such compounds and compositions, e.g., to deliver biologically active agents, such as RNAi agents, to cells and tissues.

BACKGROUND OF THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilize specific carrier molecules which are allowed selective entry into the cell. Lipid carriers, biodegradable polymers and various conjugate systems can be used to improve delivery of biologically active agents to cells.

One class of biologically active agents that is particularly difficult to deliver to cells is a biotherapeutic (including nucleosides, nucleotides, polynucleotides, nucleic acids and derivatives, such as RNAi agents). In general, nucleic acids are stable for only a limited duration in cells or plasma. The development of RNA interference, RNAi therapy, RNA drugs, antisense therapy and gene therapy, among others, has increased the need for an effective means of introducing active nucleic acid agents into cells. For these reasons, compositions that can stabilize and deliver nucleic acid-based agents into cells are of particular interest.

The most well-studied approaches for improving the transport of foreign nucleic acids into cells involve the use of viral vectors or cationic lipids. Viral vectors can be used to transfer genes efficiently into some cell types, but they generally cannot be used to introduce chemically synthesized molecules into cells.

An alternative approach is to use delivery compositions incorporating cationic lipids which interact with a biologically active agent at one part and interact with a membrane system at another part (for a review, see Felgner, 1990, Advanced Drug Delivery Reviews, 5, 162-187 and Felgner, 1993, J. Liposome Res., 3, 3-16). Such compositions are reported to contain liposomes.

Since the first description of liposomes in 1965 by Bangham (J. Mol. Biol. 13, 238-252), there has been a sustained interest and effort in developing lipid-based carrier systems for the delivery of biologically active agents. The process of introducing functional nucleic acids into cultured cells by using positively charged liposomes was first described by Philip Felgner et al. *Proc. Natl. Acad. Sci., USA*, 84, 7413-7417 (1987). The process was later demonstrated in vivo by K. L. Brigham et al., *Am. J. Med. Sci.*, 298, 278-281 (1989).

Liposomes are attractive carriers since they protect biological molecules from degradation while improving their cellular uptake. Out of the various classes of liposome, liposomes which contain cationic lipids are commonly used for delivering polyanions (e.g. nucleic acids). Such liposomes can be formed using cationic lipids alone and optionally including other lipids and amphiphiles such as phosphatidylethanolamine. It is well known in the art that both the composition of the lipid formulation as well as its method of preparation affect the structure and size of the resultant aggregate.

The use of cationic lipids for cellular delivery of biologically active agents has several advantages. The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, Trends Cell Bio., 2, 139; Xu et al., 1996, Biochemistry 35, 5616).

There is a need for further cationic lipids which facilitate the systemic and local delivery of biologically active agents such as RNAi agents to cells. There is also a need for cationic lipids which, relative to those cationic lipids that are known in the art, improve the systemic and local delivery of biologically active agents to cells. There is a further need for lipid formulations that have optimized physical characteristics for improved systemic and local delivery of biologically active agents to specific organs and to tumors, especially tumors outside the liver.

SUMMARY OF THE INVENTION

In one aspect, this invention provides for a compound of formula (I):

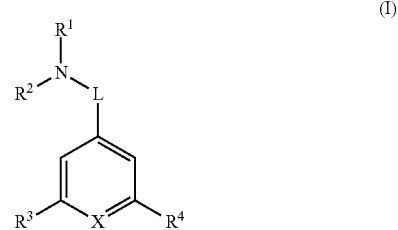

or a pharmaceutically acceptable salt thereof, wherein $R^1$-$R^4$, L and X are defined herein. The compounds of formula (I) and pharmaceutically acceptable salts thereof are cationic lipids useful in the delivery of biologically active agents to cells and tissues.

In a second aspect, this invention provides for a lipid composition comprising a compound according to formula (I) (i.e. a lipid composition of the invention), or a pharmaceutically acceptable salt thereof. In another embodiment, at least one other lipid component is present. In another embodiment the lipid composition also comprises a biologically active agent, optionally in combination with on one more other lipid components. In another embodiment the lipid composition is in the form of a liposome. In another embodiment the lipid composition is in the form of a lipid nanoparticle (LNP). In another embodiment the lipid composition is suitable for delivery to the liver. In another embodiment the lipid composition is suitable for delivery to a tumor. In another embodiment the lipid composition is suitable for immunization purposes.

In a third aspect, this invention provides for a pharmaceutical composition (i.e. formulation) comprising a lipid composition of the invention and a pharmaceutically acceptable carrier or excipient. In another embodiment at least one other lipid component is present in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the biologically active agent is a siRNA. In another embodiment the lipid composition is suitable for immunization purposes, and the biologically active agent is a RNA which encodes an immunogen.

In a fourth aspect, this invention provides a method for the treatment of a disease or condition comprising the step of administering a therapeutically effective amount of a lipid composition of the invention to a patient in need of treatment thereof. In one embodiment, the disease or condition is treatable by administering a siRNA agent.

In a fifth aspect, this invention provides for the use of a lipid composition of the invention in treating a disease or condition in a patient. In one embodiment, the disease or condition is treatable by administering an RNAi agent.

In a sixth aspect, this invention provides a method for immunizing a subject against an immunogen of interest comprising the step of administering an immunologically effective amount of a lipid composition of the invention to the subject, in combination with a RNA which encodes an immunogen.

In a seventh aspect, this invention provides for the use of a lipid composition of the invention in immunizing a subject against an immunogen of interest. The lipid is used in combination with a RNA which encodes an immunogen.

DETAILED DESCRIPTION OF THE INVENTION

The present invention provides for a compound of formula (I):

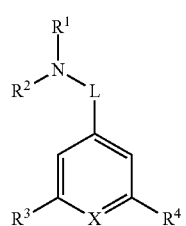

(I)

wherein:
L is $C_{1-6}$ alkylene, $C_{2-6}$ alkenylene, $C_{2-6}$ alkynylene, —$(CH_2)_r$—$C_{3-7}$ cycloalkylene-$(CH_2)_s$—, —$(CH_2)_s$—$C_{3-7}$ cycloalkenylene-$(CH_2)_s$—, —$(CH_2)_s$—$C_{3-7}$ cycloalkynylene-$(CH_2)_s$—, *—$C_{1-4}$ alkylene-L2-, *—$C_{1-4}$ alkylene-L2-$C_{1-4}$ alkylene-,

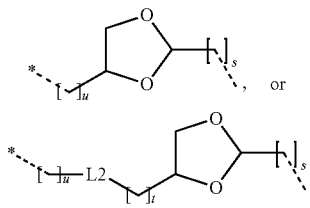

wherein in the * denotes attachment of the moiety to the $NR^1R^2$ group;
L2, attached in either direction, is —O—, —S—, —C(O)—, —C(O)O—, —OC(O)O—, —CONH—, $S(O)_2NH$—, NHCONH— or —NHCSNH—;
each s is independently 0, 1 or 2;
each t is independently 0, 1, 2, 3, or 4;
u is 0, 1, 2, 3, 4, 5, or 6;
$R^1$ and $R^2$ are each independently optionally substituted $C_{1-6}$ alkyl, optionally substituted $C_{2-6}$ alkenyl, optionally substituted $C_{2-6}$ alkynyl, optionally substituted $C_{3-7}$ cycloalkyl-$(CH_2)_s$—, optionally substituted $C_{3-7}$ cycloalkenyl-$(CH_2)_s$—, optionally substituted $C_{3-7}$ cycloalkynyl-$(CH_2)_s$—, or optionally substituted phenyl-$(CH_2)_s$—; wherein said $C_{1-6}$ alkyl, $C_{2-6}$ alkenyl, $C_{2-6}$ alkynyl, $C_{3-7}$ cycloalkyl, $C_{3-7}$ cycloalkenyl, $C_{3-7}$ cycloalkynyl, and phenyl are optionally substituted with one or two substituents each independently selected from the group consisting of: OH, $C_{1-3}$ alkoxy, COOH, and COO—$C_{1-4}$ alkyl, or $R^1$ and $R^2$ are joined together forming an optionally substituted 4-12 membered heterocyclic ring, said heterocyclic ring being optionally substituted with one to three substituents each independently selected from the group consisting of: OH, halo, $C_{1-3}$ alkyl, $C_{1-3}$ alkoxy, dimethylamino, —COO—$C_{1-4}$ alkyl, phenyl, piperidinyl, and morpholinyl;

$R^3$ and $R^4$ are each independently:
(a) —$Z^1$—$R^a$,
(b) —$Z^1$—$R^b$—$Z^2$—$R^a$,
(c) —$Z^1$—$R^b$—$Z^2$—$R^b$—$Z^3$—$R^a$,
(d) —$Z^1$—$R^b$—$Z^2$—$R^b$—$Z^3$—$R^b$—$Z^4$—$R^a$,
(e) —$R^b$—$Z^1$—$R^a$,
(f) —$R^b$—$Z^1$—$R^b$—$Z^2$—$R^a$,
(g) —$R^b$—$Z^1$—$R^b$—$Z^2$—$R^b$—$Z^3$—$R^a$,
(h) —$R^b$—$Z^1$—$R^b$—$Z^2$—$R^b$—$Z^3$—$R^b$—$Z^4$—$R^a$,
(i) —$R^c$,
(j) —$Z^1$—$R^b$—$R^c$, or
(k) —$R^b$—$Z^1$—$R^b$—$R^c$;
wherein $Z^1$, $Z^2$, $Z^3$, and $Z^4$, attached in either direction, are each independently —O—, —C(O)O—, —OC(O)O—, or —CONH—;

$R^a$ is $C_{2-22}$alkyl, $C_{2-22}$ alkenyl, or $C_{2-22}$ alkynyl;
each $R^b$ is independently $C_{1-20}$ alkylene, $C_{2-20}$ alkenylene, or $C_{2-20}$ alkynylene;

$R^c$ is
(c1) 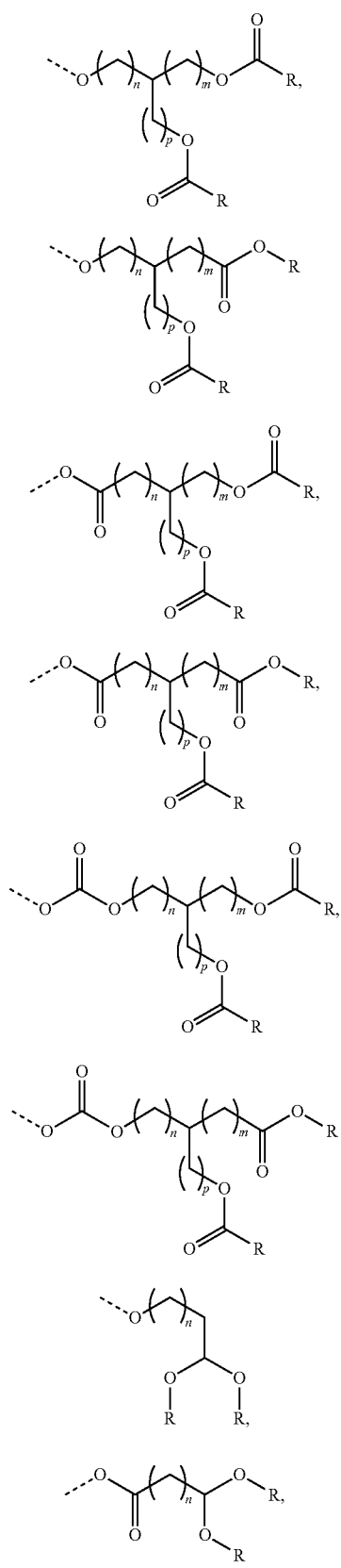
(c2)
(c3)
(c4)
(c5)
(c6)
(c7)
(c8)
-continued
(c9) 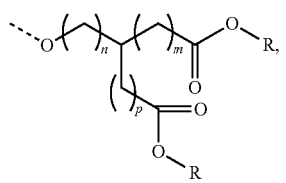
(c10) 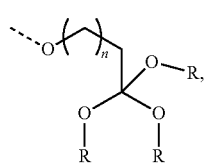
(c11) 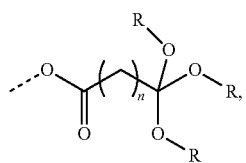
(c12) 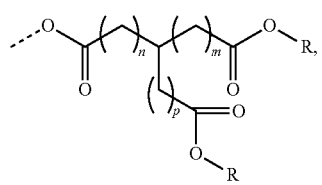
(c13) 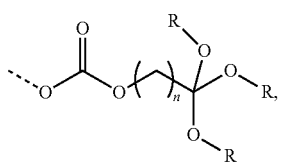
(c14) 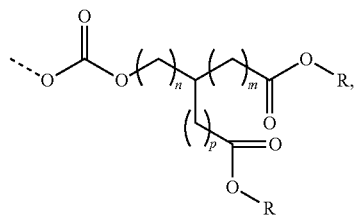
(c15) 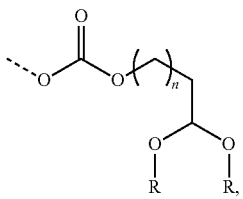
(c16) 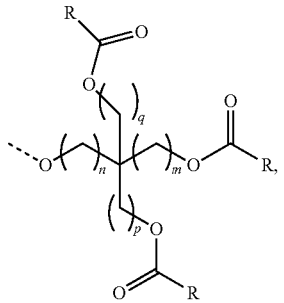

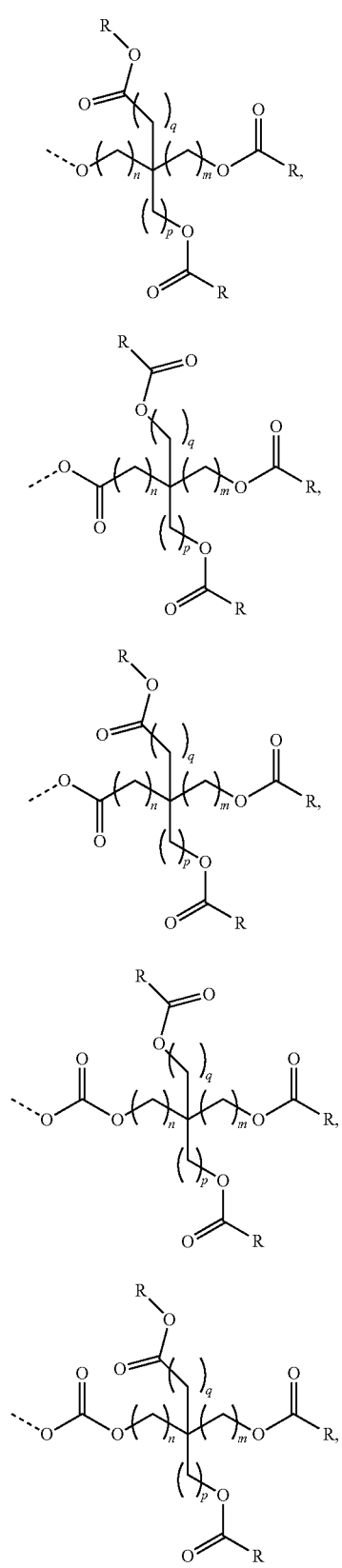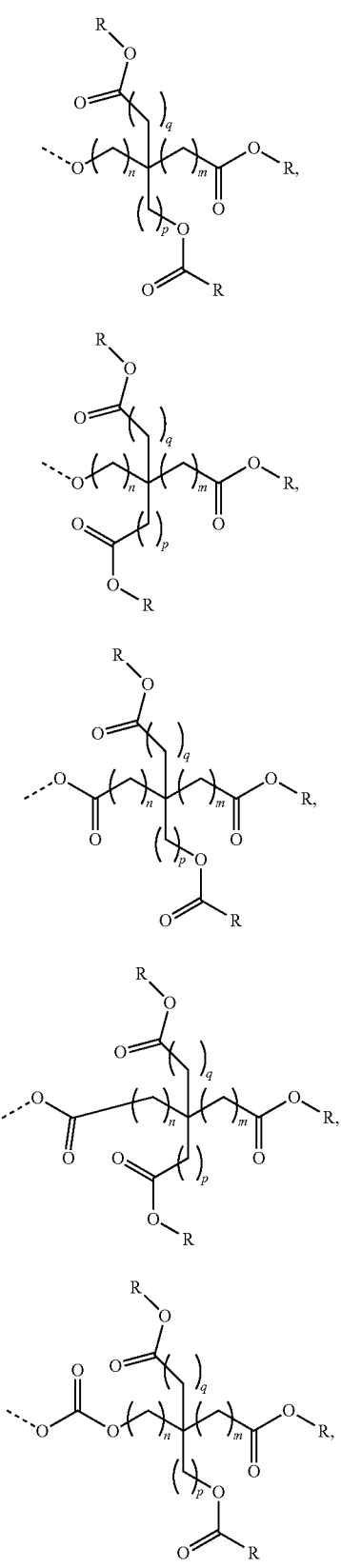

-continued (c27)
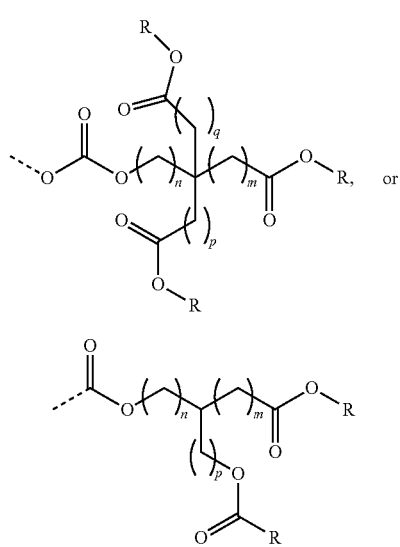

(c28)
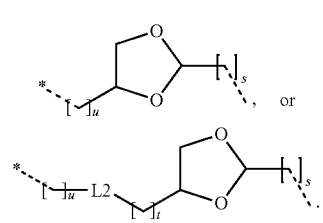

R is $C_{5-22}$ alkyl, $C_{5-22}$ alkenyl, or $C_{5-22}$ alkynyl;
n is 0-12;
m, p, and q are each independently 0, 1, 2, 3 or 4;
provided that chains (a)-(h) have 12-30 carbon atoms and chains (i)-(k) have 12-70 carbon atoms;
X is $CR^6$ or N; and
$R^6$ is H, halo, $C_{1-6}$ alkyl, or $R^4$.

EMBODIMENTS

In one embodiment $R^1$ and $R^2$ are each independently optionally substituted $C_{1-6}$ alkyl. In another embodiment $R^1$ and $R^2$ are each independently optionally substituted methyl or optionally substituted ethyl. In another embodiment $R^1$ is methyl and $R^2$ is optionally substituted ethyl. In another embodiment $R^1$ and $R^2$ are both methyl.

In another embodiment $R^1$ and $R^2$ are joined together forming an optionally substituted 4-7 membered heterocyclic ring. In another embodiment the 4-7 membered heterocyclic ring is optionally substituted azetidinyl, optionally substituted pyrrolyl, or optionally substituted piperidinyl. In another embodiment the 4-7 membered heterocyclic ring is azetidinyl, pyrrolyl, or piperidinyl each of which is optionally substituted with one OH group. In another embodiment the 4-7 membered heterocyclic ring is azetidinyl, pyrrolyl, or piperidinyl.

In another embodiment L is $C_{1-6}$ alkylene, *—$C_{1-4}$ alkylene-L2-, *—$C_{1-4}$ alkylene-L2-$C_{1-4}$ alkylene-,

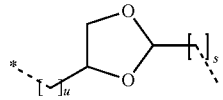
, or

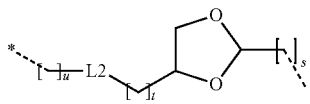

In another embodiment L is *—$C_{1-3}$ alkylene-L2-, *—$C_{1-4}$ alkylene-L2-$C_{1-2}$ alkylene-,

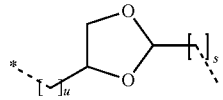

wherein s is 0 and u is 1, or

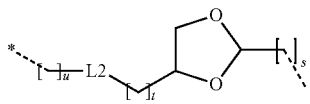

wherein s is 0, t is 1 and u is 1.

In another embodiment L is methylene, ethylene, or propylene. In another embodiment L is methylene.

In another embodiment L2, attached in either direction, is —C(O)O—, —OCOO—, or —CONH—.

In another embodiment L is *—$C_{1-3}$ alkylene-O—C(O)—.

In another embodiment L is *—$C_{1-4}$ alkylene-L2-$C_{1-2}$ alkylene-, wherein L2, attached in either direction, is —C(O)O—, or —OC(O)O—.

In another embodiment L is:

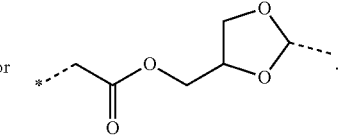

In one embodiment the L-$NR^1R^2$ group of formula (I) is selected from the list in Table 1.

TABLE 1

L—$NR^1R^2$ groups of formula (I), wherein the dashed line indicates the point of attachment to formula (I).

| Structure |
| --- |
|  |
| 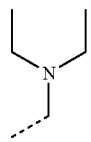 |
| 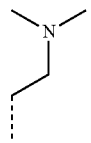 |

TABLE 1-continued
L—NR¹R² groups of formula (I), wherein the dashed line indicates the point of attachment to formula (I).
Structure
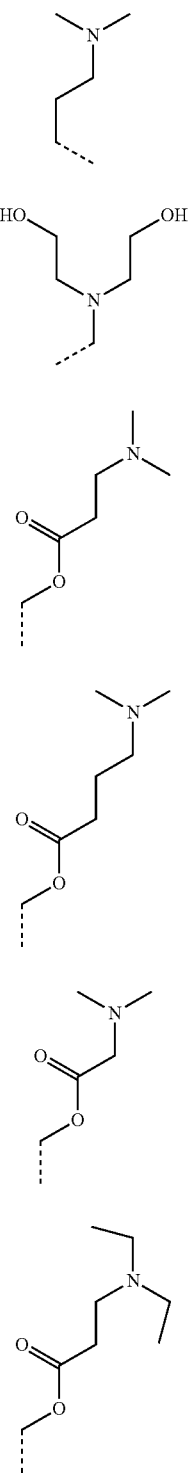
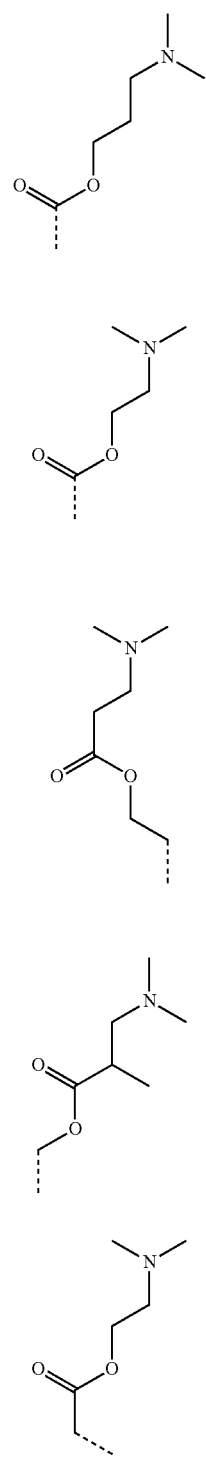

TABLE 1-continued
L—NR¹R² groups of formula (I), wherein the dashed line indicates the point of attachment to formula (I).
Structure
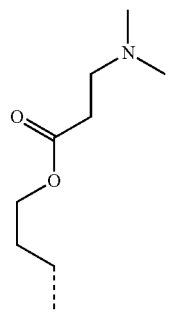
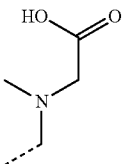
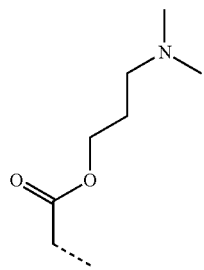
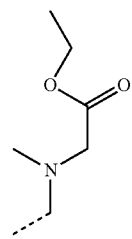
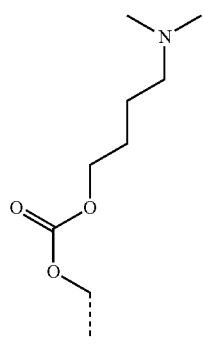
TABLE 1-continued
L—NR¹R² groups of formula (I), wherein the dashed line indicates the point of attachment to formula (I).
Structure
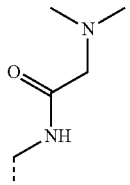
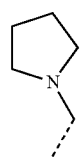
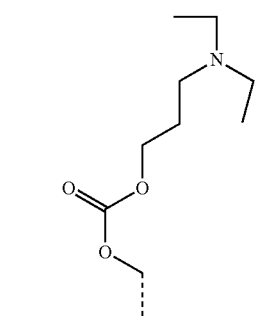
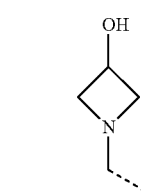
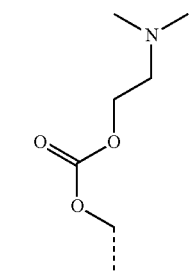
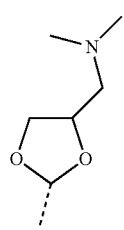

TABLE 1-continued
L—NR$^1$R$^2$ groups of formula (I), wherein the dashed line indicates the point of attachment to formula (I).
Structure
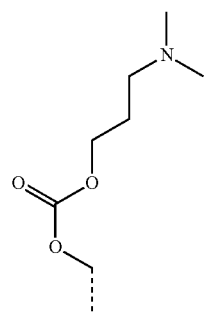
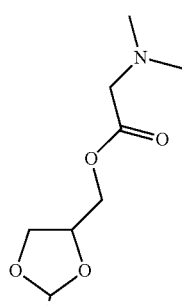
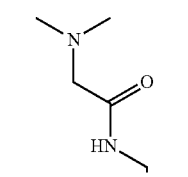
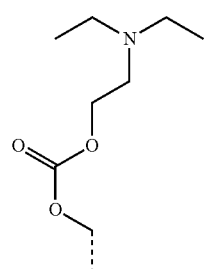
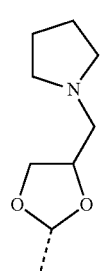
TABLE 1-continued
L—NR$^1$R$^2$ groups of formula (I), wherein the dashed line indicates the point of attachment to formula (I).
Structure
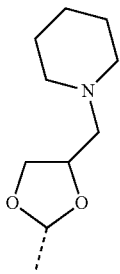
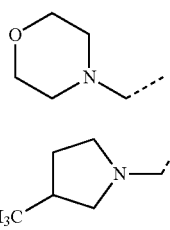
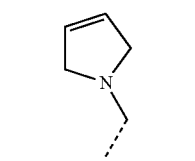
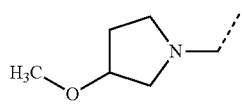
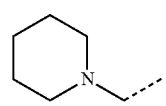
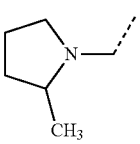
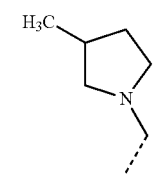
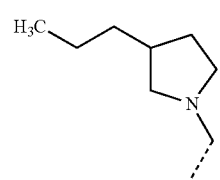

TABLE 1-continued

L—NR$^1$R$^2$ groups of formula (I), wherein the dashed line indicates the point of attachment to formula (I).

Structure

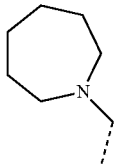

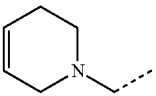

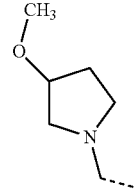

In another embodiment the L-NR$^1$R$^2$ group of formula (I) is selected from the list in Table 2.

TABLE 2

L—NR$^1$R$^2$ groups of formula (I), wherein the dashed line indicates the point of attachment to formula (I).

Structure

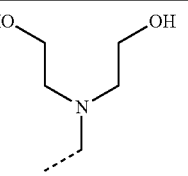

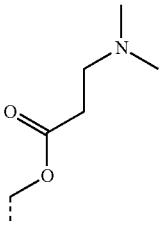

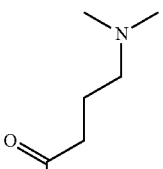

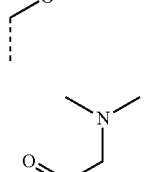

TABLE 2-continued

L—NR$^1$R$^2$ groups of formula (I), wherein the dashed line indicates the point of attachment to formula (I).

Structure

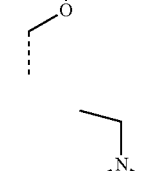

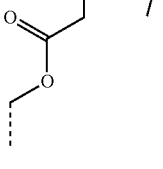

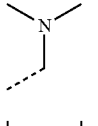

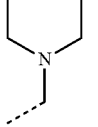

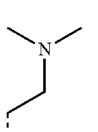

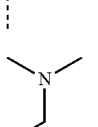

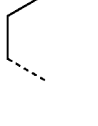

TABLE 2-continued
L—NR$^1$R$^2$ groups of formula (I), wherein the dashed line indicates the point of attachment to formula (I).
Structure
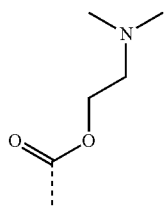
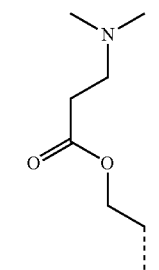
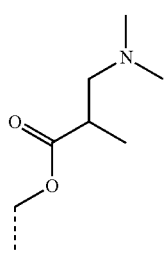
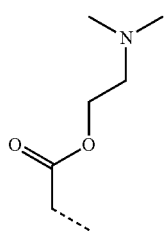
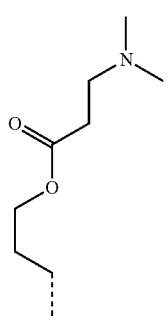
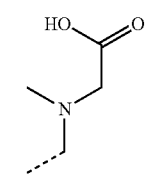
TABLE 2-continued
L—NR$^1$R$^2$ groups of formula (I), wherein the dashed line indicates the point of attachment to formula (I).
Structure
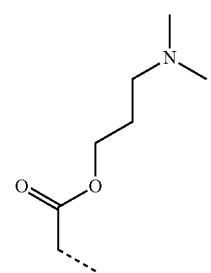
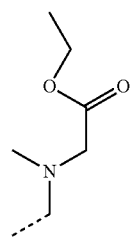
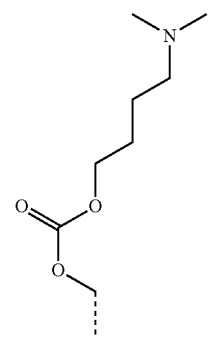
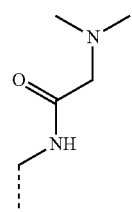
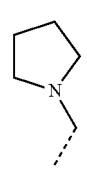

TABLE 2-continued

L—NR¹R² groups of formula (I), wherein the dashed line indicates the point of attachment to formula (I).

Structure

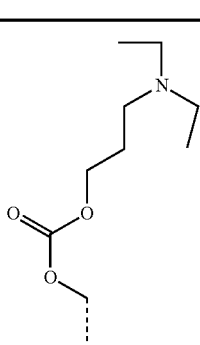

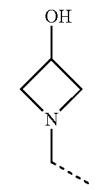

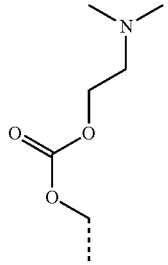

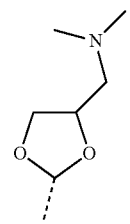

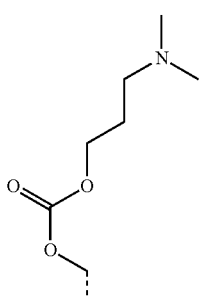

TABLE 2-continued

L—NR¹R² groups of formula (I), wherein the dashed line indicates the point of attachment to formula (I).

Structure

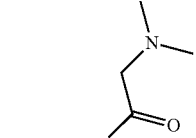

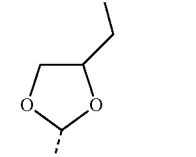

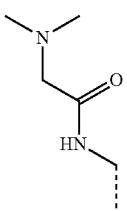

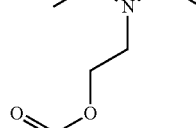

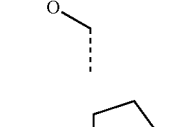

In another embodiment $R^3$ and $R^4$ are each independently:
(a) —$Z^1$—$R^a$,
(b) —$Z^1$—$R^b$—$Z^2$—$R^a$,
(c) —$Z^1$—$R^b$—$Z^2$—$R^b$—$Z^3$—$R^a$,
(e) —$R^b$—$Z^1$—$R^a$, (f) —$R^b$—$Z^1$—$R^b$—$Z^2$—$R^a$,
(g) —$R^b$—$Z^1$—$R^b$—$Z^2$—$R^b$—$Z^3$—$R^a$,
(i) —$R^c$, or
(j) —$Z^1$—$R^b$—$R^c$.

In another embodiment $R^3$ and $R^4$ are each independently:
(a) —$Z^1$—$R^a$,
(b) —$Z^1$—$R^b$—$Z^2$—$R^a$,
(c) —$Z^1$—$R^b$—$Z^2$—$R^b$—$Z^3$—$R^a$,
(e) —$R^b$—$Z^1$—$R^a$,
(f) —$R^b$—$Z^1$—$R^b$—$Z^2$—$R^a$, or
(g) —$R^b$—$Z^1$—$R^b$—$Z^2$—$R^b$—$Z^3$—$R^a$.

In another embodiment $R^3$ and $R^4$ are each independently:
(a) —$Z^1$—$R^a$,
(b) —$Z^1$—$R^b$—$Z^2$—$R^a$, or
(f) —$R^b$—$Z^1$—$R^b$—$Z^2$—$R^a$.

In another embodiment $R^3$ and $R^4$ are each independently (b) —$Z^1$—$R^b$—$Z^2$—$R^a$.

In another embodiment $R^3$ and $R^4$ are each independently (i) —$R^c$ or (j) —$Z^1$—$R^b$—$R^c$.

In another embodiment $R^4$=$R^3$.

In another embodiment $R^a$ is $C_{2-22}$ alkyl or $C_{2-22}$ alkenyl. In another embodiment $R^a$ is $C_{4-20}$ alkyl. In another embodiment $R^a$ is $C_{5-18}$ alkyl. In another embodiment $R^a$ is $C_{2-22}$ alkenyl having one to three double bonds. In another embodiment $R^a$ is $C_{10-20}$ alkenyl having one to three double bonds, suitably having one or two double bonds. In another embodiment $R^a$ is $C_{11-18}$ alkenyl having one to three double bonds, suitably one or two double bonds, suitably two double bonds.

In another embodiment each $R^b$ is independently $C_{1-20}$ alkylene. In another embodiment each $R^b$ is independently $C_{1-15}$ alkylene, suitably $C_{1-10}$ alkylene.

In another embodiment $R^c$ is (c1) or (c3). In another embodiment $R^c$ is (c1) or (c3) wherein n is 1 or 2; m is 0 or 1; and p is 1.

In another embodiment $Z^1$ is —O—, —OCO—, or —CONH—. Suitably $Z^1$ is —O—. Suitably $Z^1$ is —OCO—.

In another embodiment $Z^2$ is —OCO—, —COO—, —NHCO—, or —OCOO—. Suitably $Z^2$ is —OCO— or —COO—. Suitably $Z^2$ is —OCO—.

In another embodiment $Z^3$ is —OCO— or —COO—.

In another embodiment $R^3$ and $R^4$ are each independently (a) —$Z^1$—$R^a$, (b) —$Z^1$—$R^b$—$Z^2$—$R^a$ or (c) —$Z^1$—$R^b$—$Z^2$—$R^b$—$Z^3$—$R^a$, wherein $Z^1$ is —O—.

In another embodiment $R^3$ and $R^4$ are each independently (e) —$R^b$—$Z^1$—$R^a$, (f) —$R^b$—$Z^1$—$R^b$—$Z^2$—$R^a$ or (g) —$R^b$—$Z^1$—$R^b$—$Z^2$—$R^b$—$Z^3$—$R^a$, wherein $Z^1$ is —OCO—.

In another embodiment $R^3$ and $R^4$ are each independently (a) —$Z^1$—$R^a$ wherein $Z^1$ is —O—, —OCO—, or —CONH— and $R^a$ is $C_{12-18}$ alkenyl having one to three double bonds, suitably one or two double bonds, suitably two double bonds. Suitably $R^4$=$R^3$.

In another embodiment $R^3$ and $R^4$ are each independently (b) —$Z^1$—$R^b$—$Z^2$—$R^a$ wherein $Z^1$ is —O—, $Z^2$ is —OCO—, $R^b$ is $C_{1-15}$ alkylene, suitably $C_{2-10}$ alkylene and $R^a$ is $C_{5-18}$ alkyl or $C_{11-18}$ alkenyl having one to three double bonds. Suitably $R^4$=$R^3$.

In another embodiment $R^3$ and $R^4$ are each independently (c) —$Z^1$—$R^b$—$Z^2$—$R^b$—$Z^3$—$R^a$ wherein $Z^1$ is —O—, $Z^2$ is —O— or —OCO—, $Z^3$ is —O—, each $R^b$ is independently $C_{2-7}$ alkylene and $R^a$ is $C_{8-9}$ alkyl or $C_{17}$ alkenyl having two double bonds. Suitably $R^4$=$R^3$.

In another embodiment $R^3$ and $R^4$ are each independently (e) —$R^b$—$Z^1$—$R^a$ wherein $Z^1$ is —OCO—, $R^b$ is methylene and $R^a$ is $C_{12-18}$ alkyl or $C_{17}$ alkenyl having two double bonds. Suitably $R^4$=$R^3$.

In another embodiment $R^3$ and $R^4$ are each independently (f) —$R^b$—$Z^1$—$R^b$—$Z^2$—$R^a$ wherein $Z^1$ is —OCO—, $Z^2$ is —COO—, —NHCO—, —OCO—, —OCOO—, each $R^b$ is independently $C_{2-9}$ alkylene and $R^a$ is $C_{7-9}$ alkyl or $C_{17-18}$ alkenyl having two double bonds. Suitably $R^4$=$R^3$.

In another embodiment X is $CR^6$, wherein $R^6$ is H, chloro, bromo, or $C_{1-3}$ alkyl. Suitably X is CH.

In another embodiment X is N.

As used herein, the term "alkyl" refers to a fully saturated branched or unbranched hydrocarbon chain having the specified number of carbon atoms. For example, $C_{1-6}$ alkyl refers to an alkyl group having from 1 to 6 carbon atoms. Alkyl groups may be optionally substituted with one or more substituents as defined in formula (I). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecanyl, n-dodecanyl, n-tridecanyl, 9-methylheptadecanyl, and the like.

As used herein, the term "alkylene" refers to divalent alkyl group as defined herein above. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene, and the like.

As used herein, the term "alkenyl" refers to an unsaturated branched or unbranched hydrocarbon chain having the specified number of carbon atoms and one or more carbon-carbon double bonds within the chain. For example, $C_{2-6}$ alkenyl refers to an alkenyl group having 2 to 6 carbon atoms with one or more carbon-carbon double bonds within the chain. In certain embodiments alkenyl groups have one carbon-carbon double bond within the chain. In other embodiments, alkenyl groups have more than one carbon-carbon double bond within the chain. Alkyenyl groups may be optionally substituted with one or more substituents as defined in formula (I). Representative examples of alkenyl include, but are not limited to, ethylenyl, propenyl, butenyl, pentenyl, hexenyl and the like. Other examples of alkenyl include, but are not limited to: Z-octadec-9-enyl, Z-undec-7-enyl, Z-heptadeca-8-enyl, (9Z,12Z)-octadeca-9,12-dienyl, (8Z,11Z)-heptadeca-8,11-dienyl, and (8Z, 11Z, 14Z)-heptadeca-8,11,14-trienyl.

As used herein, the term "alkenylene" refers a divalent alkenyl group as defined herein above. Representative examples of alkenylene include, but are not limited to, ethenylene, propenylene, butenylene, pentenylene, hexenylene and the like.

As used herein, the term "alkynyl" refers to an unsaturated branched or unbranched hydrocarbon chain having the specified number of carbon atoms and one or more carbon-carbon triple bonds. For example $C_{2-6}$ alkynyl refers to an alkynyl group having from 2 to 6 carbon atoms with one or more carbon-carbon triple bonds within the chain. In certain embodiments alkynyl groups have one carbon-carbon triple bond within the chain. In other embodiments alkynyl groups have more than one carbon-carbon triple bond within the chain. Alkynyl groups may be optionally substituted with one or more substituents as defined in formula (I). Representative examples of alkynyl include, but are not limited to ethynyl, 1-propynyl, propargyl, butynyl, pentynyl, hexynyl and the like.

As used herein, the term "alkynylene" refers to a divalent alkynyl group as herein defined above. Representative examples of alkynylene include, but are not limited to ethynylene, propynylene, propargylene, butynylene, pentynlene, hexynylene and the like.

As used herein, the term "alkoxy" refers to refers to any alkyl moiety attached through an oxygen bridge (i.e. a —O—$C_{1-3}$ alkyl group wherein $C_{1-3}$ alkyl is as defined herein). Examples of such groups include, but are not limited to, methoxy, ethoxy, and propoxy.

As used herein, the term "cycloalkyl" refers to a saturated monocyclic, bicyclic or tricyclic hydrocarbon ring having the specified number of carbon atoms. For example, $C_{3-7}$ cycloalkyl refers to a cycloalkyl ring having from 3 to 7 carbon atoms. Cycloalkyl groups may be optionally substituted with one or more substituents as defined in formula (I). Representative examples of cycloalkyl include, but are not limited to, cyclopropyl, cyclobutyl, cyclopentyl, cyclohexyl, bicyclo[2.1.1]hexyl, bicyclo[2.2.1]heptyl, adamantyl and the like.

As used herein, the term "cycloalkylene" refers to a divalent cycloalkyl group as defined above.

As used herein, the term "cycloalkenyl" refers to a non-aromatic, unsaturated monocylic, bicyclic or tricyclic hydrocarbon ring having the specified number of carbon atoms and one or more carbon-carbon double bonds. For example, $C_{3-7}$ cycloalkeneyl refers to a cycloalkenyl group having from 3 to 7 carbon atoms and one or more carbon-carbon double bonds. In certain embodiments cycloalkenyl groups have one carbon-carbon double bond within the ring. In other embodiments, cycloalkenyl groups have more than one carbon-carbon double bond within the ring. Representative examples of cycloalkenyl include, but are not limited to, cyclopropenyl, cyclobutenyl, cyclopentenyl, cyclohexenyl, cycloheptenyl and the like.

As used herein, the term "cycloalkenylene" refers to a divalent cycloalkenyl group as defined herein above.

As used herein, the term "cycloalkynyl" refers to an unsaturated monocylic, bicyclic or tricyclic hydrocarbon ring having the specified number of carbon atoms and one or more carbon-carbon triple bonds. For example, $C_{3-7}$ cycloalkynyl refers to a cycloalkynyl group having from 3 to 7 carbon atoms. In certain embodiments cycloalkynyl groups have one carbon-carbon triple bond within the ring. In other embodiments, cycloalkynyl groups have more than one carbon-carbon triple bond within the ring. Representative examples of cycloalkynyl include, but are not limited to, cyclopropynyl, cyclobutynyl, cyclopentynyl, cyclohexynyl, cycloheptynyl and the like.

As used herein, the term "cycloalkynylene" refers to a divalent cycloalkynyl group as defined herein above.

As used herein, the term "halo" refers to fluoro, chloro, bromo, and iodo.

As used herein, the term "heterocyclic" refers to a 4 to 12 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic groups may be optionally substituted with one or more substituents as defined in formula (I). Heterocyclic groups are monocyclic, spiro, or fused or bridged bicyclic ring systems. Examples of monocyclic heterocyclic groups include tetrahydrofuranyl, dihydrofuranyl, 1,4-dioxanyl, morpholinyl, 1,4-dithianyl, azetidinyl, piperazinyl, piperidinyl, 1,3-dioxolanyl, imidazolidinyl, imidazolinyl, pyrrolinyl, pyrrolidinyl, tetrahydropyranyl, dihydropyranyl, 1,2,3,6-tetrahydropyridinyl, oxathiolanyl, dithiolanyl, 1,3-dioxanyl, 1,3-dithianyl, oxathianyl, thiomorpholinyl, 1,4,7-trioxa-10-azacyclododecanyl, azapanyl and the like. Examples of spiro heterocyclic rings include, but are not limited to, 1,5-dioxa-9-azaspiro[5.5]undecanyl, 1,4-dioxa-8-azaspiro[4.5]decanyl, 2-oxa-7-azaspiro[3.5] nonanyl, and the like. Fused heterocyclic ring systems have from 8 to 11 ring atoms and include groups wherein a heterocyclic ring is fused to a phenyl ring. Examples of fused heterocyclic rings include, but are not limited to decahydroqunilinyl, (4aS, 8aR)-decahydroisoquinolinyl, (4aS,8aS)-decahydroisoquinolinyl, octahydrocyclopenta[c] pyrrolyl, isoinolinyl, (3aR,7aS)-hexahydro-[1,3]dioxolo [4.5-c]pyridinyl, octahydro-1H-pyrrolo[3,4-b]pyridinyl, tetrahydroisoquinolinyl and the like.

As used herein, the term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95 enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition or base addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

General Methods for Synthesizing Cationic Lipids

The present invention also includes processes for the preparation of compounds of formula (I). In the reactions described, it could be necessary to protect reactive functional groups, for example hydroxyl, amino, iminio, thio or carboxy groups, where these are desired in the final product, to avoid their unwanted participation in the reactions.

The compounds and processes of the present invention will be better understood in connection with the following synthetic schemes, which are merely intended to illustrate methods by which the compounds may be generally prepared and are not intended to limit the scope of the invention as defined in the claims.

Final compounds of formula (I) can be prepared as described in Scheme I.

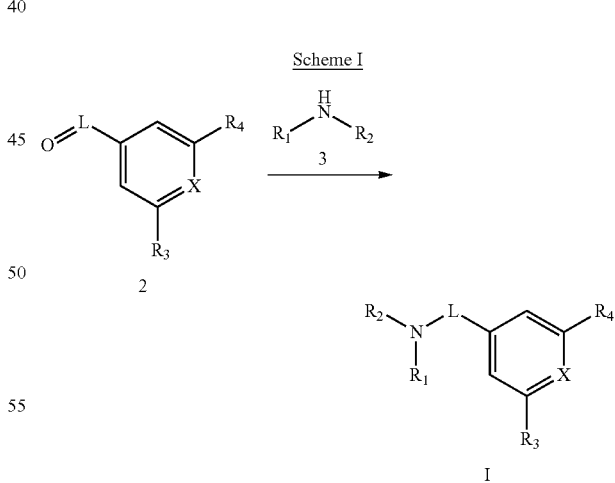

A compound of formula (I) can be prepared by reacting a compound of formula 2 with a compound of formula 3 using a suitable reducing agent (e.g. sodium acetoxyborohydride and the like) and optionally a Lewis acid (e.g. titanium tetraisopropoxide and the like) in a suitable solvent such as ethanol. The reaction can be carried out between room temperature and 80° C. and can take up to 24 hours to complete.

Compounds of formula (I) can also be prepared by proceeding as described in Scheme II.

Scheme II

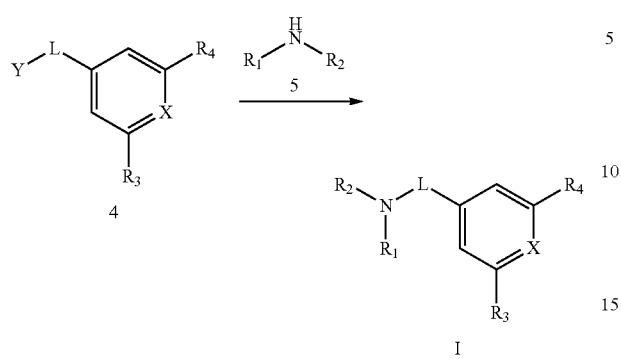

A compound of formula I can be prepared by reacting a compound of formula 4 where Y is a chloro, bromo, iodo, mesyl, tosyl, or other leaving group with a compound of formula 5 in DMF or another suitable solvent at a temperature from 20 to 180° C.

Final compounds of formula (Ia) can be prepared as described in Scheme III.

Scheme III

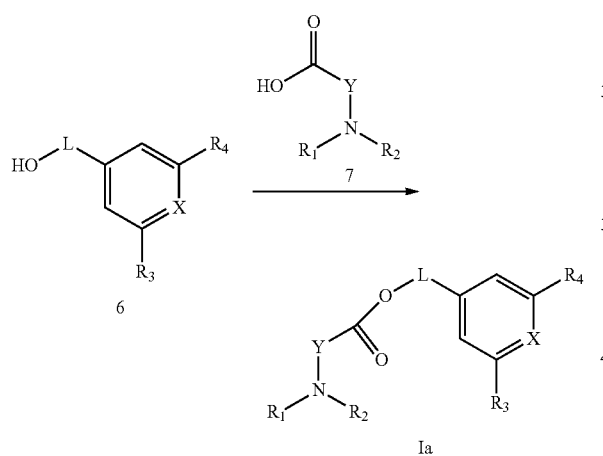

A compound of formula (Ia) can be prepared by reacting an alcohol of formula 6 with an acid of formula 7 in dichloromethane or another suitable solvent using EDC or another suitable coupling agent with optional based or catalyst, such as DMAP at a temperature from 20° C. to 150° C.

Compounds of formula 4 and 6 can be prepared from the appropriate precursor of formula 7 by methods known to those skilled in the art, for example, as described in Scheme IV.

Scheme IV

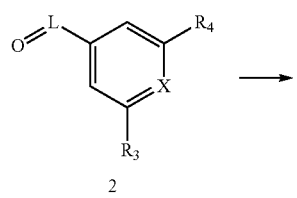

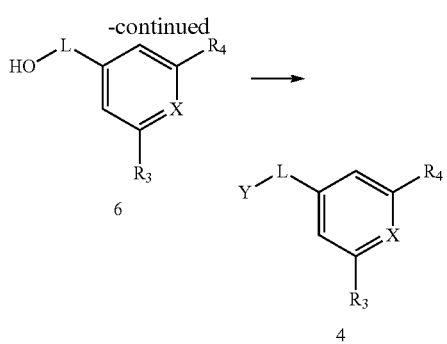

A compound of formula 6 can be prepared by reacting a compound of formula 2 with sodium borohydride or other appropriate reducing agent (e.g. diisobutylaluminum hydride, lithium borohydride, etc) in ethanol or other appropriate solvent at a temperature between −20° C. and 150° C. A compound of formula 4 can be prepared from a compound of formula 6 by reaction with mesyl anhydride or other appropriate activating agent (e.g. tosyl chloride, phosphorousoxychloride, etc) in dichloromethane or other appropriate solvent at a temperature between −20° C. and 80° C.

Compounds of formula 2 can be prepared as described in Scheme V.

Scheme V

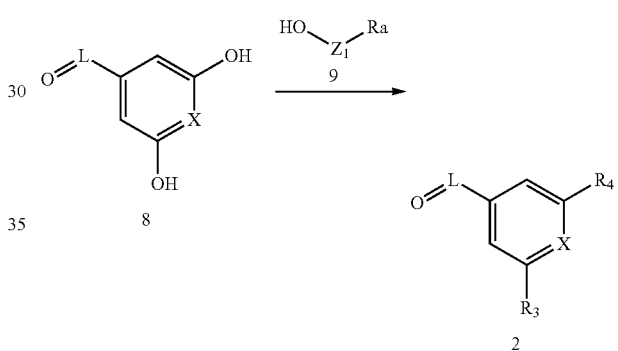

A compound of formula 2 can be prepared from a compound of formula 8 by reacting with a compound of formula 9 in the presence of DIAD or other appropriate diazo compound (e.g. DEAD, etc) with triphenylphosphine or other appropriate phosphine (e.g. trimethylphosphine) in dichloromethane or other suitable solvent at a temperature between −20° C. and 50° C.

Alternatively, compounds of formula 2 can be prepared according to Scheme VI.

Scheme VI

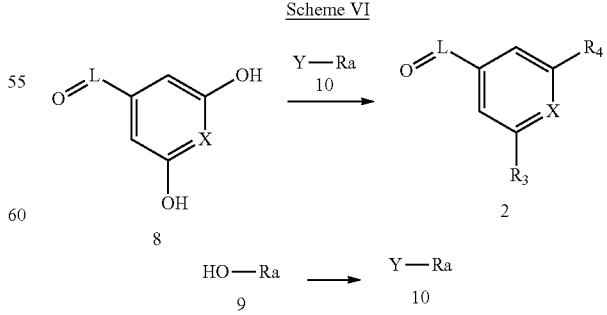

A compound of formula 2 can be prepared from a compound of formula 8 by reacting with a compound of formula 10, where Y is a halogen, mesylate, or other appropriate leaving group, in the presence of potassium carbonate or other suitable base (e.g. cesium carbonate, tribasic potassium phosphate, etc) in DMF or other suitable solvent at a temperature between 20 and 180° C. A compound of formula 10 can be prepared from a compound of formula 9 by reacting with mesyl chloride or other suitable activating agent (e.g. tosyl chloride, phosphorousoxychloride, etc) in the presence of pyridine or other suitable base in dichloromethane or other suitable solvent at a temperature between −20° C. and 180° C.

Alternatively, compounds of formula 2 can be made according to Scheme VII.

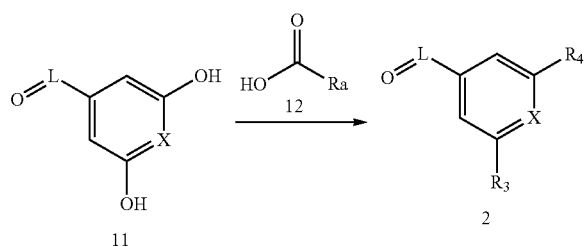

A compound of formula 2 can be prepared from a compound of formula 11 by reacting with a compound of formula 12 and EDC or other suitable coupling agent (e.g. DIC, HATU, etc) in the presence of DMAP or other appropriate catalyst and DIEA or other appropriate base in dichloromethane or other appropriate solvent (e.g. DMF, DCE, etc) at a temperature between 0° C. and 180° C.

Alternatively, compounds of formula 2 can be made according to Scheme VIII.

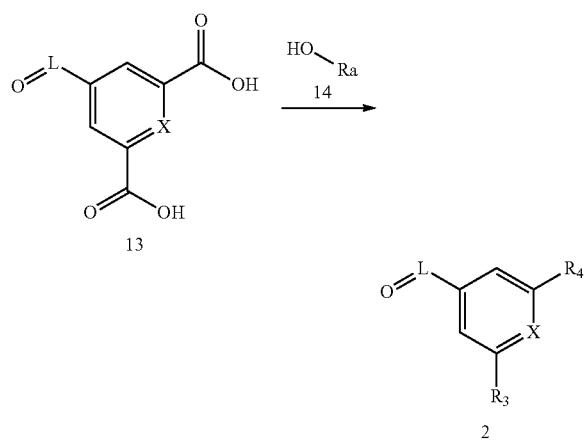

A compound of formula 2 can be prepared from a compound of formula 13 by reacting with a compound of formula 14 and EDC or other suitable coupling agent (e.g. DIC, HATU, etc) in the presence of DMAP or other appropriate catalyst and DIEA or other appropriate base in dichloromethane or other appropriate solvent (e.g. DMF, DCE, etc) at a temperature between 0° C. and 180° C.

pKa For Cationic Lipids

The compounds of formula (I) are cationic lipids useful in the delivery of biologically active agents to cells and tissues. It has been found that lipid compositions for the delivery of biologically active agents can be adjusted to preferentially target one cell type or organ over another by altering only the cationic lipid in the formulation. For example, a cationic lipid with a pKa of from about 5.1 to about 7.4 is generally effective when used in a formulation for delivery to the liver. In one embodiment, the pKa of a cationic lipid is from about 5.1 to about 7.4 for delivery to liver. In another embodiment, the pKa of a cationic lipid is from about 5.3 to about 7.0 for delivery to liver. In another embodiment, the pKa of a cationic lipid is from about 5.3 to about 6.6 for delivery to liver. For tumor delivery, a cationic lipid with a pKa of from about 5.3 to about 6.4 is particularly effective when used in a formulation for delivery of a biologically active agent to a tumor. Thus, in one embodiment, the pKa of a cationic lipid is from about 5.3 to about 6.4 for delivery to tumors. In another embodiment, the pKa of a cationic lipid is from about 5.4 to about 6.2 for delivery to tumors. In another embodiment, the pKa of the cationic lipid is from about 5.8 to about 6.1 for delivery to tumors. For immunization purposes, the pKa of a cationic lipid is usefully from 5.0 to 7.6, such as from 5.7 to 5.9 (see WO2012/006378).

Lipid Compositions

The present invention provides for a lipid composition comprising at least one compound of formula (I), i.e. a lipid composition of the invention. In one embodiment, at least one other lipid component is present. Such compositions can also contain a biologically active agent, optionally in combination with one or more other lipid components.

One embodiment of the present invention provides for a lipid composition comprising a compound of formula (I) and another lipid component. Such other lipid components include, but are not limited to, cationic lipids, neutral lipids, anionic lipids, helper lipids, and stealth lipids.

Cationic lipids suitable for use in a lipid composition of the invention include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP). In one embodiment the cationic lipid is DOTAP or DLTAP.

Neutral lipids suitable for use in a lipid composition of the invention include, for example, a variety of neutral, uncharged or zwitterionic lipids. Examples of neutral phospholipids suitable for use in the present invention include, but are not limited to: 5-heptadecylbenzene-1,3-diol (resorcinol), cholesterol hemisuccinate (CHEMS), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid is selected from the group consisting of distearoylphosphatidylcholine (DSPC) and dimyristoyl phosphatidyl ethanolamine (DMPE).

Anionic lipids suitable for use in the present invention include, but are not limited to, phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine and lysylphosphatidylglycerol.

Suitable neutral and anionic lipids also include those described in US 2009/0048197.

Helper lipids are lipids that enhance transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Helper lipids suitable for use in the present invention include, but are not limited to, cholesterol, 5-heptadecylresorcinol, and cholesterol hemisuccinate.

Stealth lipids are lipids that increase the length of time for which the nanoparticles can exist in vivo (e.g. in the blood). Stealth lipids suitable for use in a lipid composition of the invention include, but are not limited to, stealth lipids having a hydrophilic head group linked to a lipid moiety. Examples of such stealth lipids include compounds of formula (XI), as described in WO2011/076807,

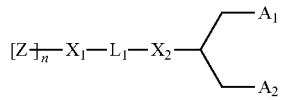

or a salt or pharmaceutically acceptable derivative thereof, wherein:

Z is a hydrophilic head group component selected from PEG and polymers based on poly(oxazoline), poly(ethyleneoxide), poly(vinyl alcohol), poly(glycerol), poly(N-vinylpyrrolidone), poly[N-(2-hydroxypropyl)methacrylamide], polysaccharides and poly(amino acid)s, wherein the polymer may be linear or branched, and wherein the polymer may be optionally substituted;

wherein Z is polymerized by n subunits;

n is a number-averaged degree of polymerization between 10 and 200 units of Z, wherein n is optimized for different polymer types;

$L_1$ is an optionally substituted $C_{1\text{-}10}$ alkylene or $C_{1\text{-}10}$ heteroalkylene linker including zero, one, two or more of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;

wherein R' is independently selected from —H, —NH—, —NH$_2$, —O—, —S—, a phosphate or an optionally substituted $C_{1\text{-}10}$ alkylene;

$X_1$ and $X_2$ are independently selected from a carbon or a heteroatom selected from —NH—, —O—, —S— or a phosphate;

$A_1$ and $A_2$ are independently selected from a $C_{6\text{-}30}$ alkyl, $C_{6\text{-}30}$ alkenyl, and $C_{6\text{-}30}$ alkynyl, wherein $A_1$ and $A_2$ may be the same or different, or wherein $A_1$ and $A_2$ together with the carbon atom to which they are attached form an optionally substituted steroid.

Specific stealth lipids include, but are not limited to, those listed in Table 3.

TABLE 3

| Stealth Lipids | |
|---|---|
| Stealth Lipid | Lipid |
| S001 | |

TABLE 3-continued

Stealth Lipids

| Stealth Lipid | Lipid |
|---|---|
| S002 | [structure: mPEG45-ester-glycine carbamate-cholesterol] |
| S003 | [structure: mPEG45-O-propyl-carbamate-cholesterol] |
| S004 | [structure: mPEG45-O-propyl-carbamate-O-dialkyl chain] |
| S005 | [structure: mPEG45-O-propyl-carbamate-O-dialkyl chain] |
| S006 | [structure: mPEG45-O-propyl-carbamate-O-dialkyl chain] |
| S007 | [structure: mPEG45-O-propyl-carbamate-O-dialkyl chain] |
| S008 | [structure: mPEG45-O-propyl-carbamate-O-dialkyl chain] |
| S009 | [structure: mPEG45-O-propyl-carbamate-O-dialkyl chain] |
| S010 | [structure: mPEG45-O-propyl-carbamate-O-glyceryl dialkyl ether] |

TABLE 3-continued

Stealth Lipids

| Stealth Lipid | Lipid |
|---|---|
| S011 | |
| S012 | |
| S013 | |
| S014 | |
| S015 | |
| S016 | |
| S017 | |
| S018 | |
| S019 | |
| S020 | |

TABLE 3-continued

Stealth Lipids

| Stealth Lipid | Lipid |
|---|---|
| S021 | 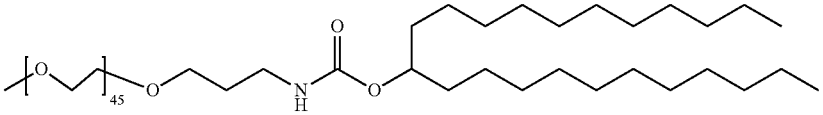 |
| S022 | 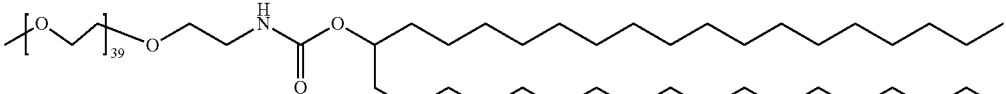 |
| S023 | 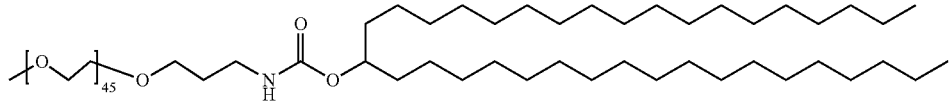 |
| S024 | 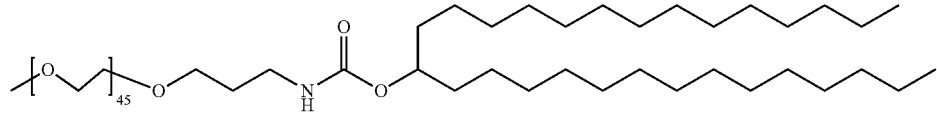 |
| S025 | 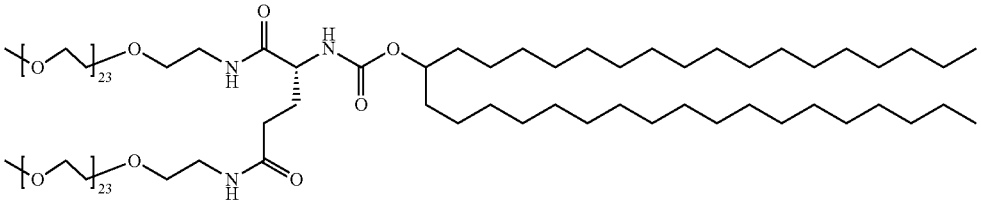 |
| S026 | 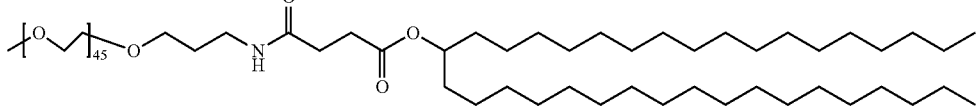 |

Other stealth lipids suitable for use in a lipid composition of the present invention and information about the biochemistry of such lipids can be found in Romberg et al., Pharmaceutical Research, Vol. 25, No. 1, 2008, p. 55-71 and Hoekstra et al., Biochimica et Biophysica Acta 1660 (2004) 41-52.

In one embodiment, the suitable stealth lipid comprises a group selected from PEG (sometimes referred to as poly(ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. Additional suitable PEG lipids are disclosed, e.g., in WO 2006/007712.

Specific suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol, PEG-dimyristylglycerol (PEG-DMG) (catalog # GM-020 from NOF, Tokyo, Japan), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000] (catalog #880150P from Avanti Polar Lipids, Alabaster, Ala., USA).

In one embodiment the stealth lipid is S010 or S011.

In another embodiment the stealth lipid is PEG-dimyristylglycerol (PEG-DMG).

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment PEG is unsubstituted. In one embodiment the PEG is substituted, e.g., by one or more alkyl, alkoxy, acyl or aryl groups. In one embodiment, the term includes PEG copolymers such as PEG-polyurethane or PEG-polypropylene (see, e.g., J. Milton Harris, Poly (ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment about 150 to about 30,000, in a sub-embodiment about 150 to about 20,000, in a sub-embodiment about 150 to about 15,000, in a sub-embodiment about 150 to about 10,000, in a sub-embodiment about 150 to about 6000, in a sub-embodiment about 150 to about 5000, in a sub-embodiment about 150 to about 4000, in a sub-embodiment about 150 to about 3000, in a sub-embodiment about 300 to about 3000, in a sub-embodiment about 1000 to about 3000, and in a sub-embodiment about 1500 to about 2500.

In certain embodiments the PEG is a "PEG-2K", also termed "PEG 2000", which has an average molecular weight of about 2000 daltons. PEG-2K is represented herein by the following formula (XIIa), wherein n is 45, meaning that the number-averaged degree of polymerization comprises about 45 subunits. However, other PEG embodiments known in the art may be used, including, e.g., those where the number-averaged degree of polymerization comprises about 23 subunits (n=23) and/or 68 subunits (n=68).

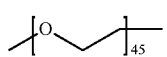

(XIIa)

The lipid compositions of the invention can also include one or more biologically active agents including, but not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (asymmetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occurring or synthetic, and may be chemically modified. In one embodiment the biologically active agent is an RNAi agent, short interfering nucleic acid (siNA), short interfering RNA (siRNA), double-stranded RNA (dsRNA), micro-RNA (miRNA), or a short hairpin RNA (shRNA) molecule. In one embodiment the biologically active agent is a RNAi agent useful for mediating RNA interference (RNAi).

Various methods for loading biologically active agents into lipid compositions, such as liposomes and lipid nanoparticles are available in the art, including both passive and active loading methods. The exact method used may be chosen based on multiple factors that include, but are not limited to, e.g., the biologically active agent to be loaded, the storage method to be used once loaded, the size of the resulting particle, and the dosage regimen contemplated. Methods include, e.g., mechanical mixing of the drug and lipids at the time the liposomes are formed or reconstituted, dissolving all components in an organic solvent and concentrating them into a dry film, forming a pH or ion gradient to draw the active agent into the interior of the liposome, creating a transmembrane potential, and ionophore mediated loading. See, e.g., PCT Publication No. WO 95/08986, U.S. Pat. Nos. 5,837,282, 5,837,282, and 7,811,602.

By "lipid nanoparticle" is meant a particle that comprises a plurality of (i.e. more than one) lipid molecules physically associated with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

The lipid nanoparticles have a size of about 1 to about 2,500 nm, about 1 to about 1,500 nm, about 1 to about 1,000 nm, in a sub-embodiment about 50 to about 600 nm, in a sub-embodiment about 50 to about 400 nm, in a sub-embodiment about 50 to about 250 nm, and in a sub-embodiment about 50 to about 150 nm. Unless indicated otherwise, all sizes referred to herein are the average sizes (diameters) of the fully formed nanoparticle, as measured by dynamic light scattering on a Malvern Zetasizer. The nanoparticle sample is diluted in phosphate buffered saline (PBS) so that the count rate is approximately 200-400 kcts. The data is presented as a weighted average of the intensity measure.

One embodiment of the present invention provides for a lipid composition comprising a compound of formula (I) and another lipid component. Another embodiment provides for a lipid composition comprising a compound of formula (I) and a helper lipid, for example cholesterol. Another embodiment provides for a lipid composition comprising a compound of formula (I), a helper lipid, for example cholesterol, and a neutral lipid, for example DSPC. Another embodiment of the present invention provides for a lipid composition comprising a compound of formula (I), a helper lipid, for example cholesterol, a neutral lipid, for example DSPC, and a stealth lipid, for example PEG-DMG, S010 or S011. Another embodiment of the present invention provides for a lipid composition comprising a compound of formula (I), a helper lipid, for example cholesterol, a neutral lipid, for example DSPC, a stealth lipid, for example PEG-DMG, S010 or S011, and a biologically active agent, for example a siRNA. Another embodiment of the present invention provides for a lipid nanoparticle comprising a compound of formula (I) a helper lipid, for example cholesterol, a neutral lipid, for example DSPC, and a stealth lipid, for example PEG-DMG, S010 or S011, and a biologically active agent, for example a siRNA.

Embodiments of the present invention also provide lipid compositions described according to the respective molar ratios of the component lipids in the formulation, wherein a slash ("/") indicates the respective components, as provided herein.

Another embodiment of the present invention is a lipid composition comprising a compound of formula (I) and a helper lipid, for example cholesterol, in a lipid molar ratio of 55-40 compound of formula (I)/55-40 helper lipid. Another embodiment provides for a lipid composition comprising a compound of formula (I), a helper lipid, for example cholesterol, and a neutral lipid, for example DPSC in a lipid molar ratio of 55-40 compound of formula (I)/55-40 helper lipid/15-5 neutral lipid. Another embodiment provides for a lipid composition comprising a compound of formula (I), a helper lipid, for example cholesterol, a neutral lipid, for example DSPC, and a stealth lipid, for example PEG-DMG, S010 or S011 in a lipid molar ratio of 55-40 compound of formula (I)/55-40 helper lipid/15-5 neutral lipid/10-1 stealth lipid.

Another embodiment of the present invention is a lipid composition comprising a compound of formula (I) and a helper lipid, for example cholesterol, in a lipid molar ratio of 50-40 compound of formula (I)/50-40 helper lipid. Another embodiment provides for a lipid composition comprising a compound of formula (I), a helper lipid, for example cholesterol, and a neutral lipid, for example DPSC in a lipid molar ratio of 50-40 compound of formula (I)/50-40 helper lipid/15-5 neutral lipid. Another embodiment provides for a lipid composition comprising a compound of formula (I), a helper lipid, for example cholesterol, a neutral lipid, for example DSPC, a stealth lipid, for example PEG-DMG, S010 or S011 in a lipid molar ratio of 50-40 compound of formula (I)/50-40 helper lipid/15-5 neutral lipid/5-1 stealth lipid.

Another embodiment of the present invention is a lipid composition comprising a compound of formula (I) and a helper lipid, for example cholesterol, in a lipid molar ratio of 47-43 compound of formula (I)/47-43 helper lipid. Another embodiment provides for a lipid composition comprising a compound of formula (I), a helper lipid, for example cholesterol, and a neutral lipid, for example DPSC in a lipid molar ratio of 47-43 compound of formula (I)/47-43 helper lipid/12-7 neutral lipid. Another embodiment provides for a lipid composition comprising a compound of formula (I), a helper lipid, for example cholesterol, a neutral lipid, for example DSPC, a stealth lipid, for example PEG-DMG, S010 or S011 in a lipid molar ratio of 47-43 compound of formula (I)/47-43 helper lipid/12-7 neutral lipid/4-1 stealth lipid.

Another embodiment of the present invention is a lipid composition comprising a compound of formula (I) and a helper lipid, for example cholesterol, in a lipid molar ratio of about 45 compound of formula (I)/about 44 helper lipid. Another embodiment provides for a lipid composition comprising a compound of formula (I), a helper lipid, for example cholesterol, and a neutral lipid, for example DPSC in a lipid molar ratio of about 45 compound of formula (I)/about 44 helper lipid/about 9 neutral lipid. Another embodiment provides for a lipid composition comprising a compound of formula (I), a helper lipid, for example cholesterol, a neutral lipid, for example DSPC, a stealth lipid, for example PEG-DMG, S010 or S011 in a lipid molar ratio of about 45 compound of formula (I)/about 44 helper lipid/about 9 neutral lipid/about 2 stealth lipid, for example PEG-DMG, S010 or S011.

Preferred compounds of formula (I) for use in the above lipid compositions are given in Examples 38, 40, 41, 42, 43, 44, 47, 52, 62, 63, 92, 93, 94 and 112. Particularly preferred compounds are given in Examples 38 and 52. Preferred biologically active agents are siRNA's.

Lipid compositions of the present invention can be further optimized by one skilled in the art by combining cationic lipids with the desired pKa range, stealth lipids, helper lipids, and neutral lipids into formulations, including, e.g., liposome formulations, lipid nanoparticles (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, formulation methods and/or dosing regimen (e.g., number of doses administered over time, actual dose in mg/kg, timing of the doses, combinations with other therapeutics, etc.). The various optimization techniques known to those of skill in the art pertaining to the above listed embodiments are considered as part of this invention.

General Methods for Making Lipid Nanoparticles

The following methods can be used to make lipid nanoparticles of the invention. To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition of the invention typically comprises providing an aqueous solution, such as citrate buffer, comprising a biologically active agent in a first reservoir, providing a second reservoir comprising an organic solution, such as an organic alcohol, for example ethanol, of the lipid(s) and then mixing the aqueous solution with the organic lipid solution. The first reservoir is optionally in fluid communication with the second reservoir. The mixing step is optionally followed by an incubation step, a filtration step, and a dilution and/or concentration step. The incubation step comprises allowing the solution from the mixing step to stand in a vessel for about 0 to about 100 hours (preferably about 0 to about 24 hours) at about room temperature and optionally protected from light. In one embodiment, a dilution step follows the incubation step. The dilution step may involve dilution with aqueous buffer (e.g. citrate buffer) e.g., using a pumping apparatus (e.g. a peristaltic pump). The filtration step is ultrafiltration. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent).

In one embodiment, the mixing step provides a clear single phase.

In one embodiment, after the mixing step, the organic solvent is removed to provide a suspension of particles, wherein the biologically active agent is encapsulated by the lipid(s), e.g. in a lipid bilayer.

The selection of an organic solvent will typically involve consideration of solvent polarity and the ease with which the solvent can be removed at the later stages of particle formation. The organic solvent, which is also used as a solubilizing agent, is preferably in an amount sufficient to provide a clear single phase mixture of biologically active agents and lipids. The organic solvent may be selected from one or more (e.g. two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, isobutanol, pentanol and hexanol.

The mixing step can take place by any number of methods, e.g., by mechanical means such as a vortex mixer.

The methods used to remove the organic solvent will typically involve diafiltration or evaporation at reduced pressures or blowing a stream of inert gas (e.g. nitrogen or argon) across the mixture.

In other embodiments, the method further comprises adding nonlipid polycations which are useful to effect the transformation of cells using the present compositions. Examples of suitable nonlipid polycations include, but are limited to, hexadimethrine bromide (sold under the brand-name POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine. In certain embodiments, the formation of the lipid nanoparticles can be carried out either in a mono-phase system (e.g. a Bligh and Dyer monophase or similar mixture of aqueous and organic solvents) or in a two-phase system with suitable mixing.

The lipid nanoparticle may be formed in a mono- or a bi-phase system. In a mono-phase system, the cationic lipid(s) and biologically active agent are each dissolved in a volume of the mono-phase mixture. Combining the two solutions provides a single mixture in which the complexes form. In a bi-phase system, the cationic lipids bind to the biologically active agent (which is present in the aqueous phase), and "pull" it into the organic phase. In one embodiment, the lipid nanoparticles are prepared by a method which comprises: (a) contacting the biologically active agent with a solution comprising noncationic lipids and a detergent to form a compound-lipid mixture; (b) contacting cationic lipids with the compound-lipid mixture to neutralize a portion of the negative charge of the biologically active agent and form a charge-neutralized mixture of biologically active agent and lipids; and (c) removing the detergent from the charge-neutralized mixture.

In one group of embodiments, the solution of neutral lipids and detergent is an aqueous solution. Contacting the biologically active agent with the solution of neutral lipids and detergent is typically accomplished by mixing together a first solution of the biologically active agent and a second solution of the lipids and detergent. Preferably, the biologically active agent solution is also a detergent solution. The amount of neutral lipid which is used in the present method is typically determined based on the amount of cationic lipid used, and is typically of from about 0.2 to 5 times the amount of cationic lipid, preferably from about 0.5 to about 2 times the amount of cationic lipid used.

The biologically active agent-lipid mixture thus formed is contacted with cationic lipids to neutralize a portion of the negative charge which is associated with the molecule of interest (or other polyanionic materials) present. The amount of cationic lipids used is typically the amount sufficient to neutralize at least 50% of the negative charge of the biologically active agent. Preferably, the negative charge will be at least 70% neutralized, more preferably at least 90% neutralized.

The methods used to remove the detergent typically involve dialysis. When organic solvents are present, removal is typically accomplished by diafiltration or evaporation at reduced pressures or by blowing a stream of inert gas (e.g. nitrogen or argon) across the mixture.

There is herein disclosed an apparatus for making a composition of the present invention. The apparatus typically includes a first reservoir for holding an aqueous solution comprising a biologically active agent and a second reservoir for holding an organic lipid solution. The apparatus also typically includes a pump mechanism configured to pump the aqueous and the organic lipid solutions into a mixing region or mixing chamber at substantially equal flow rates. In one embodiment, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof.
Methods for Delivering Biologically Active Agents and the Treatment of Disease The cationic lipids of formula (I) and lipid compostions thereof are useful in pharmaceutical compositions or formulations used for delivery of biologically active agents. Formulations containing cationic lipids of formula (I) or lipid compositions thereof may be in various forms, including, but not limited to, particle forming delivery agents including microparticles, nanoparticles and transfection agents that are useful for delivering various molecules to cells. Specific formulations are effective at transfecting or delivering biologically active agents, such as antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), short interfering RNA (siRNA), double-stranded RNA (dsRNA), micro-RNA (miRNA), and short hairpin RNA (shRNA), molecules peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (asymmetrical interfering RNA), and siRNA with 1, 2 or more mismatches between the sense and anti-sense strand to relevant cells and/or tissues, such as in a cell culture, subject or organism. The above list of biologically active agents is exemplary only, and is not intended to be limiting. Such compounds may be purified or partially purified, and may be naturally occurring or synthetic, and may be chemically modified.

Such formulations containing biologically active agents are useful, e.g., in providing compositions to prevent, inhibit, or treat diseases, conditions, or traits in a cell, subject or organism. Diseases, conditions or traits include, but are not limited to, proliferative diseases, including cancer, inflammatory disease, transplant and/or tissue rejection, autoimmune diseases or conditions, age-related disease, neurological or neurodegenerative disease, respiratory disease, cardiovascular disease, ocular disease, metabolic disease, dermatological disease, auditory disease, a liver disease, a kidney or renal disease, etc.

The amount of active agent administered per dose is an amount above the minimal therapeutic dose but below a toxic dose. The actual amount per dose may be determined by a physician depending on a number of factors, such as the medical history of the patient, the use of other therapies, the biologically active agent to be provided, and the nature of the disease. The amount of biologically active agent administered may be adjusted throughout treatment, depending on the patient's response to treatment and the presence or severity of any treatment-associated side effects. Exemplary dosages and treatment for compounds that have been approved by an appropriate regulatory agency are known and available to those skilled in the art. See, e.g., Physician's Desk Reference, 64th ed., Physician's Desk Reference Inc. (2010), Remington's Pharmaceutical Sciences, Mack Publishing Company, Philadelphia, Pa. (1985), and Remington The Science and Practice of Pharmacy, 21st ed., Lippincott Williams & Williams Publishers (2005).

In one embodiment, a single dose is administered of a biologically active agent to a patient in need thereof. In one embodiment, multiple doses are administered, wherein the multiple doses may be administered concurrently, sequentially or alternating. In one embodiment, the same formulation is administered over multiple doses. In one embodiment, the formulations differ over multiple doses. In various embodiments, the doses may be administered once a day, or for one, two, three, four or more consecutive days. In one embodiment, the doses are administered once a week. In one embodiment, the doses are administered once every other week. In one embodiment, patients receive at least two courses of a treatment regimen, and potentially more, depending on the response of the patient to the treatment. In single agent regimens, total courses of treatment are determined by the patient and physician based on observed responses and toxicity. The above dosage regimens are to be considered as non-limiting examples. Other dosage regimens are contemplated as being within the scope of the invention, and depend on the therapeutic effect desired.

The invention also provides a method for the treatment of a disease or condition comprising the step of administering a therapeutically effective amount of a lipid composition of the invention to a patient in need of treatment thereof. In one embodiment, the disease or condition is treatable by administering an siRNA agent.

The invention also provides for use of a lipid composition of the invention in treating a disease or condition in a patient. In one embodiment, the disease or condition is treatable by administering an siRNA agent.

The total amount of lipid in the composition being administered is, in one embodiment, from about 5 to about 30 mg lipid per mg biologically active agent (e.g. siRNA), in another embodiment from about 5 to about 25 mg lipid per mg biologically active agent (e.g. siRNA), in another embodiment from about 7 to about 25 mg lipid per mg biologically active agent (e.g. siRNA) and in one embodiment from about 7 to about 15 mg lipid per mg biologically active agent (e.g. siRNA).

As used herein, "treatment" includes ameliorative, curative and prophylactic treatment. As used herein, a "patient" means an animal, preferably a mammal, preferably a human, in need of treatment.

The term "therapeutically effective amount" refers to the amount of the compound of the invention and the biologically active agent (e.g. the therapeutic compound) needed to treat or ameliorate a targeted disease or condition.

The term "immunologically effective amount" refers to the amount of the compound of the invention and of RNA which encodes an immunogen needed to elicit an immune response which recognizes the immunogen (e.g. in the context of a pathogen). The term "immunogen" refers to any substance or organism that provokes an immune response when introduced into the body. The phrase "RNA which encodes an immunogen" refers to a polynucleotide, such as a messenger RNA or a replicon, that a cell or organism is capable of translating into a polypeptide according to the codon sequence of such RNA.

By "proliferative disease" as used herein is meant any disease, condition, trait, genotype or phenotype characterized by unregulated cell growth or replication as is known in the art. In one embodiment, the proliferative disease is cancer. In one embodiment, the proliferative disease is a tumor. In one embodiment, the proliferative disease includes, but are not limited to, e.g., liquid tumors such as, e.g., leukemias, e.g., acute myelogenous leukemia (AML), chronic myelogenous leukemia (CML), acute lymphocytic leukemia (ALL), multiple myeloma, and chronic lymphocytic leukemia; and solid tumors, e.g., AIDS related cancers such as Kaposi's sarcoma; breast cancers; bone cancers; brain cancers; cancers of the head and neck, non-Hodgkins lymphoma, adenoma, squamous cell carcinoma, laryngeal carcinoma, gallbladder and bile duct cancers, cancers of the retina, cancers of the esophagus, gastrointestinal cancers, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, endometrial sarcoma, multidrug resistant cancers. In one embodiment, the proliferative disease includes neovascularization associated with tumor angiogenesis, macular degeneration (e.g. wet/dry age related macular degeneration), corneal neovascularization, diabetic retinopathy, neovascular glaucoma, myopic degeneration. In one embodiment, the proliferative disease includes restenosis and polycystic kidney disease.

By "autoimmune disease" as used herein is meant any disease, condition, trait, genotype or phenotype characterized by autoimmunity as is known in the art. Autoimmune diseases include, but are not limited to, e.g., multiple sclerosis, diabetes mellitus, lupus, scleroderms, fibromyalgia, transplantation rejection (e.g. prevention of allograft rejection), pernicious anemia, rheumatoid arthritis, systemic lupus erythematosus, dermatomyositis, myasthenia gravis, lupus erythematosus, multiple sclerosis, and Grave's disease.

By "infectious disease" is meant any disease, disorder or condition associated with an infectious agent, such as a virus, bacteria, fungus, prion or parasite. The invention can be used to immunize against pathogens which cause infectious disease. Examples of such pathogens are given below.

By "neurologic disease" is meant any disease, disorder, or condition affecting the central or peripheral nervous system. Neurologic diseases include, but are not limited to, diseases or disorders of either the peripheral or the central nervous system including, e.g., Alzheimer's Disease, Aneurysm, Brain Injury, Carpal Tunnel Syndrome, Cerebral Aneurysm, Chronic Pain, Creutzfeldt-Jakob Disease, Epilepsy, Huntington's Disease, Meningitis, Seizure Disorders, and other neurologic diseases, disorders and syndromes.

By "respiratory disease" is meant any disease or condition affecting the respiratory tract. Respiratory diseases include, but are not limited to, e.g., asthma, chronic obstructive pulmonary disease (COPD), allergic rhinitis, sinusitis, allergies, impeded respiration, respiratory distress syndrome, cystic fibrosis, pulmonary hypertension or vasoconstriction and emphysema.

By "cardiovascular disease" is meant and disease or condition affecting the heart and vasculature. Cardiovascular diseases include, but are not limited to, e.g., coronary heart disease (CHD), cerebrovascular disease (CVD), aortic stenosis, peripheral vascular disease, myocardial infarction (heart attack), arrhythmia, and congestive heart failure.

By "ocular disease" as used herein is meant any disease, condition, trait, genotype or phenotype of the eye and related structures. Ocular diseases include, but are not limited to, e.g., cystoid macular edema, diabetic retinopathy, lattice degeneration, retinal vein occlusion, retinal artery occlusion, macular degeneration (e.g. age related macular degeneration such as wet AMD or dry AMD), toxoplasmosis, retinitis pigmentosa, conjunctival laceration, corneal laceration, glaucoma, and the like.

By "metabolic disease" is meant any disease or condition affecting metabolic pathways. Metabolic disease can result in an abnormal metabolic process, either congenital due to inherited enzyme abnormality (inborn errors of metabolism)

or acquired due to disease of an endocrine organ or failure of a metabolically important organ such as the liver. In one embodiment, metabolic disease includes obesity, insulin resistance, and diabetes (e.g. type I and/or type II diabetes).

By "dermatological disease" is meant any disease or condition of the skin, dermis, or any substructure therein such as a hair, a follicle, etc. Dermatological diseases, disorders, conditions, and traits can include psoriasis, ectopic dermatitis, skin cancers such as melanoma and basal cell carcinoma, hair loss, hair removal and alterations in pigmentation.

By "auditory disease" is meant any disease or condition of the auditory system, including the ear, such as the inner ear, middle ear, outer ear, auditory nerve, and any substructures therein. Auditory diseases, disorders, conditions, and traits can include hearing loss, deafness, tinnitus, vertigo, balance and motion disorders.

The term "short interfering nucleic acid" (siNA) as used herein refers to any nucleic acid molecule capable of inhibiting or down regulating gene expression or viral replication by mediating RNA interference (RNAi) or gene silencing in a sequence-specific manner. It includes short interfering RNA (siRNA), microRNA (miRNA), short interfering oligonucleotides, and chemically-modified short interfering nucleic acid molecules. siRNAs are responsible for RNA interference, the process of sequence-specific post-transcriptional gene silencing in animals and plants. siRNAs are generated by ribonuclease III cleavage from longer double-stranded RNA (dsRNA) which are homologous to, or specific to, the silenced gene target.

The term "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al., 2005, Nature Chemical Biology, 1, 216-222.

The term "RNAi inhibitor" is any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g, up-regulate or down-regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term "RNAi inhibitor" is used interchangeably with the term "siNA" in various embodiments herein.

The term "enzymatic nucleic acid" as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 JAMA 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989, 912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth et. al., 2000, Biochim. Biophys. Acta, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule, or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186, 5,741,679, 5,589,332, 5,871,914, and PCT publication Nos. WO 00/24931, WO 00/26226, WO 98/27104, and WO 99/29842.

The term "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

Formulation of Lipid Compositions

For pharmaceutical use, the lipid compositions of the invention may be administered by enteral or parenteral routes, including intravenous, intramuscular, subcutaneous, transdermal, airway (aerosol), oral, intranasal, rectal, vaginal, buccal, nasopharyngeal, gastrointestinal or sublingual administration. The administration may be systemic or topical. Topical administration may involve, e.g., catheterization, implantation, osmotic pumping, direct injection, dermal/transdermal application, stenting, ear/eye drops or portal vein administration. The compounds of formula (I) should be assessed for their biopharmaceutical properties, such as solubility and solution stability (across pH), permeability, etc., in order to select the most appropriate dosage form and route of administration for treatment of the proposed indication.

The compositions of the invention will generally, but not necessarily, be administered as a formulation in association with one or more pharmaceutically acceptable excipients. The term "excipient" includes any ingredient other than the compound(s) of the invention, the other lipid component(s) and the biologically active agent. An excipient may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

The excipient may be an aqueous solution carrier which may optionally contain a buffer (e.g. a PBS buffer) and/or a sugar.

A thorough discussion of pharmaceutically acceptable excipients is available in Gennaro, *Remington: The Science and Practice of Pharmacy* 2000, 20th edition (ISBN: 0683306472).

The compositions of the invention may be administered orally. Oral administration may involve swallowing, so that the compound enters the gastrointestinal tract, and/or buccal, lingual, or sublingual administration by which the compound enters the blood stream directly from the mouth.

The compositions of the invention can be administered parenterally. The compounds and compositions of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, e.g., by lyophilisation, may readily be accomplished using standard pharmaceutical techniques well known to the skilled person.

The solubility of the compounds and compositions used in the preparation of parenteral solutions may be increased by the use of appropriate formulation techniques, such as the incorporation of co-solvents and/or solubility-enhancing agents such as surfactants, micelle structures and cyclodextrins.

The compositions of the invention can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebuliser contains a solution or suspension of the compound(s) of the invention comprising, e.g., ethanol, aqueous ethanol, or a suitable alternative agent for dispersing, solubilising, or extending release of the compositions of the invention, a propellant(s) as solvent and an optional surfactant, such as sorbitan trioleate, oleic acid, or an oligolactic acid.

Prior to use in a dry powder or suspension formulation, the composition is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, e.g., from gelatin or hydroxypropylmethylcellulose), blisters and cartridges for use in an inhaler or insufflator may be formulated to contain a powder mix of the compound or composition of the invention, a suitable powder base such as lactose or starch and a performance modifier such as 1-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, e.g., PGLA. Modified release formulations include delayed-, sustained-, pulsed-, controlled-, targeted and programmed release.

Suitable formulations for transdermal application include a therapeutically effective amount of a compound or composition of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Lipid compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Lipid compositions of the invention can be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Suitable formulations for use in the present invention can be found, e.g., in Remington's Pharmaceutical Sciences, Mack Publishing Company, Philadelphia, Pa., 17.sup.th Ed. (1985). Often, intravenous compositions will comprise a solution of the liposomes suspended in an acceptable carrier, such as an aqueous carrier.

In one embodiment, this invention provides for a pharmaceutical composition (i.e. formulation) comprising a lipid composition of the invention and a pharmaceutically acceptable carrier or excipient. In another embodiment at least one other lipid component is present in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the biologically active agent is a siRNA.

For immunization purposes a composition will generally be prepared as an injectable, and will be administered by injection (e.g. by intramuscular injection).

The invention also provides a delivery device (e.g. syringe, nebuliser, sprayer, inhaler, dermal patch, etc.) containing a composition of the invention. This device can be used to administer a pharmaceutical composition to a subject e.g. to a human for immunization.

Cells and Organs Targeted by the Invention

The compounds, compositions, methods and uses of the invention can be used to deliver a biologically active agent to one or more of the following in a patient:

the liver or liver cells (e.g. hepatocytes);

a kidney or kidney cells;

a tumor or tumor cells;

the CNS or CNS cells (Central Nervous System, e.g. brain and/or spinal cord);

the PNS or PNS cells (Peripheral Nervous System);

a lung or lung cells;

the vasculature or vascular cells;

the skin or skin cells (e.g. dermis cells and/or follicular cells);

an eye or ocular cells (e.g. macula, fovea, cornea, retina), and an ear or cells of the ear (e.g. cells of the inner ear, middle ear and/or outer ear).

The compounds, compositions, methods and uses of the invention can also be used to deliver a biologically active agent (e.g. RNA which encodes an immunogen) to cells of the immune system.

In one embodiment, the compounds, compositions, methods and uses of the invention are for delivering a biologically active agent to liver cells (e.g. hepatocytes). In one embodiment, the compounds, compositions, methods and uses of the invention are for delivering a biologically active agent to a tumor or to tumor cells (e.g. a primary tumor or metastatic cancer cells).

For delivery of a biologically active agent to the liver or liver cells, in one embodiment a composition of the invention is contacted with the liver or liver cells of the patient as is generally known in the art, such as via parental administration (e.g. intravenous, intramuscular, subcutaneous administration) or local administration (e.g. direct injection, portal vein injection, catheterization, stenting), to facilitate delivery.

For delivery of a biologically active agent to the kidney or kidney cells, in one embodiment a composition of the invention is contacted with the kidney or kidney cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to a tumor or tumor cells, in one embodiment a composition of the invention is contacted with the tumor or tumor cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to the CNS or CNS cells (e.g. brain cells and/or spinal cord cells), in one embodiment a composition of the invention is contacted with the CNS or CNS cells (e.g. brain cells and/or spinal cord cells) of the patient as is generally known in the art, such as via parental administration (e.g. intravenous, intramuscular, subcutaneous administration) or local administration (e.g. direct injection, catheterization, stenting, osmotic pump administration (e.g. intrathecal or ventricular)), to facilitate delivery.

For delivery of a biologically active agent to the PNS or PNS cells, in one embodiment a composition of the invention is contacted with the PNS or PNS cells of the patient as is generally known in the art, such as via parental administration (e.g. intravenous, intramuscular, subcutaneous administration) or local administration (e.g. direct injection), to facilitate delivery.

For delivery of a biologically active agent to a lung or lung cells, in one embodiment a composition of the invention is contacted with the lung or lung cells of the patient as is generally known in the art, such as via parental administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a composition of the invention is contacted with the vasculature or vascular cells of the patient as is generally known in the art, such as via parental administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a composition of the invention is contacted with the skin or skin cells (e.g. dermis cells and/or follicular cells) of the patient as is generally known in the art, such as via parental administration (e.g. intravenous, intramuscular, subcutaneous administration) or local administration (e.g. direct dermal application, iontophoresis), to facilitate delivery.

For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient as is generally known in the art, such as via parental administration (e.g. intravenous, intramuscular, subcutaneous administration) or local administration (e.g. direct injection, intraocular injection, periocular injection, subretinal, iontophoresis, use of eyedrops, implants), to facilitate delivery.

For delivery of a biologically active agent to an ear or cells of the ear (e.g. cells of the inner ear, middle ear and/or outer ear), in one embodiment composition of the invention is contacted with the ear or cells of the ear (e.g. cells of the inner ear, middle ear and/or outer ear) of the patient as is generally known in the art, such as via parental administration (e.g. intravenous, intramuscular, subcutaneous administration) or local administration (e.g. direct injection), to facilitate delivery.

For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA. Such immune cells can include macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. (e.g. see WO2012/006372).

Immunization According to the Invention

For immunization purposes, the invention involves delivering a RNA which encodes an immunogen. The immunogen elicits an immune response which recognizes the immunogen, and so can be used to provide immunity against a pathogen, or against an allergen, or against a tumor antigen. Immunising against disease and/or infection caused by a pathogen is preferred.

The RNA is delivered with a lipid composition of the invention (e.g. with a liposome or LNP), and typically the invention utilises liposomes or LNPs within which immunogen-encoding RNA is encapsulated. Encapsulation within liposomes can protect RNA from RNase digestion.

In one embodiment the invention provides a liposome having a lipid bilayer encapsulating an aqueous core, wherein: (i) the lipid bilayer comprises a lipid of the invention; and (ii) the aqueous core includes a RNA which encodes an immunogen. If a composition comprises a population of liposomes with different diameters, for immunization purposes it can be useful if: (i) at least 80% by number of the liposomes have diameters in the range of 60-180 nm, and preferably in the range of 80-160 nm, and/or (ii) the average diameter (by intensity e.g. Z-average) of the population is in the range of 60-180 nm, and preferably in the range of 80-160 nm. The diameters within the plurality should ideally have a polydispersity index <0.2.

After in vivo administration of an immunization composition, the delivered RNA is released and is translated inside a cell to provide the immunogen in situ. The RNA is plus ("+") stranded, so it can be translated by cells without needing any intervening replication steps such as reverse transcription. It may also bind to TLR7 receptors expressed by immune cells, thereby initiating an adjuvant effect.

Preferred plus (+) stranded RNAs are self-replicating. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus typically a + strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is a huge amplification in the number of the introduced replicon RNAs and so the encoded immunogen becomes a major polypeptide product of the cells.

One suitable system for achieving self-replication is to use an alphavirus-based RNA replicon. These + stranded replicons are translated after delivery to a cell to give of a replicase (or replicase-transcriptase). The replicase is translated as a polyprotein which auto cleaves to provide a replication complex which creates genomic − strand copies of the + strand delivered RNA. These − strand transcripts can themselves be transcribed to give further copies of the + stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc. Mutant or wild-type viruses sequences can be used e.g. the attenuated TC83 mutant of VEEV has been used in replicons.

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non structural replicase polyprotein, it is preferred that a self-replicating RNA molecule of the invention does not encode alphavirus structural proteins. Thus a preferred self replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5) open reading frame encodes a replicase; the second (3) open reading frame encodes an immunogen. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA delivery.

A RNA molecule may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly A tail. It may also include a poly A polymerase recognition sequence (e.g. AAUAAA) near its 3' end.

A RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT transcribed RNA can function efficiently as a substrate for its self-encoded replicase.

As discussed in WO2011/005799, the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first 1, 2 or 3 5' ribonucleotides may be methylated at the 2' position of the ribose.

A RNA used with the invention for immunization purposes ideally includes only phosphodiester linkages between nucleosides, but in some embodiments it can contain phosphoramidate, phosphorothioate, and/or methylphosphonate linkages.

The amount of RNA per liposome can vary. The number of individual self-replicating RNA molecules per liposome is typically <50 e.g. <20, <10, <5, or 1-4 per liposome.

RNA molecules used with the invention for immunization purposes encode a polypeptide immunogen. After administration the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognises the corresponding pathogen (or allergen or tumor) polypeptide, but in some embodiments the polypeptide may act as a mimotope to elicit an immune response which recognises a saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in Giuliani et al. (2006) *Proc Natl Acad Sci USA* 103(29):10834-9.

*Streptococcus pneumoniae*: useful polypeptide immunogens are disclosed in WO2009/016515. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in WO02/34771 and WO2005/032582.

*Moraxella catarrhalis.*

*Bordetella pertussis*: Useful pertussis immunogens include, but are not limited to, pertussis toxin or toxoid (PT), filamentous hemagglutinin (FHA), pertactin, and agglutinogens 2 and 3.

*Staphylococcus aureus*: Useful immunogens include, but are not limited to, the polypeptides disclosed in WO2010/119343, such as a hemolysin, esxA, esxB, ferrichrome-binding protein (sta006) and/or the sta011 lipoprotein.

*Clostridium tetani*: the typical immunogen is tetanus toxoid.

*Cornynebacterium diphtheriae*: the typical immunogen is diphtheria toxoid.

*Haemophilus influenzae*: Useful immunogens include, but are not limited to, the polypeptides disclosed in WO2006/110413 and WO2005/111066.

*Pseudomonas aeruginosa*

*Streptococcus agalactiae*: useful immunogens include, but are not limited to, the polypeptides disclosed in WO02/34771.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in WO2005/002619). LcrE (WO2006/138004) and HtrA (WO2009/109860) are two preferred immunogens.

*Chlamydia pneumoniae*: Useful immunogens include, but are not limited to, the polypeptides disclosed in WO02/02606.

*Helicobacter pylori*: Useful immunogens include, but are not limited to, CagA, VacA, NAP, and/or urease (WO03/018054).

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in WO2006/091517 and WO2008/020330. Useful MNEC immunogens are disclosed in WO2006/089264. A useful immunogen for several *E. coli* types is AcfD (WO2009/104092).

*Bacillus anthracis*

*Yersinia pestis*: Useful immunogens include, but are not limited to, those disclosed in WO2007/049155 and WO2009/031043.

*Staphylococcus epidermis*

*Clostridium perfringens* or *Clostridium botulinums*

*Legionella pneumophila*

*Coxiella burnetii*

*Brucella*, such as *B. abortus, B. canis, B. melitensis, B. neotomae, B. ovis, B. suis, B. pinnipediae.*

*Francisella*, such as *F. novicida, F. philomiragia, F. tularensis.*

*Neisseria gonorrhoeae*

*Treponema pallidum*

*Haemophilus ducreyi*

*Enterococcus faecalis* or *Enterococcus faecium*

*Staphylococcus saprophyticus*

*Yersinia enterocolitica*

*Mycobacterium tuberculosis*

*Rickettsia*

*Listeria monocytogenes*

*Vibrio cholerae*

*Salmonella typhi*

*Borrelia burgdorferi*

*Porphyromonas gingivalis*

*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: immunogens include, but are not limited to, those derived from Pneumoviruses (e.g. respiratory syncytial virus, RSV), Rubulaviruses (e.g.

mumps virus), Paramyxoviruses (e.g. parainfluenza virus), Metapneumoviruses and Morbilliviruses (e.g. measles virus).

Poxviridae: immunogens include, but are not limited to, those derived from Orthopoxvirus such as Variola vera, including but not limited to, Variola major and Variola minor.

Picornavirus: immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: immunogens include, but are not limited to, those derived from a Heparnavirus, such as hepatitis A virus (HAV).

Filovirus: immunogens include, but are not limited to, those derived from a filovirus, such as an Ebola virus (including a Zaire, Ivory Coast, Reston or Sudan ebolavirus) or a Marburg virus.

Togavirus: immunogens include, but are not limited to, those derived from a Togavirus, such as a Rubivirus, an Alphavirus, or an Arterivirus. This includes rubella virus.

Flavivirus: immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: immunogens include, but are not limited to, those derived from a Pestivirus, such as Bovine viral diarrhea (BVDV), Classical swine fever (CSFV) or Border disease (BDV).

Hepadnavirus: immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: immunogens include, but are not limited to, those derived from a Rhabdovirus, such as a Lyssavirus (e.g. a Rabies virus) and Vesiculovirus (VSV).

Caliciviridae: immunogens include, but are not limited to, those derived from Caliciviridae, such as Norwalk virus (Norovirus), and Norwalk-like Viruses, such as Hawaii Virus and Snow Mountain Virus.

Coronavirus: immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: immunogens include, but are not limited to, those derived from an Oncovirus, a Lentivirus (e.g. HIV-1 or HIV-2) or a Spumavirus.

Reovirus: immunogens include, but are not limited to, those derived from an Orthoreovirus, a Rotavirus, an Orbivirus, or a Coltivirus.

Parvovirus: immunogens include, but are not limited to, those derived from Parvovirus B19.

Herpesvirus: immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: immunogens include those derived from serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp, *Alternaria* spp, *Curvularia* spp, *Hel-* minthosporium spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum*, *P. vivax*, *P. malariae* or *P. ovale*. Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale*, and Sorghum, the orders of Asterales and Urticales including herbs of the genera *Ambrosia, Artemisia*, and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

A pharmaceutical composition of the invention, particularly one useful for immunization, may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Such agonist(s) can, in some embodiments, be encapsulated with the RNA inside liposomes, but in other embodiments they are unencapsulated.

EXAMPLES

Cationic Lipids of Formula (I)

The following examples are intended to illustrate the invention and are not to be construed as being limitations thereon. Temperatures are given in degrees centigrade. If not mentioned otherwise, all evaporative concentrations are performed under reduced pressure, preferably between about 15 mm Hg and 100 mm Hg (=20-133 mbar). The structure of final products, intermediates and starting materials is confirmed by standard analytical methods, e.g., microanalysis or spectroscopic characteristics, e.g., MS, IR, or NMR. Abbreviations used are those conventional in the art, some of which are defined below.

Flash column purification is preferably carried out on silica gel using an appropriate eluent of isocratic or gradient composition.

HPLC analysis is performed on a Waters Atlantis dC18 column (4.6×150 mm, 3 mm), with gradient elution (0% to 95% acetonitrile in water modified with 0.1% v/v trifluoroacetic acid over 20 min and a flow rate of 1.4 mL/min), unless otherwise described.

1H NMR spectra were recorded on a Bruker Avance II 400 MHz spectrometer. All chemical shifts are reported in parts per million (δ) relative to tetramethylsilane. The following abbreviations are used to denote signal patterns: s=singlet, d=doublet, t=triplet, q=quartet, m=multiplet, br=broad. ES-MS data were recorded using a Waters LTC Premier mass spectrometer with a dual electrospray ionization source on an Agilent 1100 liquid chromatograph. Sulfadimethoxine [Sigma, m/z=311.0814 (M+1)] was used as a reference acquired through the LockSpray™ channel every third scan. The mass accuracy of the system has been found to be <5 ppm.

Abbreviations

C Celsius
DCM dichloromethane
deg degrees
DIEA N,N-diisopropylethylamine
DIPEA N,N-diisopropylethylamine
DMAP 4-dimethylaminopyridine
DMF N,N-dimethylformamide
DMSO dimethylsulfoxide
EDC 1-ethyl-3-(3-dimethylaminopropyl)carbodiimide
ES-MS electro spray mass spectroscopy
EtOAc ethyl acetate
EtOH ethanol
g gram
h hour(s)
HATU 2-(1H-7-azabenzotriazol-1-yl)-1,1,3,3-tetramethyluronium hexafluorophosphate
HOBt hydroxybenzotriazole
HPLC high pressure liquid chromatography
kg kilogram
L liter
LAH lithium aluminum hydride
LC liquid chromatography
LCMS liquid chromatography and mass spectrometry
MeOH methanol
MS mass spectrometry
mbar millibar
min minutes
mL milliliter(s)
mm millimeter
µM micromolar
m/z mass to charge ratio
nm nanometer
nM nanomolar
N normal
NaOEt sodium ethyloxide
NMP N-methylpyrrolidone
NMR nuclear magnetic resonance
Pd/C palladium on carbon
$PdCl_2(dppf).CH_2Cl_2$ 1,1'-bis(diphenylphosphino)ferrocene-palladium(II)dichloride dichloromethane complex
psi pounds per square inch
ppm parts per million
pTsOH p-toluenesulfonic acid
quin quintuplet
rac racemic
Rt retention time
TBAF tetrabutylammonium fluoride
TBDPS tert-butyldiphenylsilyl ether
TBTU O-(Benzotriazol-1-yl)-N,N,N',N'-tetramethyluronium tetrafluoroborate
TCEP tris(2-carboxyethyl)phosphine
TEA triethylamine
TFA trifluoroacetic acid
THF tetrahydrofuran
THP tetrahydropyran
TLC thin layer chromatography
TMS-CN trimethylsilyl cyanide
TsOH tosylic acid Synthesis of Example 1

Intermediate 1a:

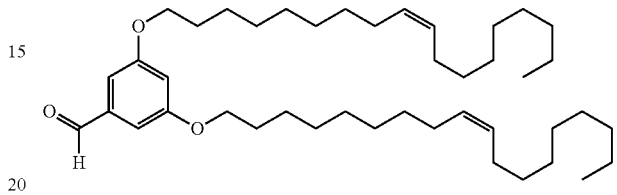

To a flask containing DMF (40 mL) was added 3,5-dihydroxybenzaldehyde (2 g, 14.2 mmol), potassium carbonate (5.88 g, 42.6 mmol) and oleylmesylate (11.3 g, 32.6 mmol). The resulting mixture was heated to 80 deg C. overnight with stirring. The reaction was cooled and water and EtOAc were added. The organic layer was collected, washed with brine, and dried over magnesium sulfate. The mixture was filtered and the filtrate concentrated under reduced pressure to a crude material that was purified on silica using heptanes/EtOAc as eluent, providing 8.53 g of the desired product.

Rf=0.56 (silica, 10% EtOAc in heptanes, UV and cerium molybdate).

Example 1 Compound

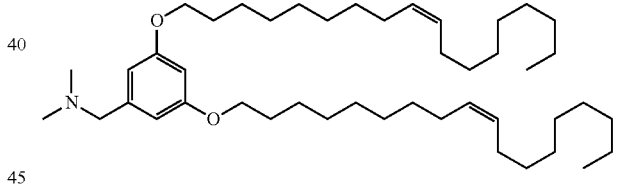

Intermediate 1a (4 g, 6.26 mmol) was stirred in EtOH (25 mL) and dimethylamine hydrochloride (1.02 g, 12.5 mmol) was added followed by TEA (1.21 mL, 8.76 mmol) and titanium tetraisopropoxide (1.8 mL, 6.3 mmol). The resulting mixture was stirred for 3 h at room temperature and sodium borohydride (355 mg, 9.39 mmol) was added in one portion. The mixture was stirred at room temperature overnight. The reaction was quenched with 7 N ammonia in MeOH (8.94 mL, 62.6 mmol) and the resulting white slurry filtered through celite with a DCM wash. The filtrate was concentrated under reduced pressure to yield a crude material that was purified on silica in 0 to 50% EtOAc in heptanes, providing 2.66 g of the desired product.

$^1$H NMR (400 MHz, $CDCl_3$) δ: 6.46 (d, J=2.0 Hz, 2H), 6.36 (t, J=2.5 Hz, 1H), 5.41-5.31 (m, 4H), 3.93 (t, J=6.9 Hzm 4H), 3.34 (s, 2H), 2.24 (s, 6H), 2.09-1.98 (m, 8H), 1.81-1.69 (m, 4H), 1.50-1.21 (m, 44H), 0.89 (t, J=7.0 Hz, 6H) ppm.

ES-MS m/z=668.8 (MH+)

Examples 2-7 were prepared using methods similar to those employed for the preparation of Example 1.

Example 2

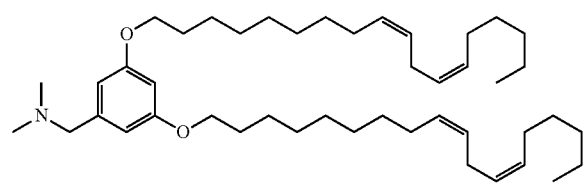 [SMILES: CCCCC/C=C\C/C=C\CCCCCCCCOc1cc(CN(C)C)cc(OCCCCCCCC/C=C\C/C=C\CCCCC)c1]

$^1$H NMR (400 MHz, CDCl$_3$) δ: 6.46 (d, J=2.5 Hz, 2H), 6.35 (t, J=2.3 Hz, 1H), 5.44-5.30 (m, 8H), 3.93 (t, J=6.5 Hz, 4H), 3.34 (s, 2H), 2.78 (t, J=6.2 Hz, 4H), 2.24 (s, 6H), 2.13-1.99 (m, 8H), 1.81-1.71 (m, 4H), 1.49-1.23 (m, 32H), 0.90 (t, J=6.8 Hz, 6H) ppm.

ES-MS m/z=664.9 (MH+)

Example 3

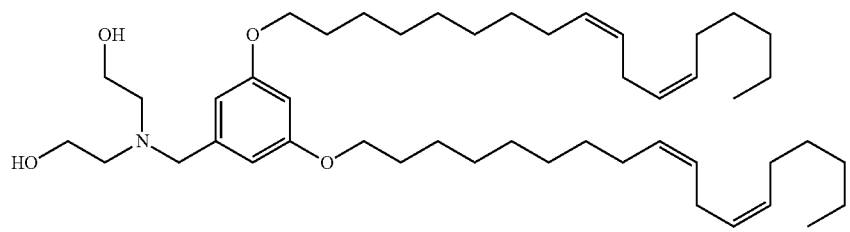 [SMILES: CCCCC/C=C\C/C=C\CCCCCCCCOc1cc(CN(CCO)CCO)cc(OCCCCCCCC/C=C\C/C=C\CCCCC)c1]

$^1$H NMR (400 MHz, CDCl$_3$) δ: 6.46-6.44 (m, 2H), 6.38-6.34 (m, 1H), 5.44-5.29 (m, 8H), 3.92 (t, J=6.5 Hz, 4H), 3.69-3.63 (m, 6H), 2.82-2.71 (m, 8H), 2.12-2.00 (m, 8H), 1.82-1.70 (m, 4H), 1.51-1.22 (m, 32H), 0.90 (t, J=6.9 Hz, 6H) ppm.

ES-MS m/z=724.6 (MH+)

Example 4

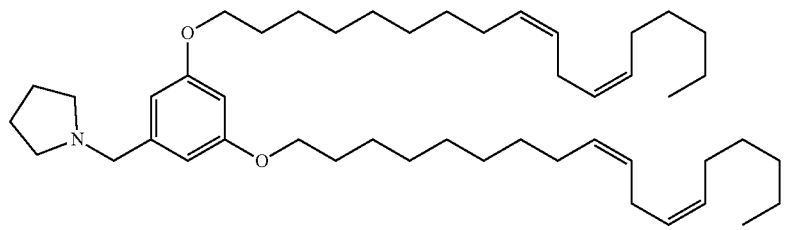 [SMILES: CCCCC/C=C\C/C=C\CCCCCCCCOc1cc(CN2CCCC2)cc(OCCCCCCCC/C=C\C/C=C\CCCCC)c1]

$^1$H NMR (400 MHz, CDCl$_3$) δ: 6.52-6.47 (m, 2H), 6.36-6.32 (m, 1H), 5.47-5.26 (m, 8H), 3.93 (t, J=6.6 Hz, 4H), 3.55 (s, 2H), 2.83-2.74 (m, 4H), 2.57-2.47 (m, 4H), 2.14-2.00 (m, 8H), 1.86-1.70 (m, 8H), 1.52-1.21 (m, 32H), 0.90 (t, J=6.8 Hz, 6H) ppm. ES-MS m/z=691.5 (MH+)

Example 5

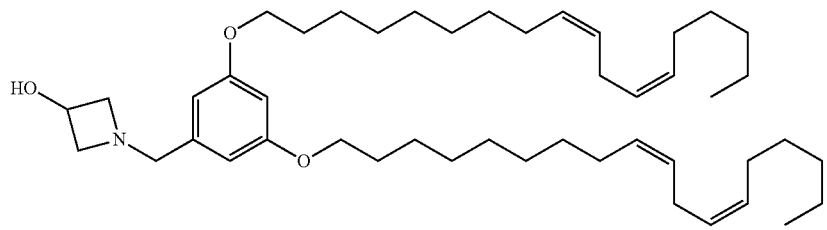 [SMILES: CCCCC/C=C\C/C=C\CCCCCCCCOc1cc(CN2CC(O)C2)cc(OCCCCCCCC/C=C\C/C=C\CCCCC)c1]

$^1$H NMR (400 MHz, CDCl$_3$) δ: 6.49 (d, J=2.0 Hz, 2H), 6.42 (t, J=2.1 Hz, 1H), 5.33-5.47 (m, 7H), 4.46 (tt, J=6.7, 3.6 Hz, 1H), 3.94 (t, J=6.7 Hz, 4H), 3.76-3.85 (m, 4H), 3.59 (d, J=10.3 Hz, 2H), 2.80 (t, J=6.5 Hz, 4H), 2.00-2.12 (m, 8H), 1.78 (dtd, J=7.8, 6.8, 5.8 Hz, 4H), 1.41-1.51 (m, 4H), 1.25-1.41 (m, 27H), 0.83-0.95 (m, J=6.8, 6.8 Hz, 5H) ppm.

ES-MS m/z=692.5 (MH+)

Example 6

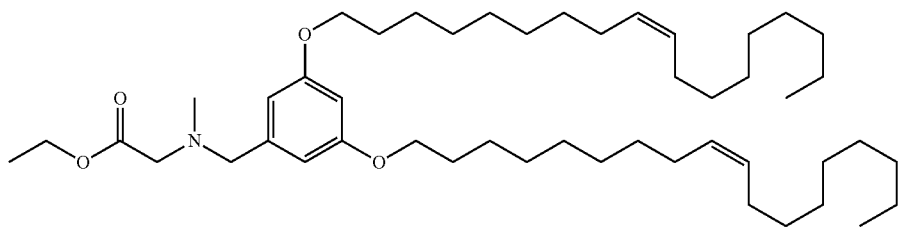 [SMILES: CCCCCCCC/C=C\CCCCCCCCOc1cc(CN(C)CC(=O)OCC)cc(OCCCCCCCC/C=C\CCCCCCCC)c1]

¹H NMR (400 MHz, CDCl₃) δ 6.50 (s, 2H), 6.36 (s, 1H), 5.39-5.32 (m, 4H), 4.18 (q, J=7.0 Hz, 2H), 3.92 (t, J=6.5 Hz, 4H), 3.60 (s, 2H), 3.24 (s, 2H), 2.40 (s, 3H), 2.10-1.95 (m, 8H), 1.80-1.60 (m, 4H), 1.50-1.15 (m, 47H), 0.88 (t, J=7.0 Hz, 6H) ppm.
ES-MS m/z=740.9 (MH+)

Example 7

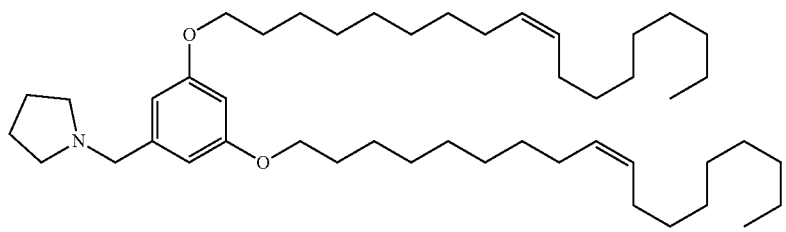 [SMILES: CCCCCCCC/C=C\CCCCCCCCOc1cc(CN2CCCC2)cc(OCCCCCCCC/C=C\CCCCCCCC)c1]

¹H NMR (400 MHz, CDCl₃) δ 6.53 (s, 2H), 6.35 (s, 1H), 5.38-5.30 (m, 4H), 3.92 (t, J=6.5 Hz, 4H), 3.62 (s, br, 2H), 2.62 (m, 4H), 2.10-1.95 (m, 8H), 1.90-1.80 (m, 4H), 1.80-1.65 (m, 4H), 1.50-1.20 (m, 43H), 0.87 (t, J=7.0 Hz, 6H) ppm.
ES-MS m/z=694.9 (MH+)

Synthesis of Example 8

Example 8

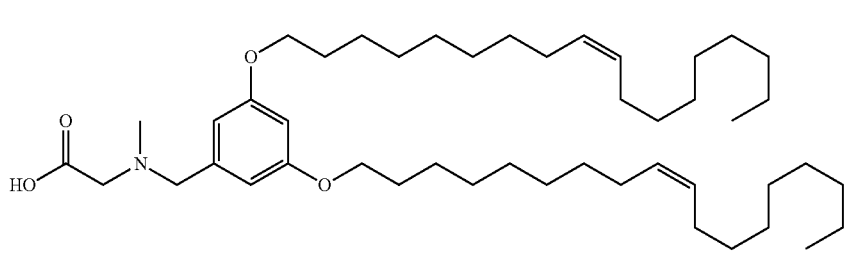

To a solution of the compound from Example 6 (160 mg, 0.22 mmol) in dioxane (7 mL) was added 50% HCl in water (6.57 mL). The mixture was heated to reflux overnight and then cooled to room temperature. The volatiles were removed under reduced pressure and the resulting material purified using strong cation exchange resin followed by column chromatography on silica using DCM/MeOH as eluent, providing 123 mg of the desired product.

¹H NMR (400 MHz, CDCl₃) δ 10.34 (s, br, 1H), 6.57 (s, 2H), 6.42 (s, 1H), 5.38-5.30 (m, 4H), 4.17 (s, 2H), 3.87 (t, J=6.5 Hz, 4H), 3.51 (s, 2H), 2.77 (s, 3H), 2.10-1.95 (m, 8H), 1.80-1.60 (m, 4H), 1.50-1.15 (m, 44H), 0.87 (t, J=7.0 Hz, 6H) ppm.
¹³C NMR (100 MHz, CDCl₃) δ 168.6, 160.6, 132.3, 129.9, 129.7, 109.0, 101.8, 68.1, 60.0, 57.6, 41.1, 31.8, 29.7, 29.5, 29.5, 29.4, 29.4, 29.2, 29.2, 27.2, 26.0, 22.6, 14.1 ppm.

Synthesis of Example 9

Intermediate 9a:

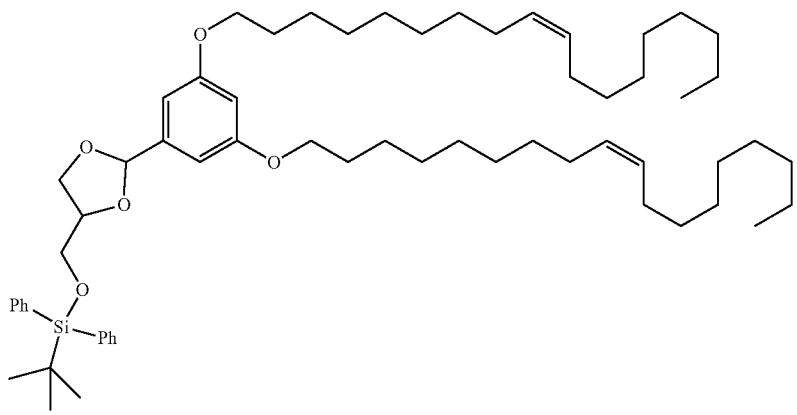 [SMILES: CCCCCCCC/C=C\CCCCCCCCOc1cc(OCCCCCCCC/C=C\CCCCCCCC)cc(C2OCC(CO[Si](c3ccccc3)(c3ccccc3)C(C)(C)C)O2)c1]

To Intermediate 1a (1 g, 1.56 mmol) in MePh (30 mL) was added TBDPS protected glycerol (0.52 g, 1.56 mmol) and TsOH monohydrate (0.03 g, 0.16 mmol). The mixture was heated to reflux overnight and then cooled to room temperature. The volatiles were removed under reduced pressure and the resulting material purified on silica using heptanes/EtOAc as eluent, providing 1.28 g of a mixture containing the desired product.

Rf=0.45 (silica, 10% EtOAc in heptanes, UV and cerium molybdate)

Intermediate 9b:

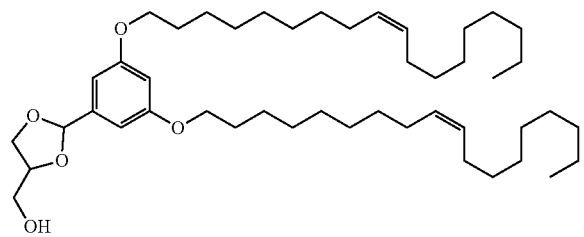 [SMILES: CCCCCCCC/C=C\CCCCCCCCOc1cc(OCCCCCCCC/C=C\CCCCCCCC)cc(C2OCC(CO)O2)c1]

To a solution of Intermediate 9a (1.28 g, 1.34 mmol) in THF (10 mL) was added TBAF (9.9 mL, 1.0 M in THF, 9.93 mmol). The resulting solution was stirred overnight at room temperature.

The volatiles were removed under reduced pressure and the resulting material purified on silica using heptanes/EtOAc as eluent, providing 638 mg (67%) of the desired product.

Rf=0.65 (silica, 50% EtOAc in heptanes, cerium molybdate)

Intermediate 9c:

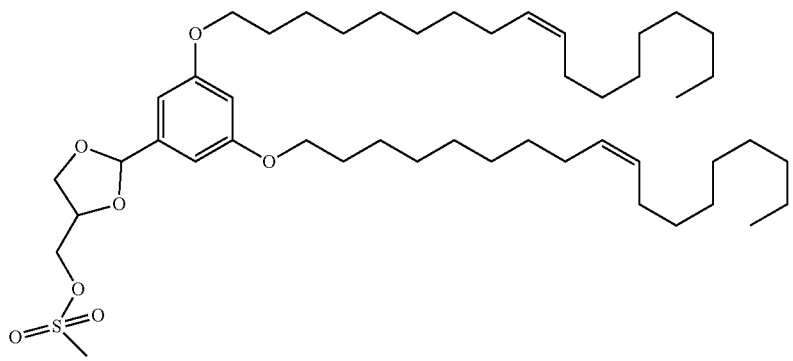 [SMILES: CCCCCCCC/C=C\CCCCCCCCOc1cc(OCCCCCCCC/C=C\CCCCCCCC)cc(C2OCC(COS(C)(=O)=O)O2)c1]

To a solution of Intermediate 9b (638 mg, 0.895 mmol) in DCM (20 mL) was added DIEA (0.78 mL, 4.5 mmol) and MsCl (0.35 mL, 4.5 mmol). The resulting solution was stirred for 30 min. The volatiles were removed under reduced pressure and the resulting material was used without further purification.

ES-MS m/z=791.4 (MH+).

Example 9 Compound

Example 9

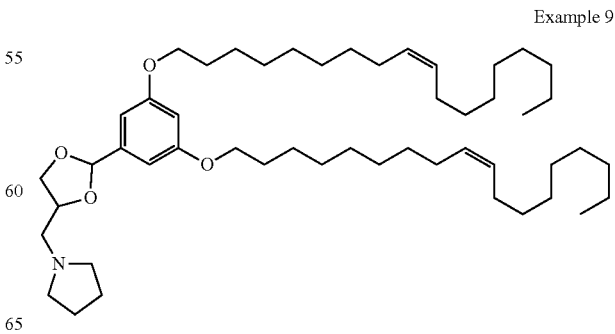

A solution of Intermediate 9c (708 mg, 0.895 mmol) was dissolved in pyrrolidine (3.0 mL, 36.2 mmol) and heated to 140 deg C. in a microwave reactor. The volatiles were removed under reduced pressure and the resulting material purified on silica using heptanes/EtOAc as eluent, providing 292 mg of the desired product.

$^1$H NMR (400 MHz, CDCl$_3$) δ 6.62 (dd, J=6.0 Hz, 2.5 Hz, 2H), 6.44-6.42 (m, 1H), 5.89 (s, 0.50H), 5.75 (s, 0.50H), 5.37-5.35 (m, 4H), 4.42-4.33 (m, 1H), 4.26-4.23 (m, 0.50H), 4.12 (dd, J=7.8 Hz, 6.8 Hz, 0.50H), 3.93 (t, J=6.3 Hz, 4H), 3.80 (dd, J=7.8 Hz, 6.8 Hz, 0.50H), 3.71-3.67 (m, 0.50H), 2.81-2.73 (m, 2H), 2.65-2.57 (m, 4H), 2.05-2.00 (m, 8H), 1.81-1.73 (m, 8H), 1.48-1.27 (m, 44H), 0.89 (m, 6H) ppm.

ES-MS m/z=766.6 (MH+).

Examples 10 and 11 were prepared using methods similar to those employed for the preparation of Example 9.

Example 10

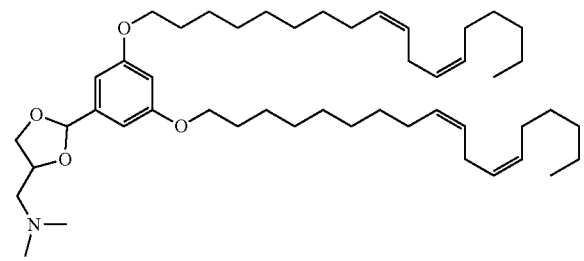 [SMILES: CCCCC/C=C\C/C=C\CCCCCCCCOc1cc(OCCCCCCCC/C=C\C/C=C\CCCCC)cc(C2OCC(CN(C)C)O2)c1]

$^1$H NMR (400 MHz, CDCl$_3$) δ 6.59-6.65 (m, 2H), 6.44 (t, J=2.3 Hz, 1H), 5.75 (s, 1H), 5.32-5.44 (m, 6H), 4.32-4.42 (m, 1H), 4.08-4.18 (m, 1H), 3.94 (t, J=6.5 Hz, 4H), 3.78 (dd, J=8.0, 6.5 Hz, 1H), 2.74-2.83 (m, 4H), 2.51-2.66 (m, 2H), 2.31-2.37 (m, 6H), 2.00-2.11 (m, 8H), 1.68-1.85 (m, 6H), 1.20-1.50 (m, 32H), 0.84-0.93 (m, 6H) ppm.

ES-MS m/z=736.5 (MH+).

Example 11

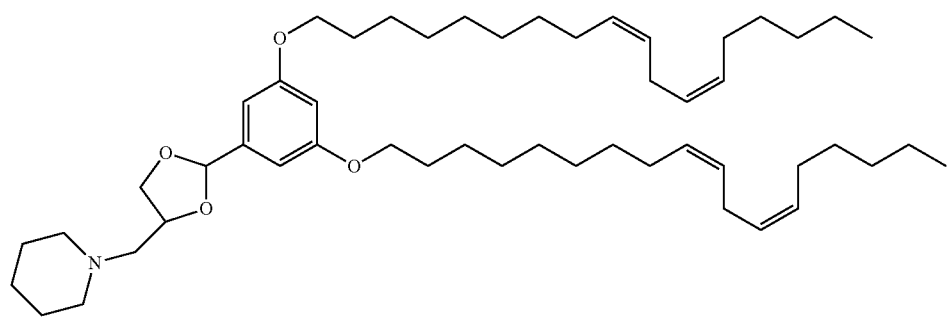 [SMILES: CCCCC/C=C\C/C=C\CCCCCCCCOc1cc(OCCCCCCCC/C=C\C/C=C\CCCCC)cc(C2OCC(CN3CCCCC3)O2)c1]

$^1$H NMR (400 MHz, CDCl$_3$) δ 6.63 (d, J=2.0 Hz, 2H), 6.45 (t, J=2.3 Hz, 1H), 5.74 (s, 1H), 5.29-5.48 (m, 8H), 4.38 (t, J=6.1 Hz, 1H), 4.07-4.15 (m, 1H), 3.96 (t, J=6.6 Hz, 4H), 3.78 (dd, J=8.1, 6.6 Hz, 1H), 2.80 (t, J=6.3 Hz, 4H), 2.62-2.72 (m, 1H), 2.50-2.62 (m, 4H), 2.40-2.50 (m, 2H), 2.08 (d, J=7.1 Hz, 4H), 1.70-1.83 (m, 4H), 1.53-1.70 (m, 7H), 1.23-1.53 (m, 34H), 0.91 (t, J=7.1 Hz, 6H) ppm.

ES-MS m/z 776.7 (MH+).

Synthesis of Example 12

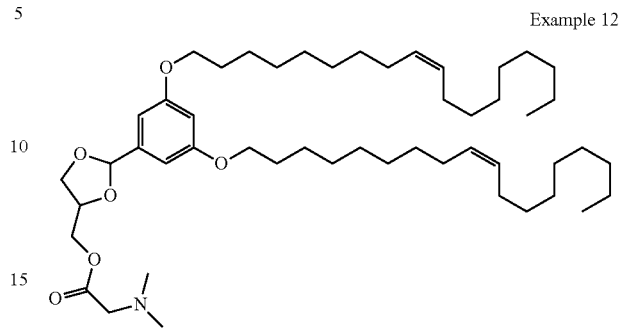

Example 12

To a solution of Intermediate 9b (2.42 g, 3.39 mmol) in DCM (30 mL) was added N,N-dimethylglycine (0.38 g, 3.73 mmol), followed by HATU (1.55 g, 4.07 mmol) and pyridine (1.1 mL, 13 mmol). The mixture was stirred at room temperature overnight. The volatiles were removed under reduced pressure and the resulting material purified on silica using heptanes/EtOAc as eluent, providing 1.14 g of the desired product.

$^1$H NMR (400 MHz, CDCl$_3$) δ 6.60 (dt, J=8.8 Hz, 2.0 Hz, 2H), 6.44-6.41 (m, 1H), 5.87 (s, 0.33H), 5.73 (s, 0.33H), 5.45 (s, 0.33H), 5.36-5.30 (m, 4H), 4.74 (m, 0.33H), 3.91 (m, 0.33H), 3.76 (m, 0.33H), 4.50-4.06 (m, 4H), 3.91 (t, J=6.5 Hz, 4H), 3.31 (s, 0.66H), 3.22 (s, 0.66H), 3.19 (s, 0.66H), 2.38 (s, 2H), 2.36 (s, 2H), 2.34 (s, 2H), 2.04-1.99 (m, 8H), 1.78-1.71 (m, 4H), 1.50-1.26 (m, 44H), 0.87 (t, J=7.0 Hz, 6H) ppm.

ES-MS m/z=798.5 (MH+).

Synthesis of Example 13

Intermediate 13a:

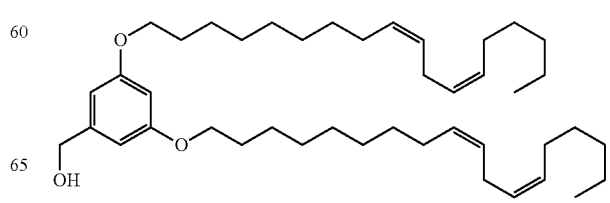

To Intermediate 1a (1.5 g, 2.4 mmol) in THF (10 mL) and MeOH (5 mL) was added sodium borohydride (0.116 g, 3.07 mmol). The resulting mixture was stirred overnight and then quenched with MeOH and water. The resulting material was extracted with EtOAc and the organic layers were dried over sodium sulfate. The material was decanted and the volatiles removed under reduced pressure. The material was used in the next step without further purification.

Example 13 Compound

Example 13

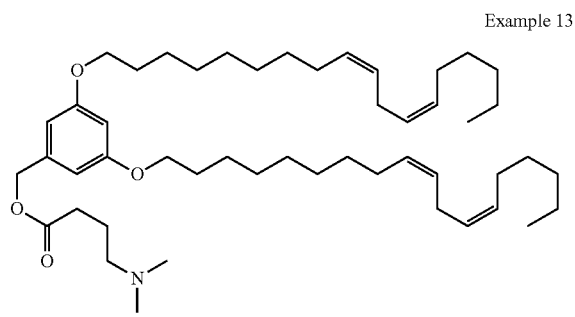 [SMILES: CCCCC/C=C\C/C=C\CCCCCCCCOc1cc(COC(=O)CCCN(C)C)cc(OCCCCCCCC/C=C\C/C=C\CCCCC)c1]

To Intermediate 13a (486 mg, 0.762 mmol) in DCM (5 mL) was added 4-dimethylaminobutanoic acid (100 mg, 0.762 mmol), followed by DIEA (0.32 mL, 1.83 mmol), DMAP (50 mg, 0.41 mmol) and EDC (175 mg, 0.92 mmol). The resulting mixture was stirred overnight at room temperature and purified directly on silica using heptanes/EtOAc as eluent, providing 319 mg (56%) of the desired product.

$^1$H NMR (400 MHz, CDCl$_3$) δ 6.48-6.45 (m, 2H), 6.41-6.38 (m, 1H), 5.44-5.29 (m, 8H), 5.04 (s, 2H), 3.92 (t, J=6.5 Hz, 4H), 2.81-2.75 (m, 4H), 2.41 (t, J=7.5 Hz, 2H), 2.29 (t, J=7.3 Hz, 2H), 2.21 (s, 6H), 2.10-2.00 (m, 8H), 1.87-1.71 (m, 6H), 1.51-1.23 (m, 32H), 0.90 (t, J=6.8 Hz, 6H) ppm.

ES-MS m/z=750.7 (MH+).

Examples 14-17 were prepared using methods similar to those employed for the preparation of Example 13.

Example 14

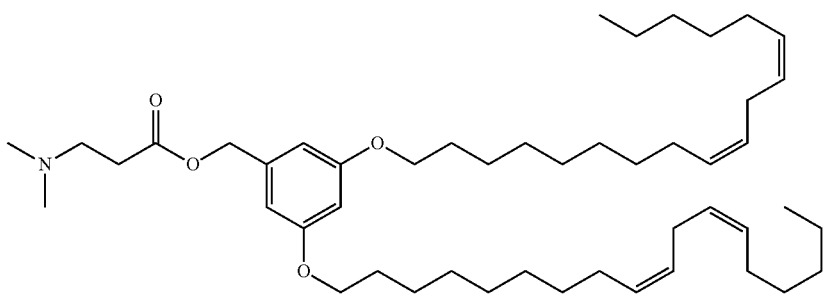 [SMILES: CCCCC/C=C\C/C=C\CCCCCCCCOc1cc(COC(=O)CCN(C)C)cc(OCCCCCCCC/C=C\C/C=C\CCCCC)c1]

$^1$H NMR (400 MHz, CDCl$_3$) δ 6.49-6.46 (m, 2H), 6.42-6.39 (m, 1H), 5.44-5.29 (m, 8H), 5.05 (s, 2H), 3.93 (t, J=6.8 Hz, 4H), 2.82-2.75 (m, 4H), 2.68-2.61 (m, 2H), 2.59-2.52 (m, 2H), 2.25 (s, 6H), 2.12-2.01 (m, 8H), 1.82-1.71 (m, 4H), 1.52-1.23 (m, 32H), 0.90 (t, J=6.8 Hz, 6H) ppm.

ES-MS m/z=736.8 (MH+).

Example 15

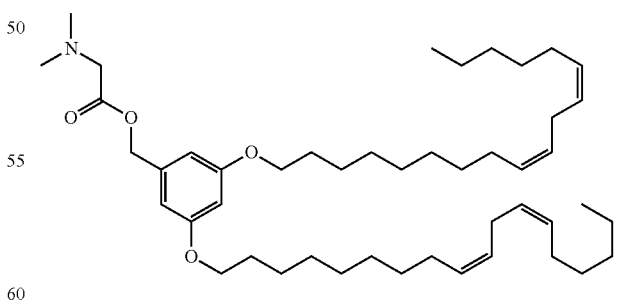

$^1$H NMR (400 MHz, CDCl$_3$) δ 6.51-6.46 (m, 2H), 6.42-6.39 (m, 1H), 5.46-5.29 (m, 8H), 5.09 (s, 2H), 3.92 (t, J=6.5 Hz, 4H), 3.23 (s, 2H), 2.83-2.75 (m, 4H), 2.37 (s, 6H), 2.12-2.00 (m, 8H), 1.83-1.70 (m, 4H), 1.50-1.23 (m, 32H), 0.89 (t, J=6.8 Hz, 6H) ppm.

ES-MS m/z=722.4 (MH+).

Example 16

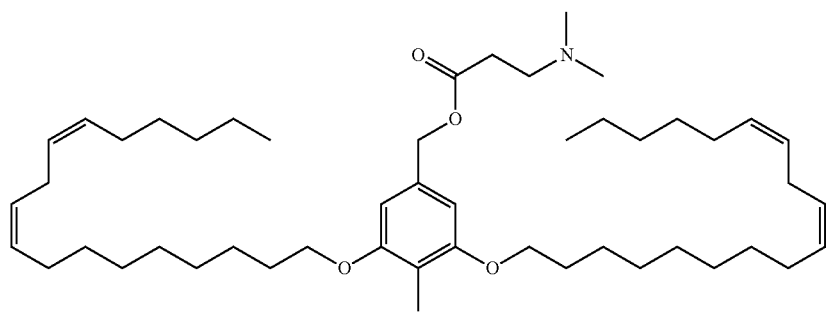 [SMILES: CCCCC/C=C\C/C=C\CCCCCCCCOc1cc(COC(=O)CCN(C)C)cc(OCCCCCCCC/C=C\C/C=C\CCCCC)c1C]

$^1$H NMR (400 MHz, CDCl$_3$) δ 6.51 (s, 2H), 5.31-5.45 (m, 8H), 5.07 (s, 2H), 3.97 (t, J=6.6 Hz, 4H), 2.80 (dd, J=6.3, 6.3 Hz, 4H), 2.68 (t, J=7.1 Hz, 2H), 2.54 (t, J=7.3 Hz, 2H), 2.27 (s, 6H), 2.04-2.13 (m, 11H), 1.76-1.85 (m, 4H), 1.46-1.53 (m, 4H), 1.26-1.45 (m, 32H), 0.92 (t, J=6.8 Hz, 5H), 0.93 (br. s., 1H) ppm.
ES-MS m/z=750.5 (MH+).

Example 17

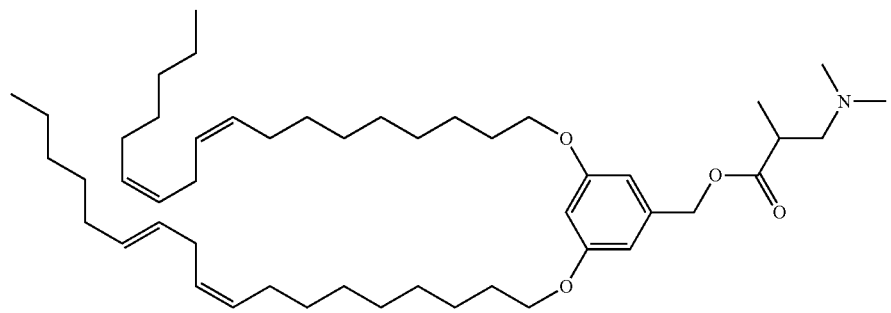 [SMILES: CCCCC/C=C\C/C=C\CCCCCCCCOc1cc(COC(=O)C(C)CN(C)C)cc(OCCCCCCCC/C=C\C/C=C/CCCCC)c1]

$^1$H NMR (400 MHz, CDCl$_3$) δ 6.40 (d, J=2.0 Hz, 2H), 6.34-6.29 (m, 1H), 5.36-5.21 (m, 8H), 4.98 (s, 2H), 3.85 (t, J=6.6 Hz, 4H), 2.70 (t, J=6.3 Hz, 4H), 2.66-2.54 (m, 2H), 2.14 (s, 6H), 1.98 (q, J=6.6 Hz, 8H), 1.72-1.64 (m, 4H), 1.42-1.34 (m, 4H), 1.33-1.16 (m, 36H), 1.10 (d, J=6.6 Hz, 3H), 0.85-0.79 (m, 6H) ppm.
ES-MS m/z=750.3 (MH+).

Synthesis of Example 18

Intermediate 18a:

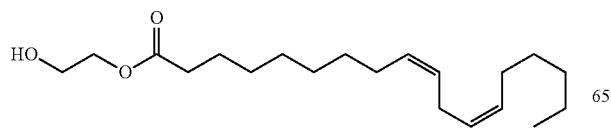

Linoleic acid (5.0 g, 17.83 mmol) was dissolved in 39.9 mL ethylene glycol with stirring. To the mixture was added EDC (5.136 g, 26.7 mmol) and HOBt (4.10 g, 26.7 mmol) followed by triethylamine (7.45 mL, 53.5 mmol). The reaction was stirred at room temperature for 48 hours and checked for completion by TLC. The crude was diluted in 100 mL dichloromethane and washed with 50 mL water and 50 mL brine. The organic layer was separated and dried over anhydrous sodium sulfate. The crude product was dry loaded onto celite and purified by silica gel chromatography 10 to 40% gradient EtOAc in heptanes. The product was recovered as a clear oil (3.884 g, 67.1%).

Rf=0.22 (silica, 20% EtOAc in heptanes, cerium molybdate).

Intermediate 18b:

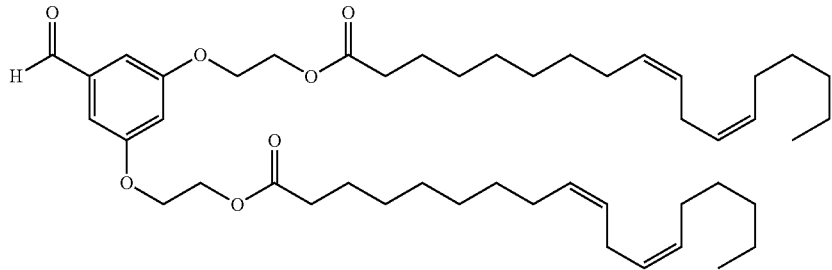 [SMILES: CCCCC/C=C\C/C=C\CCCCCCCC(=O)OCCOc1cc(C=O)cc(OCCOC(=O)CCCCCCC/C=C\C/C=C\CCCCC)c1]

Intermediate 18a (1.5 g, 4.62 mmol), 3,5-dihydroxybenzaldehyde (0.319 g, 2.311 mmol) and triphenylphosphine (1.273 g, 4.85 mmol) were dissolved in 19 mL anhydrous THF. DIAD (0.944 mL, 4.85 mmol) was added and the reaction was allowed to stir 48 hours at room temperature. The reaction was checked for completion by crude NMR using chloroform-d as solvent. The reaction mixture was directly concentrated onto celite and purified by silica gel chromatography 10 to 20% EtOAc in heptanes gradient The product was isolated as a colorless oil (1.077 g, 62.1%).

$^1$H NMR (400 MHz, CDCl$_3$) δ 9.92 (s, 1H), 7.06 (d, J=2.3 Hz, 2H), 6.76 (t, J=2.3 Hz, 1H), 5.31-5.43 (m, 8H), 4.43-4.49 (m, 4H), 4.20-4.26 (m, 4H), 2.78 (t, J=6.4 Hz, 4H), 2.37 (t, J=7.7 Hz, 4H), 2.01-2.11 (m, 8H), 1.58-1.71 (m, 5H), 1.24-1.42 (m, 30H), 0.90 (t, J=6.8 Hz, 6H) ppm.

Intermediate 18c:

Intermediate 18b (465.2 mg, 0.619 mmol) was dissolved in 4.1 mL dry ethanol under nitrogen. Sodium borohydride (46.9 mg, 1.239 mmol) was added in one portion and stirred at room temperature for 30 minutes. The reaction was monitored form completion by TLC. The reaction was quenched with acetic acid and diluted with 10 mL water and extracted into 30 mL DCM. The resulting organic layers were combined, dried over sodium sulfate, filtered and concentrated. The product was recovered as 429 mf of a clear oil.

Rf=0.55 (silica, 30% EtOAc in heptanes, cerium molybdate).

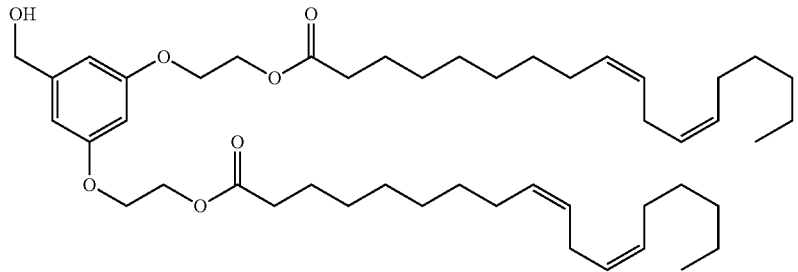 [SMILES: CCCCC/C=C\C/C=C\CCCCCCCC(=O)OCCOc1cc(CO)cc(OCCOC(=O)CCCCCCC/C=C\C/C=C\CCCCC)c1]

Example 18 Compound

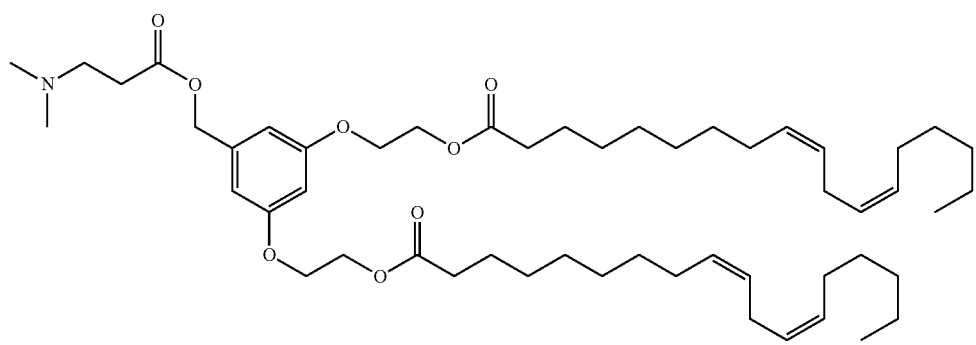

Example 18

Intermediate 18c (50 mg, 0.066 mmol) and N,N-dimethylaminopropanoic acid (10.20 mg, 0.066 mmol) were dissolved in 4 mL DCM. HATU (37.9 mg, 0.100 mmol) was added followed by triethylamine (9.25 uL, 0.066 mmol). The reaction was stirred 18 hours at room temperature and monitored by LCMS. The reaction was diluted with 100 mL DCM and 50 mL water. The organic layers were separated, then washed with brine, dried over sodium sulfate filtered and concentrated. The crude was purified by HPLC 5 to 100% 1:1 Acetonitrile: Isopropanol in water, modified with 0.1% TFA. The product was isolated as a 5.4 mg colorless oil.

$^1$H NMR (400 MHz, CDCl$_3$) δ 6.84 (s, 1H), 6.74 (d, J=1.5 Hz, 2H), 5.21-5.35 (m, 8H), 5.07 (s, 2H), 4.31 (t, J=4.8 Hz, 4H), 4.03-4.08 (m, 4H), 2.69 (t, J=6.1 Hz, 4H), 2.47-2.58 (m, 8H), 2.35-2.41 (m, 7H), 2.23-2.28 (m, 5H), 1.95-2.00 (m, 8H), 1.79-1.86 (m, 2H), 1.52-1.59 (m, 5H), 1.17-1.32 (m, 37H), 0.82 (t, J=6.8 Hz, 6H) ppm.

ES-MS m/z=867.5 (MH+).

Examples 19-23 and Example 29 were prepared using methods similar to those employed for the preparation of Example 18.

$^1$H NMR (400 MHz, CDCl$_3$) δ 6.51 (d, J=2.0 Hz, 2H), 6.42 (t, J=2.0 Hz, 1H), 5.27-5.47 (m, 8H), 5.11 (s, 2H), 4.27 (dd, J=6.4, 6.4 Hz, 4H), 4.03 (dd, J=6.1, 6.1 Hz, 4H), 3.30 (s, 2H), 2.79 (dd, J=6.4, 6.4 Hz, 4H), 2.44 (s, 6H), 2.32 (dd, J=7.5, 7.5 Hz, 4H), 2.03-2.15 (m, 12H), 1.53-1.77 (m, 14H), 1.25-1.43 (m, 32H), 0.91 (t, J=6.8 Hz, 6H) ppm.

ES-MS m/z=867.4 (MH+).

Example 19

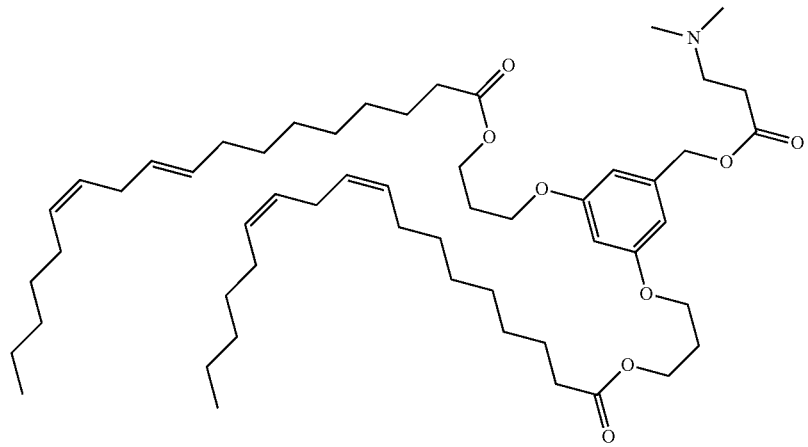 [SMILES: CCCCC/C=C\C/C=C\CCCCCCCC(=O)OCCCOc1cc(COC(=O)CCN(C)C)cc(OCCCOC(=O)CCCCCCC/C=C/C/C=C\CCCCC)c1]

$^1$H NMR (400 MHz, CDCl$_3$) δ 6.50 (d, J=2.3 Hz, 2H), 6.41 (t, J=2.3 Hz, 1H), 5.33-5.44 (m, 8H), 5.07 (s, 2H), 4.27 (t, J=6.4 Hz, 4H), 4.03 (t, J=6.1 Hz, 4H), 2.73-2.78 (m, 4H), 2.64 (d, J=7.3 Hz, 2H), 2.29-2.37 (m, 10H), 2.12 (dd, J=6.3, 6.3 Hz, 4H), 2.02-2.10 (m, 8H), 1.63 (dd, J=7.3, 7.3 Hz, 5H), 1.25-1.41 (m, 32H), 0.91 (t, J=6.8 Hz, 6H) ppm.

ES-MS m/z=880.4 (MH+).

Example 20

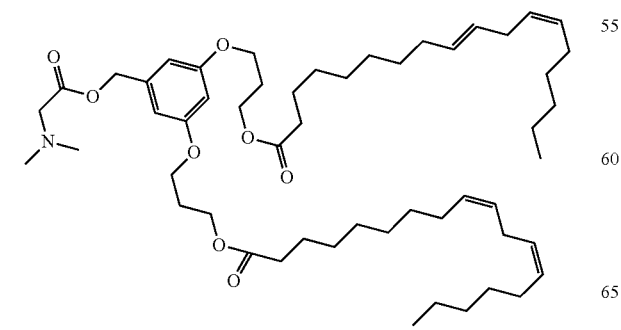

Example 21
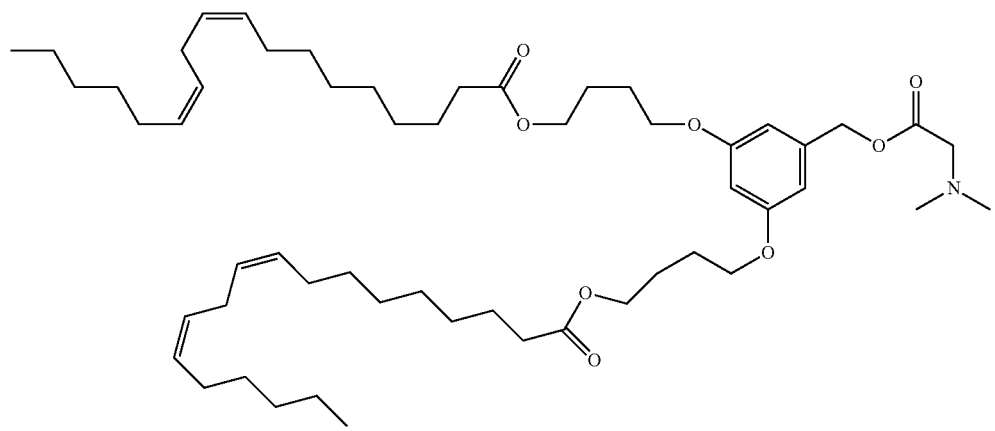 [SMILES: CCCCC/C=C\C/C=C\CCCCCCCC(=O)OCCCCOc1cc(COC(=O)CN(C)C)cc(OCCCCOC(=O)CCCCCCC/C=C\C/C=C\CCCCC)c1]
$^1$H NMR (400 MHz, CDCl$_3$) δ 6.48 (d, J=2.3 Hz, 2H), 6.40 (t, J=2.1 Hz, 1H), 5.43-5.32 (m, 8H), 5.11 (s, 2H), 4.17-4.10 (m, 4H), 3.96 (dd, J=5.6, 5.6 Hz, 4H), 3.54 (s, 2H), 3.20-3.27 (m, J=7.3 Hz, 3H), 2.81 (s, 22H), 2.77 (dd, J=6.7, 6.7 Hz, 4H), 2.63 (s, 6H), 2.30 (dd, J=7.7, 7.7 Hz, 4H), 2.01-2.08 (m, 8H), 1.86-1.78 (m, 8H), 1.66-1.58 (m, 5H), 1.42-1.37 (m, 7H), 1.37-1.23 (m, 36H), 0.91-0.87 (m, 6H) ppm.
ES-MS m/z=894.5 (MH+).
Example 22
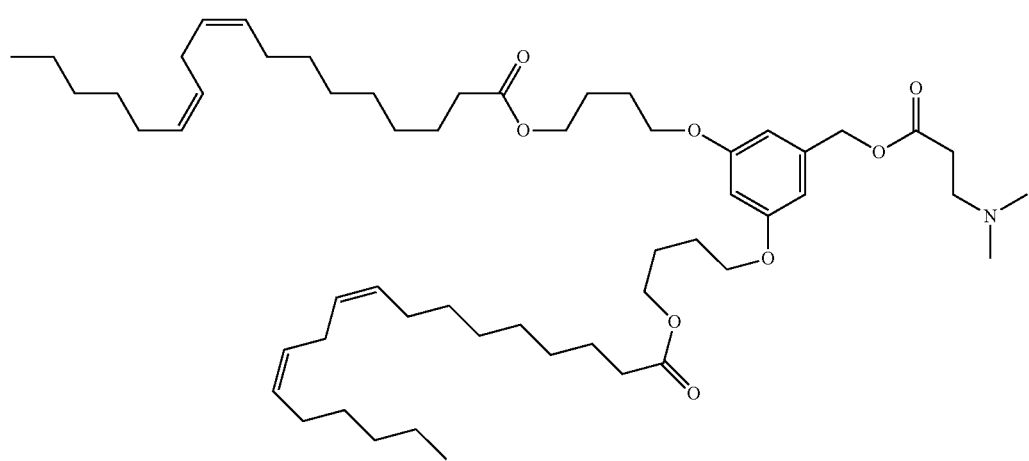 [SMILES: CCCCC/C=C\C/C=C\CCCCCCCC(=O)OCCCCOc1cc(COC(=O)CCN(C)C)cc(OCCCCOC(=O)CCCCCCC/C=C\C/C=C\CCCCC)c1]
$^1$H NMR (400 MHz, CDCl$_3$) δ: 6.48 (d, J=2.3 Hz, 2H), 6.40 (br. s, 1H), 5.32-5.43 (m, 8H), 5.11 (s, 2H), 4.10-4.17 (m, 4H), 3.96 (t, J=5.6 Hz, 4H), 3.54 (s, 2H), 3.23 (q, J=7.3 Hz, 2H), 2.77 (dd, J=6.7, 6.7 Hz, 4H), 2.63 (s, 6H), 2.30 (dd, J=7.7, 7.7 Hz, 4H), 2.02-2.07 (m, 8H), 1.79-1.88 (m, 8H), 1.58-1.68 (m, 5H), 1.23-1.39 (m, 38H), 0.89 (t, J=6.5 Hz, 7H) ppm.
ES-MS m/z=908.7 (MH+).

Example 23

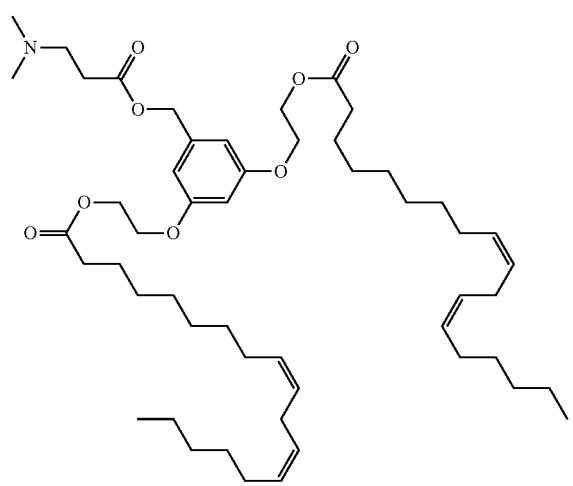 [SMILES: CCCCC/C=C\C/C=C\CCCCCCCC(=O)OCCOc1cc(COC(=O)CCN(C)C)cc(OCCOC(=O)CCCCCCC/C=C\C/C=C\CCCCC)c1]

¹H NMR (400 MHz, CDCl₃) δ 6.54 (d, J=2.3 Hz, 2H), 6.45 (t, J=2.3 Hz, 1H), 5.33-5.43 (m, 8H), 5.07 (s, 2H), 4.41-4.45 (m, 4H), 4.13-4.18 (m, 4H), 2.79 (dd, J=6.5, 6.5 Hz, 4H), 2.63-2.68 (m, 2H), 2.53-2.59 (m, 2H), 2.37 (t, J=7.7 Hz, 4H), 2.27 (s, 6H), 2.03-2.09 (m, 8H), 1.61-1.68 (m, 8H), 1.27-1.40 (m, 34H), 0.91 (t, J=6.8 Hz, 6H) ppm.

ES-MS m/z=853.7 (MH+).

Synthesis of Example 24

Intermediate 24a:

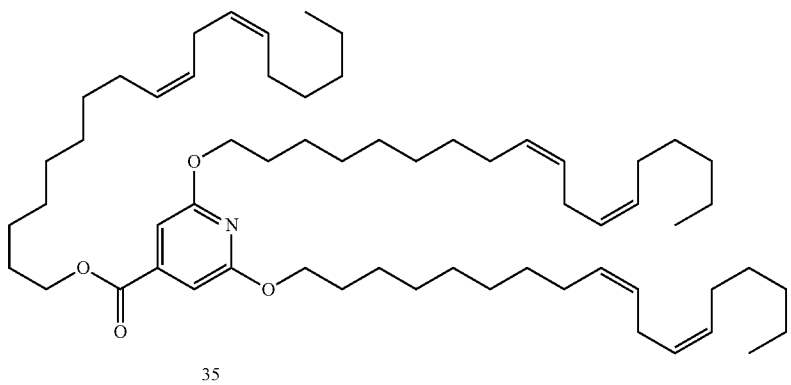

A solution of citrazinic acid (1.8 g, 11.6 mmol) in DMF (60 mL) was stirred at room temperature and linoleyl mesylate (16.0 g, 46.4 mmol) and potassium carbonate (8.02 g, 58.0 mmol) were added. The mixture was heated to 80 deg C. overnight and then cooled to room temperature and water (50 mL) and EtOAc (100 mL) were added. The organic phase was collected and dried over sodium sulfate and then the volatiles removed under reduced pressure. The resulting crude material was purified on silica using heptanes/EtOAc as eluent, providing 5.2 g of the desired product.
¹³C NMR (100 MHz, CDCl₃) δ 165.3, 163.5, 142.9, 130.2, 130.1, 130.1, 120.8, 127.9, 101.2, 66.6, 65.7, 31.6, 29.7, 29.7, 29.5, 29.4, 29.4, 29.3, 29.3, 29.1, 28.6, 27.2, 26.1, 26.0, 25.6, 22.6, 14.1 ppm.

Intermediate 24b:

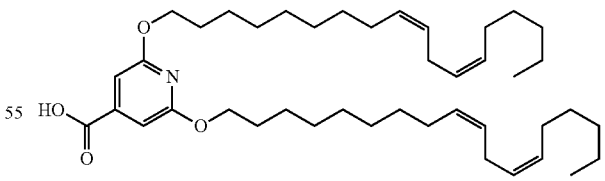

Intermediate 24a (3.06 g, 3.40 mmol) was stirred in EtOH (15 mL) and potassium hydroxide (329 mg, 5.10 mmol) was added. The cloudy solution became clear and water (10 mL) and THF (8 mL) were added. The resulting mixture was stirred overnight at room temperature and then the volatiles removed under reduced pressure. The resulting residue was purified on silica using heptanes/EtOAc as eluent, providing 1.6 g of the desired product.
ES-MS m/z=652.4 (MH+).

Example 24 Compound

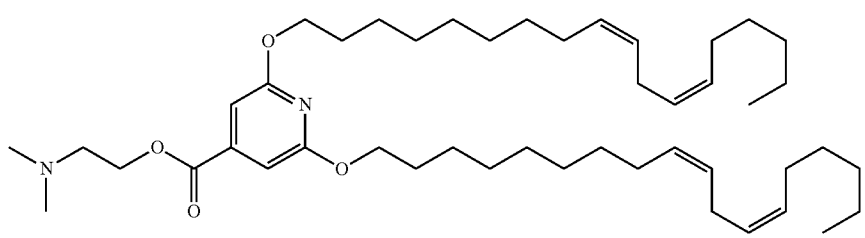
Example 24

Intermediate 24b (311 mg, 0.477 mmol) was stirred in DMF (15 mL) and HBTU (651 mg, 1.717 mmol), HOBt (120 mg, 0.444 mmol) and DIEA (0.582 mL, 3.34 mmol) were added. The reaction was stirred at room temperature overnight and the reaction poured into water (50 mL) and the resulting mixture extracted with EtOAc. The organic phases were collected and dried over sodium sulfate and then concentrated under reduced pressure. The resulting crude material was purified on silica using heptanes/EtOAc as eluent, providing 207 mg of the desired product.

$^1$H NMR (400 MHz, CDCl$_3$) δ 6.85 (s, 2H), 5.32-5.44 (m, 8H), 4.42 (t, J=8 Hz, 2H), 4.27 (t, J=8 Hz, 2H), 2.79 (t, J=8 Hz, 2H), 2.71 (t, J=8 Hz, 2H), 2.34 (s, 6H), 2.07 (dd, J=8 Hz, 8H), 1.78 (q, J=8 Hz, 4H), 1.27-1.48 (m, 32H), 0.91 (t, J=8 Hz, 6H) ppm.

ES-MS m/z=724.4 (MH+).

Example 25 was prepared using methods similar to those employed for the preparation of Example 24.

Example 25

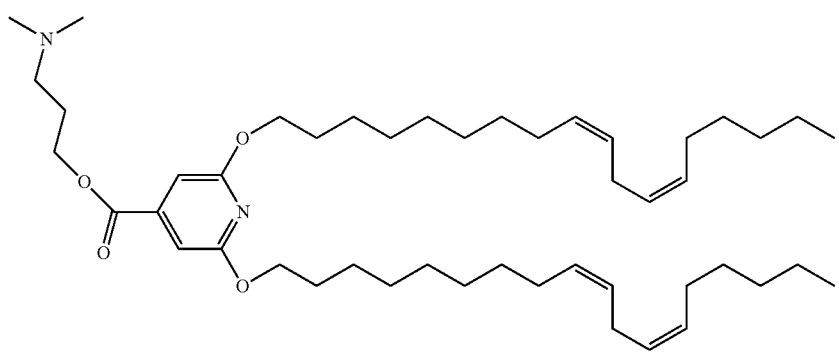 [SMILES: CCCCC/C=C\C/C=C\CCCCCCCCOc1cc(C(=O)OCCCN(C)C)cc(OCCCCCCCC/C=C\C/C=C\CCCCC)n1]

$^1$H NMR (400 MHz, CDCl$_3$) δ 6.84 (s, 2H), 5.32-5.44 (m, 8H), 4.37 (t, J=8 Hz, 2H), 4.28 (t, J=8 Hz, 4H), 2.79 (t, J=8 Hz, 4H), 2.45 (t, J=8 Hz, 2H), 2.29 (s, 6H), 2.07 (dd, J=8 Hz, 8H), 1.97 (q, J=5 Hz, 2H), 1.78 (q, J=8 Hz, 6H), 1.27-1.48 (m, 32H), 0.90 (t, J=8 Hz, 6H) ppm. ES-MS m/z=737.5 (MH+).

Synthesis of Example 26

Intermediate 26a:

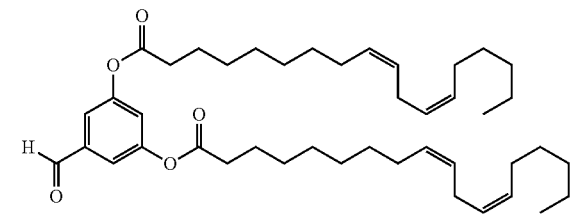 [SMILES: CCCCC/C=C\C/C=C\CCCCCCCC(=O)Oc1cc(C=O)cc(OC(=O)CCCCCCC/C=C\C/C=C\CCCCC)c1]

A solution of 3,5-dihydroxybenzaldehyde (500 mg, 3.62 mmol) in DCE (9 mL) was placed in a microwave vial and linoleic acid (2.03 g, 7.24 mmol), DIEA (1.26 mL, 7.24 mmol), DMAP (442 mg, 3.62 mmol), and EDC (1.74 g, 9.05 mmol) were added. The reaction was heated to 80 deg C. in a microwave reactor for 20 min and then stored at 4 deg C. for 2 days. The volatiles were removed under reduced pressure and the resulting material was purified on silica using heptanes/EtOAc as eluent, providing 1.44 g of the desired product.

$^{13}$C NMR (100 MHz, CDCl$_3$) δ 190.2, 171.6, 151.7, 138, 130.3, 130.0, 128.1, 127.9, 121.5, 119.9, 34.3, 31.5, 29.6, 29.4, 29.2, 29.1, 29.1, 27.2, 27.2, 25.6, 24.8, 22.6, 14.1 ppm.

Intermediate 26b:

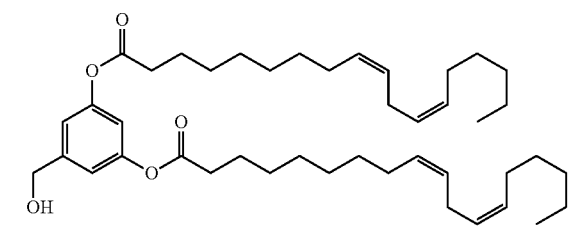 [SMILES: CCCCC/C=C\C/C=C\CCCCCCCC(=O)Oc1cc(CO)cc(OC(=O)CCCCCCC/C=C\C/C=C\CCCCC)c1]

Intermediate 26a (1.44 g, 2.17 mmol) was stirred in THF (18 mL) and EtOH (18 mL) and the resulting solution was cooled in an ice bath. Sodium borohydride (25 mg, 0.65 mmol) was added and the reaction was stirred at 0 deg C. for 1 h. The reaction was diluted with EtOAc and washed twice with water. The resulting organic layer was dried over sodium sulfate and then the volatiles were removed under reduced pressure. The crude material was purified on silica using heptanes/EtOAc followed by DCM/MeOH as eluent, providing 850 mg (59%) of the desired product.

$^{13}$C NMR (100 MHz, CDCl$_3$) δ 7.01-6.97 (m, 2H), 6.82-6.80 (m, 1H), 5.45-5.30 (m, 8H), 4.71 (s, 2H), 2.82-2.75 (m, 4H), 2.58-2.51 (m, 4H), 2.12-2.01 (m, 8H), 1.80-1.70 (m, 4H), 1.45-1.23 (m, 28H), 0.93-0.86 (m, 6H) ppm.

Example 26 Compound $^1$H NMR (400 MHz, CDCl$_3$) δ 6.97 (d, J=2.0 Hz, 2H), 6.87 (t, J=2.1 Hz, 1H), 5.27-5.48 (m, 8H), 5.10 (s, 2H), 2.78 (t, J=6.5 Hz, 4H), 2.54 (t, J=7.5 Hz, 4H), 2.41 (t, J=7.4 Hz, 2H), 2.27-2.35 (m, 2H), 2.22 (s, 6H), 2.00-2.12 (m, 8H), 1.82 (quin, J=7.3 Hz, 2H), 1.74 (quin, J=7.5 Hz, 4H), 1.23-1.46 (m, 28H), 0.89 (t, J=7.0 Hz, 6H) ppm.

ES-MS m/z=778.5 (MH+).

Example 26

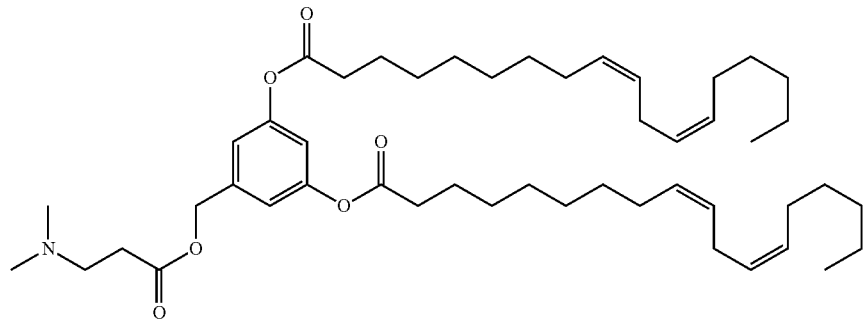

Intermediate 26b (330 mg, 0.496 mmol) in DCM (30 mL) was added 3-dimethylaminopropionic acid hydrochloride (114 mg, 0.744 mmol) EDC (143 mg, 0.744 mmol), DMAP (6 mg, 0.05 mmol) and TEA (0.277 mL, 1.98 mmol). The resulting mixture was stirred overnight at room temperature then purified directly on silica using heptanes/EtOAc followed by DCM/MeOH as eluent, providing 428 mg of the desired product as the hydrochloride salt.

$^1$H NMR (400 MHz, CDCl$_3$) δ 6.84 (s, 2H), 5.32-5.44 (m, 8H), 4.37 (t, J=8 Hz, 2H), 4.28 (t, J=8 Hz, 4H), 2.79 (t, J=8 Hz, 4H), 2.45 (t, J=8 Hz, 2H), 2.29 (s, 6H), 2.07 (dd, J=8 Hz, 8H), 1.97 (q, J=5 Hz, 2H), 1.78 (q, J=8 Hz, 6H), 1.27-1.48 (m, 32H), 0.90 (t, J=8 Hz, 6H) ppm.

ES-MS m/z=737.5 (MH+).

Example 27 was prepared using methods similar to those employed for the preparation of Example 26.

Example 27

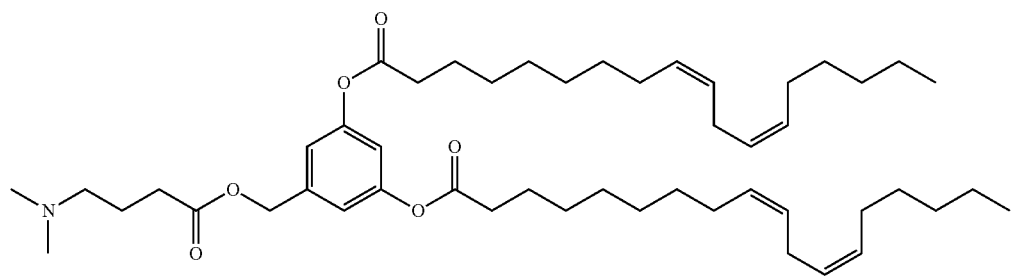 [SMILES: CCCCC/C=C\C/C=C\CCCCCCCC(=O)Oc1cc(COC(=O)CCCN(C)C)cc(OC(=O)CCCCCCC/C=C\C/C=C\CCCCC)c1]

Synthesis of Example 28

Intermediate 28a:

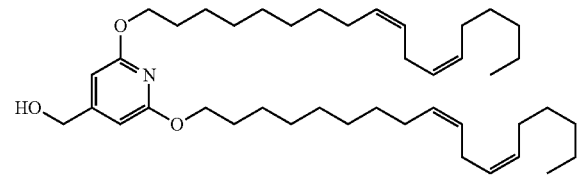 [SMILES: CCCCC/C=C\C/C=C\CCCCCCCCOc1cc(CO)cc(OCCCCCCCC/C=C\C/C=C\CCCCC)n1]

Intermediate 24b (3.5 g, 3.89 mmol) was stirred in THF (50 mL) and the solution cooled in an ice bath. To this cold solution was added lithium aluminum hydride (570 mg, 15 mmol) slowly. Following addition the reaction was allowed to warm to room temperature and stirred overnight. Ice was carefully added and the resulting mixture extracted with EtOAc. The organic layers were collected and dried over sodium sulfate and then concentrated under reduced pressure. The resulting crude material was purified on silica using heptanes/EtOAc as eluent, providing 1.3 g of the desired product.

$^1$H NMR (400 MHz, CDCl$_3$) δ 6.27 (s, 2H), 5.44-5.27 (m, 8H), 4.63 (s, 2H), 4.23 (t, J=5.7 Hz, 4H), 2.82-2.75 (m, 4H), 2.10-2.02 (m, 8H), 1.80-1.72 (m, 4H), 1.47-1.23 (m, 32H), 0.93-0.86 (m, 6H) ppm.

Example 28 Compound

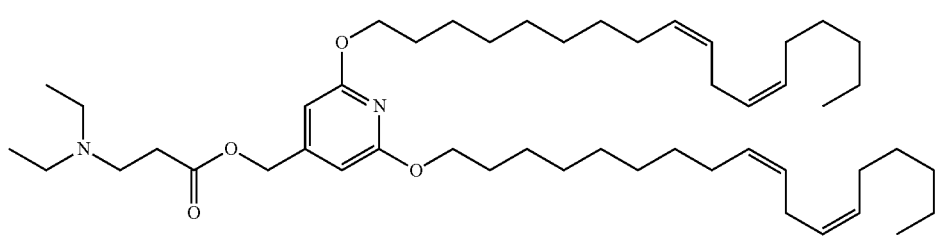

Example 28

Intermediate 28a (334 mg, 0.523 mmol) was stirred in DCM (20 mL) with 3-diethylaminopropionic acid hydrochloride (143 mg, 0.785 mmol). HATU (397 mg, 1.05 mmol) was added and the reaction was stirred overnight at room temperature. Volatiles were removed under reduced pressure and the crude material was purified on silica using heptanes/EtOAc as eluent, providing 171 mg of the desired product.

$^1$H NMR (400 MHz, CDCl$_3$) δ 6.25 (s, 2H), 5.32-5.44 (m, 8H), 5.04 (s, 2H), 4.24 (t, J=8 Hz, 4H), 2.78-2.87 (m, 6H), 2.55 (dd, J=8 Hz, 6H), 2.07 (dd, J=8 Hz, 8H), 1.78 (q, J=8 Hz, 4H), 1.27-1.48 (m, 32H), 1.05 (t, J=8 Hz, 6H), 0.91 (t, J=8 Hz, 6H) ppm.

ES-MS m/z=765.7 (MH+).

Example 29 was prepared according to Example 18.

Example 29

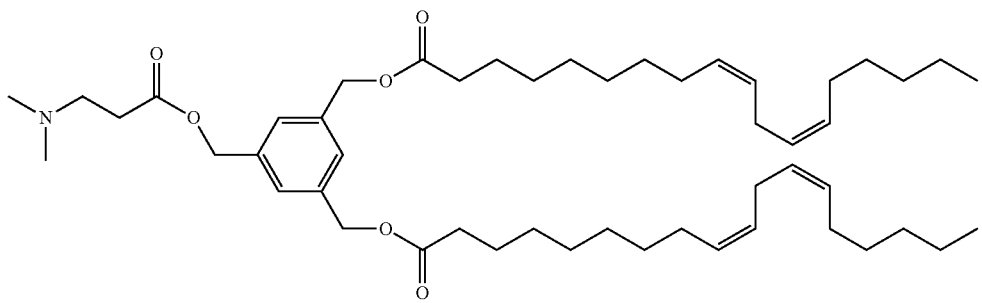 [SMILES: CCCCC/C=C\C/C=C\CCCCCCCC(=O)OCc1cc(COC(=O)CCCCCCC/C=C\C/C=C\CCCCC)cc(COC(=O)CCN(C)C)c1]

$^1$H NMR (400 MHz, CDCl$_3$) δ 7.30 (s, 3H), 5.28-5.45 (m, 8H), 5.14 (s, 2H), 5.11 (s, 4H), 2.77 (t, J=6.5 Hz, 4H), 2.61-2.70 (m, 2H), 2.51-2.59 (m, 2H), 2.37 (t, J=7.5 Hz, 4H), 2.25 (s, 6H), 2.05 (q, J=6.9 Hz, 8H), 1.59-1.73 (m, 6H), 1.22-1.43 (m, 26H), 0.89 (t, J=7.0 Hz, 6H) ppm.

ES-MS m/z=792.4 (MH+).

Examples 30-31 were prepared using methods similar to those employed for the preparation of Example 28.

Example 30

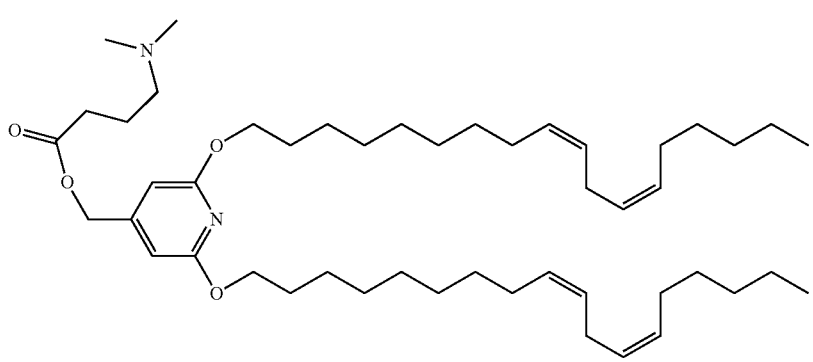 [SMILES: CCCCC/C=C\C/C=C\CCCCCCCCOc1cc(COC(=O)CCCN(C)C)cc(OCCCCCCCC/C=C\C/C=C\CCCCC)n1]

¹H NMR (400 MHz, CDCl₃) δ 6.24 (s, 2H), 5.46-5.33 (m, 8H), 5.05 (s, 2H), 4.24 (t, J=6.7 Hz, 4H), 2.81-2.72 (m, 7H), 2.66-2.61 (m, 2H), 2.34 (s, 6H), 2.02-2.11 (m, 8H), 1.80-1.72 (m, 4H), 1.49-1.40 (m, J=6.0, 13.8 Hz, 5H), 1.40-1.25 (m, 32H), 0.90 (t, J=6.9 Hz, 6H) ppm.
ES-MS m/z=751.7 (MH+).

Example 31

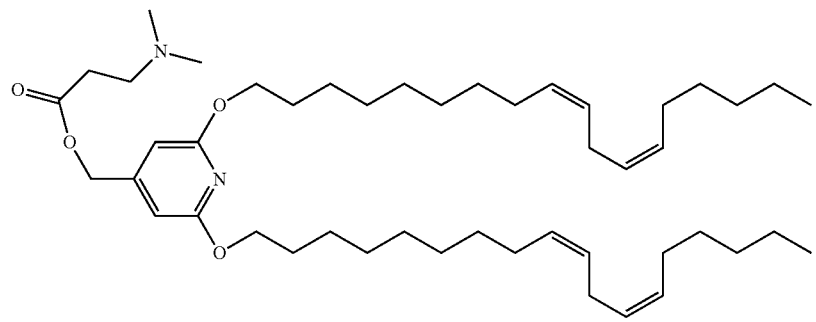 [SMILES: CCCCC/C=C\C/C=C\CCCCCCCCOc1cc(COC(=O)CCN(C)C)cc(OCCCCCCCC/C=C\C/C=C\CCCCC)n1]

¹H NMR (400 MHz, CDCl₃) δ 6.51 (d, J=2.0 Hz, 2H), 6.42 (t, J=2.0 Hz, 1H), 5.44-5.30 (m, 8H), 5.11 (s, 2H), 4.27 (t, J=6.4 Hz, 4H), 4.03 (t, J=6.1 Hz, 4H), 3.30 (s, 2H), 2.79 (t, J=6.4 Hz, 4H), 2.44 (s, 6H), 2.32 (t, J=7.5 Hz, 4H), 2.17-2.10 (m, 4H), 2.09-2.03 (m, 9H), 1.68-1.57 (m, 10H), 1.42-1.26 (m, 34H), 0.91 (t, J=6.8 Hz, 6H).
ES-MS m/z=737.5 (MH+).

Synthesis of Example 32

Intermediate 32a:

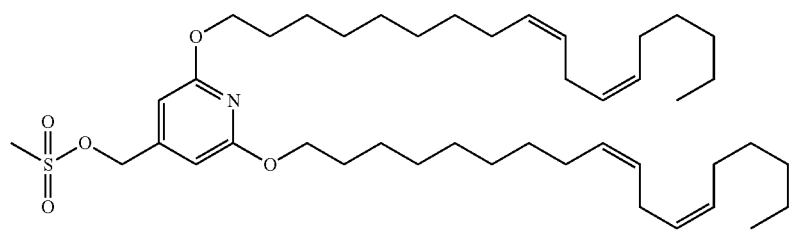 [SMILES: CCCCC/C=C\C/C=C\CCCCCCCCOc1cc(COS(C)(=O)=O)cc(OCCCCCCCC/C=C\C/C=C\CCCCC)n1]

Intermediate 28a (330 mg, 0.517 mmol) was stirred in DCM (30 mL) with TEA (0.290 mL, 2.07 mmol) and the resulting solution cooled in an ice bath. MsCl (0.08 mL, 1.0 mmol) was added and the resulting mixture was allowed to warm to room temperature with stirring for 4 h. The reaction was treated with HCl (30 mL, 1 M in water) and DCM (50 mL) and the organic layer was collected. The material was dried over sodium sulfate and the volatiles removed under reduced pressure to provide 360 mg of material that was used without further purification.

¹H NMR (400 MHz, CDCl₃) δ 6.27-6.36 (s, 2H), 5.32-5.44 (m, 10H), 5.14 (s, 1H), 4.39-4.50 (m, 1H), 4.17-4.30 (m, 5H), 3.41 (q, J=7.03 Hz, 1H), 3.01-3.06 (m, 2H), 2.74-2.84 (m, 5H), 2.07 (q, J=6.86 Hz, 10H), 1.70-1.87 (m, 5H), 1.66 (s, 2H), 1.24-1.55 (m, 34H), 0.91 (t, J=6.78 Hz, 6H) ppm.

Example 32 Compound

Example 32

Intermediate 32a (360 mg, 0.503 mmol) was stirred in DMF (3 mL) with dimethylamine (3 mL, 2 M, 11.9 mmol) and the mixture was heated in a microwave reactor to 140 deg C. for 30 min. This heating was repeated until all of the starting material had reacted as determined by TLC. The volatiles were removed under reduced pressure and the resulting crude material was purified on silica using heptanes/EtOAc as eluent, providing 123 mg of the desired product.

¹H NMR (400 MHz, CDCl₃) δ 6.27 (s, 2H), 5.32-5.44 (m, 8H), 4.26 (t, J=8 Hz, 4H), 3.33 (s, 2H) 2.80 (t, J=8 Hz, 4H), 2.26 (s, 6H), 2.07 (dd, J=8 Hz, 8H), 1.78 (q, J=5 Hz, 4H), 1.27-1.48 (m, 32H), 0.92 (t, J=8 Hz, 6H) ppm.
ES-MS m/z=665.5 (MH+).

Synthesis of Example 33

Intermediate 33a:

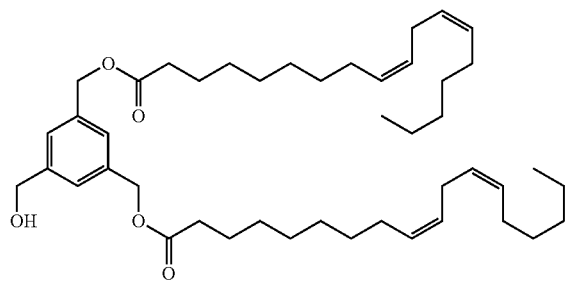 [SMILES: CCCCC/C=C\C/C=C\CCCCCCCC(=O)OCc1cc(CO)cc(COC(=O)CCCCCCC/C=C\C/C=C\CCCCC)c1]

Linoleic acid (3.42 g, 12.19 mmol) was stirred with EDC (2.33 g, 12.2 mmol) in DCM (30 mL). Once dissolved, DIEA (2.60 mL, 14.9 mmol) and DMAP (145 mg, 1.19 mmol) were added. After 10 minutes stirring, benzene-1,3,5-triyltrimethanol (1.0 g, 6.0 mmol) was added and the resulting mixture stirred at room temperature for 3 days. The volatiles were removed under reduced pressure and the resulting crude material was purified on silica using heptanes/EtOAc as eluent, providing 1.36 g of the desired product.

Rf=0.12 (silica, 20% EtOAc in heptanes, cerium molybdate).

Intermediate 33b:

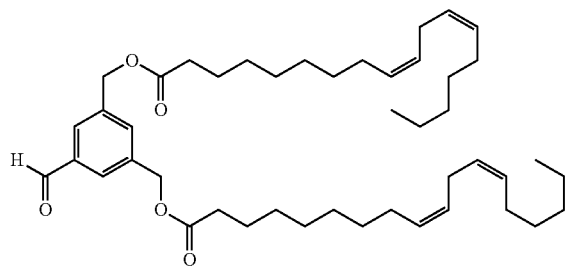 [SMILES: CCCCC/C=C\C/C=C\CCCCCCCC(=O)OCc1cc(C=O)cc(COC(=O)CCCCCCC/C=C\C/C=C\CCCCC)c1]

Intermediate 33a (214 mg, 0.309 mmol) was stirred in DCM (30 mL) and PDC (244 mg, 0.648 mmol) was added. The reaction was stirred at room temperature overnight. The volatiles were removed under reduced pressure and the resulting crude material was purified on silica using heptanes/EtOAc as eluent, providing 210 mg of the desired product.

Rf=0.44 (silica, 20% EtOAc in heptanes, cerium molybdate).

Example 33 Compound

Example 33

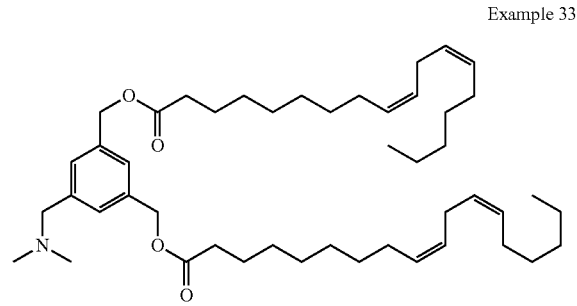 [SMILES: CCCCC/C=C\C/C=C\CCCCCCCC(=O)OCc1cc(COC(=O)CCCCCCC/C=C\C/C=C\CCCCC)cc(CN(C)C)c1]

Intermediate 33b (210 mg, 0.30 mmol) was stirred in DCE (10 mL) and dimethylamine (0.53 mL, 2.0 M in THF, 1.06 mmol) was added. Acetic acid (0.017 mL, 0.304 mmol) and sodium triacetoxyborohydride (129 mg, 0.608 mmol) were added and the material was stirred at room temperature overnight. The volatiles were removed under reduced pressure and the resulting crude material was purified on silica using heptanes/EtOAc followed by DCM/MeOH as eluent, providing 186 mg of the desired product.

$^1$H NMR (400 MHz, CDCl$_3$) δ 7.29-7.25 (m, 2H), 7.25-7.22 (m, 1H), 5.44-5.27 (m, 8H), 5.10 (s, 4H), 3.44 (s, 2H), 2.81-2.74 (m, 4H), 2.36 (t, J=7.5 Hz, 4H), 2.25 (s, 6H), 2.10-2.01 (m, 8H), 1.70-1.58 (m, 4H), 1.42-1.21 (m, 28H), 0.89 (t, J=6.9 Hz, 6H) ppm. ES-MS m/z=721.1 (MH+).

Examples 34-36 were prepared using methods similar to those employed for the preparation of Example 33.

Example 34

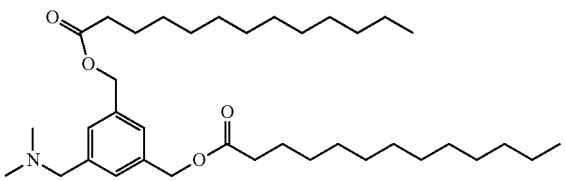 [SMILES: CCCCCCCCCCCCC(=O)OCc1cc(COC(=O)CCCCCCCCCCCC)cc(CN(C)C)c1]

$^1$H NMR (400 MHz, CDCl$_3$) δ 7.21 (s, 2H); 7.18 (s, 1H), 5.03 (s, 4H); 3.42 (br s, 2H); 2.28 (t, J=7.5 Hz, 4H); 2.22 (s, 6H); 1.61-1.53 (m, 4H); 1.27-1.15 (m, 36H); 0.81 (t, J=6.8 Hz, 6H) ppm.

ES-MS m/z=588.5 (MH+).

Example 35

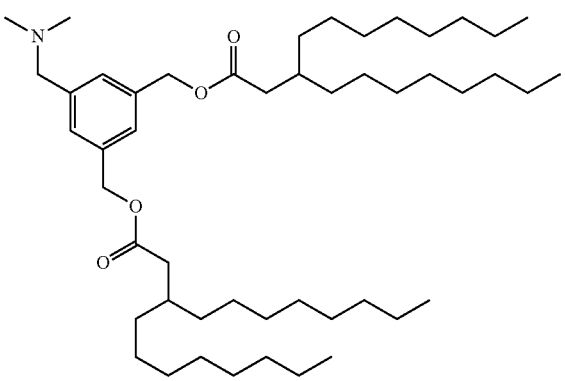 [SMILES: CCCCCCCCC(CCCCCCCC)CC(=O)OCc1cc(COC(=O)CC(CCCCCCCC)CCCCCCCC)cc(CN(C)C)c1]

$^1$H NMR (400 MHz, CDCl$_3$) δ 7.26 (s, 2H), 7.24 (s, 1H), 5.10 (s, 4H), 3.43 (s, 2H), 2.29 (d, J=7.4 Hz, 2H), 2.25 (s, 6H), 1.87 (m, 2H), 1.31-1.25 (m, 58H), 0.91-0.87 (m, 12H) ppm. ES-MS m/z=756.6 (MH+).

Example 36

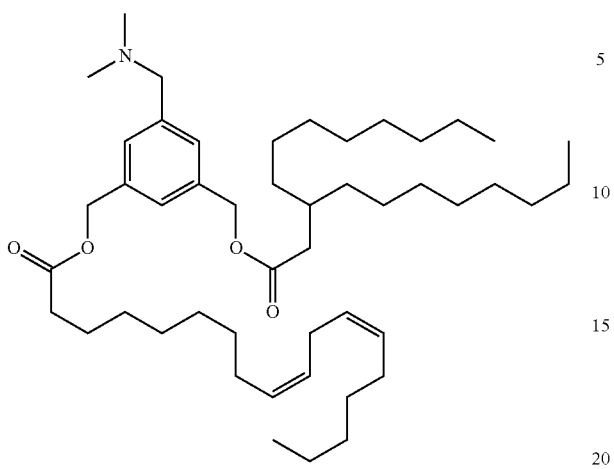

$^1$H NMR (400 MHz, CDCl$_3$) δ 7.28-7.25 (m, 2H), 7.25-7.22 (m, 1H), 5.44-5.29 (m, 4H), 5.10 (s, 4H), 3.43 (s, 2H), 2.83-2.73 (m, 2H), 2.36 (t, J=7.5 Hz, 2H), 2.29 (d, J=6.8 Hz, 2H), 2.25 (s, 6H), 2.10-2.00 (m, 4H), 1.92-1.80 (m, 1H), 1.71-1.57 (m, 2H), 1.43-1.17 (m, 42H), 0.94-0.83 (m, 9H) ppm.
ES-MS m/z=736.6 (MH+).

Synthesis of Example 37

Intermediate 37a:

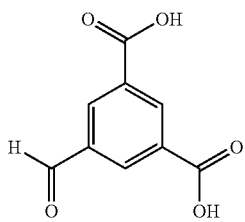

To a solution of 3-formyl-5-(methoxycarbonyl)benzoic acid (1 g, 4.80 mmol) in THF (25 mL) was added LiOH (12.01 ml, 24.02 mmol) and stirred at room temp for 16 h. Partial hydrolysis was observed. Reaction was heated to 50° C. for additional 16 h. The reaction was diluted with EtOAc (50 mL) and water (50 mL) and the pH adjusted to neutral with 1 N HCl. The organic layer was collected, washed with water (2×50 mL) and dried over sodium sulfate. The volatiles were removed under reduced pressure and the resulting material was used without further purification.

Intermediate 37b:

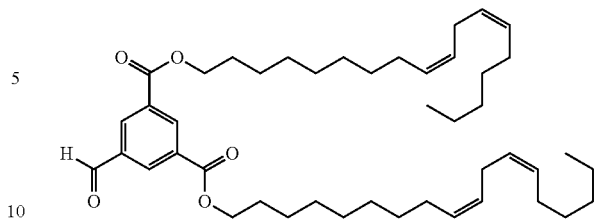

Intermediate 37a (700 mg, 0.36 mmol) was stirred in DCM (15 mL) and oxalylchloride (3.16 mL, 36 mmol) was added along with a drop of DMF. The resulting mixture was stirred overnight at room temperature. The volatiles were removed under reduced pressure and the resulting residue was redissolved in THF (10 mL). Linoleyl alcohol (2.02 g, 7.57 mmol) was added followed by TEA (2.51 mL, 18.0 mmol) and the resulting mixture was stirred in an ice bath for 3 h. The reaction was diluted with EtOAc (50 mL) and water (50 mL). The organic layer was collected, washed with water (2×50 mL) and dried over sodium sulfate. The volatiles were removed under reduced pressure and the resulting crude material was purified on silica using heptanes/EtOAc as eluent, providing 350 mg of the desired product.
ES-MS m/z=692.4 (MH+).

Intermediate 37c:

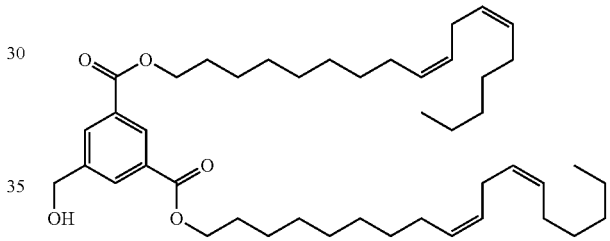

To a solution of Intermediate 37b (250 mg, 0.36 mmol) in THF (30 mL) and EtOH (15 mL) was added sodium borohydride (17.8 mg, 0.47 mmol). The reaction was stirred for 30 min at room temperature and then diluted with EtOAc (50 mL) and water (50 mL). The organic layer was collected, washed with water (2×50 mL) and dried over sodium sulfate. The volatiles were removed under reduced pressure and the resulting crude material was purified on silica using heptanes/EtOAc as eluent, providing 260 mg of the desired product.
ES-MS m/z=694.3 (MH+).

Example 37 Compound

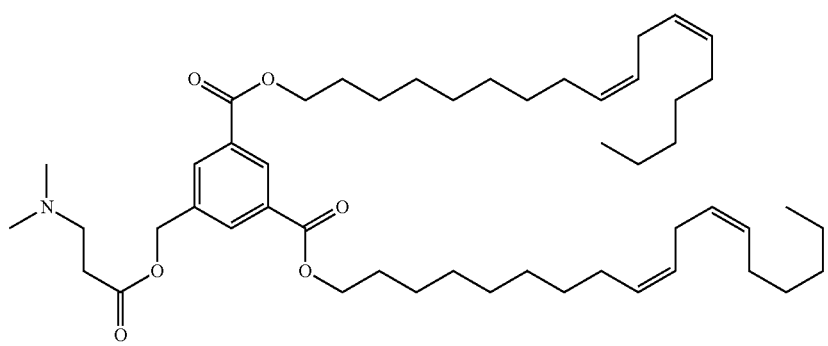

Example 37

To a solution of 3-dimethylaminopropionic acid (25 mg, 0.16 mmol) in DCM (3 mL) was added EDC (31 mg, 0.16 mmol) and DMAP (1.32 mg, 0.011 mmol) followed by TEA (0.06 mL, 0.43 mmol). The resulting solution was stirred for 30 min at room temperature and Intermediate 37c (75 mg, 0.11 mmol) was added. The reaction was stirred for 16 h and then diluted with DCM (20 mL) and water (20 mL). The organic layer was collected and washed with water (2×20 mL) and then dried over magnesium sulfate. The volatiles were removed under reduced pressure and the resulting crude material was purified on silica using heptanes/EtOAc as eluent, providing 41 mg of the desired product.

$^1$H NMR (400 MHz, CDCl$_3$) δ 8.63 (t, J=1.6 Hz, 1H), 8.20 (d, J=1.8 Hz, 2H), 5.47-5.26 (m, 8H), 5.22 (s, 2H), 4.35 (t, J=6.8 Hz, 4H), 2.89-2.74 (m, 6H), 2.74-2.65 (m, J=7.0 Hz, 2H), 2.39 (s, 6H), 2.12-1.95 (m, 8H), 1.87-1.71 (m, 4H), 1.49-1.19 (m, 33H), 0.89 (t, J=7.0 Hz, 6H) ppm.

ES-MS m/z=792.4 (MH+).

Synthesis of Example 38

Intermediate 38a:

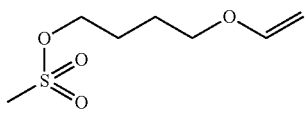

A solution of 4-(vinyloxy)butan-1-ol (50 g, 430 mmol) in DCM (430 mL) was cooled in an ice bath. To this solution was added TEA (90 mL, 646 mmol) followed by dropwise addition of methanesulfonyl chloride (36.9 ml, 473 mmol). During the second half of addition a white precipitate formed, and as addition was completed the reaction turned pale orange. The reaction was stirred overnight, allowing the ice to melt and the reaction to come to ambient temperature. The reaction was poured into a separatory funnel and diluted with 400 mL saturated sodium bicarbonate (aq) and 400 mL EtOAc. The layers were separated and the aqueous layer was extracted with 300 mL EtOAc two more times. The EtOAc layers were washed with 200 mL saturated sodium bicarbonate followed by water, and the EtOAc layer was then dried over sodium sulfate, and filtered. The filtrate was concentrated under reduced pressure to provide 84 g, (100%) of the desired product.

$^1$H NMR (400 MHz, CDCl$_3$) δ 6.47 (dd, J=6.8, 14.3 Hz, 1H), 4.29 (t, J=6.3 Hz, 2H), 4.19 (dd, J=2.0, 14.3 Hz, 1H), 4.02 (dd, J=2.0, 6.8 Hz, 1H), 3.74 (t, J=5.9 Hz, 2H), 3.03 (s, 3H), 1.96-1.85 (m, 2H), 1.86-1.73 (m, 2H) ppm.

Intermediate 38b:

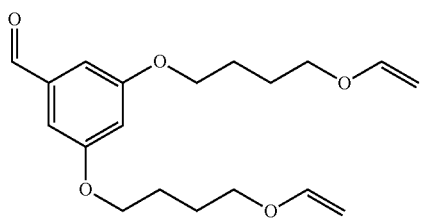 [SMILES: C=COCCCCOc1cc(C=O)cc(OCCCCOC=C)c1]

Intermediate 38a (84 g, 435 mmol) was stirred in DMF (400 mL) and 3,5-dihydroxybenzaldehyde (27.3 g, 198 mmol) was added followed by potassium carbonate (109 mg, 791 mmol). The reaction was heated to 80 deg C. overnight. After cooling to room temperature, the reaction was diluted with EtOAc (600 mL) and water (700 mL). The organic layer was collected and the aqueous layer was extracted again with EtOAc (300 mL). The organic layers were combined and washed with water (4×300 mL), dried over sodium sulfate, and then the volatiles were removed under reduced pressure. The resulting crude material was purified on silica using heptanes/EtOAc as eluent, providing 56 g of the desired product.

ES-MS m/z=335.1 (MH+).

Intermediate 38c:

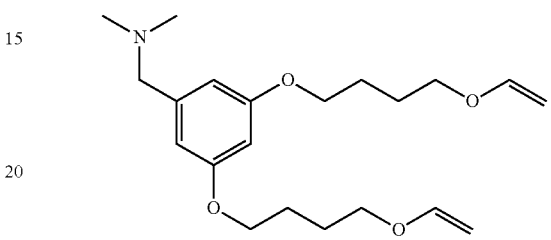

Intermediate 38b (37 g, 111 mmol) was stirred with dimethylamine (116 mL, 2 M in THF, 332 mmol) and acetic acid (6.33 mL, 111 mmol) in DCM (400 mL). To this mixture was added sodium triacetoxyborohydride (58.6 g, 277 mmol) and the reaction was stirred at room temperature overnight. To the reaction was added saturated sodium bicarbonate (800 mL) and EtOAc (1000 mL). The organic phase was collected and the aqueous phase was extracted with EtOAc (500 mL). The combined organic phases were dried over sodium sulfate and the volatiles removed under reduced pressure. The resulting crude material was purified on silica using heptanes/EtOAc as eluent, providing 34 g of the desired product.

ES-MS m/z=364.9 (MH+).

Intermediate 38d:

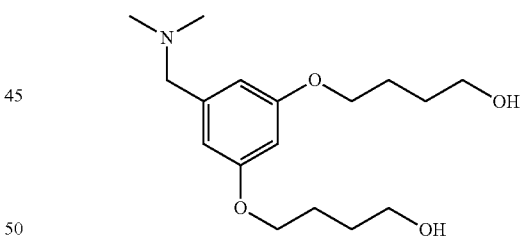

To a solution of Intermediate 38c (42 g, 116 mmol) in EtOAc (200 mL) was added HCl (87 mL, 4 M in dioxane, 348 mmol). Once the reaction was complete, as monitored by TLC, saturated aqueous sodium bicarbonate (500 mL) was added and the pH was adjusted to 10 by the addition of solid potassium carbonate. EtOAc (600 mL) was added and the organic layer was collected. The aqueous layer was extracted with EtOAc (3×500 mL) and the combined organic layers were dried over sodium sulfate. The volatiles were removed under reduced pressure to provide 35 g of material that was used without further purification.

$^1$H NMR (400 MHz, CDCl$_3$) δ 6.50 (d, J=2.3 Hz, 2H), 6.37 (t, J=2.3 Hz, 1H), 4.01 (t, J=6.1 Hz, 4H), 3.79-3.68 (m, 6H), 3.36 (s, 2H), 2.26 (s, 6H), 1.93-1.82 (m, 4H), 1.82-1.67 (m, 4H) ppm.

Example 38 Compound

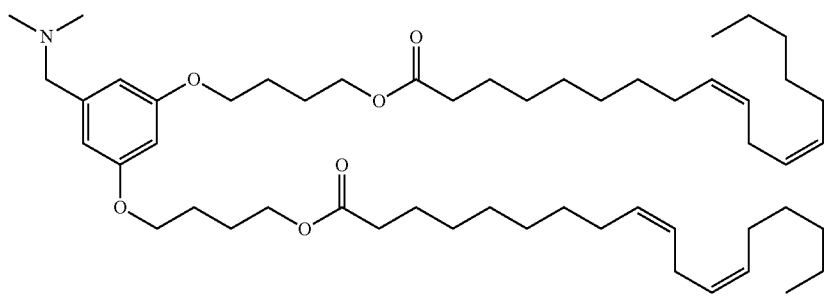

Example 38

To a solution of Intermediate 36 (10 g, 32 mmol) in DCM (161 mL) was added DMAP (392 mg, 3.21 mmol), DIEA (16.8 mL, 96 mmol) and linoleic acid (18.9 g, 67.4 mmol). EDC (14.8 g, 77 mmol) was added and the material was allowed to stir at room temperature overnight. Saturated aqueous sodium bicarbonate (500 mL) was added and the resulting mixture was extracted with EtOAc (3×600 mL). The combined organic layers were dried over sodium sulfate and then the volatiles removed under reduced pressure. The resulting crude material was purified on silica using heptanes/EtOAc as an eluent to provide 18.6 g of the desired material.

$^1$H NMR (400 MHz, CDCl$_3$) δ 6.50 (br s, 2H), 6.36 (br s, 1H), 5.28-5.45 (m, 8H), 4.14 (t, J=6.05 Hz, 4H), 3.98 (t, J=5.70 Hz, 4H), 3.39 (br s, 2H), 2.78 (t, J=6.55 Hz, 4H), 2.16-2.41 (m, 10H), 1.98-2.12 (m, 8H), 1.77-1.90 (m, 8H), 1.52-1.71 (m, 4H), 1.20-1.43 (m, 28H), 0.90 (t, J=6.85 Hz, 6H) ppm.

ES-MS m/z=836.7 (MH+).

Synthesis of Example 39

Intermediate 39a:

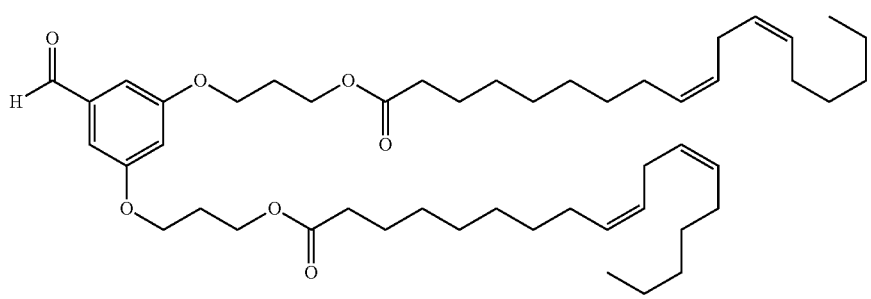 [SMILES: CCCCC/C=C\C/C=C\CCCCCCCC(=O)OCCCOc1cc(C=O)cc(OCCCOC(=O)CCCCCCC/C=C\C/C=C\CCCCC)c1]

This material was prepared in a manner similar to the preparation of Intermediate 18b using linoleic acid and 1,3-propanediol as starting materials.

Rf=0.74 (silica, 40% EtOAc in Heptane, UV and cerium molybdate).

Example 39 Compound

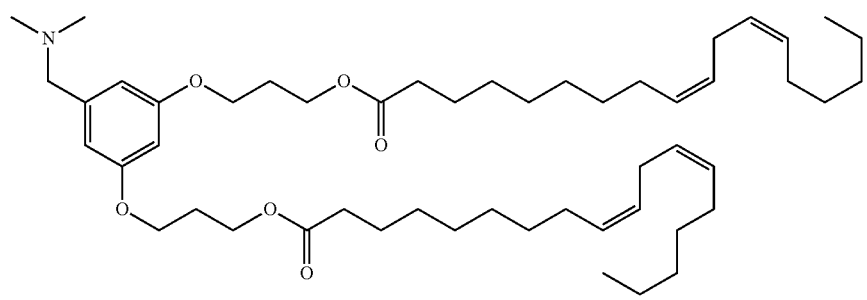

Example 39

To a solution of Intermediate 39a (2.42 g, 3.11 mmol) in DCE (20 mL) was added dimethylamine (3.25 mL, 2.0 M in THF, 6.5 mmol) and acetic acid (0.18 mL, 3.1 mmol) followed by sodium triacetoxyborohydride (1.32 g, 6.21 mmol). The reaction was stirred at room temperature overnight and then saturated aqueous sodium bicarbonate was added followed by DCM. The organic layer was collected and then washed with additional saturated aqueous sodium bicarbonate. The resulting aqueous layer was back extracted with DCM and the organic layers combined and dried over sodium sulfate. The volatiles removed under reduced pressure. The resulting crude material was purified on silica using heptanes/EtOAc followed by DCM/MeOH as an eluent to provide 1.4 g of the desired material.

$^1$H NMR (400 MHz, CDCl$_3$) δ 0.89 (t, J=8.00 Hz, 6H) 1.21-1.43 (m, 28H) 1.55-1.71 (m, 4H) 1.98-2.14 (m, 12H) 2.25 (s, 6H) 2.30 (t, J=7.65 Hz, 4H) 2.77 (t, J=8.00 Hz, 4H) 3.35 (s, 2H) 4.02 (t, J=6.15 Hz, 4H) 4.25 (t, J=6.40 Hz, 4H) 5.24-5.52 (m, 8H) 6.35 (t, J=2.26 Hz, 1H) 6.48 (d, J=2.26 Hz, 2H) ppm.

ES-MS m/z=809.2 (MH+).

Examples 40-64 were prepared using similar methods to those employed for the preparation of Example 39.

Example 40

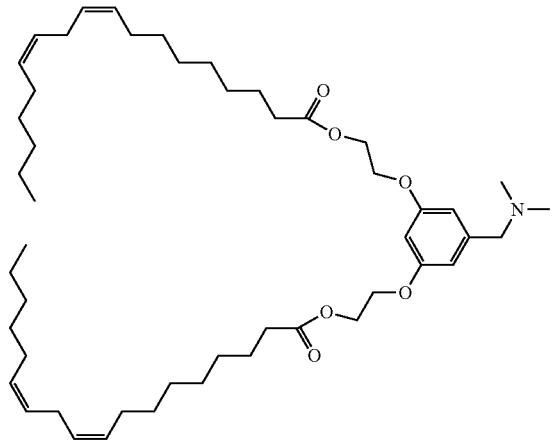 [SMILES: CCCCC/C=C\C/C=C\CCCCCCCC(=O)OCCOc1cc(CN(C)C)cc(OCCOC(=O)CCCCCCC/C=C\C/C=C\CCCCC)c1]

$^1$H NMR (400 MHz, CDCl$_3$) δ 0.88 (t, J=8.00 Hz, 6H) 1.22-1.42 (m, 28H) 1.56-1.71 (m, 4H) 1.98-2.10 (m, 8H) 2.23 (s, 6H) 2.34 (t, J=7.53 Hz, 4H) 2.76 (t, J=6.53 Hz, 4H) 3.34 (s, 2H) 4.08-4.20 (m, 4H) 4.35-4.46 (m, 4H) 5.26-5.44 (m, 8H) 6.38 (t, J=2.26 Hz, 1H) 6.51 (d, J=2.26 Hz, 2H) ppm.

ES-MS m/z=781.3 (MH+).

Example 41

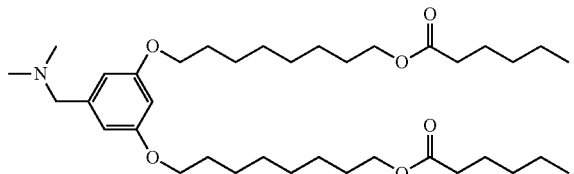

$^1$H NMR (400 MHz, CDCl$_3$) δ 0.90 (t, J=8.00 Hz, 6H) 1.29-1.52 (m, 24H) 1.63 (quin, J=7.45 Hz, 8H) 1.71-1.82 (m, 4H) 2.26 (s, 6H) 2.30 (t, J=7.58 Hz, 4H) 3.37 (s, 2H) 3.93 (t, J=6.57 Hz, 4H) 4.06 (t, J=6.69 Hz, 4H) 6.35 (t, J=2.27 Hz, 1H) 6.47 (d, J=2.27 Hz, 3H) ppm.

ES-MS m/z=620.2 (MH+).

Example 42

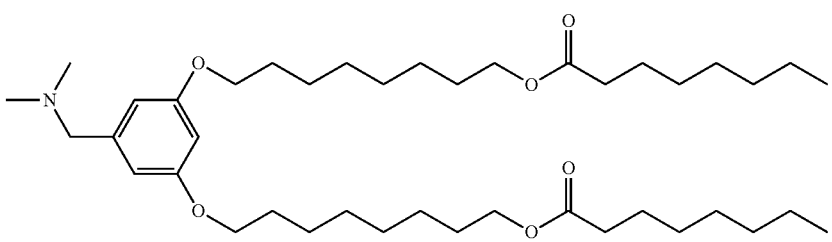 [SMILES: CCCCCCCC(=O)OCCCCCCCCOc1cc(CN(C)C)cc(OCCCCCCCCOC(=O)CCCCCCC)c1]

¹H NMR (400 MHz, CDCl₃) δ 0.88 (t, J=8.00 Hz, 6H) 1.19-1.50 (m, 32H) 1.55-1.68 (m, 8H) 1.71-1.85 (m, 4H) 2.21-2.39 (m, 10H) 3.40 (br. s., 2H) 3.94 (t, J=6.44 Hz, 4H) 4.07 (t, J=6.69 Hz, 4H) 6.36 (t, J=2.27 Hz, 1H) 6.49 (d, J=2.02 Hz, 2H) ppm.
ES-MS m/z=676.6 (MH+).
Example 43
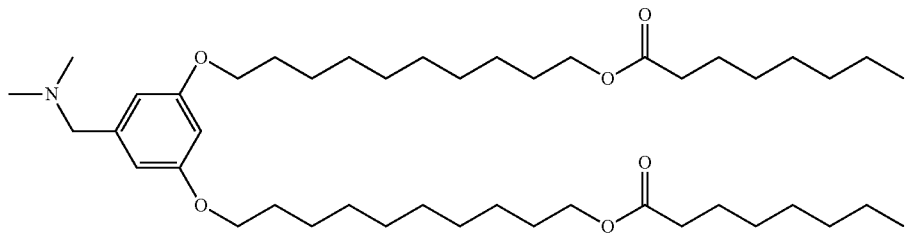 [SMILES: CCCCCCCC(=O)OCCCCCCCCCCOc1cc(CN(C)C)cc(OCCCCCCCCCCOC(=O)CCCCCCC)c1]
¹H NMR (400 MHz, CDCl₃) δ 0.88 (t, J=8.00 Hz, 6H) 1.21-1.50 (m, 40H) 1.62 (quin, J=6.95 Hz, 8H) 1.70-1.82 (m, 4H) 2.25 (s, 6H) 2.29 (t, J=7.58 Hz, 4H) 3.35 (s, 2H) 3.93 (t, J=6.57 Hz, 4H) 4.06 (t, J=6.82 Hz, 4H) 6.35 (t, J=2.27 Hz, 1H) 6.46 (d, J=2.27 Hz, 2H) ppm.
ES-MS m/z=732.1 (MH+).
Example 44
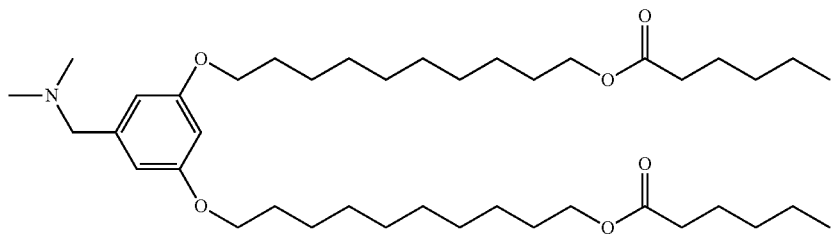 [SMILES: CCCCCC(=O)OCCCCCCCCCCOc1cc(CN(C)C)cc(OCCCCCCCCCCOC(=O)CCCCC)c1]
¹H NMR (400 MHz, CDCl₃) δ 0.89 (t, J=8.00 Hz, 6H) 1.23-1.51 (m, 32H) 1.57-1.69 (m, 8H) 1.70-1.82 (m, 4H) 2.24-2.39 (m, 10H) 3.43 (br. s., 2H) 3.94 (t, J=6.57 Hz, 4H) 4.06 (t, J=6.69 Hz, 4H) 6.37 (t, J=2.15 Hz, 1H) 6.50 (d, J=1.52 Hz, 2H) ppm.
ES-MS m/z=676.6 (MH+).
Example 45
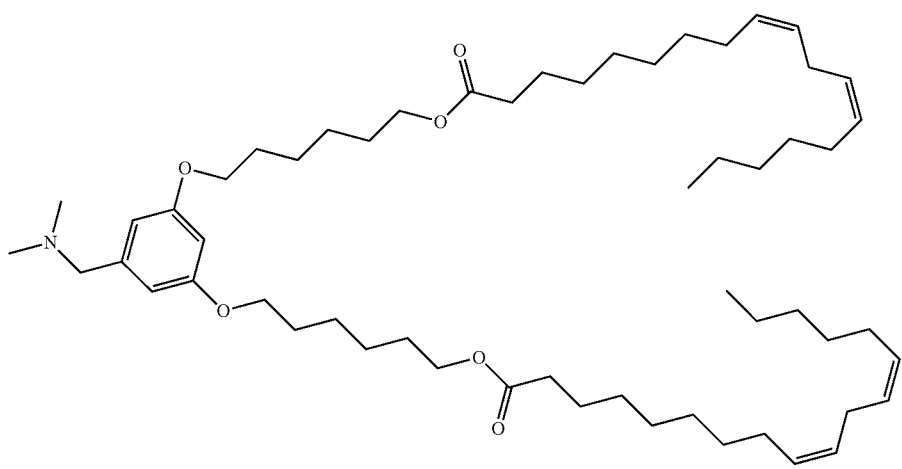 [SMILES: CCCCC/C=C\C/C=C\CCCCCCCC(=O)OCCCCCCOc1cc(CN(C)C)cc(OCCCCCCOC(=O)CCCCCCC/C=C\C/C=C\CCCCC)c1]

$^1$H NMR (400 MHz, CDCl$_3$) δ 0.90 (t, J=8.00 Hz, 6H) 1.23-1.52 (m, 36H) 1.65 (dt, J=14.59, 7.48 Hz, 8H) 1.73-1.83 (m, 4H) 1.99-2.11 (m, 8H) 2.24 (s, 6H) 2.30 (t, J=7.58 Hz, 4H) 2.78 (t, J=6.57 Hz, 4H) 3.39 (br. s., 2H) 3.94 (t, J=6.44 Hz, 4H) 4.08 (t, J=6.69 Hz, 4H) 5.25-5.49 (m, 8H) 6.35 (t, J=2.27 Hz, 1H) 6.46 (d, J=2.27 Hz, 2H) ppm.
ES-MS m/z=893.8 (MH+).
Example 46
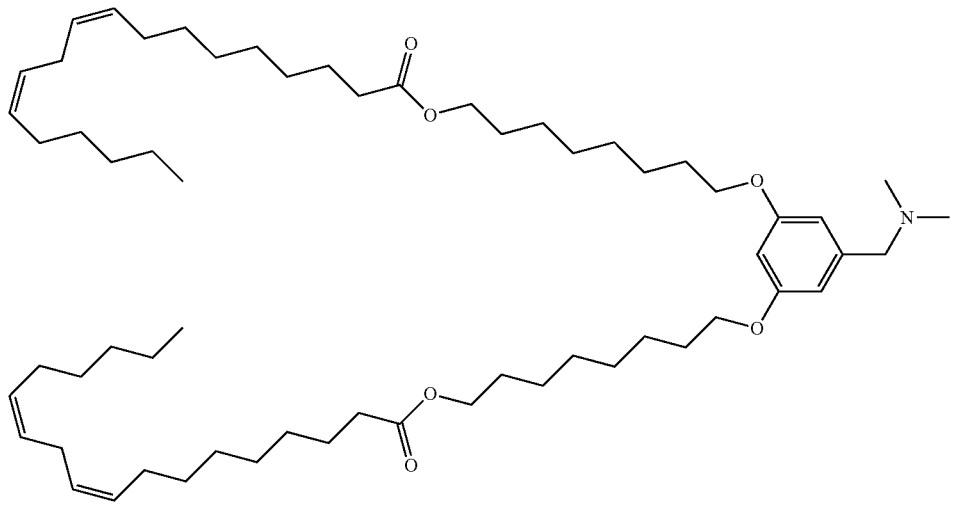 [SMILES: CCCCC/C=C\C/C=C\CCCCCCCC(=O)OCCCCCCCCOc1cc(CN(C)C)cc(OCCCCCCCCOC(=O)CCCCCCC/C=C\C/C=C\CCCCC)c1]
$^1$H NMR (400 MHz, CDCl$_3$) δ 0.89 (t, J=8.00 Hz, 6H) 1.23-1.51 (m, 44H) 1.55-1.69 (m, 8H) 1.71-1.82 (m, 4H) 1.99-2.11 (m, 8H) 2.24 (s, 6H) 2.30 (t, J=7.58 Hz, 4H) 2.78 (t, J=6.57 Hz, 4H) 3.35 (s, 2H) 3.93 (t, J=6.57 Hz, 4H) 4.07 (t, J=6.69 Hz, 4H) 5.28-5.45 (m, 8H) 6.35 (t, J=2.27 Hz, 1H) 6.46 (d, J=2.27 Hz, 2H) ppm.
ES-MS m/z=948.8 (MH+).
Example 47
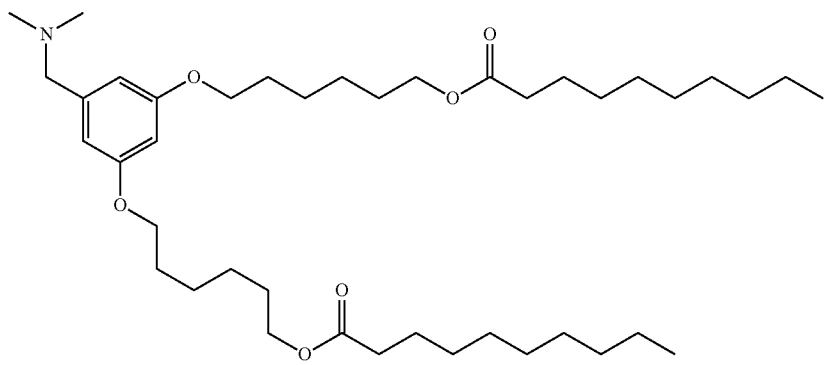 [SMILES: CCCCCCCCCC(=O)OCCCCCCOc1cc(CN(C)C)cc(OCCCCCCOC(=O)CCCCCCCCC)c1]
$^1$H NMR (400 MHz, CDCl$_3$) δ 6.49-6.43 (m, 2H), 6.37-6.32 (m, 1H), 4.07 (t, J=6.6 Hz, 4H), 3.93 (t, J=6.4 Hz, 4H), 3.35 (s, 2H), 2.29 (t, J=7.6 Hz, 4H), 2.25 (s, 6H), 1.84-1.72 (m, 4H), 1.72-1.55 (m, 8H), 1.55-1.36 (m, 8H), 1.36-1.16 (m, 24H), 0.88 (t, J=6.8 Hz, 6H) ppm.
ES-MS m/z=676.4 (MH+).

Example 48
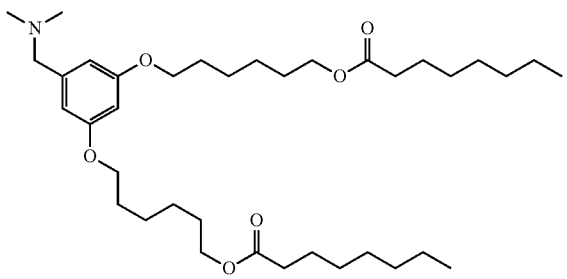 [SMILES: CCCCCCCC(=O)OCCCCCCOc1cc(CN(C)C)cc(OCCCCCCOC(=O)CCCCCCC)c1]
¹H NMR (400 MHz, CDCl₃) δ: 6.65-6.58 (m, 2H), 6.44-6.39 (m, 1H), 4.07 (t, J=6.6 Hz, 4H), 3.96 (t J=6.3 Hz, 4H), 3.72 (s, 2H), 2.52 (s, 6H), 2.29 (t, J=7.5 Hz, 4H), 1.84-1.73 (m, 4H), 1.72-1.56 (m, 8H), 1.55-1.36 (m, 8H), 1.36-1.18 (m, 16H), 0.91-0.84 (m, 6H) ppm.
ES-MS m/z=620.4 (MH+).
Example 49
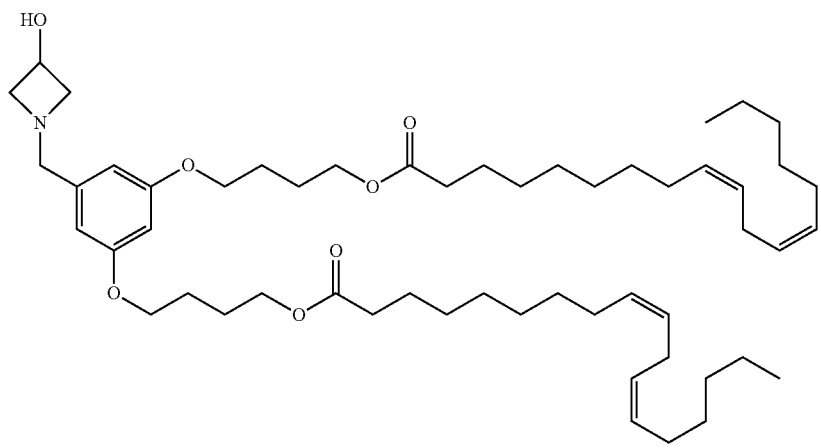 [SMILES: CCCCC/C=C\C/C=C\CCCCCCCC(=O)OCCCCOc1cc(CN2CC(O)C2)cc(OCCCCOC(=O)CCCCCCC/C=C\C/C=C\CCCCC)c1]
¹H NMR (400 MHz, CDCl₃) δ 6.45 (d, J=2.01 Hz, 2H) 6.35 (t, J=1.00 Hz 1H), 5.31-5.44 (m, 8H), 4.11-4.19 (m, 5H), 3.97 (t, J=1.00 Hz, 4H), 3.65-3.76 (m, 2H), 3.60 (s, 2H), 2.79 (t, J=1.00 Hz, 4H), 2.32 (t, J=7.53 Hz, 4H), 2.07 (q, J=6.78 Hz, 8H), 1.80-1.89 (m, 8H), 1.64 (d, J=16.81 Hz, 6H), 1.24-43 (m, 31H), 0.91 (t, J=1.00 Hz, 6H) ppm.
ES-MS m/z=864.6 (MH+).
Example 50
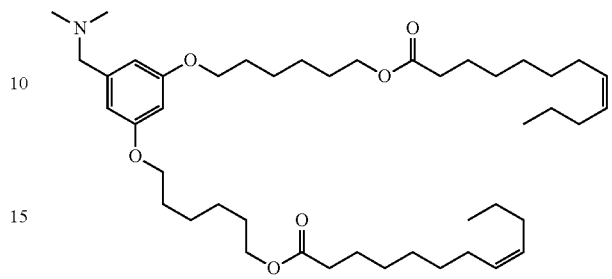
¹H NMR (400 MHz, CDCl₃) δ 6.48 (d, J=2.0 Hz, 2H), 6.35 (t, J=2.2 Hz, 1H), 5.43-5.25 (m, 4H), 4.08 (t, J=6.8 Hz, 4H), 3.94 (t, J=6.4 Hz, 4H), 3.38 (s, 2H), 2.30 (t, J=7.6 Hz, 4H), 2.27 (s, 6H), 2.07-1.90 (m, 8H), 1.85-1.70 (m, 4H), 1.71-1.55 (m, 8H), 1.55-1.29 (m, 24H), 0.90 (t, J=7.4 Hz, 6H) ppm.
ES-MS m/z=728.5 (MH+).
Example 51
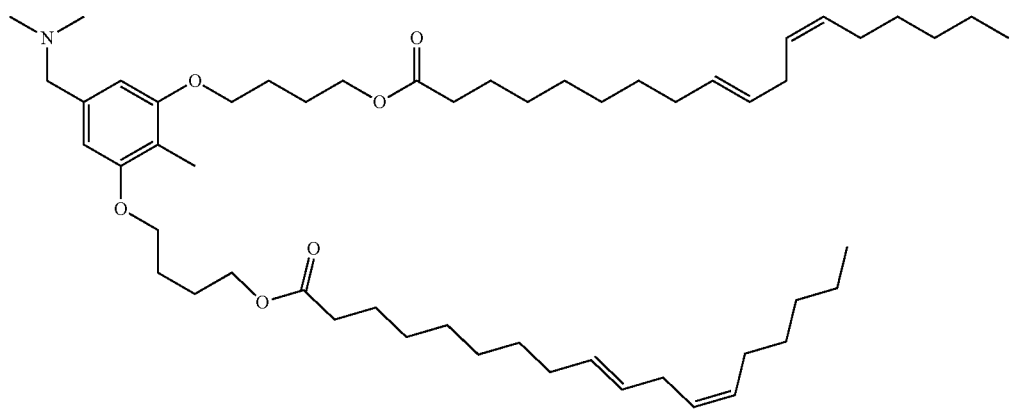 [SMILES: CCCCC/C=C\C/C=C/CCCCCCCC(=O)OCCCCOc1cc(CN(C)C)cc(OCCCCOC(=O)CCCCCCC/C=C/C/C=C\CCCCC)c1C]

¹H NMR (400 MHz, CDCl₃) δ 6.48 (s, 2H), 5.32-5.44 (m, 8H), 4.17 (t, J=8 Hz, 4H), 4.01 (t, J=8 Hz, 4H), 3.37 (s, 2H), 2.79 (t, J=8 Hz, 4H), 2.32 (t, J=8 Hz, 4H), 2.25 (s, 6H), 2.10 (s, 3H), 2.08 (dd, J=8 Hz, 8H), 1.87 (q, J=5 Hz, 8H), 1.64 (m, 4H), 1.27-1.48 (m, 28H), 0.90 (t, J=8 Hz, 6H) ppm.
ES-MS m/z=851.5 (MH+).
Example 52
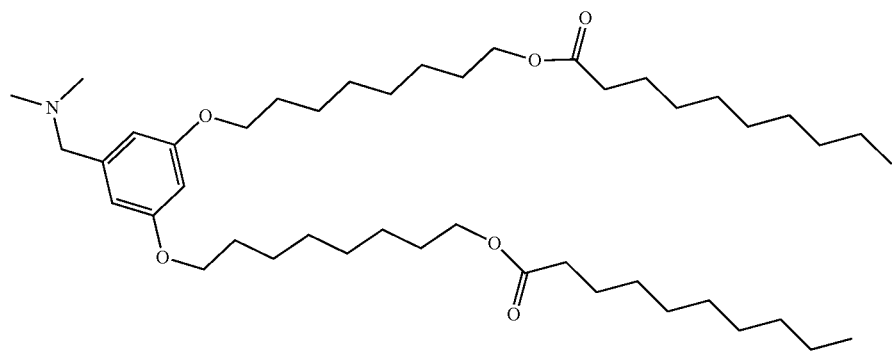 [SMILES: CCCCCCCCCC(=O)OCCCCCCCCOc1cc(CN(C)C)cc(OCCCCCCCCOC(=O)CCCCCCCCC)c1]
¹H NMR (400 MHz, CDCl₃) δ 0.88 (t, J=8.00 Hz, 6H) 1.18-1.50 (m, 40H) 1.56-1.70 (m, 8H) 1.70-1.81 (m, 4H) 2.24 (s, 6H) 2.30 (t, J=7.53 Hz, 4H) 3.34 (s, 2H) 3.93 (t, J=6.53 Hz, 4H) 4.06 (t, J=6.78 Hz, 4H) 6.35 (t, J=2.26 Hz, 1H) 6.46 (d, J=2.26 Hz, 2H) ppm.
ES-MS m/z=732.5 (MH+).
Example 53
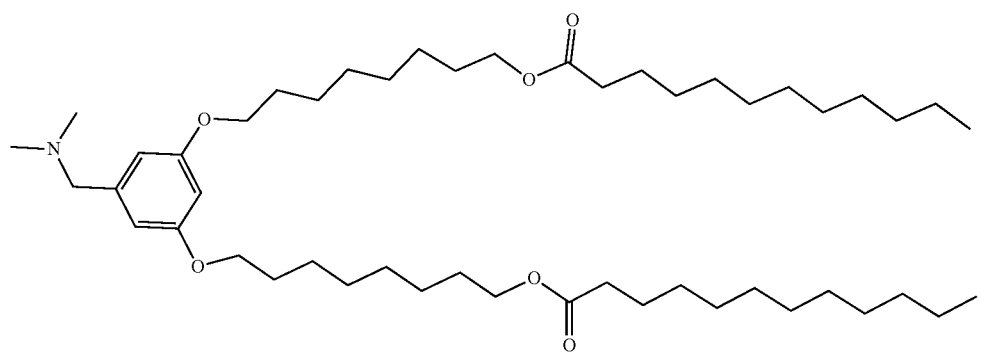 [SMILES: CCCCCCCCCCCC(=O)OCCCCCCCCOc1cc(CN(C)C)cc(OCCCCCCCCOC(=O)CCCCCCCCCCC)c1]
¹H NMR (400 MHz, CDCl₃) δ 0.83-0.97 (m, 6H) 1.19-1.51 (m, 48H) 1.56-1.68 (m, 8H) 1.71-1.83 (m, 4H) 2.24 (s, 6H) 2.30 (t, J=7.53 Hz, 4H) 3.34 (s, 2H) 3.93 (t, J=6.53 Hz, 4H) 4.06 (t, J=6.78 Hz, 4H) 6.35 (t, J=2.26 Hz, 1H) 6.46 (d, J=2.01 Hz, 2H) ppm.
ES-MS m/z=788.6 (MH+).

Example 54
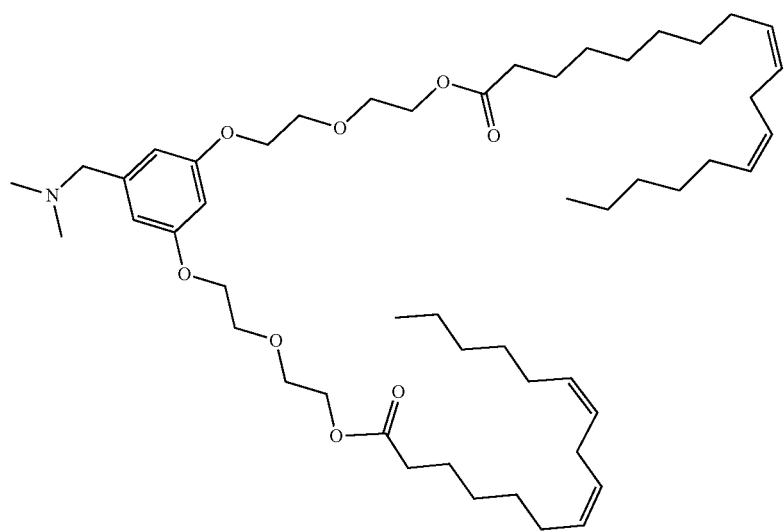 [SMILES: CCCCC/C=C\C/C=C\CCCCCCCC(=O)OCCOCCOc1cc(CN(C)C)cc(OCCOCCOC(=O)CCCCC/C=C\C/C=C\CCCCC)c1]
$^1$H NMR (400 MHz, CDCl$_3$) δ 6.59 (br s, 2H), 6.44 (br s, 1H), 5.27-5.44 (m, 8H), 4.26 (t, J=4.9 Hz, 4H), 4.13 (t, J=4.65 Hz, 4H), 3.85 (t, J=4.65 Hz, 4H), 3.77 (t, J=4.9 Hz, 4H), 3.50 (br s, 2H), 2.77 (t, J=6.65 Hz, 4H), 2.21-2.52 (m, 10H), 1.96-2.12 (m, 8H), 1.55-1.70 (m, 4H), 1.19-1.45 (m, 28H), 0.89 (t, J=6.90 Hz, 6H) ppm.
ES-MS m/z=869.8 (MH+).
Example 55
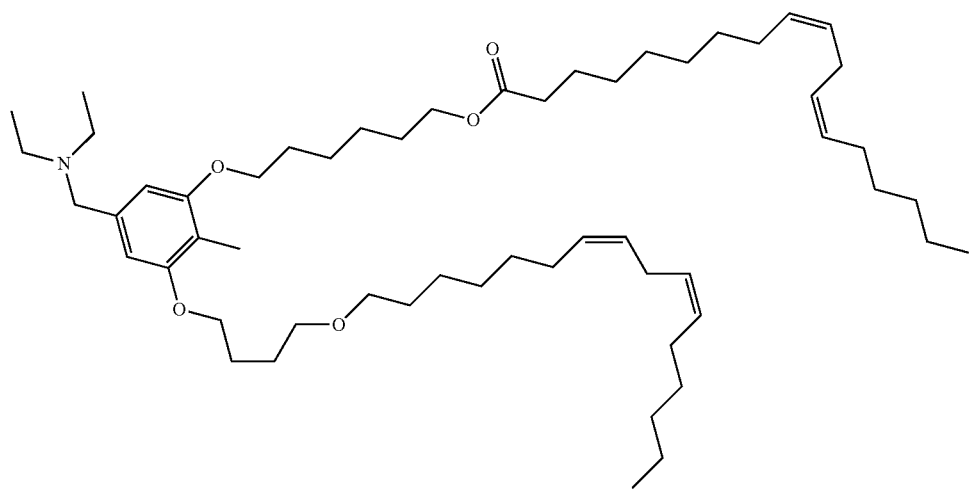 [SMILES: CCCCC/C=C\C/C=C\CCCCCCCC(=O)OCCCCCCOc1cc(CN(CC)CC)cc(OCCCCOCCCCCC/C=C\C/C=C\CCCCC)c1C]
$^1$H NMR (400 MHz, CDCl$_3$) δ 6.52 (s, 2H), 5.32-5.44 (m, 8H), 4.16 (t, J=8 Hz, 4H), 4.00 (t, J=8 Hz, 4H), 3.52 (s, 2H), 2.79 (t, J=8 Hz, 4H), 2.54 (dd, J=8 Hz, 4H), 2.32 (t, J=8 Hz, 4H), 2.09 (s, 3H), 2.08 (dd, J=8 Hz, 8H), 1.87 (q, J=5 Hz, 8H), 1.64 (m, 4H), 1.27-1.48 (m, 28H), 1.06 (t, J=8 Hz, 6H), 0.91 (t, J=8 Hz, 6H) ppm.
ES-MS m/z=878.6 (MH+).

Example 56

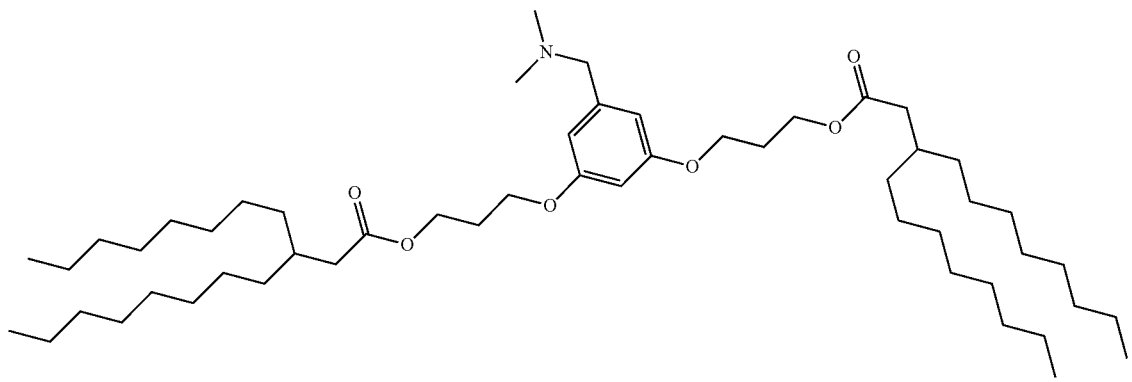 [SMILES: CCCCCCCCC(CCCCCCCC)CC(=O)OCCCOc1cc(CN(C)C)cc(OCCCOC(=O)CC(CCCCCCCC)CCCCCCCC)c1]

¹H NMR (400 MHz, CDCl₃) δ 6.48 (d, J=2.02 Hz, 2H) 6.35 (t, J=2.27 Hz, 1H) 4.25 (t, J=6.32 Hz, 4H) 4.03 (t, J=6.19 Hz, 4H) 3.35 (s, 2H) 2.20-2.30 (m, 10H) 2.10 (quin, J=6.25 Hz, 4H) 1.84 (br. s., 2H) 1.19-1.36 (m, 56H) 0.81-0.97 (m, 12H) ppm.
ES-MS m/z=845.7 (MH+).

¹H NMR (400 MHz, CDCl₃) δ 6.54 (d, J=2.3 Hz, 2H), 6.37 (t, J=2.25 Hz, 1H), 5.25-5.46 (m, 8H), 4.26 (t, J=4.8 Hz, 4H), 4.11 (t, J=4.75 Hz, 4H), 3.85 (t, J=4.75 Hz, 4H), 3.77 ((t, J=4.9 Hz, 4H), 3.48 (s, 2H), 2.77 (t, J=6.5 Hz, 4H), 2.50 (q, J=7.1 Hz, 4H), 2.34 (t, J=7.7 Hz, 4H), 1.98-2.13 (m, 8H), 1.55-1.70 (m, 4H), 1.22-1.42 (m, 28H), 1.03 (t, J=7.2 Hz, 6H), 0.89 (t, J=6.9 Hz, 6H) ppm.
ES-MS m/z=897.9 (MH+).

Example 57

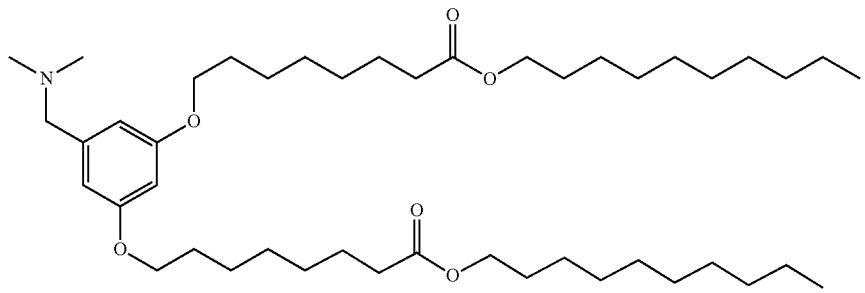 [SMILES: CCCCCCCCCCOC(=O)CCCCCCCOc1cc(CN(C)C)cc(OCCCCCCCC(=O)OCCCCCCCCCC)c1]

¹H NMR (400 MHz, CDCl₃) δ 6.51-6.45 (m, 2H), 6.38-6.33 (m, 1H), 4.06 (t, J=6.8 Hz, 4H), 3.93 (t, J=6.5 Hz, 4H), 3.40 (s, 2H), 2.30 (t, J=7.5 Hz, 4H), 2.28 (s, 6H), 1.82-1.71 (m, 4H), 1.70-1.56 (m, 8H), 1.54-1.20 (m, 40H), 0.93-0.84 (m, 6H) ppm.
ES-MS m/z=732.4 (MH+).

Example 58

Example 59

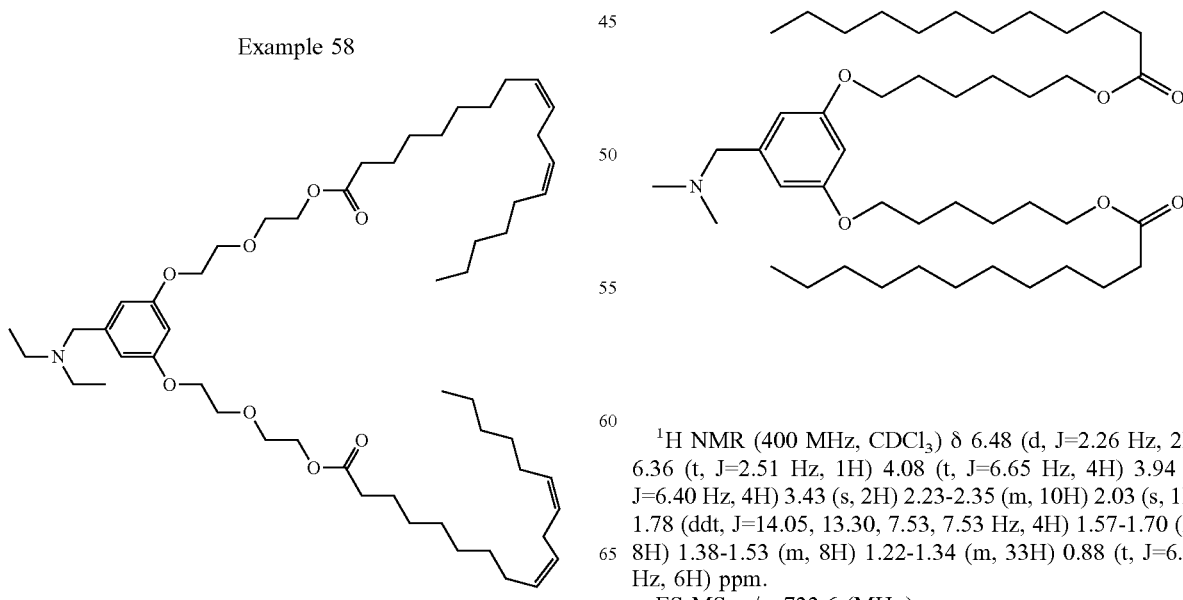

¹H NMR (400 MHz, CDCl₃) δ 6.48 (d, J=2.26 Hz, 2H) 6.36 (t, J=2.51 Hz, 1H) 4.08 (t, J=6.65 Hz, 4H) 3.94 (t, J=6.40 Hz, 4H) 3.43 (s, 2H) 2.23-2.35 (m, 10H) 2.03 (s, 1H) 1.78 (ddt, J=14.05, 13.30, 7.53, 7.53 Hz, 4H) 1.57-1.70 (m, 8H) 1.38-1.53 (m, 8H) 1.22-1.34 (m, 33H) 0.88 (t, J=6.02 Hz, 6H) ppm.
ES-MS m/z=733.6 (MH+).

Example 60
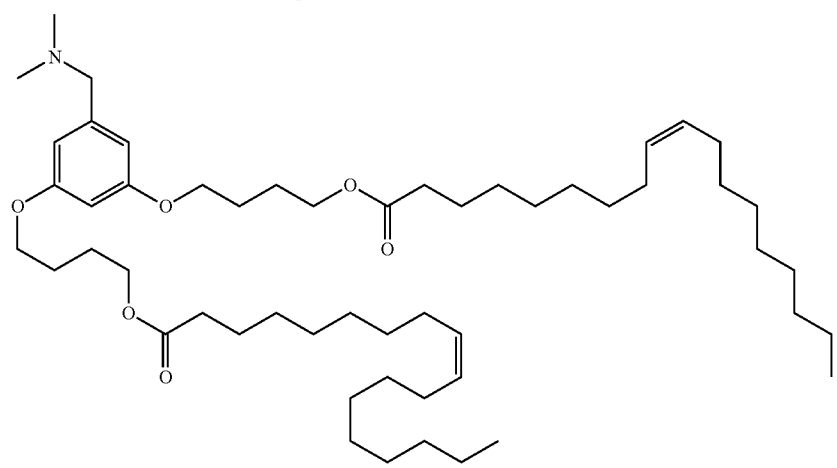 [SMILES: CCCCCCCC/C=C\CCCCCCCC(=O)OCCCCOc1cc(CN(C)C)cc(OCCCCOC(=O)CCCCCCC/C=C\CCCCCCCC)c1]
$^1$H NMR (400 MHz, CDCl$_3$) δ 6.49 (br. s., 2H), 6.36 (t, J=2.0 Hz, 1H), 5.44-5.28 (m, 4H), 4.15 (t, J=5.8 Hz, 4H), 3.98 (t, J=5.8 Hz, 4H), 3.36 (br. s., 2H), 2.38-2.18 (m, 10H), 2.10-1.95 (m, 8H), 1.92-1.76 (m, 8H), 1.71-1.56 (m, J=7.3, 7.3 Hz, 4H), 1.30 (d, J=15.6 Hz, 40H), 0.90 (t, J=6.5 Hz, 6H) ppm.
ES-MS m/z=840.7 (MH+).
Example 61
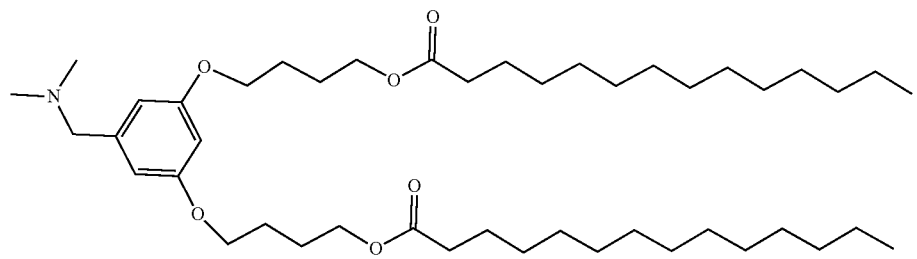
$^1$H NMR (400 MHz, CDCl$_3$) δ 6.54 (br s, 2H) 6.37 (br s, 1H) 4.14 (t, J=6.30 Hz, 4H) 3.98 (t, J=5.65 Hz, 4H) 3.48 (br s, 2H) 2.22-2.51 (m, 10H) 1.73-1.93 (m, 8H) 1.62 (m, 4H) 1.19-1.49 (m, 40H) 0.88 (t, J=6.9 Hz, 6H) ppm.
ES-MS m/z=732.7 (MH+).
Example 62
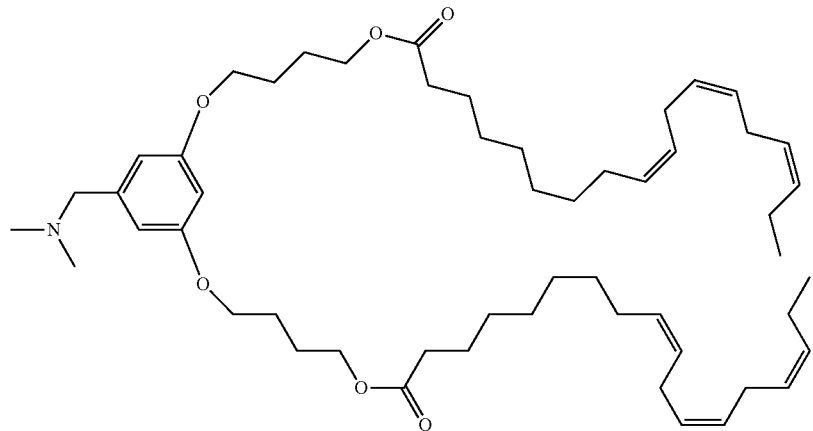 [SMILES: CC/C=C\C/C=C\C/C=C\CCCCCCCC(=O)OCCCCOc1cc(CN(C)C)cc(OCCCCOC(=O)CCCCCCC/C=C\C/C=C\C/C=C\CC)c1]

$^1$H NMR (400 MHz, CDCl$_3$) δ 6.51 (d, J=1.8 Hz, 2H), 6.36 (t, J=2.3 Hz, 1H), 5.55-5.18 (m, 12H), 4.15 (t, J=5.5 Hz, 4H), 3.98 (t, J=5.6 Hz, 4H), 3.41 (br. s., 2H), 2.82 (t, J=6.0 Hz, 8H), 2.39-2.22 (m, 10H), 2.17-2.00 (m, 8H), 1.92-1.74 (m, 9H), 1.71-1.55 (m, 4H), 1.45-1.22 (m, 16H), 0.99 (t, J=7.5 Hz, 6H) ppm.
ES-MS m/z=833.0 (MH+).

Example 63

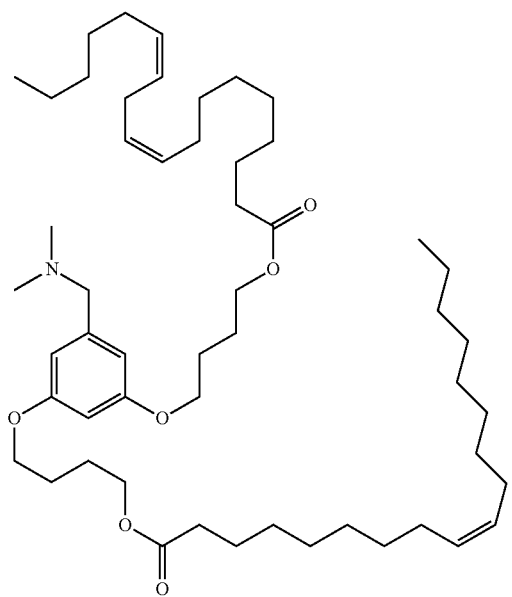 [SMILES: CCCCC/C=C\C/C=C\CCCCCCCC(=O)OCCCCOc1cc(CN(C)C)cc(OCCCCOC(=O)CCCCCCC/C=C\CCCCCCCC)c1]

$^1$H NMR (400 MHz, CDCl$_3$) δ 6.51 (s, 2H), 6.37 (t, J=2.0 Hz, 1H), 5.49-5.23 (m, 6H), 4.15 (t, J=6.5 Hz, 4H), 3.99 (t, J=5.6 Hz, 4H), 3.42 (br. s., 2H), 2.79 (t, J=6.7 Hz, 2H), 2.39-2.21 (m, 10H), 2.18-1.95 (m, 8H), 1.94-1.73 (m, 8H), 1.73-1.55 (m, 4H), 1.44-1.19 (m, 34H), 0.95-0.86 (m, J=4.0, 6.8, 6.8 Hz, 6H) ppm.
ES-MS m/z=838.7 (MH+).

Example 64

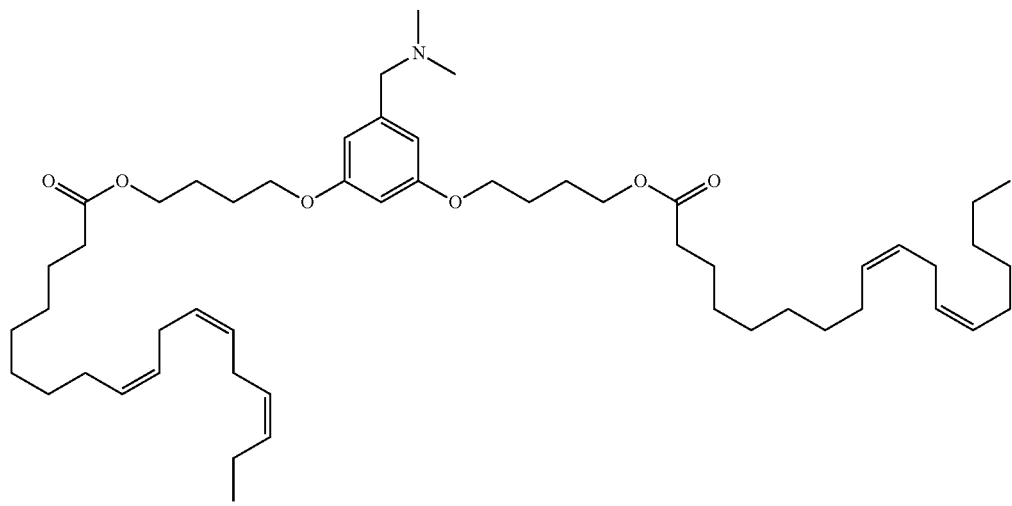 [SMILES: CC/C=C\C/C=C\C/C=C\CCCCCCCC(=O)OCCCCOc1cc(CN(C)C)cc(OCCCCOC(=O)CCCCCCC/C=C\C/C=C\CCCCC)c1]

$^1$H NMR (400 MHz, CDCl$_3$) δ 6.48 (d, J=2.0 Hz, 2H), 6.35 (t, J=2.3 Hz, 1H), 5.48-5.27 (m, 10H), 4.15 (t, J=5.8 Hz, 4H), 3.98 (t, J=5.8 Hz, 4H), 3.36 (s, 2H), 2.90-2.73 (m, 6H), 2.32 (t, J=7.7 Hz, 4H), 2.26 (s, 6H), 2.16-2.00 (m, 8H), 1.93-1.75 (m, 8H), 1.64 (t, J=7.3 Hz, 4H), 1.44-1.22 (m, 22H), 0.99 (t, J=7.5 Hz, 3H), 0.91 (t, J=7.0 Hz, 3H) ppm.
ES-MS m/z=835.0 (MH+).

Synthesis of Example 65

Intermediate 65a:

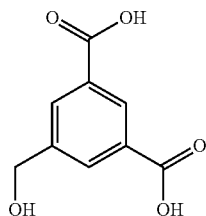 [SMILES: O=C(O)c1cc(CO)cc(C(=O)O)c1]

To a solution of diethyl 5-(hydroxymethyl)isophthalate (509 mg, 2.02 mmol) in THF (5 mL) was added NaOH (5.04 mL, 1.0 M in water, 5.04 mmol). The reaction was stirred for 3 days at room temperature. Volatiles were removed under reduced pressure and the resulting material was used without further purification.

Intermediate 65b:

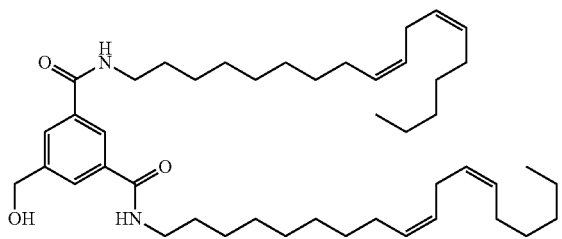

Intermediate 65a (168 mg, 0.694 mmol) was stirred in DCM (25 mL) and EDC (399 mg, 2.08 mmol) and HOBt (319 mg, 2.08 mmol) were added followed by TEA (0.481 mL, 3.47 mmol). The reaction was stirred at room temperature for 5 min and the linoleyl amine hydrochloride (419 mg, 1.39 mmol) was added. The reaction was stirred overnight at room temperature and then diluted with DCM (100 mL) and water (100 mL). The organic layer was collected and washed with water (2×50 mL) and dried over magnesium sulfate. The volatiles were removed under reduced pressure. The resulting crude material was purified on silica using heptanes/EtOAc as an eluent to provide 150 mg of the desired material.

ES-MS m/z=691.4 (MH+).

Example 65 Compound

Example 65

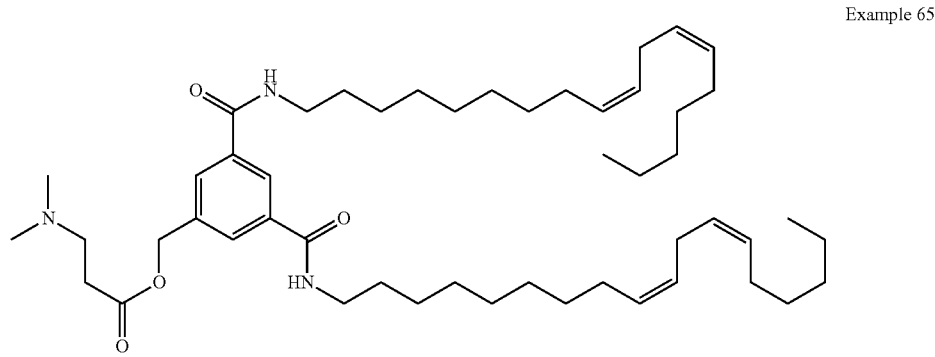 [SMILES: CCCCC/C=C\C/C=C\CCCCCCCCNC(=O)c1cc(COC(=O)CCN(C)C)cc(C(=O)NCCCCCCCC/C=C\C/C=C\CCCCC)c1]

Example 65 was prepared from Intermediate 65b using conditions similar to those used in preparation of Example 37.

$^1$H NMR (400 MHz, CDCl$_3$) δ 8.11 (t, J=1.5 Hz, 1H), 7.89 (d, J=1.5 Hz, 2H), 6.43 (t, J=5.6 Hz, 2H), 5.25-5.48 (m, 8H), 5.19 (s, 2H), 3.33-3.53 (m, 4H), 2.77 (t, J=6.5 Hz, 4H), 2.60-2.70 (m, 2H), 2.49-2.60 (m, 2H), 2.26 (s, 6H), 2.05 (q, J=6.9 Hz, 8H), 1.55-1.71 (m, 4H), 1.18-1.47 (m, 32H), 0.89 (t, J=7.0 Hz, 6H) ppm.

ES-MS m/z=790.4 (MH+).

Example 66 was prepared using methods similar to those employed for the preparation of Example 65.

Example 66

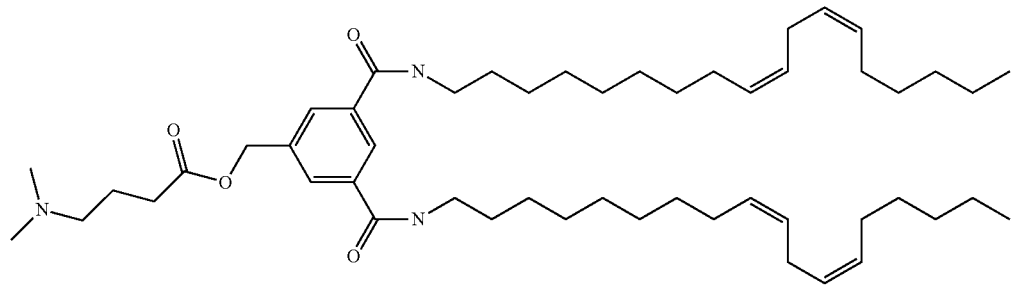 [SMILES: CCCCC/C=C\C/C=C\CCCCCCCCNC(=O)c1cc(COC(=O)CCCN(C)C)cc(C(=O)NCCCCCCCC/C=C\C/C=C\CCCCC)c1]

$^1$H NMR (400 MHz, CDCl$_3$) δ 8.11 (t, J=1.6 Hz, 1H), 7.88 (d, J=1.5 Hz, 2H), 6.50 (t, J=5.6 Hz, 2H), 5.20-5.48 (m, 8H), 5.15 (s, 2H), 3.31-3.55 (m, 4H), 2.66-2.85 (m, 4H), 2.41 (t, J=7.4 Hz, 2H), 2.28 (t, J=7.3 Hz, 2H), 2.20 (s, 6H), 2.04 (q, J=6.9 Hz, 8H), 1.82 (q, J=7.4 Hz, 2H), 1.54-1.67 (m, 4H), 1.17-1.45 (m, 32H), 0.88 (t, J=7.0 Hz, 6H) ppm.

ES-MS m/z=804.5 (MH+).

Synthesis of Example 67

Intermediate 67a:

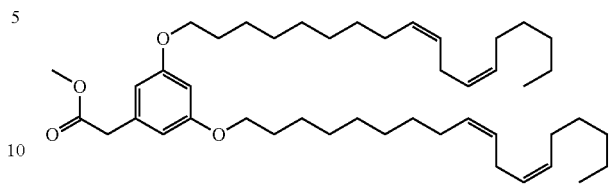

To a solution of methyl-3-(3,5-dihydroxyphenyl)acetate (1.0 g, 5.4 mmol) in DMF (25 mL) was added linoleyl mesylate (4.16 g, 12.1 mmol) and potassium carbonate (3.0 g, 21.6 mmol). The reaction was heated to 100 deg C. for 4 h after which the reaction was cooled to room temperature and water (100 mL) was added. The resulting mixture was extracted with EtOAc (3×50 mL). The organic layers were combined, washed with brine, dried over sodium sulfate, and the volatiles were removed under reduced pressure. The resulting crude material was purified on silica using n-hexane/EtOAc as the eluent to yield 3.3 g of the desired product.

ES-MS m/z=680 (MH+).

Intermediate 67b:

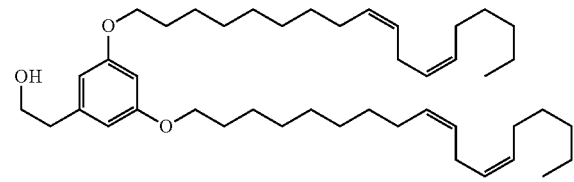 [SMILES: CCCCC/C=C\C/C=C\CCCCCCCCOc1cc(CCO)cc(OCCCCCCCC/C=C\C/C=C\CCCCC)c1]

Intermediate 67a (3.3 g, 4.8 mmol) was stirred in THF (50 mL) and cooled in an ice bath. A solution of lithium aluminum hydride (370 mg, 97 mmol) in THF (3 mL) was added slowly to the stirring reaction. Following the addition the reaction was stirred at room temperature for 3 h. The material was then cooled again in an ice bath and water (5 mL) and EtOAc (5 mL) were added. After 10 minutes, the resulting slurry was filtered through celite and the filtrate concentrated under reduced pressure to provide 2.8 g of material that was used without further purification.

Example 67 Compound

Intermediate 13a (82.5 mg, 0.130 mmol) was dissolved in dry $CDCl_3$ (2 mL) 4-nitrophenyl carbonochloridate (28.7 mg, 0.142 mmol) was added followed by pyridine (0.011 mL, 0.129 mmol). This was stirred at 50 deg C. for 30 minutes. After this time the heat was turned off and the reaction was let stir overnight at room temperature. The reaction was checked by TLC which indicates complete consumption of SM. The intermediate was concentrated and redissolved in dichloromethane (3 mL), 3-(dimethylamino) propan-1-ol (66.8 mg, 0.648 mmol) was added followed by

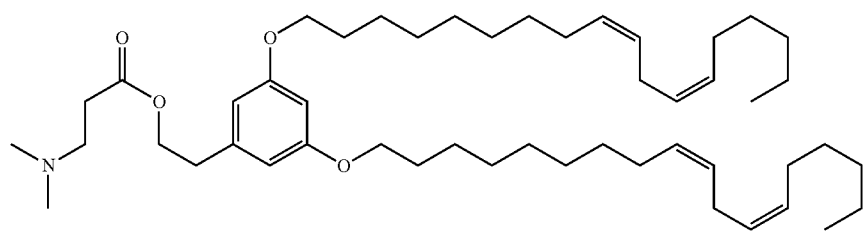

Example 67

Intermediate 67b (75 mg, 0.12 mmol) in DCM (3 mL) was added 3-dimethylaminopropionic acid hydrochloride (26 mg, 0.17 mmol) and HATU (88 mg, 0.23 mmol) followed by TEA (0.016 mL, 0.12 mmol). The reaction was stirred overnight at room temperature and then water (2 mL) was added. The mixture was extracted with DCM (3×5 mL) and the combined organic layers dried over sodium sulfate. The volatiles were removed under reduced pressure and the resulting crude material was purified on silica using DCM/MeOH as an eluent to provide 72 mg of the desired material.

$^1$H NMR (400 MHz, $CDCl_3$) δ 6.32-6.37 (m, 3H), 5.28-5.44 (m, 8H), 4.37 (t, J=7.2 Hz, 2H), 3.92 (t, J=6.6 Hz, 4H), 3.36 (t, J=6.4 Hz, 2H), 2.86-2.92 (m, 8H), 2.75-2.81 (m, 6H), 2.06 (ddd, J=6.7, 6.7, 6.7 Hz, 8H), 1.71-1.80 (m, 4H), 1.41-1.49 (m, 4H), 1.24-1.41 (m, 32H), 0.90 (t, J=7.1 Hz, 6H) ppm.

ES-MS m/z=750.5 (MH+).

DMAP (3.16 mg, 0.026 mmol). The reaction was stirred 72 h at room temperature. The reaction was quenched with water (2 mL) and extracted into additional DCM (3×5 mL). The organic layers were concentrated. The crude material was purified on silica using 0 to 6% MeOH in DCM as eluent to yield 47 mg of the desired product.

$^1$H NMR (400 MHz, $CDCl_3$) δ 6.51 (d, J=2.3 Hz, 2H), 6.42 (t, J=2.3 Hz, 1H), 5.32-5.48 (m, 8H), 5.09 (s, 2H), 4.23 (t, J=6.7 Hz, 2H), 3.94 (t, J=6.5 Hz, 4H), 2.80 (dd, J=6.4, 6.4 Hz, 4H), 2.37 (t, J=7.0 Hz, 2H), 2.24 (s, 6H), 1.99-2.16 (m, 8H), 1.82-1.91 (m, 2H), 1.72-1.82 (m, 4H), 1.41-1.50 (m, 5H), 1.27-1.41 (m, 29H), 0.83-0.97 (m, J=6.8, 6.8 Hz, 5H) ppm.

ES-MS m/z=766.5 (MH+).

Example 69 was prepared using methods similar to those described for Intermediate 33a and Example 68.

Synthesis of Example 68

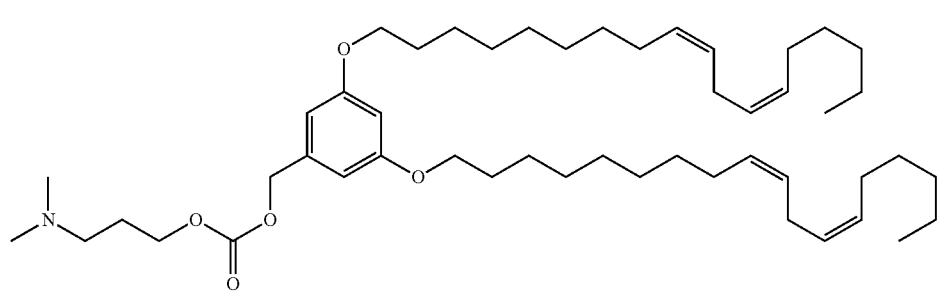

Example 68

Example 69
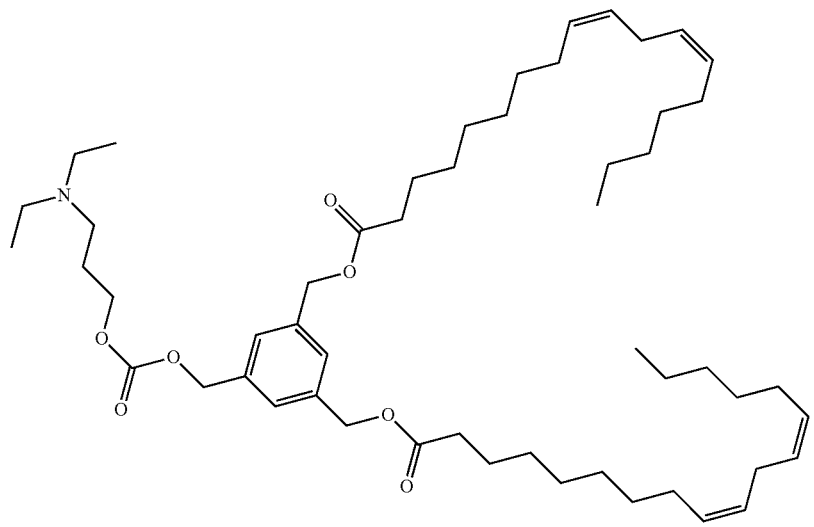 [SMILES: CCCCC/C=C\C/C=C\CCCCCCCC(=O)OCc1cc(COC(=O)CCCCCCC/C=C\C/C=C\CCCCC)cc(COC(=O)OCCCN(CC)CC)c1]
¹H NMR (400 MHz, CDCl₃) δ 7.33 (s, 2H), 7.31 (s, 1H), 5.25-5.45 (m, 8H), 5.16 (s, 2H), 5.11 (s, 4H), 4.22 (t, J=6.5 Hz, 2H), 2.73-2.82 (m, 4H), 2.43-2.55 (m, 6H), 2.37 (t, J=7.5 Hz, 4H), 2.01-2.09 (m, 8H), 1.83 (quin, J=6.5 Hz, 2H), 1.57-1.71 (m, 5H), 1.21-1.42 (m, 28H), 1.01 (t, J=7.2 Hz, 6H), 0.89 (t, J=6.8 Hz, 6H) ppm.
ES-MS m/z=850.6 (MH+).
Examples 70 and 71 were prepared using methods similar to those employed for the preparation of Example 69.
Example 70
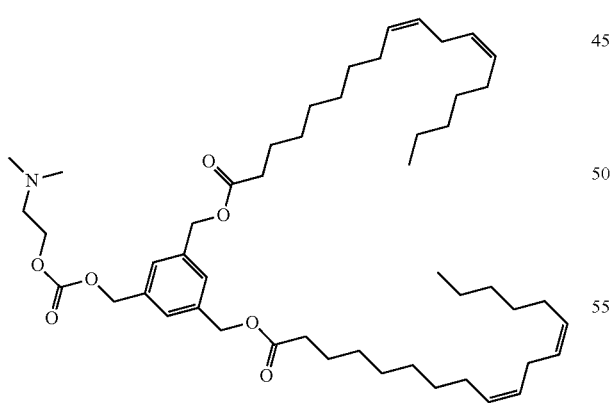
¹H NMR (400 MHz, CDCl₃) δ 7.33 (s, 2H), 7.30 (s, 1H), 5.29-5.43 (m, 8H), 5.16 (s, 2H), 5.11 (s, 4H), 4.25 (t, J=5.8 Hz, 2H), 2.77 (t, J=6.5 Hz, 4H), 2.60 (t, J=5.8 Hz, 2H), 2.37 (t, J=7.7 Hz, 4H), 2.29 (s, 6H), 2.05 (q, J=6.8 Hz, 8H), 1.52-1.75 (m, 4H), 1.24-1.40 (m, 29H), 0.88 (t, J=6.8 Hz, 5H) ppm.
ES-MS m/z=808.5 (MH+).

Example 71

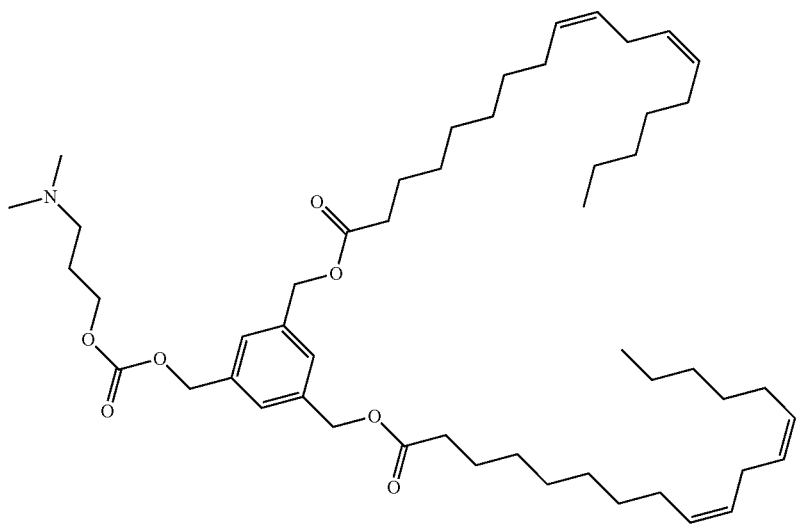 [SMILES: CCCCC/C=C\C/C=C\CCCCCCCC(=O)OCc1cc(COC(=O)CCCCCCC/C=C\C/C=C\CCCCC)cc(COC(=O)OCCCN(C)C)c1]

¹H NMR (400 MHz, CDCl₃) δ 7.34 (s, 2H), 7.32 (s, 1H), 5.29-5.45 (m, 8H), 5.17 (s, 2H), 5.12 (s, 4H), 4.24 (t, J=6.5 Hz, 2H), 2.79 (t, J=6.5 Hz, 4H), 2.34-2.41 (m, 6H), 2.24 (s, 6H), 2.06 (q, J=6.7 Hz, 8H), 1.87 (quin, J=6.5 Hz, 2H), 1.61-1.72 (m, 4H), 1.25-1.42 (m, 29H), 0.91 (t, J=7.0 Hz, 6H) ppm.

ES-MS m/z=822.6 (MH+).

Example 72 was prepared using methods similar to those used in the synthesis of Intermediate 26b and Example 68.

Example 72

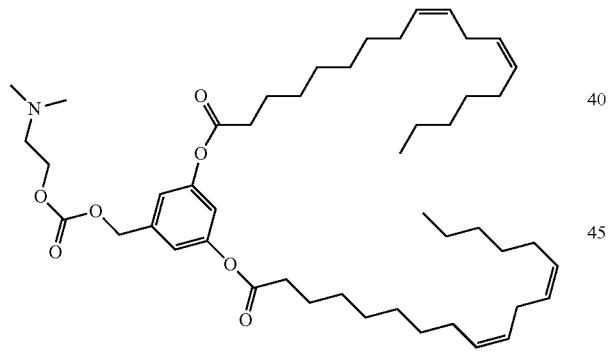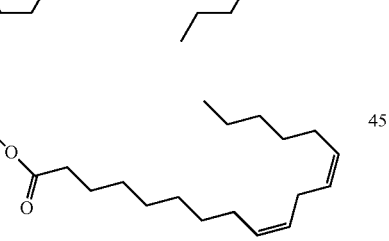

¹H NMR (400 MHz, CDCl₃) δ 7.01 (d, J=2.0 Hz, 2H), 6.89 (t, J=2.1 Hz, 1H), 5.30-5.46 (m, 8H), 5.14 (s, 2H), 4.26 (t, J=5.8 Hz, 2H), 2.79 (t, J=6.4 Hz, 4H), 2.61 (t, J=5.8 Hz, 2H), 2.54 (t, J=7.5 Hz, 4H), 2.29 (s, 6H), 2.01-2.11 (m, 8H), 1.74 (dt, J=14.7, 7.5 Hz, 4H), 1.24-1.46 (m, 31H), 0.90 (t, J=7.0 Hz, 6H) ppm.

ES-MS m/z=780.4 (MH+).

Example 73 was prepared using procedures similar to those used in the synthesis of Intermediate 13a and Example 68.

Example 73

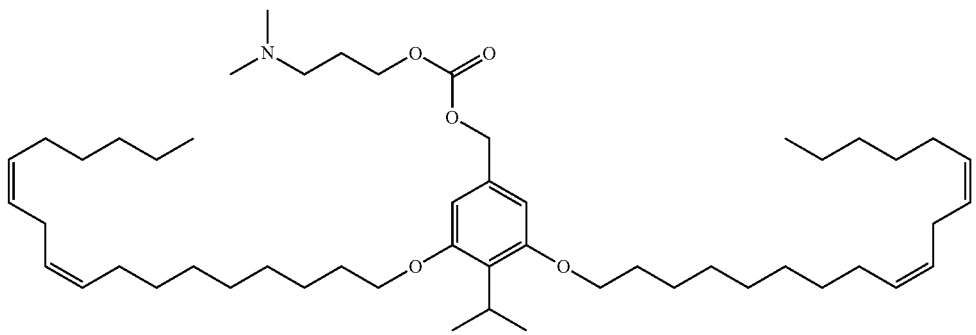 [SMILES: CCCCC/C=C\C/C=C\CCCCCCCCOc1cc(COC(=O)OCCCN(C)C)cc(OCCCCCCCC/C=C\C/C=C\CCCCC)c1C(C)C]

$^1$H NMR (400 MHz, CDCl$_3$) δ 6.52 (s, 2H), 5.50-5.25 (m, 8H), 5.07 (s, 2H), 4.21 (t, J=6.5 Hz, 2H), 3.93 (t, J=6.4 Hz, 4H), 3.63 (quin, J=7.1 Hz, 1H), 2.79 (t, J=6.4 Hz, 4H), 2.36 (t, J=7.5 Hz, 2H), 2.22 (s, 6H), 2.06 (q, J=6.8 Hz, 8H), 1.92-1.71 (m, 6H), 1.56-1.41 (m, 4H), 1.41-1.20 (m, 34H), 0.90 (t, J=6.8 Hz, 3H) ppm.

ES-MS m/z=810.1 (MH+).

Examples 74 and 75 were prepared using methods similar to those employed for the preparation of Example 73.

Example 74

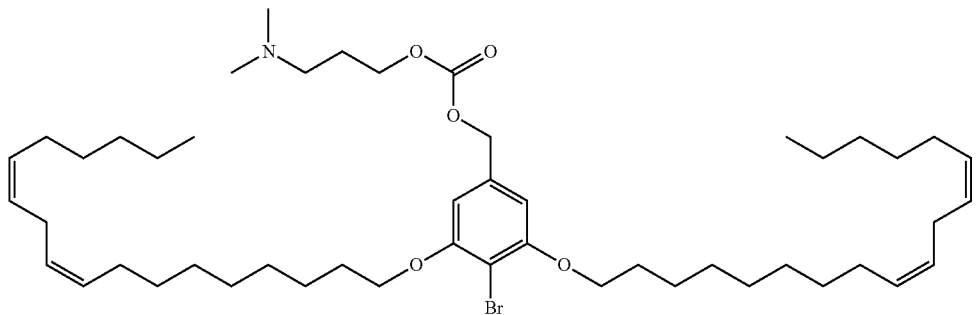

$^1$H NMR (400 MHz, CDCl$_3$) δ 6.55 (s, 2H), 5.44-5.30 (m, 8H), 5.08 (s, 2H), 4.22 (t, J=6.7 Hz, 2H), 4.02 (t, J=6.5 Hz, 4H), 2.78 (t, J=6.3 Hz, 4H), 2.35 (t, J=7.4 Hz, 2H), 2.22 (s, 6 H), 2.06 (q, J=6.7 Hz, 8H), 1.90-1.77 (m, 6H), 1.55-1.46 (m, 4H), 1.42-1.22 (m, 28H), 0.89 (t, J=6.8 Hz, 6H) ppm.

ES-MS m/z=846.3 (MH+) (bromine isotope pattern observed).

Example 75

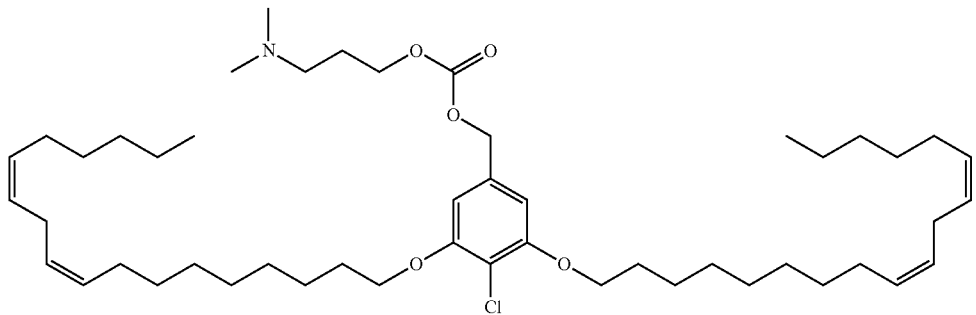 [SMILES: CCCCC/C=C\C/C=C\CCCCCCCCOc1cc(COC(=O)OCCCN(C)C)cc(OCCCCCCCC/C=C\C/C=C\CCCCC)c1Cl]

$^1$H NMR (400 MHz, CDCl$_3$) δ 6.59 (d, J=2.8 Hz, 1H), 6.48 (d, J=2.8 Hz, 1H), 5.51-5.29 (m, 8H), 5.26 (s, 2H), 4.25 (t, J=6.5 Hz, 2H), 4.00 (t, J=6.5 Hz, 2H), 3.94 (t, J=6.5 Hz, 2H), 2.80 (t, J=6.4 Hz, 4H), 2.38 (t, J=7.0 Hz, 2H), 2.24 (s, 6H), 2.07 (q, J=6.7 Hz, 8H), 1.91-1.75 (m, 6H), 1.55-1.44 (m, 4H), 1.44-1.24 (m, 30H), 0.91 (t, J=6.8 Hz, 6H) ppm.

ES-MS m/z=802.8 (MH+) (chloro isotope pattern observed).

Synthesis of Example 76

Intermediate 76a:

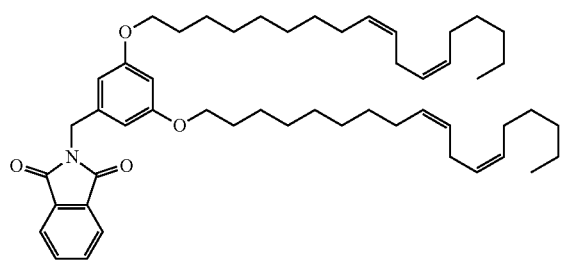 [SMILES: CCCCC/C=C\C/C=C\CCCCCCCCOc1cc(CN2C(=O)c3ccccc3C2=O)cc(OCCCCCCCC/C=C\C/C=C\CCCCC)c1]

Intermediate 13a (120 mg, 0.188 mmol), isoindoline-1,3-dione (34.6 mg, 0.235 mmol) and triphenylphosphine (64.2 mg, 0.245 mmol) were dissolved THF (1.5 mL). DIAD (0.044 mL, 0.226 mmol) was then added dropwise. The reaction was stirred at room temperature for 16 hours. Reaction was checked for completion by LCMS. The reaction was concentrated then washed with water then brine and dried over sodium sulfate and reconcentrated. Desired product was obtained as a mixture with triphenylphosphine oxide to yield 144.0 mg of material.

Intermediate 76b:

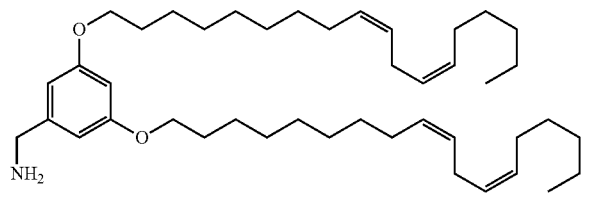 [SMILES: CCCCC/C=C\C/C=C\CCCCCCCCOc1cc(CN)cc(OCCCCCCCC/C=C\C/C=C\CCCCC)c1]

Intermediate 76a (144 mg, 0.188 mmol, mixture) was dissolved in EtOH (3.7 mL). Hydrazine (0.030 mL, 0.940 mmol) was added and the reaction was heated for 4 hours at 50 deg C. The reaction was monitored for completion by LCMS. The reaction was concentrated and suspended in DCM (10 mL). Reaction was filtered. Filtrate was then loaded on to DCM pre-equilibrated SCX 2 g column. The column was washed with 3CV of DCM and product was eluted with DCM+5% 7N ammonia in methanol to recover 57 mg of the desired product.

ES-MS m/z=636.5 (MH+).

Example 76 Compound

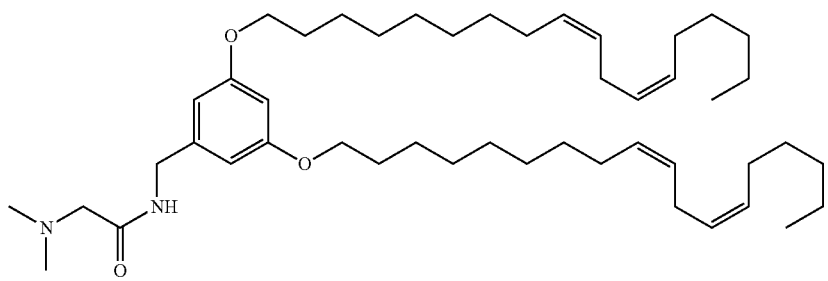

Example 76

Intermediate 76b (36.1 mg, 0.057 mmol), 2-(dimethylamino)acetic acid hydrochloride (23.77 mg, 0.170 mmol) and HATU (43.2 mg, 0.114 mmol) were dissolved in DCM (4 mL). Triethylamine (0.032 mL, 0.227 mmol) was then added and the reaction was stirred 18 hours at room temperature and checked by LCMS. The reaction was quenched with water (2 mL) and extracted into additional DCM (3×5 mL). The reaction was purified by silica gel chromatography in 0 to 5% MeOH in DCM to provide 20 mg of the desired product.

$^1$H NMR (400 MHz, CDCl$_3$) δ 7.34 (br. s., 1H), 6.43 (d, J=2.0 Hz, 2H), 6.40-6.33 (m, 1H), 5.54-5.30 (m, 8H), 4.40 (d, J=6.1 Hz, 2H), 3.94 (t, J=6.6 Hz, 4H), 3.01 (s, 2H), 2.80 (t, J=6.3 Hz, 4H), 2.30 (s, 6H), 2.13-1.98 (m, 8H), 1.70-1.82 (m, J=6.6 Hz, 4H), 1.53-1.23 (m, 41H), 0.91 (t, J=7.1 Hz, 6H) ppm.

ES-MS m/z=721.5 (MH+).

Synthesis of Example 77

Intermediate 77a:

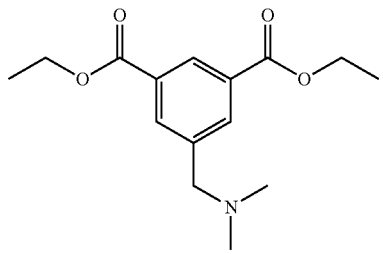 [SMILES: CCOC(=O)c1cc(CN(C)C)cc(C(=O)OCC)c1]

In a round bottom flask, diethyl 5-(hydroxymethyl)isophthalate (15.53 g, 47.6 mmol) and DIPEA (10.39 mL, 59.5 mmol) were taken into chloroform (40 mL). The resulting suspension was stirred for 1 h. To the resulting suspension was added toluenesulfonic anhydride (10 g, 39.6 mmol), and the reaction stirred at ambient temperature. After 20 h, the reaction solution was added dropwise to dimethylamine (60 ml, 120 mmol) over ~30 minutes to control exothermic reaction below reflux. The reaction was stirred at ambient temperature for 3 h. The reaction was diluted with dichloromethane (200 mL), saturated aqueous sodium bicarbonate (200 mL), and water (50 mL). The layers were separated and the aqueous was extracted with dichloromethane (3×100 mL). The combined organics were washed with saturated aqueous sodium bicarbonate (3×100 mL). The organics were dried over sodium sulfate, filtered and concentrated under reduced pressure. The residue was purified by flash chromatography (silica gel, 0%-10% methanol in dichloromethane) followed by flash chromatography (silica-gel, 0%-100% ethyl acetate in dichloromethane, 0%-10% methanol in ethylacetate) to provide 7.3 g of the desired product.

$^1$H NMR (400 MHz, CDCl$_3$) δ 1.44 (t, J=7.2 Hz, 6H); 2.29 (s, 6H); 3.55 (s, 2H); 4.43 (q, J=7.1 Hz, 4H); 8.20 (d, J=1.5 Hz, 2H); 8.61 (t, J=1.5 Hz, 1H) ppm.

Intermediate 77b:

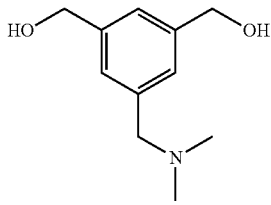

In a round bottom flask, LAH (2.480 g, 65.3 mmol) was taken into tetrahydrofuran (50 mL) and the reaction placed in an ambient water bath. Intermediate 77a (7.3 g, 26.1 mmol) dissolved in THF (10 mL) and added dropwise over 10 minutes to the LAH suspension to maintain exothermic reaction below reflux. The resulting green suspension was stirred overnight at ambient temperature, at which time it had changed to dark grey. The reaction was diluted to 150 mL with additional THF and quenched with water (2.5 mL) by dropwise addition to maintain temperature below reflux. After stirring at ambient temperature for 15 minutes, The reaction was further quenched with 2.5 M aqueous NaOH (5 mL) by dropwise addition over 5 minutes. The reaction was stirred at ambient temperature for 5 minutes and water (7.5 mL) were added dropwise over 1 min, at which point the suspension became white. The reaction was stirred at ambient temperature for 2 h, after which the salts were filtered through celite with ethyl acetate washing. The filtrate was collected and concentrated under reduced pressure to provide viscous colorless oil. The material was dissolved into dichloromethane and purified by flash column chromatography (silica gel 0%-50% methanol in dichloromethane). Product fractions were collected and solvents were removed under reduced pressure to provide colorless oil. The material was dissolved into dichloromethane (100 mL) and filtered. Washing the residue with ethyl acetate resulted in additional precipitate. Solvents were removed under reduced pressure and the material was redissolved in ethyl acetate (100 mL), filtered, and solvents were removed under reduced pressure to provide 4 g of the desired product.

$^1$H NMR (400 MHz, CDCl$_3$) δ 2.21 (s, 6H); 3.37 (s, 2H); 3.77 (br s, 2H); 4.56 (s, 4H); 7.16 (s, 2H); 7.21 (s, 1H) ppm.

Intermediate 77c:

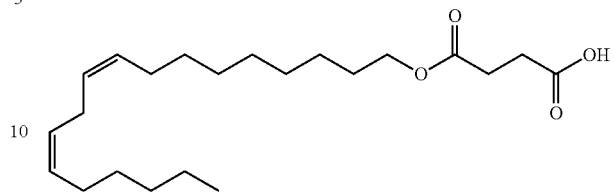

In a borosilicate glass vial, linoleyl alcohol (2 g, 7.51 mmol) and DMAP (0.046 g, 0.375 mmol) are stirred in chloroform (7 mL). Succinic anhydride (1.127 g, 11.26 mmol) is added and the reaction is stirred at ambient temperature. After 3 days the reaction was purified directly via flash column chromatography (silica-gel, 0-10% methanol in dichloromethane), which provided 2.73 g of the desired product.

$^1$H NMR (400 MHz, CDCl$_3$) δ 0.91 (t, J=7.0 Hz, 3H); 1.27-1.41 (m, 17H); 1.64 (m, 2H); 2.07 (dd, J=7.0, 13.8 Hz, 4H); 2.62-2.73 (m, 4H); 2.79 (t, J=6.7 Hz, 2H); 4.11 (t, J=6.8 Hz, 2H); 5.32-5.44 (m, 4H) ppm.

Example 77 Compound

Example 77

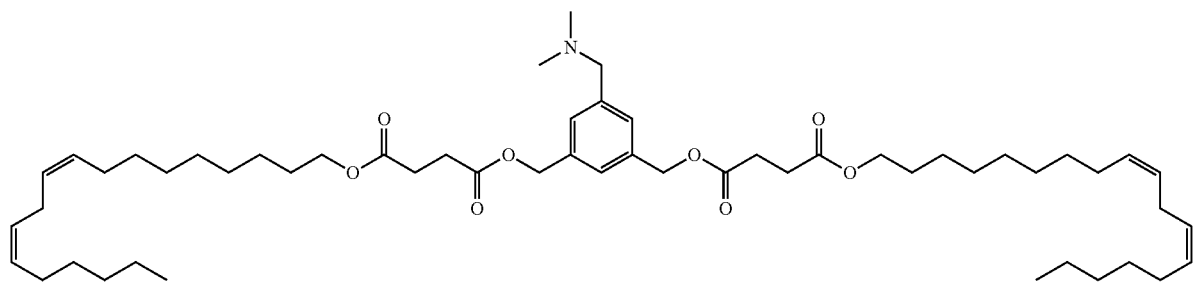

In a borosilicate glass vial, Intermediate 77b (250 mg, 1.280 mmol) was stirred in dichloromethane (10 mL). DIPEA (0.671 ml, 3.84 mmol), DMAP (15.64 mg, 0.128 mmol), EDC (736 mg, 3.84 mmol), and the material from Intermediate 77c (1032 mg, 2.82 mmol) were added sequentially. The reaction was sealed and stirred at ambient temperature. After 2 days, the reaction was purified directly by flash column chromatography (silica gel, equilibrated with 1% formic acid in dichloromethane, purification with 0%-10% methanol in dichloromethane) to provide 916 mg of the desired product.

$^1$H NMR (400 MHz, CDCl$_3$) δ 8.24 (s, 0.5H, formate); 7.55 (s, 2H); 7.41 (s, 1H); 5.43-5.31 (m, 8H); 5.20 (s, 4H); 4.16 (s, 2H); 4.08 (t, J=6.8 Hz, 4H); 2.79 (t, J=6.8 Hz, 4H); 2.75 (s, 6H); 2.75-2.66 (m, 8H); 2.06 (q, J=6.6 Hz, 8H); 1.66-1.59 (m, 4H); 1.40-1.27 (m, 32H); 0.90 (t, J=6.5 Hz, 6H) ppm.

ES-MS m/z=892.7 (MH+).

Example 78 was prepared using methods similar to those used in the synthesis of Intermediate 18a and Example 77.

Example 78

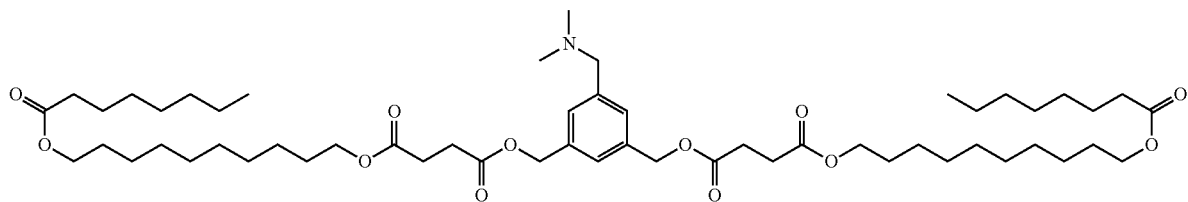 [SMILES: CCCCCCCC(=O)OCCCCCCCCCCOC(=O)CCC(=O)OCc1cc(COC(=O)CCC(=O)OCCCCCCCCCCOC(=O)CCCCCCC)cc(CN(C)C)c1]

¹H NMR (400 MHz, CDCl₃) δ 8.37 (s, 1.6H, formate); 7.42 (s, 2H); 7.38 (s, 1H); 5.18 (s, 4H); 4.10-4.05 (m, 10H); 2.74-2.65 (m, 14H); 2.31 (t, J=7.5 Hz, 4H); 1.66-1.59 (m, 12H); 1.40-1.25 (m, 40H); 0.90 (t, J=7.0 Hz, 6H) ppm.
ES-MS m/z=960.9 (MH+)

Synthesis of Example 79

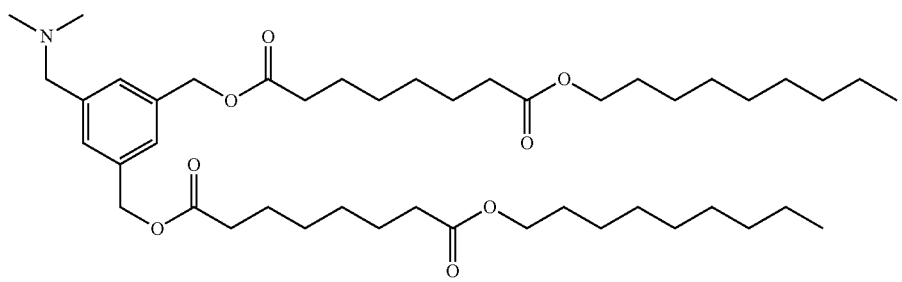 [SMILES: CCCCCCCCCOC(=O)CCCCCCC(=O)OCc1cc(COC(=O)CCCCCCC(=O)OCCCCCCCCC)cc(CN(C)C)c1]

In a 250 ml round-bottom flask equipped with a stirbar, suberic acid (5 g, 28.7 mmol) and EDC (6.60 g, 34.4 mmol) are dissolved in DCM (150 mL). DIPEA (15.04 ml, 86 mmol) is added, followed by DMAP (1.403 g, 11.48 mmol) and mixture is stirred at room temperature for 1 hr before addition of 1-Nonanol (5.01 ml, 28.7 mmol). Mixture stirred at room temperature overnight. The volatiles were removed under reduced pressure and the resulting material was purified by silica gel chromatography using heptanes/EtOAc as the eluent to provide 1 g of the desired product. The desired product was prepared using the procedure used to generate Example 77.
¹H NMR (400 MHz, CDCl₃) δ 7.26 (s, 2H), 7.23 (s, 1H), 5.10 (s, 4H), 4.05 (t, J=6.8 Hz, 4H), 3.44 (s, 2H), 2.36 (t, J=7.7 Hz, 4H), 2.31-2.25 (m, 10H), 1.69-1.58 (m, 12H), 1.36-1.27 (m, 32H), 0.88 (t, J=7.0 Hz, 6H) ppm.
ES-MS m/z=760.4 (MH+).

¹H NMR (400 MHz, CDCl₃) δ 7.27 (s, 2H), 7.24 (s, 1H), 5.11 (s, 4H), 4.07 (t, J=6.8 Hz, 4H), 3.44 (s, 2H), 2.37 (t, J=7.7 Hz, 4H), 2.30 (t, J=7.5 Hz, 4H), 2.26 (s, 6H), 1.67-1.59 (m, 12H), 1.33-1.29 (m, 32H), 0.90 (t, J=8.0 Hz, 6H) ppm.
ES-MS m/z=760.4 (MH+).

Example 80 was prepared using methods similar to those employed for the preparation of Example 79.

Example 80

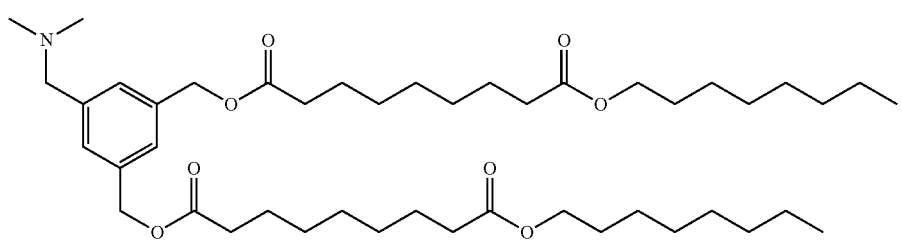 [SMILES: CCCCCCCCOC(=O)CCCCCCCC(=O)OCc1cc(COC(=O)CCCCCCCC(=O)OCCCCCCCC)cc(CN(C)C)c1]

Synthesis of Example 81

Intermediate 81a:

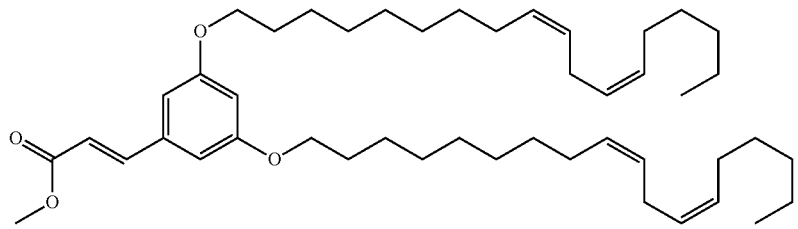

Trimethyl phosphonoacetate (357 mg, 1.96 mmol) was added to a suspension of NaH (78 mg, 1.96 mmol) in THF (10 mL) which was stirring in an ice bath. After 10 min, the starting aldehyde (1 g, 1.63 mmol), made using a procedure analogous to that in Example 1a, was dissolved in THF (5 mL) and added slowly. The reaction was stirred for 1 h and then ice cold water (5 mL) was added and the resulting mixture was extracted with EtOAc (3×30 mL). The combined organic layers were dried over sodium sulfate and concentrated under reduced pressure. The resulting material was purified by silica gel chromatography using heptanes/EtOAc as eluent to provide 1.2 g of the desired material.

Rf=0.77 (silica, 10% ethyl acetate in hexane, UV)

Intermediate 81b:

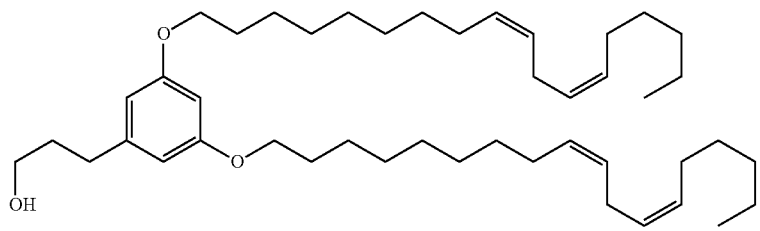 [SMILES: CCCCC/C=C\C/C=C\CCCCCCCCOc1cc(CCCO)cc(OCCCCCCCC/C=C\C/C=C\CCCCC)c1]

Intermediate 81a (2.6 g, 3.7 mmol) in THF (75 mL) was cooled in an ice bath and lithium aluminum hydride (300 mg, 7.9 mmol) was added in portions. The reaction was stirred for 45 min in cooling bath and then quenched with ice cold water. The resulting material was filtered through celite and the filtrate concentrated under reduced pressure. The resulting material was purified by silica gel chromatography using heptanes/EtOAc as eluent to provide 2.5 g of the desired material.

Rf=0.21 (silica, 10% EtOAc in hexane, UV and cerium molybdate)

Example 81 Compound

Example 81 was prepared from Intermediate 81b using the methods similar to those used for the synthesis of Example 13.

$^1$H NMR (400 MHz, CDCl$_3$) δ 6.34 (d, J=2.0 Hz, 2H), 6.32 (d, J=2.3 Hz, 1H), 5.27-5.47 (m, 8H), 4.16 (t, J=6.5 Hz, 2H), 3.93 (t, J=6.5 Hz, 4H), 2.92-3.03 (m, 2H), 2.80 (dd, J=6.4, 6.4 Hz, 4H), 2.61-2.69 (m, 4H), 2.58 (s, 6H), 2.07 (q, J=6.9 Hz, 8H), 1.91-2.03 (m, 2H), 1.71-1.85 (m, J=7.8 Hz, 4H), 1.42-1.52 (m, 4H), 1.23-1.41 (m, 29H), 0.91 (t, J=6.8 Hz, 6H) ppm.

ES-MS m/z=764.6 (MH+).

Synthesis of Example 82

Intermediate 82a:

The starting alcohol (1.0 g, 2.8 mmol), made using chemistry as for Intermediate 18a, was stirred in acetone (25 mL) and cooled in an ice bath. Jones' reagent (2.27 mL, 2.5 M, 5.67 mmol) was added dropwise and the ice bath was removed. After 1 h stirring, MeOH (5 mL) was added followed by EtOAc (220 mL). The resulting mixture was washed with 1:1 water:brine and then brine. The resulting organic layer was dried over sodium sulfate and then the volatiles were removed under reduced pressure. The crude material was purified by silica gel chromatography using heptanes/EtOAc as eluent to provide 672 mg of the desired material.

$^{13}$C NMR (100 MHz, CDCl$_3$) δ 6.178.3, 173.8, 130.2, 130.0, 128.0, 127.9, 63.0, 34.2, 31.5, 30.4, 29.6, 29.3, 29.2, 29.1, 27.2, 25.6, 24.9, 23.7, 22.5, 14.1 ppm.

Example 82 Compound

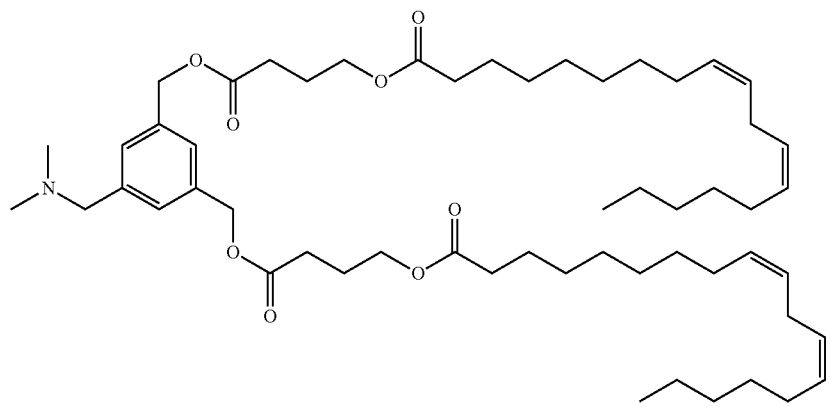 [SMILES: CCCCC/C=C\C/C=C\CCCCCCCC(=O)OCCCC(=O)OCc1cc(COC(=O)CCCOC(=O)CCCCCCC/C=C\C/C=C\CCCCC)cc(CN(C)C)c1]

Intermediate 82a (672 mg, 1.83 mmol) was stirred in DCE (40 mL). EDC (501 mg, 2.6 mmol) was added followed by the material from Intermediate 77b (170 mg, 0.87 mmol) as a solution in DCE (10 mL). TEA (0.485 mL, 3.48 mmol) and DMAP (21 mg, 0.17 mmol) were added and the reaction was stirred for 3 days at room temperature. The reaction was concentrated under reduced pressure and the crude material was purified by silica gel chromatography using heptanes/ EtOAc as eluent to provide 359 mg of the desired material.

$^1$H NMR (400 MHz, CDCl$_3$) δ 7.31-7.28 (m, 2H), 7.25-7.23 (m, 1H), 5.44-5.28 (m, 8H), 5.12 (s, 4H), 4.11 (t, J=6.4 Hz, 4H), 2.81-2.73 (m, 4H), 2.46 (t, J=7.4 Hz, 4H), 2.32-2.24 (m, 9H), 2.09-1.94 (m, 12H), 1.69-1.51 (m, 5H), 1.42-1.22 (m, 28H), 0.89 (t, J=6.9 Hz, 6H) ppm.

ES-MS m/z=892.7 (MH+).

Examples 83-88 were prepared using methods similar to those employed for the preparation of Example 82.

Example 83

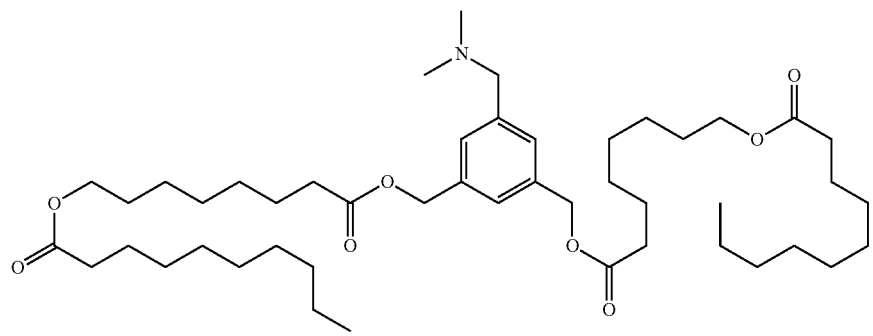 [SMILES: CCCCCCCCCC(=O)OCCCCCCCC(=O)OCc1cc(COC(=O)CCCCCCCOC(=O)CCCCCCCCC)cc(CN(C)C)c1]

¹H NMR (400 MHz, CDCl₃) δ 7.28-7.25 (m, 2H), 7.24-7.21 (m, 1H), 5.10 (s, 4H), 4.05 (t, J=6.8 Hz, 4H), 3.43 (s, 2H), 2.36 (t, J=7.6 Hz, 4H), 2.29 (t, J=7.6 Hz, 4H), 2.25 (s, 6H), 1.72-1.52 (m, 12H), 1.42-1.14 (m, 36H), 0.95-0.75 (m, 6H) ppm.
ES-MS m/z=788.4 (MH+).

Example 84

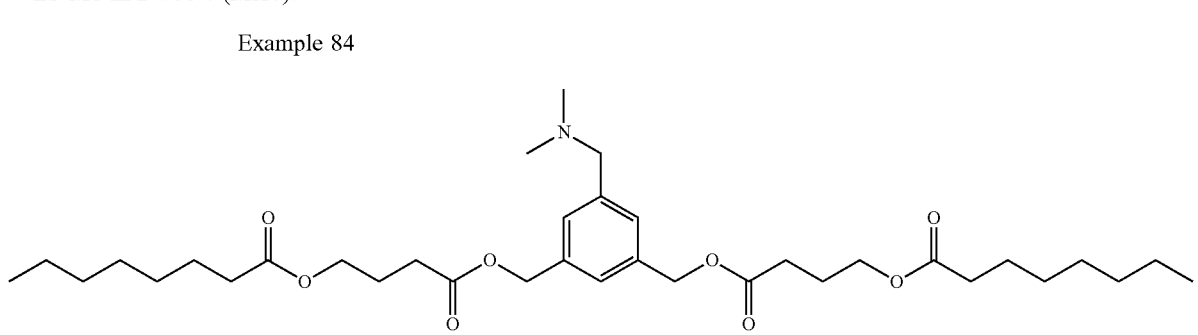

¹H NMR (400 MHz, CDCl₃) δ 8.33 (s, 1H, formate); 7.54 (s, 2H); 7.39 (s, 1H); 5.17 (s, 4H), 4.15 (s, 2H), 4.12 (t, J=6.4 Hz, 4H); 2.74 (s, 6H); 2.50 (t, J=7.4 Hz, 4H); 2.30 (t, J=7.5 Hz, 4H); 2.04-1.97 (m, 4H); 1.65-1.58 (m, 4H); 1.34-1.23 (m, 16H); 0.88 (t, J=6.7 Hz, 6H) ppm. LCMS m/z=620.2 (MH+).

Example 85

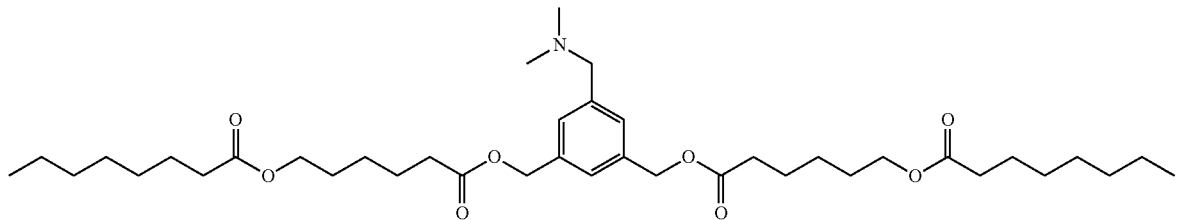 [SMILES: CCCCCCCC(=O)OCCCCCC(=O)OCc1cc(COC(=O)CCCCCOC(=O)CCCCCCC)cc(CN(C)C)c1]

¹H NMR (400 MHz, CDCl₃) δ 8.30 (s, 0.6H, formate); 7.54 (s, 2H); 7.40 (s, 1H); 5.15 (s, 4H); 4.15 (s, 2H); 4.06 (t, J=6.5 Hz, 4H); 2.74 (s, 6H); 2.42 (t, J=7.5 Hz, 4H); 2.29 (t, J=7.5 Hz, 4H); 1.73-1.58 (m, 12H); 1.44-1.36 (m, 4H); 1.34-1.23 (m, 16H); 0.88 (t, J=6.3 Hz, 6H) ppm. LCMS m/z=676.2 (MH+).

Example 86

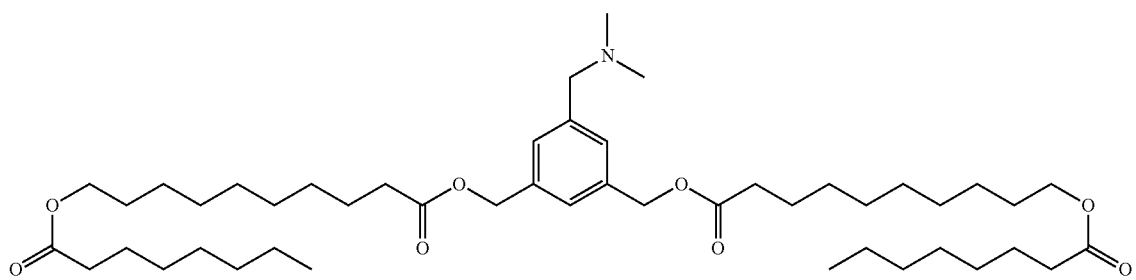 [SMILES: CCCCCCCC(=O)OCCCCCCCCCC(=O)OCc1cc(COC(=O)CCCCCCCCCOC(=O)CCCCCCC)cc(CN(C)C)c1]

¹H NMR (400 MHz, CDCl₃) δ 7.50 (s, 2H); 7.38 (s, 1H); 5.14 (s, 4H); 4.06 (t, J=6.8 Hz, 4H); 3.97 (s, 2H); 2.63 (s, 6H); 2.39 (t, J=7.7 Hz, 4H); 2.30 (t, J=7.5 Hz, 4H); 1.69-1.59 (m, 12H); 1.38-1.25 (m, 36H); 0.89 (t, J=7.0, 6H) ppm.
LCMS m/z=788.8 (MH+).

Example 87

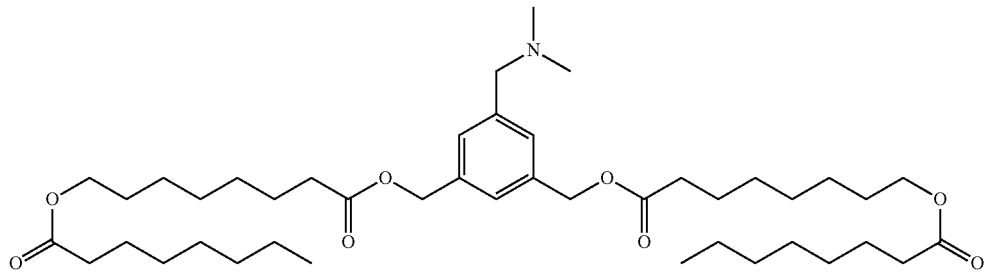 [SMILES: CCCCCCCC(=O)OCCCCCCCC(=O)OCc1cc(COC(=O)CCCCCCCOC(=O)CCCCCCC)cc(CN(C)C)c1]

$^1$H NMR (400 MHz, CDCl$_3$) δ 7.52 (s, 2H); 7.38 (s, 1H); 5.15 (s, 4H); 4.06 (t, J=6.7 Hz, 4H); 3.99 (s, 2H); 2.65 (s, 6H); 2.40 (t, J=7.5 Hz, 4H); 2.30 (t, J=7.5Hs, 4H); 1.70-1.59 (m, 12H); 1.38-1.25 (m, 28H); 0.89 (t, J=6.8 Hz, 6H) ppm. LCMS m/z=732.8 (MH+).

Example 88

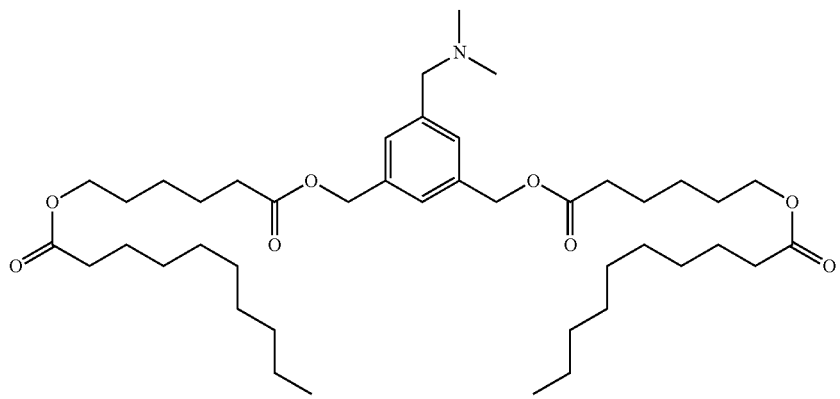 [SMILES: CCCCCCCCCC(=O)OCCCCCC(=O)OCc1cc(COC(=O)CCCCCOC(=O)CCCCCCCCC)cc(CN(C)C)c1]

$^1$H NMR (400 MHz, CDCl$_3$) δ 7.54 (s, 2H); 7.38 (s, 1H); 5.15 (s, 4H); 4.07 (t, J=6.7 Hz, 4H); 4.02 (s, 2H); 2.66 (s, 6H); 2.42 (t, J=7.5 Hz, 4H); 2.30 (t, J=7.7 Hz, 4H); 1.74-1.58 (m, 12H); 1.45-1.37 (m, 4H); 1.35-1.22 (m, 24H); 0.89 (t, J=7.0 Hz, 6H) ppm.
LCMS m/z=732.8 (MH+).

Synthesis of Example 89

Intermediate 89a:

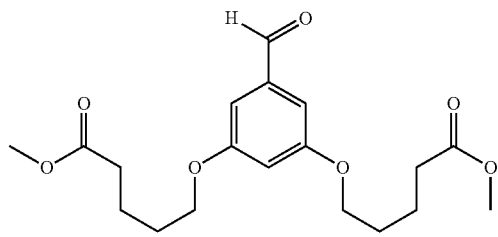 [SMILES: COC(=O)CCCCOc1cc(C=O)cc(OCCCCC(=O)OC)c1]

To a solution of 3,5-dihydroxybenzaldehyde (1.0 g, 7.24 mmol) in acetone (35 mL) was added methyl 5-bromopentanoate (3.53 g, 18.1 mmol). Potassium carbonate (3.0 g, 22 mmol) was added and the reaction was heated to reflux in an oil bath. After heating overnight, the reaction was cooled to room temperature and allowed to stir for 4 days. The volatiles were removed under reduced pressure and the material was resuspended in DCM. The resulting mixture was filtered and the filtrate was concentrated under reduced pressure to a crude material that was purified by silica gel chromatography using heptanes/EtOAc as eluent to provide 824 mg of the desired material.

$^1$H NMR (400 MHz, CDCl$_3$) δ 9.89 (s, 1H), 6.99 (s, 2H), 6.68 (s, 1H), 4.01 (m, 4H), 3.68 (s, 6H), 2.41 (m, 4H), 1.84 (m, 8H) ppm.

Intermediate 89b:

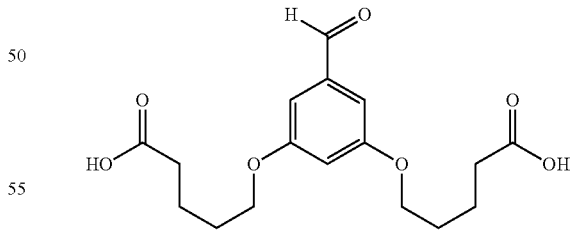

Intermediate 89a (824 mg, 2.25 mmol) was stirred in EtOH (15 mL). Potassium hydroxide (505 mg, 9.0 mmol) and water (5 mL) were added and the reaction was stirred at room temperature for 3 h. The material was then diluted with EtOAc (100 mL) and washed with 1 M HCl (2×50 mL). The resulting organic phase was dried over sodium sulfate and concentrated under reduced pressure to provide 710 mg of the desired material.

¹H NMR (400 MHz, DMSO-d₆) δ 9.90 (s, 1H), 7.03 (s, 2H), 6.81 (s, 1H), 4.02 (m, 4H), 2.29 (m, 4H), 1.6-1.8 (m, 8H) ppm.

Intermediate 89c

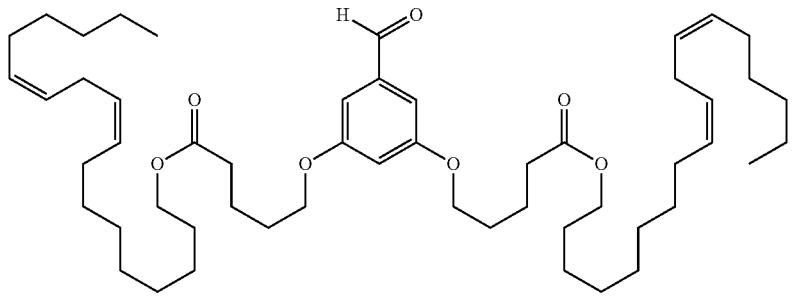 [SMILES: CCCCC/C=C\C/C=C\CCCCCCCCOC(=O)CCCCOc1cc(C=O)cc(OCCCCC(=O)OCCCCCCCC/C=C\C/C=C\CCCCC)c1]

Intermediate 89b (710 mg, 2.1 mmol) was stirred in DCM (20 mL). Linoleyl alcohol (1.40 g, 5.25 mmol) was added along with DMAP (64 mg, 0.52 mmol) and paratoluenesulfonic acid monohydrate (100 mg, 0.52 mmol). EDC (1.0 g, 5.25 mmol) was then added and the reaction was stirred at room temperature for 48 h. The material was purified directly by silica gel chromatography using heptanes/EtOAc as eluent to provide 1.32 g of material containing the desired product and about 30% linoleyl alcohol. The material was carried on without further purification.

Example 89 Compound

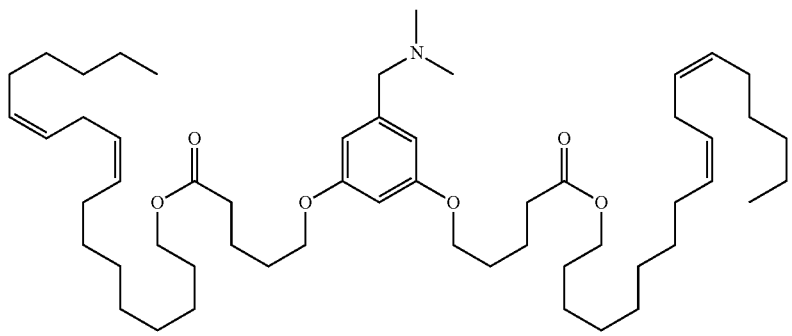 [SMILES: CCCCC/C=C\C/C=C\CCCCCCCCOC(=O)CCCCOc1cc(CN(C)C)cc(OCCCCC(=O)OCCCCCCCC/C=C\C/C=C\CCCCC)c1]

Example 89 was prepared from Intermediate 89c using methods similar to those described in Example 33.

¹H NMR (400 MHz, CDCl₃) δ 6.46 (d, J=2.20 Hz, 2H), 6.33 (t, J=2.30 Hz, 1H), 5.27-5.45 (m, 8H), 4.07 (t, J=6.80 Hz, 4H), 3.88-4.01 (m, 4H), 3.34 (s, 2H), 2.78 (t, J=6.65 Hz, 4H), 2.33-2.44 (m, 4H), 2.24 (s, 6H), 1.98-2.13 (m, 8H), 1.75-1.88 (m, 8H), 1.55-1.70 (m, 4H), 1.22-1.43 (m, 32H), 0.90 (t, J=6.90 Hz, 6H) ppm.

ES-MS m/z=865.8 (MH+).

Example 90 was prepared using methods similar to those employed for the preparation of Example 89.

Example 90

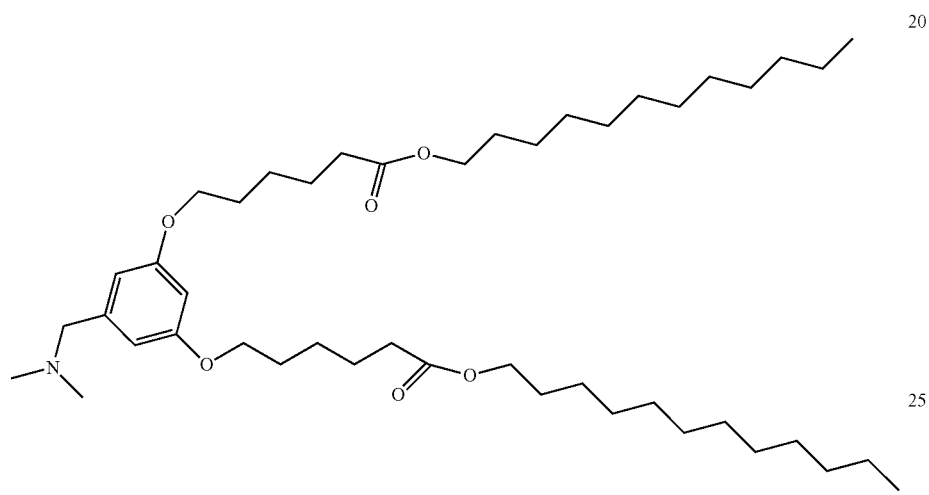 [SMILES: CCCCCCCCCCCCOC(=O)CCCCCOc1cc(CN(C)C)cc(OCCCCCC(=O)OCCCCCCCCCCCC)c1]

¹H NMR (400 MHz, CDCl₃) δ 6.48 (br. s., 2H) 6.35 (br. s., 1H) 4.00-4.11 (m, 4H) 3.94 (t, J=6.44 Hz, 4H) 2.34 (t, J=7.45 Hz, 5H) 2.27 (br. s., 3H) 1.57-1.85 (m, 12H) 1.40-1.57 (m, 4H) 1.20-1.39 (m, 40H) 0.80-0.98 (m, 6H) ppm.

ES-MS m/z=733.9 (MH+).

Synthesis of Example 91

Intermediate 91a:

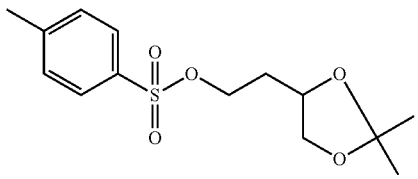

To a suspension of 2-(2,2-dimethyl-1,3-dioxolan-4-yl)ethanol (10 g, 68.4 mmol) in DCM (100 mL) was added pyridine (25 mL). Toluenesulfonic anhydride (26.8 g, 82 mmol) was added and the reaction was stirred overnight at room temperature. The volatiles were removed under reduced pressure and the resulting material was purified by silica gel chromatography using heptanes/EtOAc as eluent to provide 8.92 g of the desired material.

¹H NMR (400 MHz, CDCl₃) δ 7.82-7.77 (m, 2H), 7.38-7.32 (m, 2H), 4.21-4.07 (m, 3H), 4.05-3.99 (m, 1H), 3.55-3.49 (m, 1H), 2.45 (s, 3H), 1.97-1.83 (m, 2H), 1.34 (s, 3H), 1.29 (s, 3H) ppm.

Intermediate 91b:

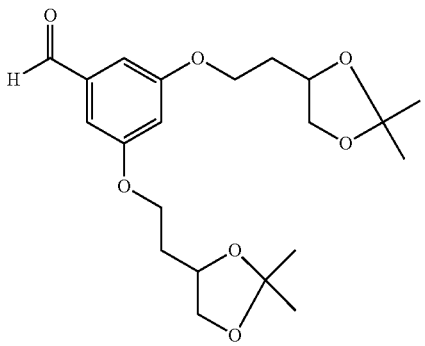 [SMILES: CC1(C)OCC(CCOc2cc(C=O)cc(OCCC3COC(C)(C)O3)c2)O1]

To a flask containing Intermediate 91a (8.92 g, 29.7 mmol) was added 3,5-dihydroxybenzaldehyde (1.9 g, 13.8 mmol) and DMF (50 mL). Potassium carbonate (5.7 g, 41.3 mmol) was added and the reaction was heated to 80 deg C. overnight. The reaction was cooled and water was added. The resulting material was extracted with EtOAc and the combined organic layers were dried over sodium sulfate. The volatiles were removed under reduced pressure and the resulting residue was purified by silica gel chromatography using heptanes/EtOAc as eluent to provide 1.9 g of the desired product.

¹H NMR (400 MHz, CDCl₃) δ 9.89 (s, 1H), 7.02-6.99 (m, 2H), 6.72-6.68 (m, 1H), 4.36-4.26 (m, 2H), 4.18-4.07 (m, 6H), 3.68-3.62 (m, 2H), 2.10-2.02 (m, 4H), 1.43 (s, 3H), 1.37 (s 3H) ppm.

Intermediate 91c:

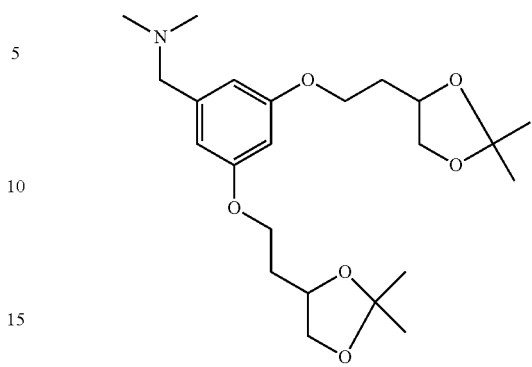

Intermediate 91b (1.4 g, 3.55 mmol) was stirred in DCE (35 mL). Dimethylamine (7.10 mL, 2 M in THF, 14.2 mmol) was added followed by acetic acid (0.20 mL, 3.6 mmol) and then sodium triacetoxyborohydride (1.88 g, 8.87 mmol). The reaction was capped and allowed to stir at room temperature overnight. The reaction was quenched with saturated aqueous sodium bicarbonate and the resulting mixture extracted with EtOAc. The combined organic layers were dried over sodium sulfate and concentrated under reduced pressure to 1.34 g of a crude material that was used without further purification.

Intermediate 91d:

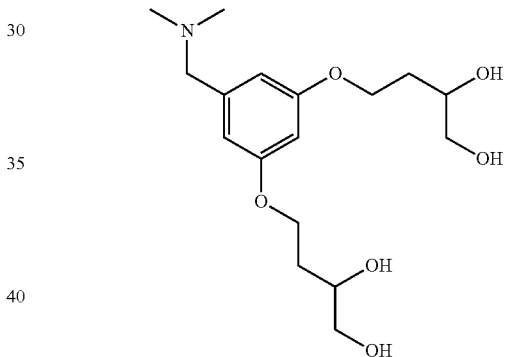

Intermediate 91c (1.34 g, 3.16 mmol) was stirred in MeOH (20 mL). Concentrated aqueous HCl (0.19 mL, 6.33 mmol) was added and the reaction was stirred at room temperature overnight. The volatiles were removed under reduced pressure and the material was used without further purification.

ES-MS m/z=344.2 (MH+).

Example 91 Compound

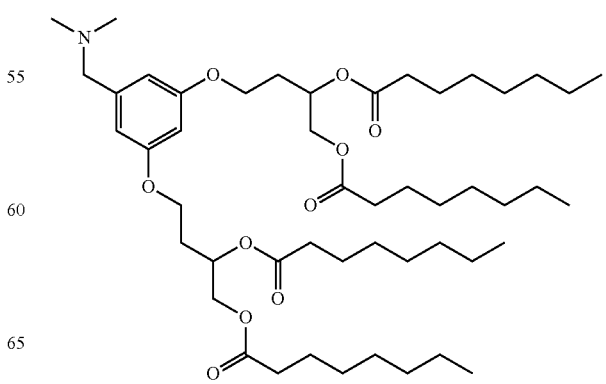

Intermediate 91d (1.0 g, 2.63 mmol) was stirred in DMF (6 mL) until dissolved. DCM (6 mL) was added, followed by pyridine (1.7 mL, 21 mmol) and DMAP (0.096 mg, 0.79 mmol). Octanoyl chloride (2.14 g, 13.16 mmol) was slowly added to the stirring reaction and the resulting mixture was allowed to stir for 3 days at room temperature. The reaction was diluted with water and saturated aqueous sodium bicarbonate and the resulting mixture was extracted with DCM and EtOAc. The combined organic layers were dried over sodium sulfate and the volatiles removed under reduced pressure. The material was purified using silica gel that had been prewashed with 1% acetic acid (by volume) in DCM. The compound was eluted with EtOAc/heptanes and the fractions containing product were washed with saturated aqueous sodium bicarbonate. The resulting organics were dried over sodium sulfate and then concentrated under reduced pressure. The resulting material was purified a second time on silica using heptanes/EtOAc as eluent to yield 1.65 g of the desired product $^1$H NMR (400 MHz, CDCl$_3$) δ 6.59 (br s, 2H) 6.36 (br s, 1H) 5.25-5.37 (m, 2H) 4.35 (dd, J=12.05, 3.26 Hz, 2H) 4.12 (dd, J=11.92, 6.15 Hz, 2H) 3.91-4.09 (m, 4H) 3.58 (br s, 2H) 2.25-2.55 (m, 14H) 2.01-2.13 (m, 4H) 1.49-1.70 (m, 8H) 1.13-1.39 (m, 32H) 0.77-0.99 (m, 12H) ppm.

ES-MS m/z=848.6 (MH+).

Examples 92-94 were prepared using methods similar to those employed for the preparation of Example 91.

Example 92

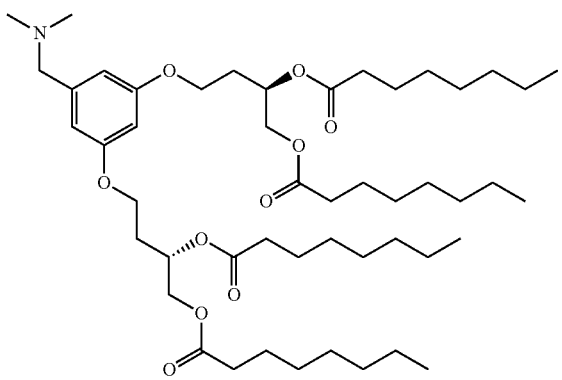 [SMILES: CCCCCCCC(=O)OC[C@@H](CCOc1cc(CN(C)C)cc(OCC[C@@H](COC(=O)CCCCCCC)OC(=O)CCCCCCC)c1)OC(=O)CCCCCCC]

$^1$H NMR (400 MHz, CDCl$_3$) δ 0.74-0.97 (m, 12H) 1.14-1.40 (m, 32H) 1.51-1.71 (m, 8H) 2.07 (q, J=5.94 Hz, 4H) 2.21-2.46 (m, 14H) 3.44 (s., 2H) 3.89-4.07 (m, 4H) 4.12 (dd, J=11.92, 6.15 Hz, 2H) 4.34 (dd, J=12.05, 3.26 Hz, 2H), 5.20-5.40 (m, 2H) 6.32 (t, J=2.26 Hz, 1H) 6.49 (d, J=2.01 Hz, 2H) ppm.

ES-MS m/z=848.3 (MH+).

Example 93

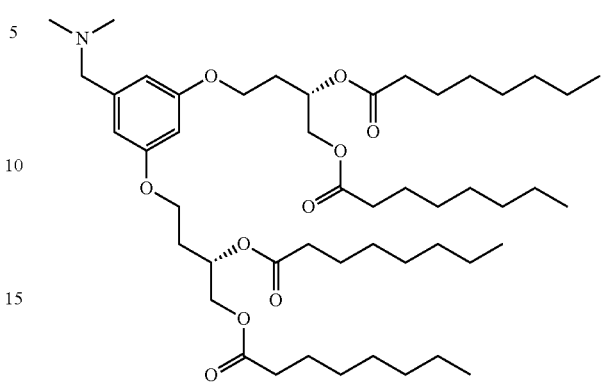

$^1$H NMR (400 MHz, CDCl$_3$) δ 0.87 (m, 12H) 1.14-1.38 (m, 32H) 1.48-1.72 (m, 8H) 2.07 (q, J=6.19 Hz, 4H) 2.22-2.41 (m, 14H) 3.44 (s., 2H) 3.87-4.07 (m, 4H) 4.12 (dd, J=11.92, 6.15 Hz, 2H) 4.34 (dd, J=12.05, 3.26 Hz, 2H) 5.20-5.40 (m, 2H) 6.32 (t, J=2.26 Hz, 1H) 6.49 (d, J=2.01 Hz, 2H) ppm.

ES-MS m/z=848.3 (MH+).

Example 94

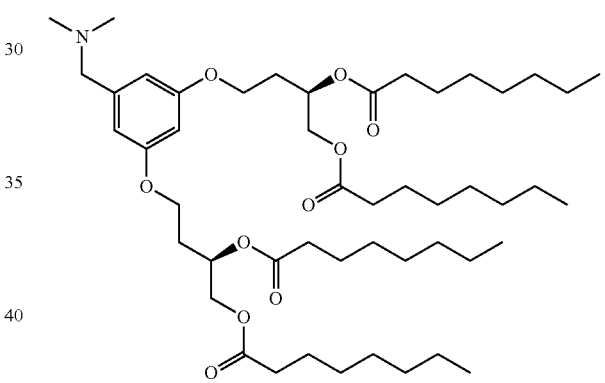

$^1$H NMR (400 MHz, CDCl$_3$) δ 0.87 (m, 12H) 1.12-1.40 (m, 32H) 1.47-1.71 (m, 8H) 2.07 (q, J=6.44 Hz, 4H) 2.18-2.38 (m, 14H) 3.47 (s, 2H) 3.85-4.06 (m, 4H) 4.12 (dd, J=11.92, 6.15 Hz, 2H) 4.34 (dd, J=11.92, 3.39 Hz, 2H) 5.20-5.40 (m, 2H) 6.33 (t, J=2.26 Hz, 1H) 6.49 (d, J=2.01 Hz, 2H) ppm.

ES-MS m/z=848.3 (MH+).

Synthesis of Example 95

Intermediate 95a:

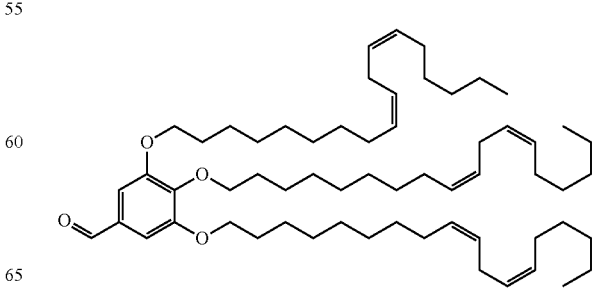

3,4,5-trihydroxybenzaldehyde (600 mg, 3.89 mmol), LinOMs (4427 mg, 12.85 mmol) and potassium carbonate (2690 mg, 19.47 mmol) were mixed in DMF (30 ml) and heated to 80 deg C. overnight. The reaction mixture was poured into ice-water (100 ml) and extracted with diethyl ether (100 ml×2). The organic phase was collected and dried over sodium sulfate and the volatiles removed under reduced pressure. The residue was purified by chromatography on silica gel using heptanes/EtOAc as eluent to provide 2.76 g, of the desired material.

$^1$H NMR (400 MHz, CDCl$_3$) δ 9.84 (s, 1H), 7.72 (dd, J=5.77, 3.26 Hz, 1H), 7.50-7.58 (m, 1H), 7.09 (s, 2H), 5.22-5.47 (m, 13H), 4.23 (t, J=6.02 Hz, 1H), 3.94-4.12 (m, 7H), 2.78 (t, J=6.40 Hz, 7H), 2.06 (q, J=6.69 Hz, 13H), 1.78-1.91 (m, 5H), 1.73-1.78 (m, 2H), 1.70 (dd, J=11.42, 5.40 Hz, 1H), 1.58 (s, 1H), 1.42-1.55 (m, 8H) 1.22-1.42 (m, 51H) 0.82-0.98 (m, 13H) ppm.

Example 95 Compound

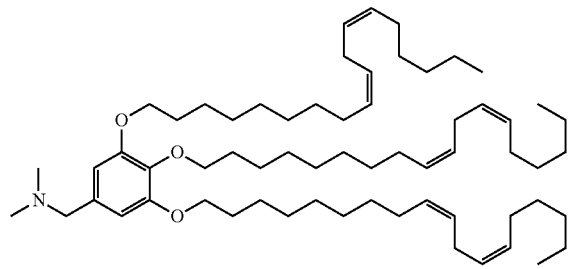 [SMILES: CCCCC/C=C\C/C=C\CCCCCCCCOc1cc(CN(C)C)cc(OCCCCCCCC/C=C\C/C=C\CCCCC)c1OCCCCCCCC/C=C\C/C=C\CCCCC]

Example 95 was prepared from Intermediate 95a using the reaction conditions similar to those used in the preparation of Example 33.

$^1$H NMR (400 MHz, CDCl$_3$) δ 6.50 (s, 2H), 5.44-5.29 (m, 12H), 4.00-3.91 (m, 6H), 3.32 (s, 2H), 2.81-2.75 (m, 6H), 2.24 (s, 6H), 2.10-2.01 (m, 12H), 1.85-1.65 (m, 8H), 1.52-1.24 (m, 50H), 0.92-0.86 (m, 9H) ppm.

$^{13}$C NMR (100 MHz, CDCl$_3$) δ 152.9, 137.5, 134.1, 130.2, 130.1, 130.1, 128.0, 127.9, 107.3, 73.3, 69.0, 64.7, 45.4, 31.3, 30.3, 29.7, 29.7, 29.6, 29.6, 29.5, 29.4, 29.4, 29.3, 29.3, 27.3, 27.2, 27.2, 26.1, 25.6, 22.6, 14.1 ppm.

Synthesis of Example 96

Intermediate 96a:

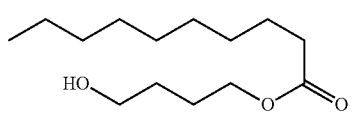 [SMILES: CCCCCCCCCC(=O)OCCCCO]

To a solution of butanediol (3.54 g, 39.3 mmol) in DCM (80 mL) was added pyridine (1.65 mL, 20.4 mmol) and DMAP (0.38 g, 3.2 mmol). Decanoyl chloride (3.0 g, 15.7 mmol) was added and the reaction was stirred at room temperature for 1 h. Volatiles were removed under reduced pressure and the resulting material was purified by silica gel chromatography using heptanes/EtOAc as eluent to yield 3.3 g of the desired product.

$^1$H NMR (400 MHz, CDCl$_3$) δ 4.1 (m, 2H), 3.7 (m, 2H), 2.3 (m, 2H), 1.7 (m, 2H), 1.6 (m, 4H), 1.3 (m, 12H), 0.9 (m, 3H) ppm.

Intermediate 96b:

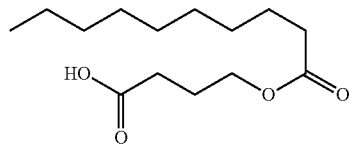 [SMILES: CCCCCCCCCC(=O)OCCCC(=O)O]

Intermediate 96b was prepared from Intermediate 98a and using conditions similar to those used in the synthesis of Intermediate 84a.

$^1$H NMR (400 MHz, CDCl$_3$) δ 4.1 (m, 2H), 2.5 (m, 2H), 2.3 (m, 2H), 2.0 (m, 2H), 1.6 (m, 2H), 1.3 (m, 12H), 0.9 (m, 3H) ppm.

Intermediate 96c:

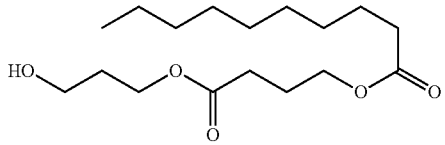 [SMILES: CCCCCCCCCC(=O)OCCCC(=O)OCCCO]

Intermediate 98c was prepared from Intermediate 98b and 1,3-propanediol using conditions similar to those employed in the preparation of Intermediate 18a.

$^1$H NMR (400 MHz, CDCl$_3$) δ 4.3 (m, 2H), 4.1 (m, 2H), 3.7 (m, 2H), 2.4 (m, 2H), 2.3 (m, 2H), 2.0 (m, 2H), 1.9 (m, 3H), 1.6 (m, 2H), 1.3 (m, 12H), 0.9 (m, 3H) ppm.

Intermediate 96d:

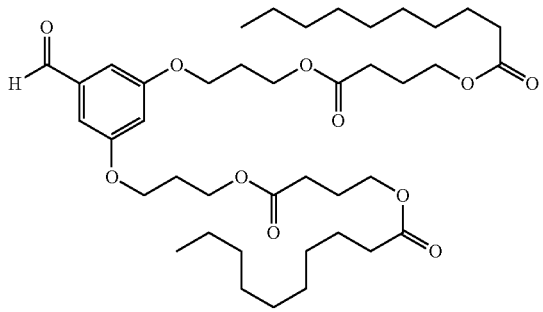 [SMILES: CCCCCCCCCC(=O)OCCCC(=O)OCCCOc1cc(C=O)cc(OCCCOC(=O)CCCOC(=O)CCCCCCCCC)c1]

Intermediate 96d was prepared from Intermediate 98c using the conditions similar to those employed in the synthesis of Intermediate 18b.

$^1$H NMR (400 MHz, CDCl$_3$) δ δ 9.9 (s, 1H), 7.0 (s, 2H), 6.7 (s, 1H), 4.3 (m, 4H), 4.1 (m, 8H), 2.4 (m, 4H), 2.3 (m, 4H), 2.2 (m, 4H), 2.0 (m, 4H), 1.6 (m, 4H), 1.3 (m, 24H), 0.9 (m, 6H) ppm.

Example 96 Compound

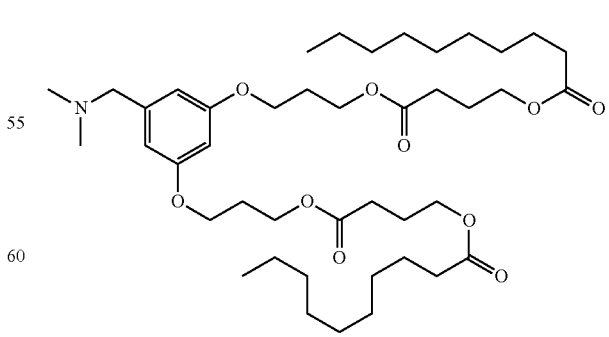

Example 96 was prepared from Intermediate 96d using the reaction conditions similar to those used in the synthesis of Example 33.

¹H NMR (400 MHz, CDCl₃) δ 0.81-0.92 (m, 6H) 1.18-1.37 (m, 24H) 1.53-1.67 (m, 4H) 1.96 (quin, J=6.90 Hz, 4H) 2.09 (quin, J=6.27 Hz, 4H) 2.23 (s, 6H) 2.28 (t, J=7.53 Hz, 4H) 2.40 (t, J=7.53 Hz, 4H) 3.33 (s, 2H) 4.02 (t, J=6.02 Hz, 4H) 4.09 (t, J=6.00 Hz, 4H) 4.26 (t, J=6.27 Hz, 4H) 6.33 (t, J=2.26 Hz, 1H) 6.47 (d, J=2.26 Hz, 2H) ppm.

ES-MS m/z=764.5 (MH+).

Synthesis of Example 97

Intermediate 97a:

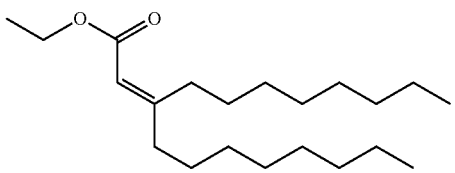 [SMILES: CCCCCCCCC(=CC(=O)OCC)CCCCCCCC]

A solution of 9-heptadecanone (15 g, 59 mmol) and triethylphosphonoacetate (13.2 g, 59 mmol) was stirred in THF (100 mL). To this reaction was added NaOEt (26.4 mL, 21% in EtOH, 70.7 mmol) and the resulting solution was heated to reflux for 48 h. The reaction was acidified with 1 M HCl and then diluted with EtOAc. The organic layer was collected and washed with saturated aqueous sodium bicarbonate. The resulting organic material was dried over sodium sulfate and the volatiles removed under reduced pressure to yield a crude material that was purified by silica gel chromatography using heptanes/EtOAc as eluent, providing 11.7 g of the desired product.

¹H NMR (400 MHz, CDCl₃) δ 5.62 (s, 1H) 4.01-4.26 (m, 2H) 2.49-2.68 (m, 2H) 2.13 (m, 2H) 1.44 (dd, J=7.33, 4.80 Hz, 4H) 1.17-1.35 (m, 23H) 0.83-0.98 (m, 6H) ppm.

Intermediate 97b:

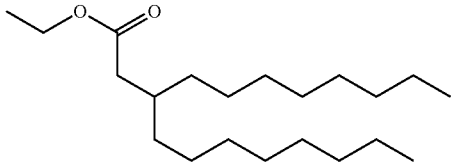 [SMILES: CCCCCCCCC(CCCCCCCC)CC(=O)OCC]

Intermediate 97a (11.75 g, 36.2 mmol) was stirred in DCM (16.5 mL) and MeOH (165 mL). Pd/C (3.85 g, 10% Pd) was added and the reaction flask was fitted with a balloon filled with hydrogen. The reaction was stirred at room temperature for 24 h. The reaction was degassed with nitrogen and filtered through celite with a wash of DCM and MeOH. The filtrate was collected and the volatiles removed under reduced pressure to provide 10.6 g of material that was used without further purification.

¹H NMR (400 MHz, CDCl₃) δ 4.13 (q, J=7.16 Hz, 2H) 2.39 (t, J=7.45 Hz, 2H) 2.22 (d, J=6.82 Hz, 2H) 1.84 (br. s., 1H) 1.56 (t, J=7.20 Hz, 2H) 1.19-1.36 (m, 27H) 0.81-0.95 (m, 6H) ppm.

Intermediate 97c:

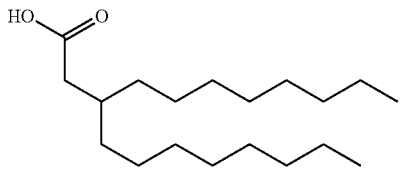 [SMILES: CCCCCCCCC(CCCCCCCC)CC(=O)O]

Intermediate 97b (10.6 g, 32.5 mmol) was stirred with NaOH (9.74 mL, 10 M, 97.4 mmol) in MeOH (100 mL) and DCM (10 mL). The reaction was heated to reflux overnight. Aqueous HCl was added to neutralize the solution, the volatiles were removed under reduced pressure and the resulting material was taken back up in DCM. The organics were washed with aqueous saturated sodium bicarbonate and the resulting aqueous layer was extracted with DCM. The combined organics were dried over magnesium sulfate, filtered, and concentrated under reduced pressure. The material was purified by silica gel chromatography using heptanes/EtOAc as eluent. The resulting material was taken up in DCM and loaded onto an NH₂ functionalized column. The column was washed with DCM and then DCM/MeOH. The product was eluted with acidic methanol and the eluent concentrated under reduced pressure. The residue was taken up in DCM and washed with saturated aqueous sodium bicarbonate, dried over magnesium sulfate, filtered, and concentrated under reduced pressure to provide 6.5 g of the desired product.

¹H NMR (400 MHz, CDCl₃) δ 2.28 (d, J=7.07 Hz, 2H) 1.86 (br. s., 1H) 1.15-1.44 (m, 28H) 0.82-0.97 (m, 6H) ppm.

Intermediate 97d:

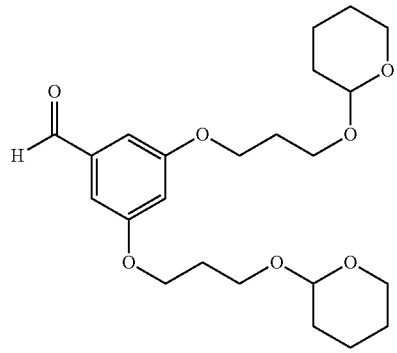 [SMILES: O=Cc1cc(OCCCOC2CCCCO2)cc(OCCCOC2CCCCO2)c1]

A solution of 3,5-dihydroxybenzaldehyde (3 g, 22 mmol) and 2-(3-bromopropoxy)tetrahydro-2H-pyran (8.11 mL, 47.8 mmol) were stirred in DMF (100 mL). Potassium carbonate (15 g, 109 mmol) was added and the reaction was heated to 80 deg C. overnight. The reaction was diluted with brine and EtOAc, followed by saturated aqueous sodium bicarbonate. The resulting mixture was filtered and the organic layer was collected, dried over sodium sulfate, and the volatiles removed under reduced pressure. The resulting material was purified by silica gel chromatography using heptanes/EtOAc as eluent to provide 3.8 g of the desired material.

¹H NMR (400 MHz, CDCl₃) δ 9.88 (s, 1H) 6.84-7.12 (m, 2H) 6.68 (t, J=2.40 Hz, 1H) 4.52-4.76 (m, 1H) 4.13 (t, J=6.32 Hz, 2H) 3.78-4.05 (m, 2H) 3.44-3.73 (m, 2H) 1.97-2.27 (m, 2H) 1.79-1.92 (m, 1H) 1.67-1.79 (m, 1H) 1.41-1.67 (m, 4H) ppm.

Intermediate 97e:

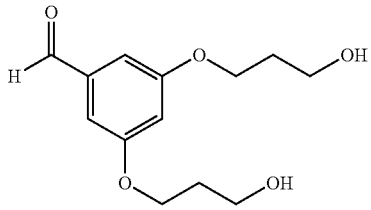 [SMILES: O=Cc1cc(OCCCO)cc(OCCCO)c1]

Intermediate 97f:

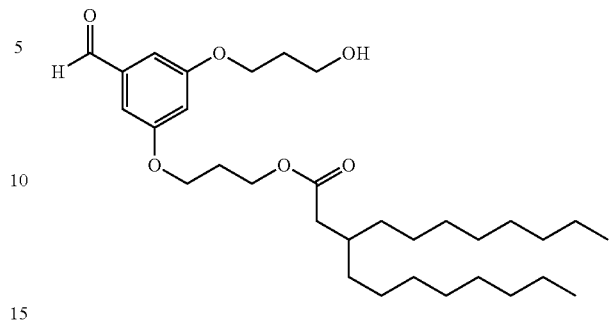

Intermediate 97d (2.6 g, 6.15 mmol) was stirred in MeOH (40 mL) and THF (40 mL) and HCl (24.6 mL, 1 N in water, 24.6 mmol). The reaction was stirred at room temperature for 4 h. Saturated aqueous sodium bicarbonate was added and the reaction was concentrated under reduced pressure. The resulting mixture was extracted with dichloromethane and the combined organics were dried over sodium sulfate. The volatiles were removed under reduced pressure and the resulting material was purified by silica gel chromatography using heptanes/EtOAc as eluent to provide 1.4 g of the desired material.

$^1$H NMR (400 MHz, CDCl$_3$) δ 9.90 (s, 1H) 7.03 (d, J=2.27 Hz, 2H) 6.73 (t, J=2.27 Hz, 1H) 4.17 (t, J=6.06 Hz, 4H) 3.88 (t, J=5.81 Hz, 4H) 1.98-2.20 (m, 4H) ppm.

Intermediate 97e (1.0 g, 3.93 mmol), the acid from Intermediate 99c (1.41 g, 4.72 mmol), EDC (0.90 g, 4.7 mmol), DIEA (2.06 mL, 11.8 mmol), and DMAP (0.48 g, 3.93 mmol) were dissolved in DCE (20 mL) and the resulting solution was split into two portions. Each portion was heated in a microwave reactor for 20 min at 70 deg C. The resulting mixtures were combined and purified directly by silica gel chromatography using heptanes/EtOAc as eluent to provide 680 mg of the desired material.

$^1$H NMR (400 MHz, CDCl$_3$) δ 9.90 (s, 1H) 7.02 (ddd, J=7.83, 2.27, 1.26 Hz, 1H) 6.72 (t, J=2.27 Hz, 1H) 4.22-4.35 (m, 2H) 4.13-4.22 (m, 2H) 4.09 (t, J=6.06 Hz, 1H) 3.88 (q, J=5.81 Hz, 2H) 2.25 (d, J=6.82 Hz, 2H) 1.99-2.19 (m, 4H) 1.84 (br. s., 1H) 1.14-1.38 (m, 30H) 0.89 (td, J=6.95, 3.54 Hz, 6H) ppm.

Intermediate 97g:

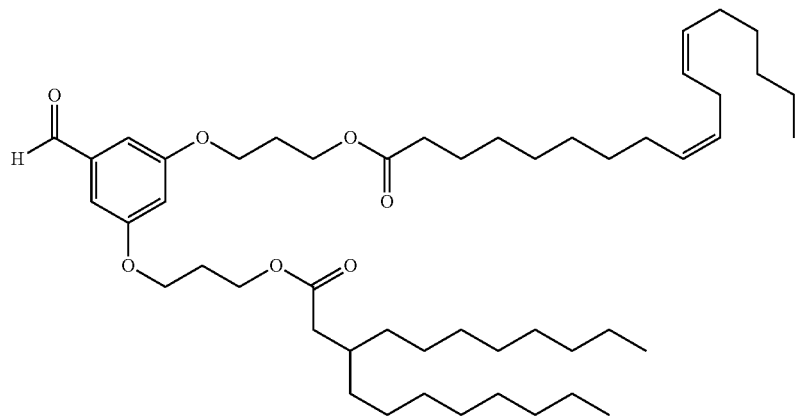 [SMILES: CCCCC/C=C\C/C=C\CCCCCCCC(=O)OCCCOc1cc(C=O)cc(OCCCOC(=O)CC(CCCCCCCC)CCCCCCCC)c1]

Intermediate 97g was prepared from Intermediate 99f using the conditions used to prepare Intermediate 18a.

$^1$H NMR (400 MHz, CDCl3) δ 9.90 (s, 1H) 7.01 (d, J=2.27 Hz, 2H) 6.70 (t, J=2.27 Hz, 1H) 5.28-5.44 (m, 4H) 4.27 (t, J=6.32 Hz, 4H) 4.02-4.17 (m, 4H) 2.78 (t, J=6.44 Hz, 2H) 2.32 (t, J=7.45 Hz, 2H) 2.25 (d, J=6.82 Hz, 2H) 2.14 (quin, J=6.19 Hz, 4H) 1.98-2.09 (m, 4H) 1.84 (br. s., 1H) 1.58-1.70 (m, 2H) 1.18-1.41 (m, 42H) 0.77-0.99 (m, 9H) ppm.

Example 97 Compound

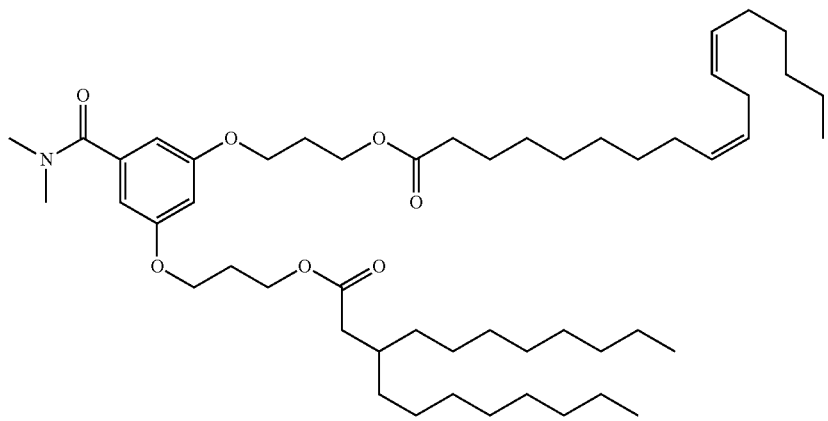 [SMILES: CCCCC/C=C\C/C=C\CCCCCCCC(=O)OCCCOc1cc(OCCCOC(=O)CC(CCCCCCCC)CCCCCCCC)cc(C(=O)N(C)C)c1]

Example 97 was prepared from Intermediate 97g using conditions similar to those used to prepare Example 39.

$^1$H NMR (400 MHz, CDCl$_3$) δ 6.49 (br. s., 2H) 6.27-6.43 (m, 1H) 5.29-5.46 (m, 4H) 4.26 (t, J=6.32 Hz, 4H) 4.03 (t, J=6.19 Hz, 4H) 3.36 (br. s., 2H) 2.78 (t, J=6.57 Hz, 2H) 2.18-2.39 (m, 10H) 1.96-2.18 (m, 8H) 1.84 (br. s., 1H) 1.48-1.73 (m, 4H) 1.17-1.47 (m, 40H) 0.74-1.03 (m, 9H) ppm.

ES-MS m/z=827.6 (MH+).

Synthesis of Example 98

Intermediate 98a:

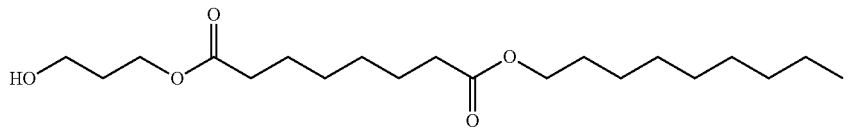 [SMILES: CCCCCCCCCOC(=O)CCCCCCC(=O)OCCCO]

Intermediate 98a was prepared from Intermediate 79a using conditions similar to those employed in the preparation of Intermediate 18a.

Rf=0.51 (silica, 5% MeOH in DCM, cerium molybdate).

Example 98 Compound

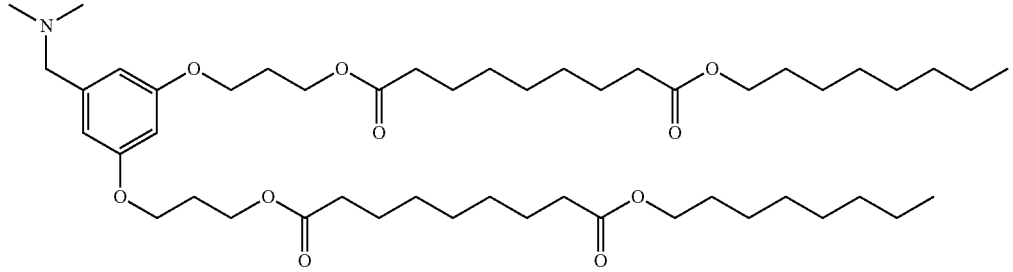 [SMILES: CCCCCCCCOC(=O)CCCCCCCC(=O)OCCCOc1cc(CN(C)C)cc(OCCCOC(=O)CCCCCCCC(=O)OCCCCCCCC)c1]

Example 98 was prepared from Intermediate 98a using conditions similar to those described for the preparation of Example 33.

$^1$H NMR (400 MHz, CDCl$_3$) δ 6.47 (s, 2H), 6.34 (s, 1H), 4.25 (t, J=6.3 Hz, 4H), 4.07-4.01 (m, 8H), 3.34 (s, 2H), 2.29 (q, J=7.2 Hz, 8H), 2.24 (s, 6H), 2.09 (quin, J=6.2 Hz, 4H), 1.65-1.58 (m, 12H), 1.31-1.28 (m, 32H), 0.88 (t, J=6.8 Hz, 6H) ppm.

ES-MS m/z=848.5 (MH+).

Synthesis of Example 99

Intermediate 99a:

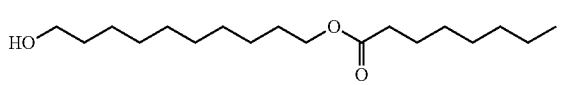 [SMILES: CCCCCCCC(=O)OCCCCCCCCCCO]

Prepared from 1,10-decanediol and octanoyl chloride using conditions similar to those used in the preparation of Intermediate 96a.

$^1$H NMR (400 MHz, CDCl$_3$) δ 4.06 (t, J=6.65 Hz, 2H), 3.64 (t, J=6.65 Hz, 2H), 2.29 (t, J=7.65 Hz, 2H), 1.50-1.70 (m, 5H), 1.18-1.41 (m, 19H), 0.88 (t, J=7.28 Hz, 3H) ppm.

Intermediate 99b:

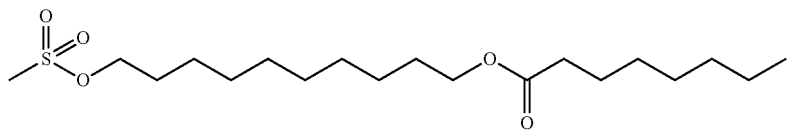 [SMILES: CCCCCCCC(=O)OCCCCCCCCCCOS(C)(=O)=O]

A mixture of Intermediate 99a (3.34 g, 11.1 mmol) and triethylamine (6.2 mL, 44 mmol) in DCM (40 mL) was stirred in an ice bath and MsCl (1.04 mL, 13.3 mmol) was added. The reaction was allowed to warm to room temperature and was stirred overnight. The reaction was then poured into ice water. The resulting organic phase was collected, dried over sodium sulfate, and concentrated under reduced pressure to yield 4.2 g of material that was used without further purification.

$^1$H NMR (400 MHz, CDCl$_3$) δ 4.23 (t, J=6.57 Hz, 1H), 4.06 (t, J=6.82 Hz, 2H), 3.15 (s, 1H), 3.01 (s, 1H), 2.30 (t, J=7.58 Hz, 2H), 1.75 (dd, J=8.08, 6.82 Hz, 1H), 1.62 (t, J=6.95 Hz, 5H), 1.40 (t, J=7.33 Hz, 4H), 1.18-1.34 (m, 17H), 0.89 (t, J=7.10 Hz, 3H) ppm.

Example 99 Compound

The final compound was then obtained from Intermediate 99b by following procedures similar to those used in the preparation of Intermediate 97d and Example 33.

$^1$H NMR (400 MHz, CDCl$_3$) δ 7.54 (s, 2H); 7.38 (s, 1H); 5.15 (s, 4H); 4.07 (t, J=6.7 Hz, 4H); 4.02 (s, 2H); 2.66 (s, 6H); 2.42 (t, J=7.5 Hz, 4H); 2.30 (t, J=7.7 Hz, 4H); 1.74-1.58 (m, 12H); 1.45-1.37 (m, 4H); 1.35-1.22 (m, 24H); 0.89 (t, J=7.0 Hz, 6H) ppm.

LCMS m/z=732.8 (MH+).

Example 100 was prepared using methods similar to those employed for the preparation of Example 99.

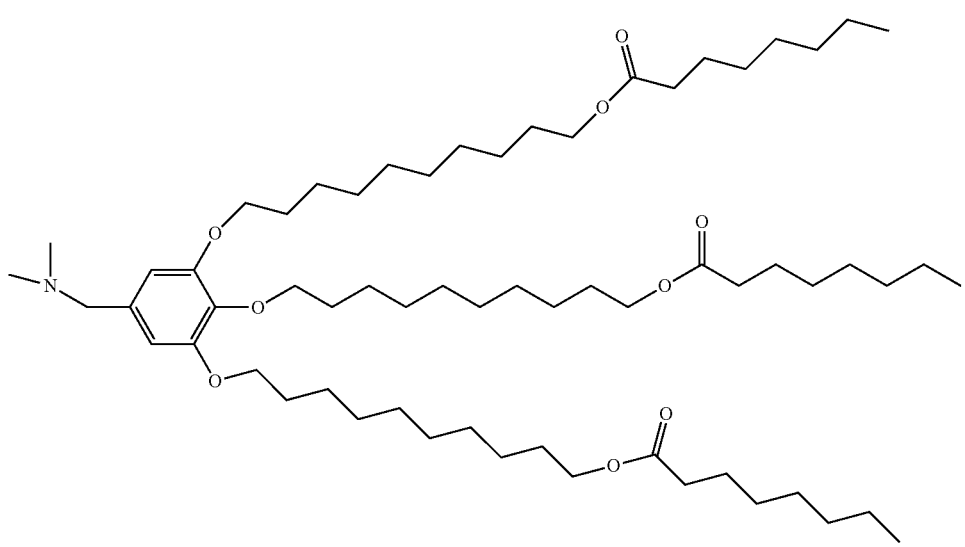 [SMILES: CCCCCCCC(=O)OCCCCCCCCCCOc1cc(CN(C)C)cc(OCCCCCCCCCCOC(=O)CCCCCCC)c1OCCCCCCCCCCOC(=O)CCCCCCC]

Example 100

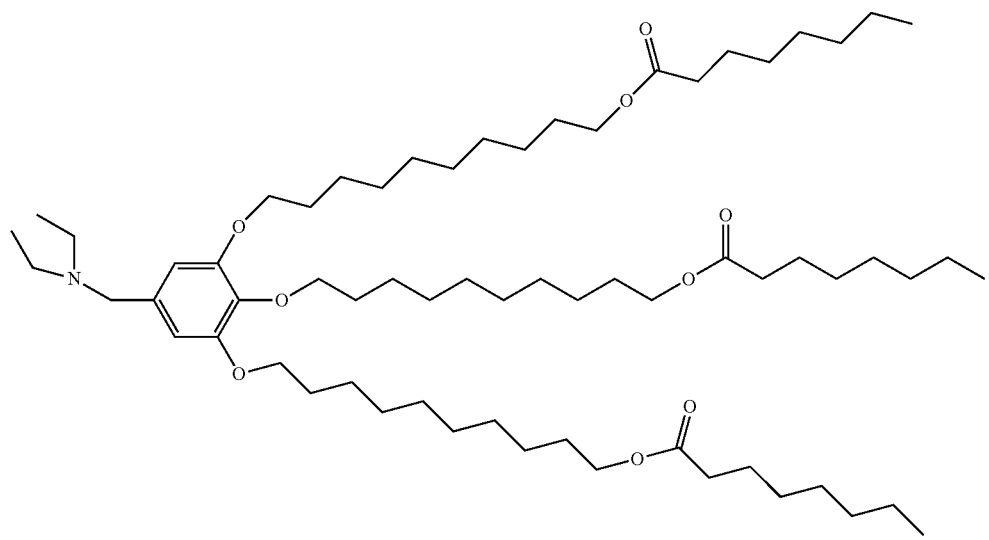 [SMILES: CCCCCCCC(=O)OCCCCCCCCCCOc1cc(CN(CC)CC)cc(OCCCCCCCCCCOC(=O)CCCCCCC)c1OCCCCCCCCCCOC(=O)CCCCCCC]

Intermediate 77b was reacted with the acid prepared analogously to Intermediate 79a, and Intermediate 97c under the conditions used to prepare Example 77.

Example 101

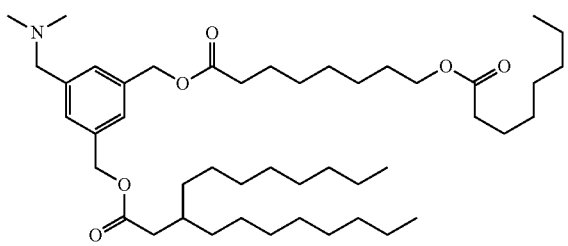 [SMILES: CCCCCCCCC(CCCCCCCC)CC(=O)OCc1cc(COC(=O)CCCCCCCOC(=O)CCCCCCC)cc(CN(C)C)c1]

$^1$H NMR (400 MHz, CDCl$_3$) δ 7.27 (s, 2H), 7.24 (s, 1H), 5.11 (s, 4H), 4.06 (t, J=6.8 Hz, 2H), 3.44 (s, 2H), 2.37 (t, J=7.5 Hz, 2H), 2.32-2.29 (m, 4H), 2.26 (s, 6H), 1.88 (m, 1H), 1.70-1.59 (m, 6H), 1.35-1.26 (m, 42H), 0.89 (t, J=6.8 Hz, 9H) ppm.

ES-MS m/z=744.4 (MH+).

Synthesis of Example 102

Intermediate 102a

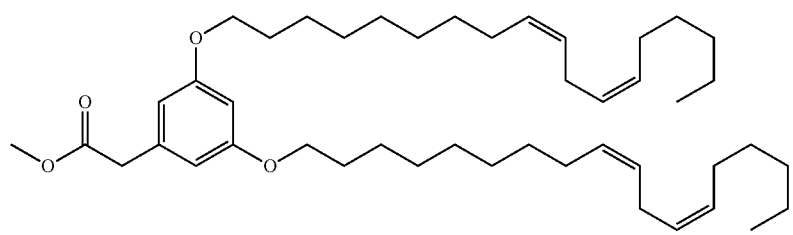 [SMILES: CCCCC/C=C\C/C=C\CCCCCCCCOc1cc(CC(=O)OC)cc(OCCCCCCCC/C=C\C/C=C\CCCCC)c1]

To a suspension of potassium carbonate (12.1 g, 88 mmol) in dimethyl formamide (100 mL) was added methyl 2-(3,5-dihydroxyphenyl)acetate (4.0 g, 22 mmol) and linoleyl mesylate (16.6 g, 48 mmol). The reaction was heated in a 100° C. bath for 4 h, then allowed to cool to ambient temperature. Water (100 mL) was added, and the reaction was extracted with ethyl acetate (3×100 mL). The combined organic layers were washed with brine, dried over sodium sulfate and concentrated under reduced pressure. The residue was purified by silica gel chromatography using ethyl acetate and n-hexane as eluent to provide the desired compound.

ES-MS m/z=680 (MH+).

Intermediate 102b:

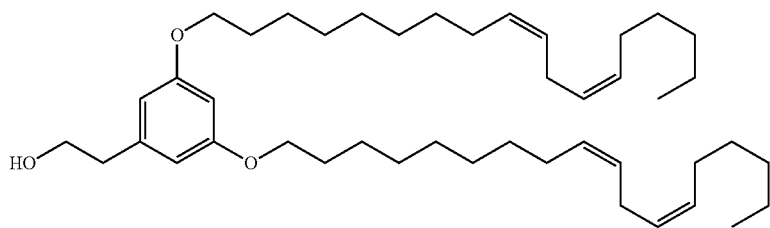 [SMILES: CCCCC/C=C\C/C=C\CCCCCCCCOc1cc(CCO)cc(OCCCCCCCC/C=C\C/C=C\CCCCC)c1]

To a suspension of lithium aluminum hydride (671 mg, 17.6 mmol) in tetrahydrofuran (50 mL) was slowly added a solution of Intermediate 104a (6 g, 8.8 mmol) in THF (38 mL). The reaction was then stirred at ambient temperature for 3 h, at which time the reaction was cooled in a 0° C. bath and quenched with water (5 mL) and ethyl acetate (5 mL). The reaction was stirred for 10 min, then filtered over celite. The filtrate was concentrated under reduced pressure to provide the desired compound.

ES-MS m/z=652 (MH+).

Intermediate 102c:

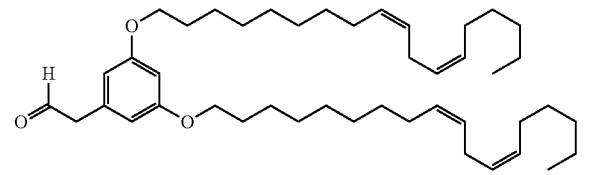 [SMILES: CCCCC/C=C\C/C=C\CCCCCCCCOc1cc(CC=O)cc(OCCCCCCCC/C=C\C/C=C\CCCCC)c1]

To a solution of Intermediate 102b (5.3 g, 8.1 mmol) in dichloromethane (86 mL) was added Dess-Martin periodinane (10.3 g, 24 mmol). The reaction was stirred at ambient temperature for 2 h, at which time the reaction was quenched by the addition of aqueous sodium bicarbonate solution. The reaction was extracted with dichloromethane and the combined organic layers were dried over sodium sulfate and concentrated under reduced pressure. The residue was purified with silica-gel chromatography using ethyl acetate and n-hexane as eluent to provide the desired compound.

ES-MS m/z=649 (MH+).

Example 102 Compound

To a solution of Intermediate 102c (2.5 g, 3.8 mmol) in ethanol (10 mL) and tetrahydrofuran (10 mL) was added dimethylamine hydrochloride (627 mg, 5.7 mmol), followed by triethylamine (1.1 mL, 7.7 mmol) and titanium (IV) isopropoxide (2.1 g, 7.7 mmol). The reaction was stirred at ambient temperature, at which time sodium borohydride (216 mg, 5.7 mmol) was added. The reaction was stirred at ambient temperature for an additional 10 h. The reaction was quenched by slow addition of water (2 mL), and the resultant mixture was filtered through celite. The residue was washed with tetrahydrofuran and the combined filtrates were concentrated under reduced pressure. The residue was purified by silica-gel chromatography, using methanol in dichloromethane with 0.1% ammonium hydroxide as eluent, to provide the desired compound.

$^1$H NMR (400 MHz, CDCl$_3$) δ 6.36 (d, J=2.3 Hz, 2H); 6.32 (t, J=2.0 Hz, 1H); 5.44-5.32 (m, 8H); 3.93 (t, J=6.5 Hz, 4H); 2.81-2.74 (m, 6H); 2.62-2.58 (m, 2H); 2.36 (s, 6H); 2.08 (t, J=6.9 Hz, 4H); 2.06 (t, J=6.9 Hz, 4H); 1.78 (quin, J=7.0 Hz, 4H); 1.48-1.27 (m, 32H), 0.90 (t, J=7.0 Hz, 6H).

ES-MS m/z=678.7 (MH+).

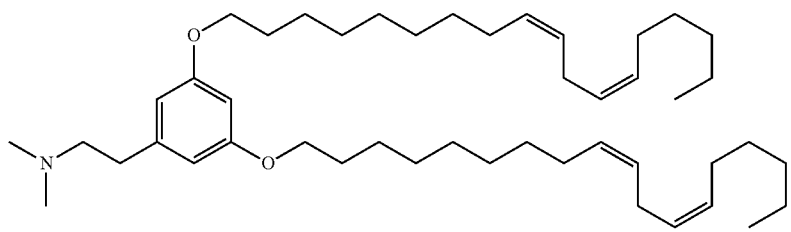 [SMILES: CCCCC/C=C\C/C=C\CCCCCCCCOc1cc(CCN(C)C)cc(OCCCCCCCC/C=C\C/C=C\CCCCC)c1]

Synthesis of Example 103

Intermediate 103a:

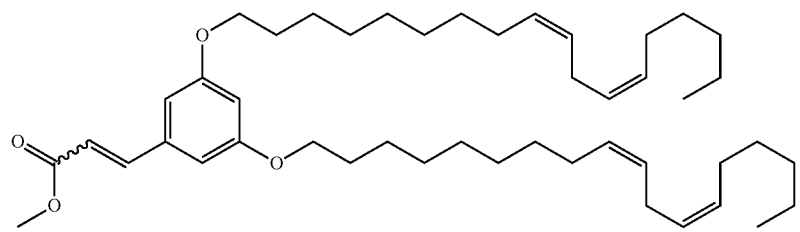 [SMILES: CCCCC/C=C\C/C=C\CCCCCCCCOc1cc(C=CC(=O)OC)cc(OCCCCCCCC/C=C\C/C=C\CCCCC)c1]

To a suspension of sodium hydride (60% dispersion, 18 mmol) in tetrahydrofuran (50 mL), cooled in a 0° C. bath, was added trimethylphosphonoacetate (1.0 g, 18 mmol). The reaction was stirred for 10 minutes, then a solution of the aldehyde, prepared using conditions similar to those in Example 1a, (7.5 g, 12 mmol) in tetrahydrofuran (25 mL) was added slowly. The reaction was stirred for an additional 1 h, then ice-water (5 mL) was added. The reaction was extracted with ethyl acetate (3×100 mL), and the combined organic phases were dried over sodium sulfate and concentrated under reduced pressure. The residue was purified by silica-gel chromatography with ethyl acetate and n-hexane as eluent to provide the desired compound.

Rf=0.77 (silica, 10% EtOAc in hexane, UV).

Intermediate 103b:

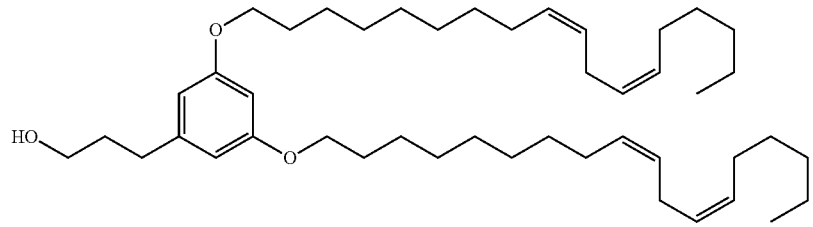 [SMILES: CCCCC/C=C\C/C=C\CCCCCCCCOc1cc(CCCO)cc(OCCCCCCCC/C=C\C/C=C\CCCCC)c1]

To a solution Intermediate 103a (7.7 g, 11.1 mmol) in THF (100 mL), cooled in a 0° C. bath, was added lithium aluminum hydride (927 mg, 24 mmol). The reaction was stirred for 45 minutes, then ice-water was added slowly. The resulting mixture was filtered through celite and the filtrate concentrated under reduced pressure. The residue was purified by silica-gel chromatography with ethyl acetate and n-hexane as eluent to provide the desired compound.

Rf=0.21 (silica, 10% EtOAc in hexane, UV and cerium molybdate).

Intermediate 103c:

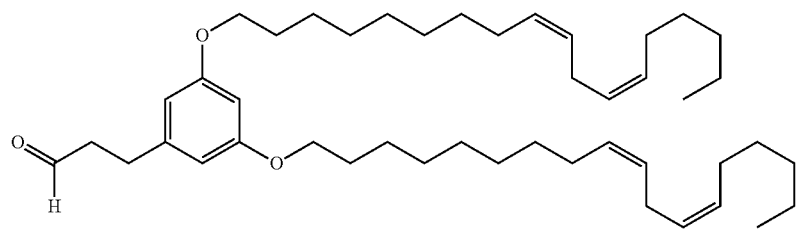 [SMILES: CCCCC/C=C\C/C=C\CCCCCCCCOc1cc(CCC=O)cc(OCCCCCCCC/C=C\C/C=C\CCCCC)c1]

A solution of Intermediate 105b (2.5 g, 3.8 mmol) in tetrahydrofuran (40 mL) was added to a second solution of 2-iodoxybenzoic acid (2.3 g, 8.3 mmol) in DMSO (8 mL). The reaction was stirred at ambient temperature for 2 h. The reaction was diluted with ether and filtered through celite. Water was added, and the reaction was extracted with dichloromethane. The combined organic layers were dried over sodium sulfate and concentrated under reduced pressure. The residue was purified by silica-gel chromatography with ethyl acetate and n-hexane as eluent to provide the desired compound.

Rf=0.75 (silica, 10% EtOAc in hexane, UV and cerium molybdate).

Example 103 Compound

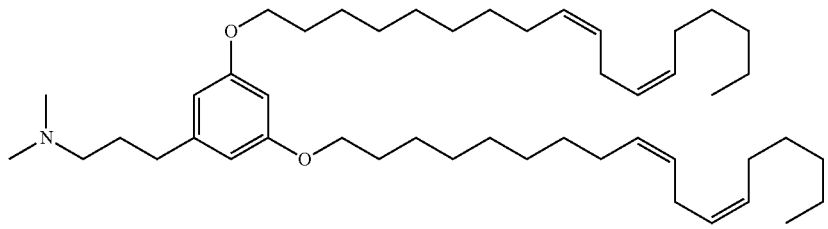 [SMILES: CCCCC/C=C\C/C=C\CCCCCCCCOc1cc(CCCN(C)C)cc(OCCCCCCCC/C=C\C/C=C\CCCCC)c1]

To a solution of Intermediate 103c (2.0 g, 3.0 mmol) in ethanol (40 mL) was added dimethylamine hydrochloride (742 mg, 9.0 mmol), triethylamine (913 mg, 9.0 mmol), and titanium (IV) isopropoxide (2.5 g, 9.0 mmol). The reaction was stirred at amine temperature for 10 h, at which time sodium borohydride (172 mg, 4.5 mmol) was added. The reaction was stirred at ambient temperature for an additional 10 h, at which time water (2 mL) was added. The reaction was filtered through celite and the residue washed with tetrahydrofuran. The filtrate was concentrated under reduced pressure. The residue was purified by silica-gel chromatography with methanol and dichloromethane eluent modified with 0.1% ammonium hydroxide to provide the desired compound.

$^1$H NMR (400 MHz, CDCl$_3$) δ 6.26 (d, J=2.0 Hz, 2H), 6.21 (t, J=2.3 Hz, 1H), 5.22-5.35 (m, 8H), 3.84 (t, J=6.7 Hz, 4H), 2.71 (t, J=6.3 Hz, 4H), 2.49 (t, J=7.8 Hz, 2H), 2.22 (t, J=7.3 Hz, 2H), 2.15 (s, 6H), 1.98 (q, J=6.9 Hz, 8H), 1.65-1.74 (m, J=7.0 Hz, 6H), 1.33-1.42 (m, 5H), 1.15-1.33 (m, 33H), 0.82 (t, J=6.8 Hz, 6H) ppm.

ES-MS m/z=692.5 (MH+).

Synthesis of Example 104

Intermediate 104a:

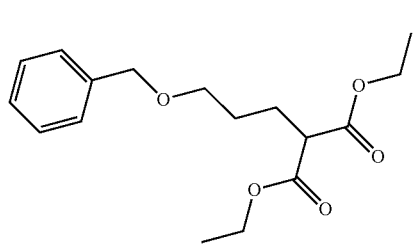 [SMILES: CCOC(=O)C(CCCOCc1ccccc1)C(=O)OCC]

To a suspension of sodium hydride (1.05 g, 26 mmol) in tetrahydrofuran (40 mL), was added diethyl malonate (7 g, 44 mmol). Once evolution of gas had ceased, ((3-bromopropoxy)methyl)benzene (5 g, 22 mmol) was added. The reaction mixture was heated in a 90° C. bath for 6 h, then cooled to ambient temperature. The reaction was diluted with diethyl ether (100 mL) and washed with water (100 mL). The aqueous layer was separated and extracted with diethyl ether (2×100 mL). The combined organic layers were dried over magnesium sulfate and concentrated under reduced pressure. The residue was purified by silica-gel chromatography with ethyl acetate and heptanes as eluent to provide the desired compound.

$^1$H NMR (400 MHz, CDCl$_3$) δ 7.31-7.38 (m, 4H), 7.25-7.31 (m, 1H), 4.50 (s, 2H), 4.10-4.27 (m, 7H), 3.50 (t, J=6.3 Hz, 2H), 3.32-3.41 (m, 2H), 1.93-2.08 (m, 2H), 1.60-1.73 (m, 2H), 1.20-1.38 (m, 10H) ppm.

Intermediate 104b:

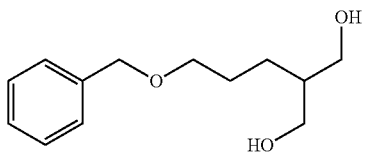 [SMILES: OCC(CO)CCCOCc1ccccc1]

To a solution of Intermediate 104a (7 g, 23 mmol) in tetrahydrofuran (100 mL), cooled in a 0° C. bath, was added lithium aluminum hydride (2.58 g, 68 mmol). The cooling bath was removed and the mixture was stirred at ambient temperature overnight. Ice was added to the reaction, and the mixture was extracted with ethyl acetate. The organic phase was dried over sodium sulfate and concentrated under reduced pressure. The residue was purified by silica-gel chromatography with ethyl acetate and heptanes as eluent to provide the desired compound.

$^1$H NMR (400 MHz, CDCl$_3$) δ 7.27-7.39 (m, 5H), 4.51 (s, 2H), 3.75-3.88 (m, 2H), 3.60-3.73 (m, 2H), 3.41-3.55 (m, 2H), 2.39 (t, J=5.1 Hz, 2H), 1.76 (dt, J=7.2, 3.5 Hz, 1H), 1.59-1.71 (m, 3H), 1.32-1.45 (m, 2H)

Intermediate 104c:

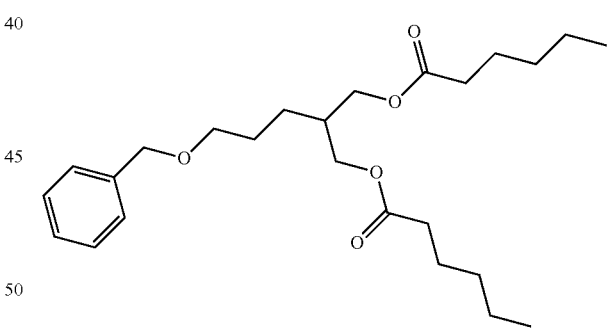

To a mixture of Intermediate 104b (600 mg, 2.7 mmol), pyridine (466 mg, 5.9 mmol) and 4-(dimethylamino)pyridine (16 mg, 0.13 mmol) in dichloromethane (30 mL) was added hexanoyl chloride (792 mg, 5.9 mmol). The reaction was stirred at ambient temperature for 1 h, then was poured into 6M aqueous HCl (20 mL). The mixture was extracted with diethyl ether (2×40 mL). The combined organic phases were dried over sodium sulfate and concentrated under reduced pressure. The residue was purified by silica-gel chromatography with ethyl acetate and heptanes as eluent to provide the desired compound.

$^1$H NMR (400 MHz, CDCl$_3$) δ 7.27-7.39 (m, 5H), 4.43 (s, 2H), 3.96-4.06 (m, 4H), 3.39-3.42 (t, 2H), 2.20-2.24 (t, 4H), 1.94 (m, 1H), 1.52-1.60 (m, 8H), 1.39 (m, 2H), 1.17-1.26 (m, 10H), 0.80-0.85 (t, 6H) ppm.

Intermediate 104d:

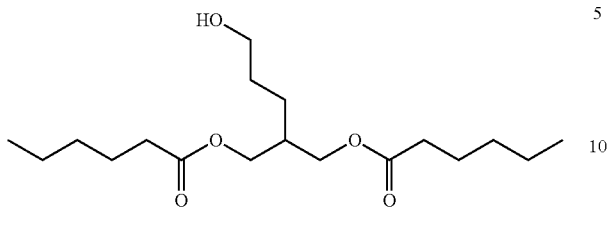

Intermediate 104c (1 g, 2.4 mmol) and palladium (10% by weight on carbon, 20 mg) were taken into methanol (10 mL). The reaction was pressurized with hydrogen to 54 psi and stirred at ambient temperature overnight. The pressure was released and the reaction was filtered. The filtrate was concentrated under reduced pressure to provide the desired compound.

$^1$H NMR (400 MHz, CDCl$_3$) δ 4.06-4.14 (m, 4H), 3.66-3.70 (m, 2H), 2.03-2.06 (m, 1H), 1.59-1.69 (m, 6H), 1.46-1.48 (m, 2H), 1.29-1.36 (m, 10H), 0.89-0.93 (m, 6H) ppm.

Intermediate 104e

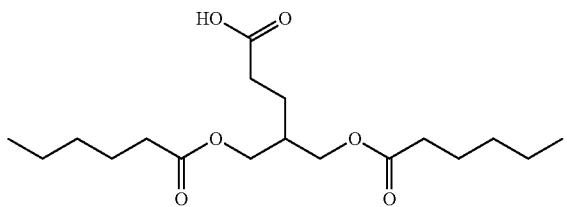 [SMILES: CCCCCC(=O)OCC(CCC(=O)O)COC(=O)CCCCC]

To a solution of Intermediate 104d (760 mg, 2.3 mmol) in acetone (10 mL), cooled in a 0° C. bath, was added Jones' reagent (2 M, 1.8 mmol). The reaction was stirred at ambient temperature for 2 h. Methanol (1 mL) was added and the reaction was stirred for 5 min, then concentrated under reduced pressure. The residue was taken into ethyl acetate (50 mL) and water (540 mL), and the organic phase was collected, dried over sodium sulfate, and concentrated under reduced pressure. The residue was purified by silica-gel chromatography with ethyl acetate and heptanes as eluent to provide the expected product.

ES-MS m/z=343 (M-H-).

Intermediate 104f:

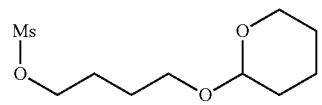 [SMILES: CS(=O)(=O)OCCCCOC1CCCCO1]

To a mixture of the THP protected 1,4-butanediol (9.2 g, 53 mmol) and methanesulfonyl chloride (7.26 g, 63 mmol) in dichloromethane (50 mL), cooled in a 0° C. bath, was added triethylamine (16.0 g, 158 mmol). The cooling bath was removed, and the reaction was stirred at ambient temperature for 30 minutes. The reaction was poured into ice water. The organic phase was separated, dried over sodium sulfate, and concentrated under reduced pressure to provide the desired compound.

$^1$H NMR (400 MHz, CDCl$_3$) δ 4.49-4.51 (m, 1H), 4.22 (t, 2H), 3.69-3.80 (m, 2H), 3.33-3.47 (m, 2H), 2.95 (s, 3H), 1.44-1.83 (m, 11H) ppm.

Intermediate 104g:

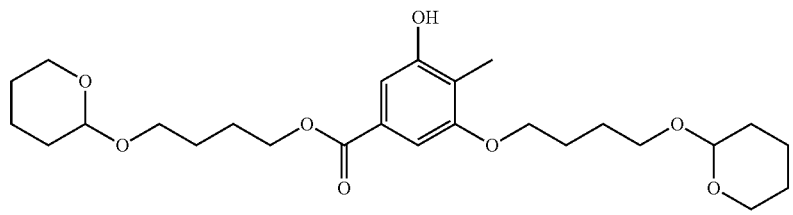 [SMILES: Cc1c(O)cc(C(=O)OCCCCOC2CCCCO2)cc1OCCCCOC1CCCCO1]

A mixture of Intermediate 104f (20.4 g, 81 mmol), 3,5-dihydroxy-4-methylbenzoic acid (4.12 g, 25 mmol), and potassium carbonate (13.55 g, 98 mmol) in dimethylformamide (100 mL) was heated in an 80° C. bath overnight. The reaction was cooled to ambient temperature and poured into ice-water (150 mL). The mixture was extracted with diethyl ether (2×150 mL) and the combined organic phases were dried over sodium sulfate and concentrated under reduced pressure. The residue was purified by silica-gel chromatography with ethyl acetate and heptanes as eluent to provide the desired compound.

ES-MS m/z=479 (M-1).

Intermediate 104h:

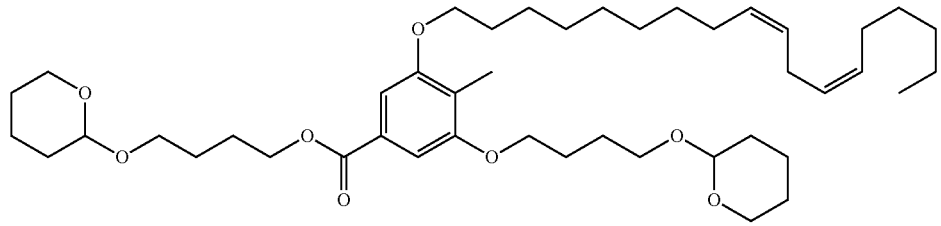 [SMILES: CCCCC/C=C\C/C=C\CCCCCCCCOc1cc(C(=O)OCCCCOC2CCCCO2)cc(OCCCCOC2CCCCO2)c1C]

A mixture of Intermediate 104g (2.07 g, 4.3 mmol), linoleyl mesylate (1.78 g, 5.2 mmol) and potassium carbonate (2.38 g, 17.2 mmol) in dimethylformamide (20 mL) was heated in an 80° C. bath overnight. The reaction was cooled to ambient temperature and poured into ice-water. The mixture was extracted with diethyl ether (2×100 mL). The organic phases were combined, dried over sodium sulfate, and concentrated under reduced pressure. The residue was purified by silica-gel chromatography with ethyl acetate and heptanes as eluent to provide the desired product.

$^1$H NMR (400 MHz, CDCl$_3$) δ 7.20 (s, 2H), 5.34-5.42 (m, 4H), 4.60-4.63 (m, 2H), 4.36 (t, 2H), 4.00-4.08 (m, 4H), 3.83-3.86 (m, 4H), 3.47-3.51 (m, 4H), 2.80 (t, 2H), 2.16 (s, 3H), 2.06-2.08 (m, 5H), 1.73-1.84 (m, 14H), 1.51-1.60 (m, 20H), 1.29-1.37 (m, 18H), 0.90 (m, 4H) ppm.

Intermediate 104i:

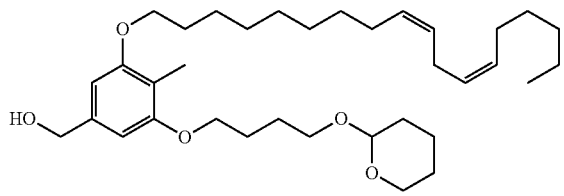 [SMILES: CCCCC/C=C\C/C=C\CCCCCCCCOc1cc(CO)cc(OCCCCOC2CCCCO2)c1C]

To a solution of Intermediate 104h (1.55 g, 2.1 mmol) in tetrahydrofuran (25 mL), cooled in a 0° C. bath, was added lithium aluminum hydride (89 mg, 2.3 mmol). The cooling bath was removed and the reaction was stirred overnight. Ice was added, and the mixture was extracted with ethyl acetate. The organic phase was separated, dried over sodium sulfate, and concentrated under reduced pressure. The residue was purified by silica-gel chromatography using ethyl acetate and heptanes as eluent to provide the desired compound.

$^1$H NMR (400 MHz, CDCl$_3$) δ 6.54 (s, 2H), 5.34-5.44 (m, 4H), 3.97-4.03 (m, 4H), 3.85-3.87 (m, 2H), 3.49-3.52 (m, 2H), 2.80 (t, 2H), 2.11 (s, 3H), 2.07-2.08 (m, 4H), 1.72-1.90 (m, 18H), 1.26-1.35 (m, 16H), 0.91 (t, 4H) ppm.

Intermediate 104j:

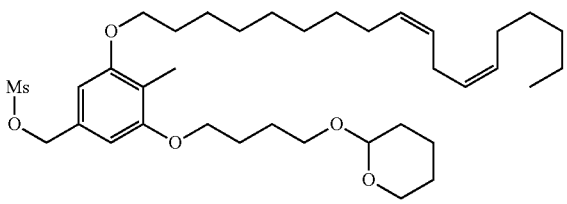 [SMILES: CCCCC/C=C\C/C=C\CCCCCCCCOc1cc(COS(C)(=O)=O)cc(OCCCCOC2CCCCO2)c1C]

To a mixture of Intermediate 104i (580 mg, 1.0 mmol) and methanesulfonyl chloride (143 mg, 1.2 mmol) in dichloromethane (20 mL), cooled in a 0° C. bath, was added triethylamine (420 mg, 4.2 mmol). The cooling bath was removed and the reaction was stirred at ambient temperature for 30 minutes, at which time the reaction was poured into ice-water. The organic phase was collected, dried over sodium sulfate, and concentrated under reduced pressure to provide the desired compound.

ES-MS m/z=586 (M−50).

Intermediate 104k:

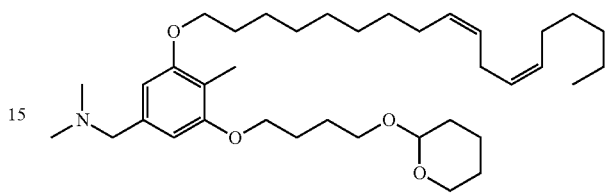

Intermediate 104j (660 mg, 1.0 mmol), sodium iodide (600 mg, 4.0 mmol), and dimethylamine (2 M in tetrahydrofuran, 2 mL) were taken into dimethylformamide (5 mL). The reaction was sealed and heated to 120° C. by microwave irradiation for 40 minutes. The reaction was cooled to ambient temperature and concentrated under reduced pressure. The residue was taken into ethyl acetate (50 mL) and washed with water (50 mL). The organic phase was collected, dried over sodium sulfate and concentrated under reduced pressure. The residue was purified by silica gel chromatography using dichloromethane and methanol as eluent to provide the desired compound.

ES-MS m/z=586.3 (MH+).

Intermediate 104l:

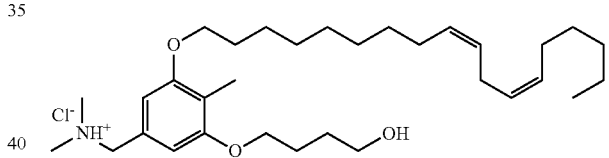

To a solution of Intermediate 104k (520 mg, 0.89 mmol) in methanol (10 mL) was added aqueous HCl (2 M, 2 mL). The reaction was stirred at ambient temperature for 30 minutes, then concentrated under reduced pressure. The residue was taken into toluene (3 mL) and concentrated under reduced pressure to provide the desired compound ES-MS m/z=502.3 (MH+).

Example 104 Compound

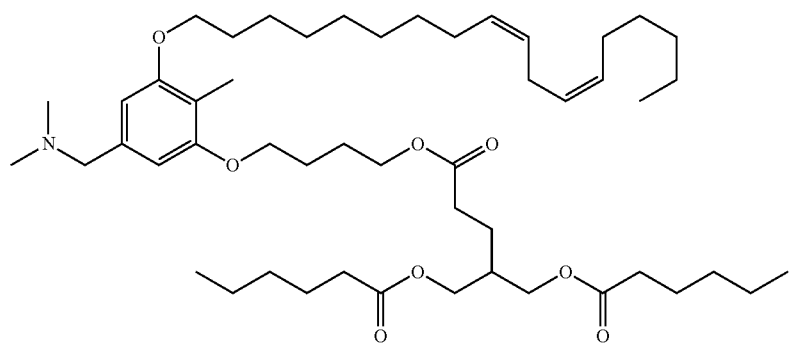 [SMILES: CCCCC/C=C\C/C=C\CCCCCCCCOc1cc(CN(C)C)cc(OCCCCOC(=O)CCC(COC(=O)CCCCC)COC(=O)CCCCC)c1C]

To a solution of Intermediate 104e (250 mg, 0.73 mmol) was added EDCI (167 mg, 0.871 mmol), diisopropylethylamine (0.190 mL, 1.1 mmol) and 4-(dimethylamino)pyridine (1.8 mg, 0.015 mmol). The reaction was stirred for 1 h at ambient temperature, then the alcohol of Experiment 1041 (480 mg, 0.892 mmol) was added. The reaction was stirred at ambient temperature overnight and then concentrated under reduced pressure. The residue was purified by silica gel chromatography with dichloromethane and methanol with 1% acetic acid modifier. Product containing fractions were washed with sodium bicarbonate solution and concentrated under reduced pressure. The residue was repurified by silica gel chromatography with ethyl acetate and heptanes as eluent to provide the desired compound.

$^1$H NMR (400 MHz, CDCl$_3$) δ 6.48 (s, 1H), 6.47 (s, 1H), 5.32-5.44 (m, 4H), 3.95-4.19 (m, 10H), 3.37 (s, 2H), 2.80 (t, J=8 Hz, 2H), 2.42 (t, J=8 Hz, 2H), 2.32 (t, J=8 Hz, 4H), 2.25 (s, 6H), 2.10 (s, 3H), 2.08 (dd, J=8 Hz, 4H), 1.86 (q, J=5 Hz, 4H), 1.64 (m, 4H), 1.27-1.48 (m, 24H), 0.91 (t, J=8 Hz, 9H) ppm.

ES-MS m/z=828.4 (MH+).

Synthesis of Example 105

Intermediate 105a:

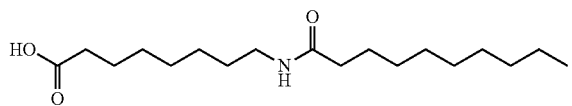 [SMILES: CCCCCCCCCC(=O)NCCCCCCCC(=O)O]

To a solution of decanoyl chloride (3.73 g, 20 mmol) and pyridine (3.10 g, 39 mmol) in dichloromethane (50 mL) was added 8-aminocaprylic acid (3.27 g, 21 mmol). The mixture was stirred at ambient temperature for 2 h. The mixture was diluted with water and dichloromethane, and the aqueous phase was adjusted to pH between 4 and 6 with 1N aqueous HCl and sodium bicarbonate solutions. The organic phase was separated and washed with water. The organic phase was dried over magnesium sulfate and concentrated under reduced pressure. The residue was purified by silica-gel chromatography with ethyl acetate and heptanes as eluent to provide the desired compound.

Rf=0.25 (silica, 5% MeOH in DCM, cerium molybdate).
Example 105 Compound

Example 105 was prepared from Intermediate 105a using conditions similar to those described for the synthesis of Example 77.

$^1$H NMR (400 MHz, CDCl$_3$) δ 7.21 (s, 2H), 7.18 (s, 1H), 5.90 (t, J=5.4 Hz, 2H), 5.05 (s, 4H), 3.38 (s, 2H), 3.17 (q, J=6.9 Hz, 4H), 2.31 (t, J=7.5 Hz, 4H), 2.20 (s, 6H), 2.11 (t, J=7.7 Hz, 4H), 1.62-1.53 (m, 8H), 1.46-1.39 (m, 4H), 1.27-1.21 (m, 36H), 0.82 (t, J=6.9 Hz, 6H) ppm.

ES-MS m/z=786.5 (MH+).

Synthesis of Example 106

Intermediate 106a

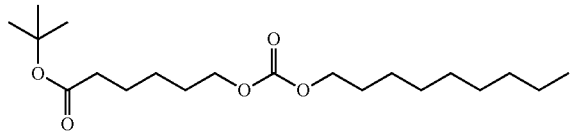 [SMILES: CCCCCCCCCOC(=O)OCCCCCC(=O)OC(C)(C)C]

To a solution of 4-nitrophenylchloroformate (3.75 g, 19 mmol), 4-(dimethylamino)pyridine (0.65 g, 5.3 mmol) and pyridine (3.15 g, 40 mmol) in dichloromethane (30 mL) was added tert-butyl 6-hydroxyhexanoate (2.5 g, 13 mmol). The reaction was stirred at ambient temperature overnight. Nonanol (5.75 g, 40 mmol) was added and the mixture was stirred at ambient temperature overnight. The mixture was concentrated under reduced pressure, and the residue was purified by silica-gel chromatography with ethyl acetate and heptanes as eluent to provide the desired compound.

Rf=0.58 (silica, 20% EtOAc in Heptane, cerium molybdate).

Intermediate 106b:

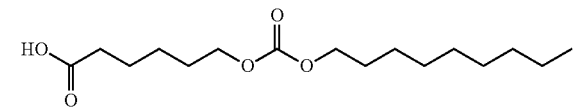 [SMILES: CCCCCCCCCOC(=O)OCCCCCC(=O)O]

A solution of Intermediate 106a (2.42 g, 6.7 mmol) in trifluoroacetic acid (3.0 mL) was swirled for 1 min, then concentrated under reduced pressure. The residue was taken into dichloromethane (10 mL), and concentrated under reduced pressure to provide the desired compound.

$^1$H NMR (400 MHz, CDCl$_3$) δ 10.20 (s, br, 1H), 4.18-4.13 (m, 4H), 2.45 (t, J=7.3 Hz, 2H), 1.76-1.64 (m, 6H), 1.50-1.27 (m, 14H), 0.89 (m, 3H) ppm.

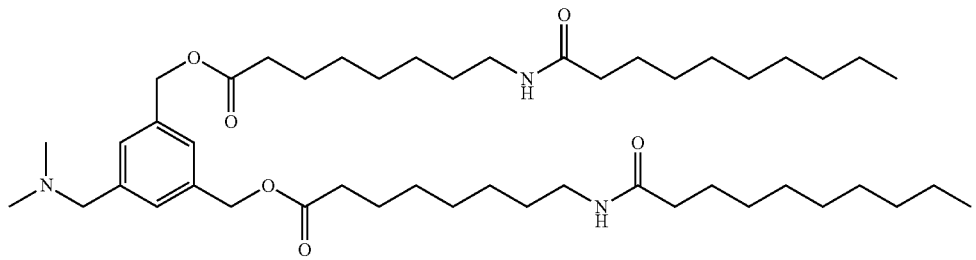

Example 106 Compound

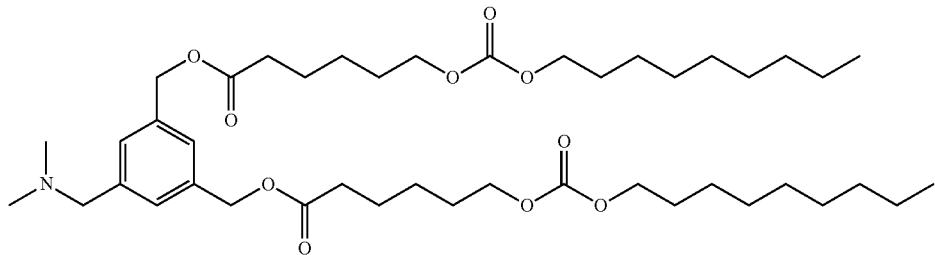 [SMILES: CCCCCCCCCOC(=O)OCCCCCC(=O)OCc1cc(COC(=O)CCCCCOC(=O)OCCCCCCCCC)cc(CN(C)C)c1]

Example 106 was prepared from Intermediate 106b using conditions similar to those employed in the synthesis of Example 77.

$^1$H NMR (400 MHz, CDCl$_3$) δ 7.26 (s, 2H), 7.23 (s, 1H), 5.10 (s, 4H), 4.12 (t, J=6.7 Hz, 8H), 3.43 (s, 2H), 2.38 (t, J=7.5 Hz, 4H), 2.25 (s, 6H), 1.73-1.62 (m, 12H), 1.46-1.27 (m, 28H), 0.88 (m, 6H) ppm.

ES-MS m/z=764.3 (MH+).

Synthesis of Example 107

Intermediate 107a

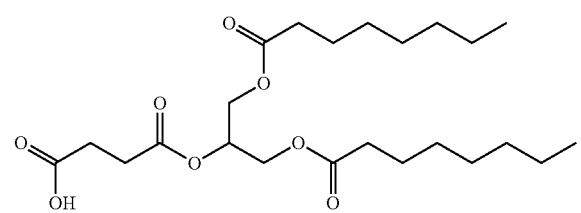 [SMILES: CCCCCCCC(=O)OCC(COC(=O)CCCCCCC)OC(=O)CCC(=O)O]

To a solution of 1,3-dicaprylin (1.0 g, 2.9 mmol) in toluene (12 mL) was added succinic anhydride (0.320 g, 3.2 mmol). The reaction was sealed and heated under microwave irradiation at 140° C. for 40 minutes. The reaction was cooled to ambient temperature and concentrated under reduced pressure. The residue was suspended in DCM and filtered through celite. The filtrate is concentrated under reduced pressure to provide the desired compound.

$^1$H NMR (400 MHz, CDCl$_3$) δ 13.26 (s, br, 1H), 5.32-5.26 (m, 1H), 4.35-4.28 (m, 2H), 4.23-4.15 (m, 2H), 2.70-2.65 (m, 4H), 2.38-2.31 (m, 4H), 1.70-1.55 (m, 4H), 1.40-1.20 (m, 16H), 0.91-0.88 (m, 6H) ppm.

Example 107 Compound

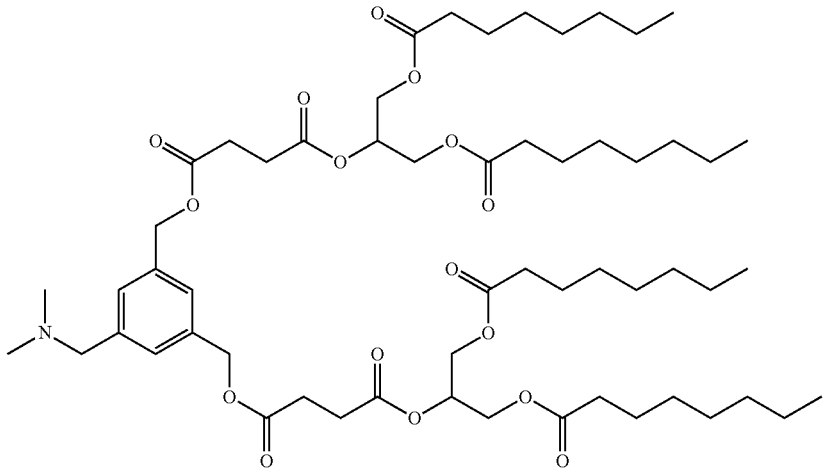 [SMILES: CCCCCCCC(=O)OCC(COC(=O)CCCCCCC)OC(=O)CCC(=O)OCc1cc(COC(=O)CCC(=O)OC(COC(=O)CCCCCCC)COC(=O)CCCCCCC)cc(CN(C)C)c1]

Example 107 was prepared from Intermediate 107a using conditions similar to those described for the synthesis of Example 77.

$^1$H NMR (400 MHz, CDCl$_3$) δ 7.27 (s, 2H), 7.23 (s, 1H), 5.30-5.25 (m, 2H), 5.13 (s, 4H), 4.34-4.28 (m, 4H), 4.21-4.13 (m, 4H), 3.43 (s, 2H), 2.70-2.67 (m, 8H), 2.35-2.30 (m, 8H), 2.25 (s, 6H), 1.65-1.58 (m, 8H), 1.32-1.27 (m, 32H), 0.88 (m, 12H) ppm.

ES-MS m/z=1048.5 (MH+).

Synthesis of Example 108

Intermediate 108a:

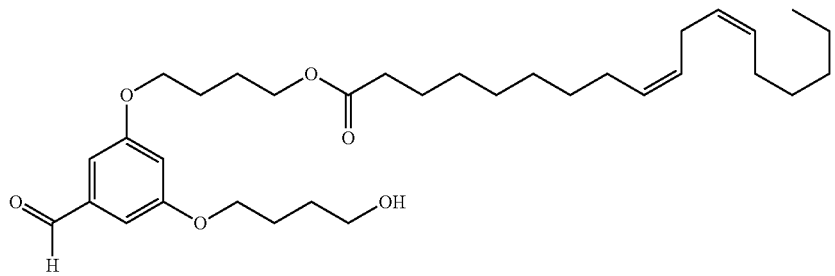 [SMILES: CCCCC/C=C\C/C=C\CCCCCCCC(=O)OCCCCOc1cc(C=O)cc(OCCCCO)c1]

To a solution of linoleic acid (2.33 g, 8.3 mmol) in dichloroethane (21 mL) was added EDCI (2.41 g, 12.6 mmol), DIPEA (1.63 g, 12.6 mmol), and DMAP (0.10 g, 0.84 mmol). The diol, prepared using conditions similar to those in Example 99e, was added and the reaction was sealed and heated under microwave irradiation at 80° C. for 20 minutes. The reaction was cooled to ambient temperature and concentrated under reduced pressure. The residue was purified by silica-gel chromatography with ethyl acetate and heptanes as eluent, followed by methanol and dichloromethane as eluent to provide the desired compound.

$^1$H NMR (400 MHz, CDCl$_3$) δ 9.90 (s, 1H), 7.00 (d, J=2.3 Hz, 1H), 6.69 (d, J=2.3 Hz, 1H), 5.22-5.47 (m, 4H), 4.15 (t, J=6.1 Hz, 2H), 3.97-4.10 (m, 2H), 2.77 (t, J=6.5 Hz, 2H), 2.31 (t, J=7.7 Hz, 2H), 1.97-2.14 (m, 4H), 1.72-1.97 (m, 5H), 1.46-1.70 (m, 4H), 1.23-1.45 (m, 15H), 0.89 (t, J=6.8 Hz, 3H) ppm.

Intermediate 108b:

To a solution of dodec-8-enoic acid (60.1 mg, 0.30 mmol) in dichloroethane (690 uL) was added EDCI (79 mg, 0.41 mmol), diisopropylethylamine (53 mg, 0.41 mmol), and 4-(dimethylamino)pyridine (3.4 mg, 0.03 mmol). Intermediate 110a (150 mg, 0.28 mmol) was added, and the reaction was sealed and heated under microwave irradiation at 80° C. for 20 minutes. The reaction was concentrated under reduced pressure. The residue was purified by silica-gel chromatography with ethyl acetate and heptanes as eluent followed by methanol and dichloromethane as eluent to provide the desired compound.

$^1$H NMR (400 MHz, CDCl$_3$) δ 9.90 (s, 1H), 7.00 (d, J=2.3 Hz, 2H), 6.69 (t, J=2.3 Hz, 1H), 5.23-5.45 (m, 6H), 4.15 (t, J=6.1 Hz, 4H), 4.03 (t, J=5.9 Hz, 4H), 2.77 (t, J=6.5 Hz, 2H), 2.31 (t, J=7.7 Hz, 4H), 1.94-2.12 (m, 8H), 1.75-1.94 (m,

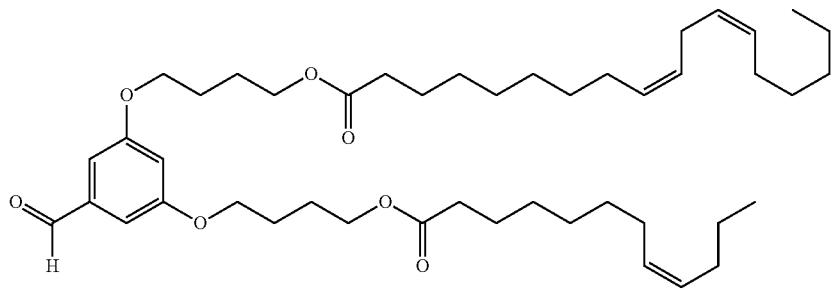 [SMILES: CCC/C=C\CCCCCCC(=O)OCCCCOc1cc(C=O)cc(OCCCCOC(=O)CCCCCCC/C=C\C/C=C\CCCCC)c1]

8H), 1.51-1.72 (m, 6H), 1.21-1.45 (m, 23H), 0.79-1.02 (m, 6H) ppm.

Example 108 Compound

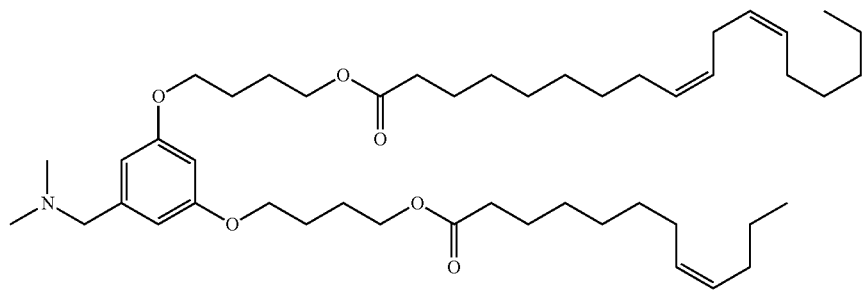 [SMILES: CCC/C=C\CCCCCCC(=O)OCCCCOc1cc(CN(C)C)cc(OCCCCOC(=O)CCCCCCC/C=C\C/C=C\CCCCC)c1]

Example 108 was prepared from Intermediate 108b using conditions similar to those employed in the synthesis of Example 33.

$^1$H NMR (400 MHz, CDCl$_3$) δ 6.48 (d, J=2.26 Hz, 2H) 6.35 (t, J=1.00 Hz, 1H) 5.37 (d, J=4.77 Hz, 5H) 4.15 (s, 4H) 3.98 (s, 4H) 3.36 (s, 2H) 2.74-2.83 (m, 2H) 2.32 (t, J=7.53 Hz, 4H) 2.25 (s, 6H) 1.96-2.11 (m, 8H) 1.77-1.91 (m, 8H) 1.60 (s, 8H) 1.27-1.43 (m, 23H) 0.88-0.95 (m, 6H) ppm.

ES-MS m/z=754.5 (MH+).

Example 109 was prepared using methods similar to those employed for the preparation of Example 108.

Example 109

Intermediate 110b:

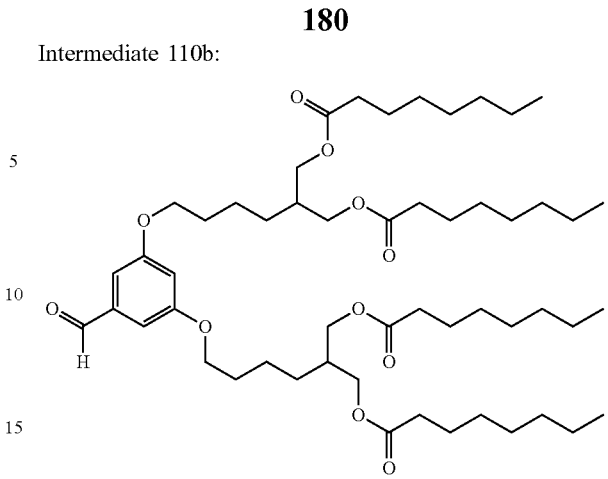

$^1$H NMR (400 MHz, CDCl$_3$) δ 6.49 (d, J=2.01 Hz, 2H) 6.36 (t, J=4.30 Hz, 1H) 5.37 (d, J=5.77 Hz, 4H) 4.11-4.19 (m, 4H) 3.98 (t, J=5.65 Hz, 4H) 3.40 (s, 2H) 2.79 (t, J=6.65 Hz, 2H) 2.23-2.34 (m, 10H) 2.07 (d, J=7.78 Hz, 5H) 1.79-1.90 (m, 9H) 1.23-1.40 (m, 44H) 0.86-0.94 (m, 9H) ppm.

ES-MS m/z=854.5 (MH+).

Synthesis of Example 110

Intermediate 110a:

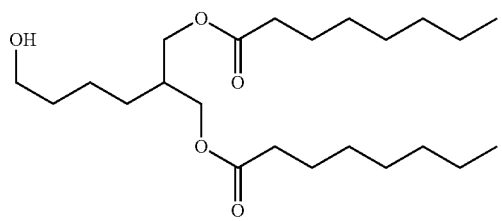 [SMILES: CCCCCCCC(=O)OCC(CCCCO)COC(=O)CCCCCCC]

Intermediate 110a was prepared using conditions similar to those employed in the synthesis of Intermediate 104d. This intermediate was used directly in the next step without purification.

Intermediate 110b was prepared from Intermediate 110a using conditions similar to those employed in the synthesis of Intermediate 104f and Intermediate 104g.

$^1$H NMR (400 MHz, CDCl$_3$) δ 9.87 (s, 1H), 6.97 (s, 2H), 6.67 (s, 1H), 3.96-4.11 (m, 12H), 2.29 (t, 8H), 2.00 (m, 2H), 1.76-1.82 (m, 4H), 1.58-1.61 (m, 12H), 1.41-1.45 (m, 4H), 1.25-1.27 (m, 34H), 0.87 (t, 12H) ppm.

Example 110 Compound

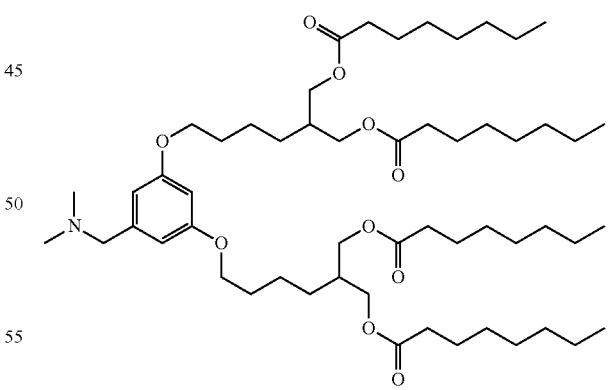

Example 110 was prepared from Intermediate 110c using conditions similar to those described for the preparation of Example 33.

$^1$H NMR (400 MHz, CDCl$_3$) δ 6.49-6.44 (m, 2H), 6.35-6.31 (m, 1H), 4.14-4.01 (m, 8H), 3.97-3.90 (m, 4H), 3.35 (s, 2H), 2.34-2.27 (m, 8H), 2.25 (s, 6H), 2.08-1.98 (m, 2H), 1.82-1.71 (m, 4H), 1.68-1.38 (m, 16H), 1.36-1.19 (m, 32H), 0.93-0.84 (m, 12H) ppm.

ES-MS m/z=932.6 (MH+).

Synthesis of Example 111

Intermediate 111a:

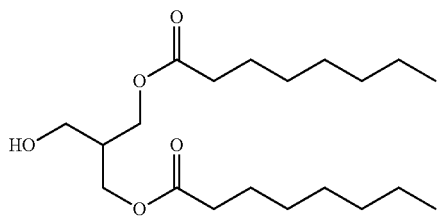 [SMILES: CCCCCCCC(=O)OCC(CO)COC(=O)CCCCCCC]

To a solution of octanoyl chloride (12.3 g, 75 mmol) in dichloromethane (50 mL) was added DMAP (1.84, 15 mmol) and pyridine (11.9 g, 150 mmol). The mixture was stirred at ambient temperature for 5 min, then 2-(hydroxymethyl)-1,3-propanediol (4.0 g, 38 mmol) was added. The reaction was stirred at ambient temperature overnight, then was concentrated under reduced pressure. The residue was purified by silica-gel chromatography with ethyl acetate and heptane to provide the desired product.

Rf=0.21 (silica, 20% EtOAc in heptanes, cerium molybdate).

Intermediate 111b:

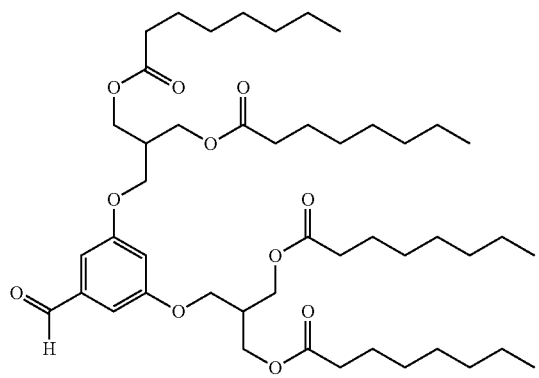 [SMILES: CCCCCCCC(=O)OCC(COC(=O)CCCCCCC)COc1cc(C=O)cc(OCC(COC(=O)CCCCCCC)COC(=O)CCCCCCC)c1]

Intermediate 111b was prepared from Intermediate 111a using conditions similar to those used to prepare Intermediate 18b.

Rf=0.44 (silica, 20% EtOAc in heptanes, cerium molybdate).

Example 111 Compound

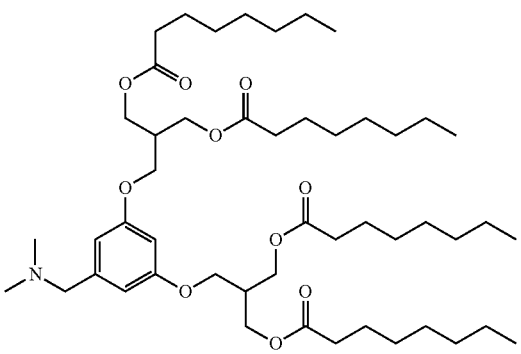 [SMILES: CCCCCCCC(=O)OCC(COC(=O)CCCCCCC)COc1cc(CN(C)C)cc(OCC(COC(=O)CCCCCCC)COC(=O)CCCCCCC)c1]

Example 111 was prepared from Intermediate 111b using conditions similar to those employed to prepare Example 33.

$^1$H NMR (400 MHz, CDCl$_3$) δ 6.51 (s, 2H), 6.37 (s, 1H), 4.25-4.22 (m, 8H), 4.00-3.98 (m, 4H), 3.52 (s, br, 2H), 2.53-2.50 (m, 2H), 2.34-2.30 (m, 14H), 1.65-1.58 (m, 8H), 1.31-1.25 (m, 32H), 0.87 (m, 12H) ppm.

ES-MS m/z=848.4 (MH+).

Example 112

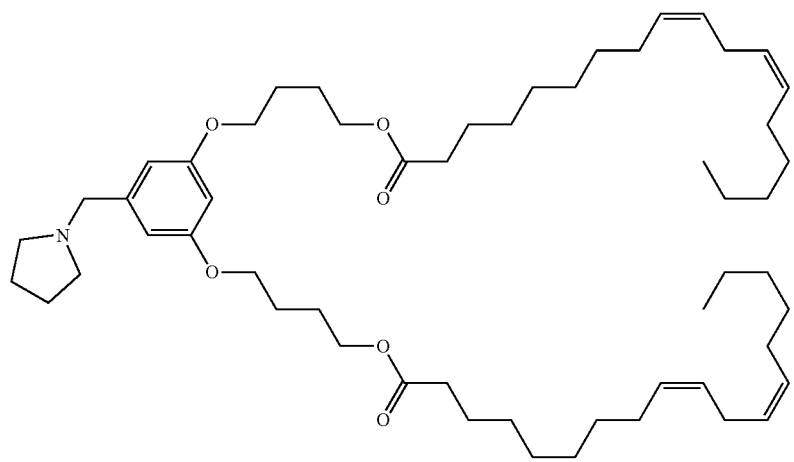 [SMILES: CCCCC/C=C\C/C=C\CCCCCCCC(=O)OCCCCOc1cc(CN2CCCC2)cc(OCCCCOC(=O)CCCCCCC/C=C\C/C=C\CCCCC)c1]

Example 112 was prepared from Intermediate 38b using conditions similar to those employed to prepare Example 38.

$^1$H NMR (400 MHz, CDCl$_3$) δ 6.52 (s, 2H), 6.35 (s, 1H), 5.44-5.32 (m, 8H), 4.15 (t, J=5.6 Hz, 4H), 3.98 (t, J=5.1 Hz, 4H), 3.57 (s, 2H), 2.79 (t, J=6.4 Hz, 4H), 2.54 (br s, 4H), 2.32 (t, J=7.5 Hz, 4H), 2.07 (q, J=6.7 Hz, 8H), 1.79-1.90 (m, 12H), 1.68-1.59 (m, 5H), 1.42-1.27 (m, 27H), 0.91 (t, J=6.8 Hz, 6H) ppm.

ES-MS m/z=862.8 (MH+).

Lipid Compositions

The lipid nanoparticles (LNPs) were formed by mixing equal volumes of lipids dissolved in alcohol with siRNA dissolved in a citrate buffer by an impinging jet process. The lipid solution contains a cationic lipid compound of the invention, a helper lipid (cholesterol), an optional neutral lipid (DSPC) and a PEG (PEG) lipid at a concentration of 8-16 mg/mL with a target of 12 mg/mL in an alcohol. The relative molar ratios of each lipid component in the formulations of this invention are reported in Tables 4 and 5. The siRNA to total lipid ratio is approximately 0.05 (wt/wt). Where a LNP formulation contains four lipid components, the molar ratios correspond to the type of lipid as it appears in the first four columns of the table, in the order that they appear. The ratio of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate: sodium chloride buffer pH 4-6, with a target of 4.5-5.5. The LNPs are formed by mixing equal volumes of lipid solution in ethanol with siRNA dissolved in a citrate buffer by an impinging jet process through a mixing device with ID ranging from 0.25 to 2.0 mm at a flow rate from 10 to 640 mL/min. The mixed LNP solution is held at room temperature for 0-24 hrs prior to a dilution step. The solution is then concentrated and diafiltered with suitable buffer by ultrafiltration process using membranes with a MW cutoff from 30 to 500 KD. The final product is sterile filtered and stored at 4° C.

siRNA's

The siRNA used in the lipid nanoparticles described above was made up of double stranded siRNA sequences specific to a target mRNA sequence.

1. FVII siRNA Duplex Sequence

```
                                       (SEQ ID NO: 1)
5' UUu AAU UGA AAC cAA GAc Auu 3'

(SEQ ID NO: 2)
5' uGu cuu GGu uuc AAu uAA Auu 3'
```

2. PLK1-424 siRNA Duplex Sequence

```
                                       (SEQ ID NO: 3)
5' UAU UUA AgG AGG GUG AuC Uuu 3'

(SEQ ID NO: 4)
5' AGA Uca CCC Ucc uuA AAU auu 3'
```

The following abbreviations are used in these sequences:
A=adenosine
U=uridine
G=guanosine
C=cytosine
a=2'-O-methyl-adenosine
u=2'-O-methyl-uridine
g=2'-O-methyl-guanosine
c=2'-O-methyl-cytosine pKa Measurements Unless indicated otherwise, all pKa's referred to herein were measured at standard temperature and pressure. Also, unless otherwise indicated, all references to pKa are references to pKa measured using the following technique.

2 mM solution of lipid in ethanol was prepared by weighing the lipid and then dissolving it in ethanol. 0.3 mM solution of fluorescent probe TNS in ethanol:methanol 9:1 was prepared by first making 3 mM solution of TNS in methanol and then diluting to 0.3 mM with ethanol.

An aqueous buffer containing 200 mM sodium phosphate dibasic and 100 mM citric acid was prepared. The buffer was split into twelve parts and the pH adjusted either with 12N HCl or 6N NaOH to 4.21-4.33, 4.86-4.99, 5.23-5.37, 5.46-5.54, 5.65-5.74, 5.82-5.89, 6.09-6.18, 6.21-6.32, 6.45-6.52, 6.66-6.72, 6.83-6.87, 7.19-7.28. 400 uL of 2 mM lipid solution and 800 uL of 0.3 mM TNS solution were mixed.

Using the Hamilton Microlab Star high throughput liquid handler and Hamilton run control software Software, 7.5 uL of probe/lipid mix were added to 242.5 uL of buffer in a 1 mL 96 well plate (model NUNC 260252, Nalgae Nunc International). This was done with all twelve buffers.

After mixing in 1 mL 96 well plate, 100 uL of each probe/lipid/buffer mixture was transferred to a 250 uL black with clear bottom 96 well plate (model COSTAR 3904, Corning).

The fluorescence measurements are carried out on the SpectraMax M5 spectrophotometer using software SoftMax pro 5.2 and following parameters:

Read Mode: Fluorescence, Top read
Wavelengths: Ex 322 nm, Em 431 nm, Auto Cutoff On 420 nm
Sensitivity: Readings 6, PMT: Auto
Automix: Before: Off
Autocalibrate: On
Assay plate type: 96 Well Standard clrbtm
Wells to read: Read entire plate
Settling time: Off
Column Way. Priority: Column priority
Carriage Speed: Normal
Auto read: Off After the measurement, the background fluorescence value of an empty well on the 96 well plate was subtracted from each probe/lipid/buffer mixture. The fluorescence intensity values were then normalized to the value at lowest pH. The normalized fluorescence intensity vs. pH chart was then plotted in the Microsoft Excel software. The twelve points were connected with a smooth line.

The point on the line at which the normalized fluorescence intensity was equal to 0.5 was found. The pH corresponding to normalized fluorescence intensity equal to 0.5 was found and was considered the pKa of the lipid.

The pKa determined using this method is precise to about 0.1 pKa units.

Polydispersity Index (PDI) Measurements

Unless indicated otherwise, all PDIs referred to herein are the PDI of the fully formed nanoparticle, as measured by dynamic light scattering on a Malvern Zetasizer. The nanoparticle sample was diluted in phosphate buffered saline (PBS) so that the count rate was approximately 200-400 kcts. The data is presented in Tables 4 and 5 as a weighted average of the intensity measure.

The Particle size of the Lipid Nanoparticle

Unless indicated otherwise, all particle size measurements referred to in Tables 4 and 5 are the Z-average particle size of the fully formed nanoparticle, as measured by dynamic light scattering on a Malvern Zetasizer. The nanoparticle sample was diluted in phosphate buffered saline (PBS) so that the count rate is approximately 200-400 kcts.

Biological Assays

Mouse Factor VII Dosing

Female CD-1 mice were received from Harlan Labs and maintained on standard lab chow and water ad libitum. The animals weighed approximately 25 grams at time of dosing. Formulated Factor VII siRNA was administered as a single dose intravenously via the lateral tail vein. Approximately 48 hours after injection, the mice were euthanized by $CO_2$ inhalation followed by exsanguination through the vena cava. The blood was collected in tubes containing 0.105M sodium citrate anticoagulant for plasma Factor VII activity analysis.

Factor VII Activity Assay

Plasma collected from injected mice was assayed for Factor VII enzyme activity using the Biophen FVII kit from Hyphen Biomedical (catalog number 221304). An assay standard curve was prepared using pooled plasma aliquots from the vehicle control animals. All samples were diluted to fall within the linear range of the standard curve and Factor VII activity relative to control plasma was reported.

Lipid nanoparticles comprising lipid compounds of formula (I) and the FVII siRNA duplex sequence listed above were tested in the Factor VII Activity Assay. The results of this assay are given in Table 4 below as a percent knock down of plasma Factor VII enzyme activity at a dose of 0.3 mg/kg and 0.03 mg/kg.

TABLE 4

Factor VII Activity Assay Results Using FVII siRNA Lipid Nanoparticles

| Cationic Lipid of Formula (I) | Helper Lipid | Neutral Lipid | Stealth Lipid | [1]Lipid Molar ratio | Size (nm) | PDI | [2]pKa | KD FVII 0.3 mg/kg | KD FVII 0.03 mg/kg |
|---|---|---|---|---|---|---|---|---|---|
| Ex. 1 | Chol | DSPC | S010 | 45/44/9/2 | 87.16 | 0.124 | 5.59 | — | 30.8 |
| Ex. 1 | Chol | DSPC | PEG-DMG | 45/44/9/2 | 98.2 | 0.05 | 5.59 | 75.1 | — |
| Ex. 2 | Chol | DSPC | S010 | 45/44/9/2 | 92.85 | 0.067 | 5.57 | — | 55 |
| Ex. 2 | Chol | DSPC | PEG-DMG | 45/44/9/2 | 97.4 | 0.04 | 5.46 | 95.5 | — |
| Ex. 14 | Chol | DSPC | S010 | 45/44/9/2 | 81.74 | 0.059 | 6.11 | — | — |
| Ex. 26 | Chol | DSPC | S010 | 45/44/9/2 | 121.6 | 0.046 | 6.45 | — | — |
| Ex. 26 | Chol | DSPC | PEG-DMG | 45/44/9/2 | 104.3 | 0.04 | 6.45 | 58.1 | — |
| Ex. 31 | Chol | DSPC | S010 | 45/44/9/2 | 81.16 | 0.049 | 6.01 | — | — |
| Ex. 33 | Chol | DSPC | S010 | 45/44/9/2 | 79.15 | 0.042 | 5.85 | — | — |
| Ex. 33 | Chol | DSPC | PEG-DMG | 45/44/9/2 | 107.8 | 0.06 | 5.75 | 90.4 | — |
| Ex. 34 | Chol | DSPC | S010 | 45/44/9/2 | 113.8 | 0.036 | 5.95 | — | — |
| Ex. 34 | Chol | DSPC | PEG-DMG | 45/44/9/2 | 126.0 | 0.06 | 5.61 | 0 | — |
| Ex. 38 | Chol | DSPC | S010 | 45/44/9/2 | 120 | 0.04 | 5.93 | — | 43.6 |
| Ex. 38 | Chol | DSPC | PEG-DMG | 45/44/9/2 | 108.0 | 0.02 | 5.9 | 99 | — |
| Ex. 39 | Chol | DSPC | S010 | 45/44/9/2 | 122.9 | 0.044 | 5.91 | — | — |
| Ex. 40 | Chol | DSPC | S010 | 45/44/9/2 | 94.28 | 0.062 | 6.17 | — | 8.2 |
| Ex. 40 | Chol | DSPC | PEG-DMG | 45/44/9/2 | 110.9 | 0.02 | 6.17 | 89.8 | — |
| Ex. 41 | Chol | DSPC | S010 | 45/44/9/2 | 170.7 | 0.119 | 5.83 | — | — |
| Ex. 42 | Chol | DSPC | S010 | 45/44/9/2 | 120 | 0.084 | 5.93 | — | 92.8 |
| Ex. 43 | Chol | DSPC | S010 | 45/44/9/2 | 121.9 | 0.066 | 5.85 | — | — |
| Ex. 43 | Chol | DSPC | PEG-DMG | 45/44/9/2 | 157.8 | 0.08 | 5.85 | 97.4 | — |
| Ex. 44 | Chol | DSPC | S010 | 45/44/9/2 | 172.9 | 0.077 | 5.66 | — | — |
| Ex. 45 | Chol | DSPC | S010 | 45/44/9/2 | 102.8 | 0.072 | 5.57 | — | — |
| Ex. 46 | Chol | DSPC | S010 | 45/44/9/2 | 102.4 | 0.135 | 6.18 | — | — |
| Ex. 47 | Chol | DSPC | S010 | 45/44/9/2 | 125.9 | 0.035 | 6.07 | — | — |
| Ex. 47 | Chol | DSPC | PEG-DMG | 45/44/9/2 | 109.3 | 0.06 | 6.07 | 99 | — |
| Ex. 48 | Chol | DSPC | S010 | 45/44/9/2 | 152.3 | 0.105 | 5.93 | — | — |
| Ex. 49 | Chol | DSPC | S010 | 45/44/9/2 | 111.1 | 0.046 | 5.99 | — | — |
| Ex. 50 | Chol | DSPC | S010 | 45/44/9/2 | 126 | 0.056 | 5.92 | — | — |
| Ex. 51 | Chol | DSPC | S010 | 45/44/9/2 | 103.2 | 0.052 | 5.91 | — | — |
| Ex. 52 | Chol | DSPC | S010 | 45/44/9/2 | 145.4 | 0.052 | 5.96 | — | 73.5 |
| Ex. 52 | Chol | DSPC | PEG-DMG | 45/44/9/2 | 109.4 | 0.1 | 5.96 | — | 72.5 |
| Ex. 53 | Chol | DSPC | S010 | 45/44/9/2 | 113.3 | 0.079 | 6.03 | — | — |
| Ex. 53 | Chol | DSPC | PEG-DMG | 45/44/9/2 | 129.1 | 0.1 | 5.84 | 96.6 | — |
| Ex. 55 | Chol | DSPC | S010 | 45/44/9/2 | 106.9 | 0.043 | 6.37 | — | — |
| Ex. 55 | Chol | DSPC | PEG-DMG | 45/44/9/2 | 101.9 | 0.10 | 6.03 | 98.0 | — |
| Ex. 56 | Chol | DSPC | S010 | 45/44/9/2 | 99.47 | 0.114 | 5.93 | — | — |
| Ex. 56 | Chol | DSPC | PEG-DMG | 45/44/9/2 | 110.1 | 0.01 | 5.71 | 71.0 | — |
| Ex. 57 | Chol | DSPC | S010 | 45/44/9/2 | 123.8 | 0.059 | 5.94 | — | — |
| Ex. 57 | Chol | DSPC | PEG-DMG | 45/44/9/2 | 108.4 | 0.03 | 5.94 | 96.7 | — |
| Ex. 58 | Chol | DSPC | S010 | 45/44/9/2 | 138.9 | 0.022 | 5.9 | — | 15.25 |
| Ex. 58 | Chol | DSPC | PEG-DMG | 45/44/9/2 | 120.6 | 0.06 | 6.02 | 78.1 | — |
| Ex. 59 | Chol | DSPC | S010 | 45/44/9/2 | 92.56 | 0.064 | 6.09 | — | 48.24 |
| Ex. 60 | Chol | DSPC | S010 | 45/44/9/2 | 95.55 | 0.098 | 6.21 | — | 49.75 |
| Ex. 61 | Chol | DSPC | S010 | 45/44/9/2 | 81.79 | 0.076 | 5.82 | — | 0 |
| Ex. 62 | Chol | DSPC | S010 | 45/44/9/2 | 102.5 | 0.066 | 5.9 | — | 85.8 |
| Ex. 63 | Chol | DSPC | S010 | 45/44/9/2 | 91.66 | 0.057 | 5.92 | — | 75 |
| Ex. 69 | Chol | DSPC | S010 | 45/44/9/2 | 98.13 | 0.053 | 5.3 | — | — |
| Ex. 77 | Chol | DSPC | S010 | 45/44/9/2 | 154.1 | 0.014 | 6.09 | — | — |
| Ex. 78 | Chol | DSPC | S010 | 45/44/9/2 | 178.2 | 0.043 | 6.02 | — | — |
| Ex. 79 | Chol | DSPC | S010 | 45/44/9/2 | | | 6.48 | — | — |

TABLE 4-continued

Factor VII Activity Assay Results Using FVII siRNA Lipid Nanoparticles

| Cationic Lipid of Formula (I) | Helper Lipid | Neutral Lipid | Stealth Lipid | [1]Lipid Molar ratio | Size (nm) | PDI | [2]pKa | KD FVII 0.3 mg/kg | KD FVII 0.03 mg/kg |
|---|---|---|---|---|---|---|---|---|---|
| Ex. 82 | Chol | DSPC | S010 | 45/44/9/2 | 119.2 | 0.064 | 6.03 | — | — |
| Ex. 83 | Chol | DSPC | S010 | 45/44/9/2 | 128.5 | 0.005 | 6.15 | — | — |
| Ex. 85 | Chol | DSPC | S010 | 45/44/9/2 | | | 5.72 | — | — |
| Ex. 86 | Chol | DSPC | S010 | 45/44/9/2 | 120.3 | 0.058 | 5.84 | — | 0 |
| Ex. 86 | Chol | DSPC | PEG-DMG | 45/44/9/2 | 128.7 | 0.05 | 5.81 | 55.3 | — |
| Ex. 87 | Chol | DSPC | S010 | 45/44/9/2 | 159.2 | 0.089 | 6.07 | — | — |
| Ex. 88 | Chol | DSPC | S010 | 45/44/9/2 | 152.4 | 0.046 | 5.99 | — | — |
| Ex. 89 | Chol | DSPC | S010 | 45/44/9/2 | 101.5 | 0.076 | 6.02 | — | — |
| Ex. 90 | Chol | DSPC | S010 | 45/44/9/2 | 87.54 | 0.073 | 5.81 | — | — |
| Ex. 91 | Chol | DSPC | S010 | 45/44/9/2 | 111.9 | 0.053 | 6.01 | — | — |
| Ex. 91 | Chol | DSPC | PEG-DMG | 45/44/9/2 | 124.3 | 0.06 | 6.01 | 99.0 | — |
| Ex. 92 | Chol | DSPC | S010 | 45/44/9/2 | 117.3 | 0.065 | 5.92 | — | 89.4 |
| Ex. 93 | Chol | DSPC | S010 | 45/44/9/2 | 121.5 | 0.071 | 6.00 | — | 89.71 |
| Ex. 94 | Chol | DSPC | S010 | 45/44/9/2 | 116.4 | 0.073 | 6.16 | — | 90 |
| Ex. 96 | Chol | DSPC | S010 | 45/44/9/2 | 197.3 | 0.14 | 5.71 | — | — |
| Ex. 97 | Chol | DSPC | S010 | 45/44/9/2 | 98.01 | 0.106 | 5.82 | — | — |
| Ex. 98 | Chol | DSPC | S010 | 45/44/9/2 | 164.6 | 0.096 | 5.94 | — | — |
| Ex. 99 | Chol | DSPC | S010 | 45/44/9/2 | 96.61 | 0.061 | 5.75 | — | — |
| Ex. 100 | Chol | DSPC | S010 | 45/44/9/2 | 105.9 | 0.121 | 6.17 | — | 26.9 |
| Ex. 100 | Chol | DSPC | PEG-DMG | 45/44/9/2 | 106.4 | 0.07 | 5.69 | 94.0 | — |
| Ex. 101 | Chol | DSPC | S010 | 45/44/9/2 | | | 6.32 | — | — |
| Ex. 104 | Chol | DSPC | S010 | 45/44/9/2 | | | 6.02 | — | — |
| Ex. 106 | Chol | DSPC | S010 | 45/44/9/2 | 149.3 | 0.083 | 6.04 | — | — |
| Ex. 107 | Chol | DSPC | S010 | 45/44/9/2 | 191.7 | 0.071 | 6.11 | — | — |
| Ex. 109 | Chol | DSPC | S010 | 45/44/9/2 | 91.98 | 0.09 | 5.98 | — | 68.97 |
| Ex. 110 | Chol | DSPC | S010 | 45/44/9/2 | 183.3 | 0.071 | 5.66 | — | — |
| Ex. 111 | Chol | DSPC | S010 | 45/44/9/2 | 161.9 | 0.048 | 6.27 | — | — |
| Ex. 112 | Chol | DSPC | PEG-DMG | 45/44/9/2 | 96.1 | 0.1 | 6.08 | — | 86 |

[1]The order of the lipid types as they appear in the molar ratio corresponds to the order in which the lipids appear in the first four columns of the table.
[2]pKa refers to the pKa of the cationic lipid of formula (I)

LS411N Xenograft Assay:

Female Nu/Nu mice (6-8 weeks old) were implanted subcutaneously with $5 \times 10^6$ LS411N cells. Tumor growth was monitored by caliper measurement before treatment initiation. Mice bearing 150-250 mm$^3$ subcutaneous tumors were randomized and enrolled in the study. The stock siRNA formulations were diluted to 0.3 m/ml with PBS for dosing. Animals enrolled in different groups received a single daily bolus IV injection of 3 mg/kg siRNA for three days. Tumors were harvested 24 hours post last injection to assess target gene regulation by qRT-PCR.

Lipid nanoparticles comprising lipid compounds of formula (I) and the PLK1-424 siRNA duplex sequence listed above were tested in the LS411 N Xenograft Assay. The results of this assay are given in Table 5 below as a percent knock down of PLK-1 mRNA as compared to the control when administered as a single daily dose for three days at a dose of 3 mg/kg.

TABLE 5

Lipid Nanoparticles Comprising PLK1-424 siRNA and Results of the LS411N Xenograph Assay.

| Cationic Lipid of Formula (I) | Neutral Lipid | Helper Lipid | Stealth Lipid | [3]Lipid Molar ratio | Size (nm) | PDI | [4]pKa | LS411 KD 3 × 3 mg/Kg |
|---|---|---|---|---|---|---|---|---|
| Example 1 | Chol | DSPC | S010 | 45/44/9/2 | 74.56 | 0.152 | 5.59 | — |
| Example 2 | Chol | DSPC | S011 | 45/44/9/2 | 88.19 | 0.1 | 5.57 | — |
| Example 38 | Chol | DSPC | S010 | 45/44/9/2 | 116.8 | 0.036 | 5.93 | 60 |
| Example 38 | Chol | DSPC | PEG-DSG | 45/44/9/2 | 116.8 | 0.036 | 5.93 | 58 |
| Example 39 | Chol | DSPC | S010 | 45/44/9/2 | 114.3 | 0.039 | 5.91 | 55 |
| Example 42 | Chol | DSPC | S010 | 45/44/9/2 | 181.1 | 0.06 | 5.93 | 50 |
| Example 43 | Chol | DSPC | S010 | 45/44/9/2 | 150.7 | 0.046 | 5.85 | 40 |
| Example 52 | Chol | DSPC | S010 | 45/44/9/2 | 132.2 | 0.06 | 5.96 | 50 |
| Example 52 | Chol | DSPC | PEG-DSG | 45/44/9/2 | 132.2 | 0.06 | 5.96 | 69 |
| Example 57 | Chol | DSPC | S010 | 45/44/9/2 | 116.3 | 0.038 | 5.94 | 60 |
| Example 63 | Chol | DSPC | PEG_DSG | 45/44/9/2 | 108.6 | 0.047 | 5.9 | 66 |
| Example 91 | Chol | DSPC | S010 | 45/44/9/2 | 136.1 | 0.032 | 6.01 | 45 |

[3] The order of the lipid types as they appear in the molar ratio corresponds to the order in which the lipids appear in the first four columns of the table.
[4]pKa refers to the pKa of the cationic lipid of formula (I)

Immunization Studies:

BALB/c were immunized with liposomes comprising DSPC, cholesterol, and various lipids of the invention (or, for comparison, the cationic lipid 1,2-dilinoleyloxy-N,N-dimethyl-3-aminopropane or 'DLinDMA'). The liposomes encapsulated 0.1 µg of "vA317" self-replicating RNA replicon which encodes respiratory syncytial virus F protein (see WO2012/031043). As a negative control, mice received 1 µg of "naked" replicon. Doses were given either on days 0 & 21 or days 0 & 42. Immune responses were assessed 2 weeks after each dose (2wp1, 2wp2), and in some cases also at 4 weeks after the second dose (4wp2). Four series of experiments were performed, each with its own naked control. In all experiments sera were assessed in two pools, and anti-RSV-F titers are shown in Table 6 below.

TABLE 6

Immunization titers against RSV protein F.

| Cationic Lipid of Formula (I) | Course | 2 wp1 pool 1 | 2 wp1 pool 2 | 2 wp2 pool 1 | 2 wp2 pool 2 | 4 wp2 pool 1 | 4 wp2 pool 2 |
|---|---|---|---|---|---|---|---|
| Naked | A | 115 | 264 | 692 | 5371 | — | — |
| DLinDMA | A | 819 | 954 | 18318 | 21731 | — | — |
| Example 2 | A | 217 | 259 | 12785 | 8232 | — | — |
| Example 13 | A | 495 | 620 | 7157 | 12316 | — | — |
| Example 14 | A | 1234 | 2089 | 44059 | 45246 | — | — |
| Example 9 | A | 1832 | 1352 | 29707 | 18788 | — | — |
| Naked | B | 155 | 48 | 3264 | 1440 | 4747 | 1954 |
| DLinDMA | B | 13 | 4 | 18290 | 5538 | 13936 | 7020 |
| Example 12 | B | 88 | 128 | 4550 | 4828 | 4787 | 3972 |
| Naked | A | 219 | 255 | 855 | 1052 | 1157 | 1726 |
| DLinDMA | A | 4336 | 6460 | 19155 | 19141 | 26504 | 28008 |
| Example 26 | A | 4 | 4 | 10 | 10 | 10 | 10 |
| Example 14 | A | 3098 | 3539 | 12785 | 14582 | 13687 | 18851 |
| Example 25 | A | 1217 | 1883 | 1611 | 1156 | 2850 | 1767 |
| Naked | A | 2699 | 905 | 5253 | 5491 | 4323 | 5008 |
| DLinDMA | A | 4585 | 3390 | 60395 | 56229 | 50799 | 35992 |
| Example 14 | A | 1192 | 1206 | 34906 | 28736 | 21375 | 21347 |
| Example 66 | A | 75 | 75 | 75 | 75 | 75 | 75 |
| Example 68 | A | 1031 | 494 | 11315 | 7800 | 12963 | 17734 |
| Example 81 | A | 1779 | 1553 | 24648 | 15304 | 41921 | 34684 |
| Example 29 | A | 2101 | 3584 | 12529 | 18669 | 23930 | 37278 |
| Example 70 | A | 1416 | 3110 | 31550 | 20124 | 18779 | 18358 |
| Example 69 | A | 2853 | 4481 | 23851 | 20793 | 19075 | 21504 |

Course: A = days 0 & 21; B = days 0 & 42.

ENUMERATED EMBODIMENTS

Embodiment 1

The present invention provides for a compound of formula (I):

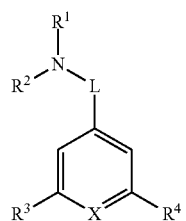

(I)

wherein:

L is $C_{1-6}$ alkylene, $C_{2-6}$ alkenylene, $C_{2-6}$ alkynylene, $—(CH_2)_t C_{3-7}$ cycloalkylene-$(CH_2)_s—$, $—(CH_2)_s—C_{3-7}$ cycloalkenylene-$(CH_2)_s—$, $—(CH_2)_s—C_{3-7}$ cycloalkynylene-$(CH_2)_s—$, *—$C_{1-4}$ alkylene-L2-, *—$C_{1-4}$ alkylene-L2-$C_{1-4}$ alkylene-,

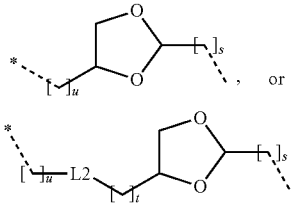

wherein in the * denotes attachment of the moiety to the $NR^1R^2$ group;

L2, attached in either direction, is —O—, —S—, —C(O)—, —C(O)O—, —OC(O)O—, —CONH—, $S(O)_2NH—$, NHCONH— or —NHCSNH—;

each s is independently 0, 1 or 2;
each t is independently 0, 1, 2, 3, or 4;
u is 0, 1, 2, 3, 4, 5, or 6;

$R^1$ and $R^2$ are each independently optionally substituted $C_{1-6}$ alkyl, optionally substituted $C_{2-6}$ alkenyl, optionally substituted $C_{2-6}$ alkynyl, optionally substituted $C_{3-7}$ cycloalkyl-$(CH_2)_s—$, optionally substituted $C_{3-7}$ cycloalkenyl-$(CH_2)_s—$, optionally substituted $C_{3-7}$ cycloalkynyl-$(CH_2)_s—$, or optionally substituted phenyl-$(CH_2)_s—$; wherein said $C_{1-6}$ alkyl, $C_{2-6}$ alkenyl, $C_{2-6}$ alkynyl, $C_{3-7}$ cycloalkyl, $C_{3-7}$ cycloalkenyl, $C_{3-7}$ cycloalkynyl, and phenyl are optionally substituted with one or two substituents each independently selected from the group consisting of: OH, $C_{1-3}$ alkoxy, COOH, and COO—$C_{1-4}$ alkyl, or $R^1$ and $R^2$ are joined together forming an optionally substituted 4-12 membered heterocyclic ring, said heterocyclic ring being optionally substituted with one to three substituents each independently selected from the group consisting of: OH, halo, $C_{1-3}$ alkyl, $C_{1-3}$ alkoxy, dimethylamino, —COO—$C_{1-4}$ alkyl, phenyl, piperidinyl, and morpholinyl;

$R^3$ and $R^4$ are each independently:
  (a) —$Z^1$—$R^a$,
  (b) —$Z^1$—$R^b$—$Z^2$—$R^a$,
  (c) —$Z^1$—$R^b$—$Z^2$—$R^b$—$Z^3$—$R^a$,
  (d) —$Z^1$—$R^b$—$Z^2$—$R^b$—$Z^3$—$R^b$—$Z^4$—$R^a$,
  (e) —$R^b$—$Z^1$—$R^a$,
  (f) —$R^b$—$Z^1$—$R^b$—$Z^2$—$R^a$,
  (g) —$R^b$—$Z^1$—$R^b$—$Z^2$—$R^b$—$Z^3$—$R^a$,
  (h) —$R^b$—$Z^1$—$R^b$—$Z^2$—$R^b$—$Z^3$—$R^b$—$Z^4$—$R^a$,
  (i) —$R^c$,
  (j) —$Z^1$—$R^b$—$R^c$, or
  (k) —$R^b$—$Z^1$—$R^b$—$R^c$;

wherein $Z^1$, $Z^2$, $Z^3$, and $Z^4$, attached in either direction, are each independently —O—, —C(O)O—, —OC(O)O—, or —CONH—;

$R^a$ is $C_{2-22}$ alkyl, $C_{2-22}$ alkenyl, or $C_{2-22}$ alkynyl;

each $R^b$ is independently $C_{1-20}$ alkylene, $C_{2-20}$ alkenylene, or $C_{2-20}$ alkynylene;

$R^c$ is

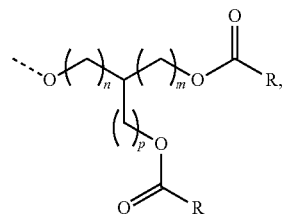 (c1)

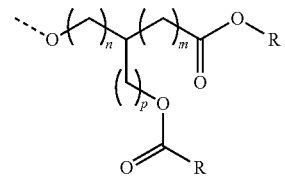 (c2)

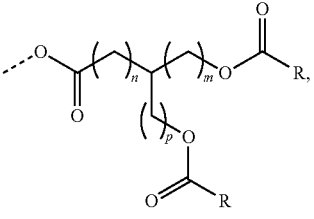 (c3)

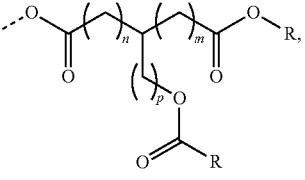 (c4)

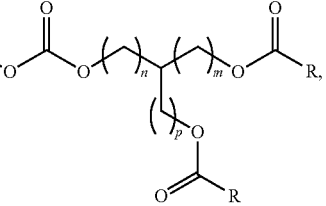 (c5)

-continued

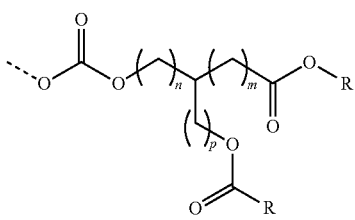 (c6)

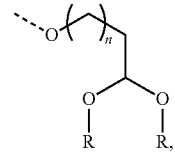 (c7)

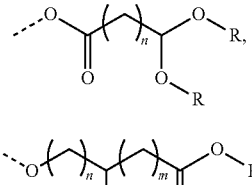 (c8)

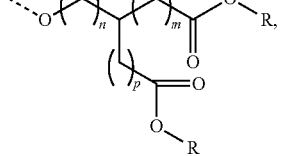 (c9)

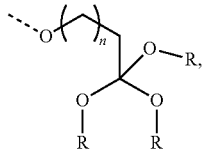 (c10)

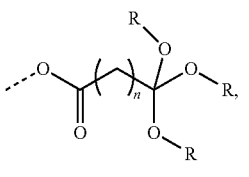 (c11)

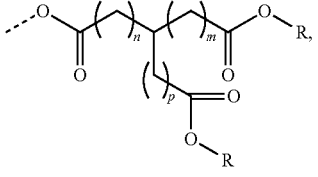 (c12)

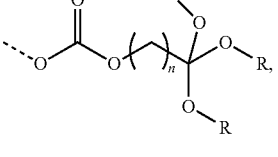 (c13)

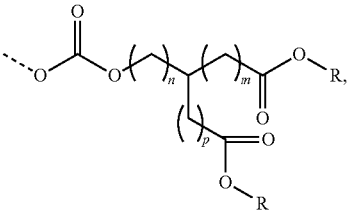 (c14)

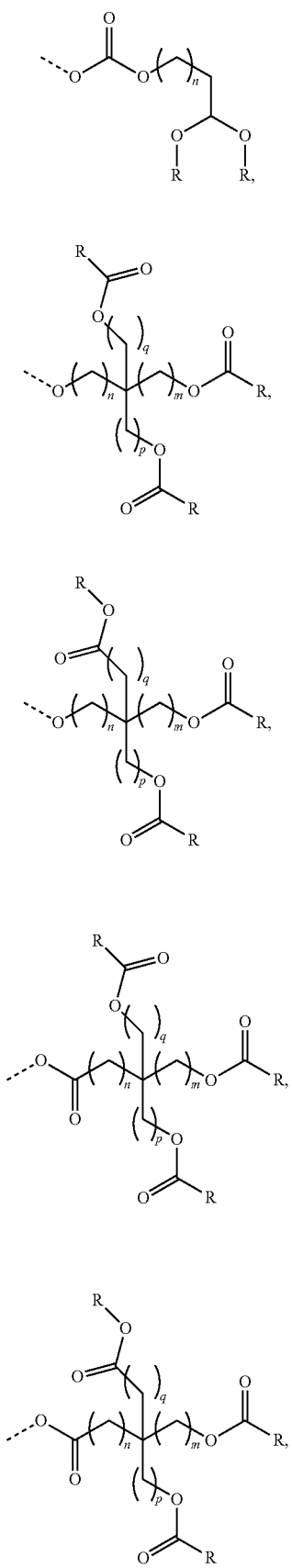
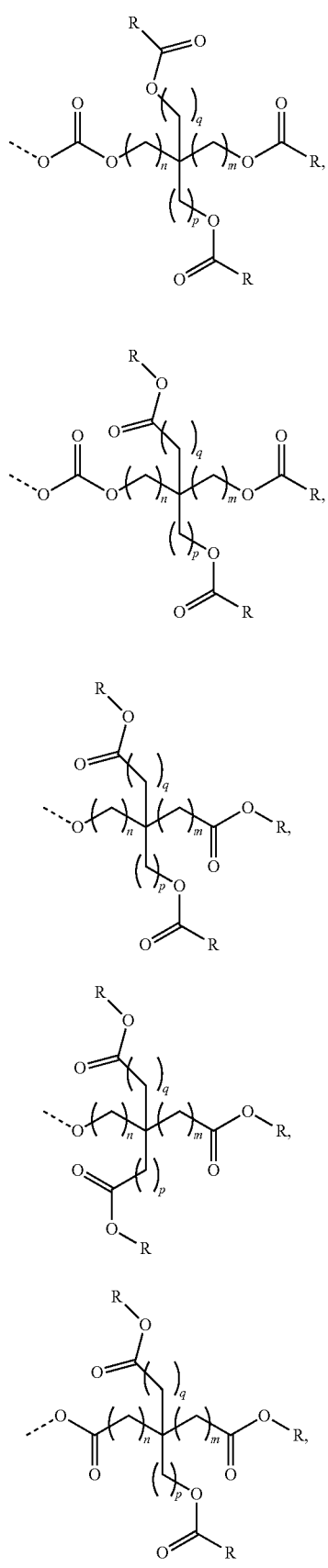

-continued

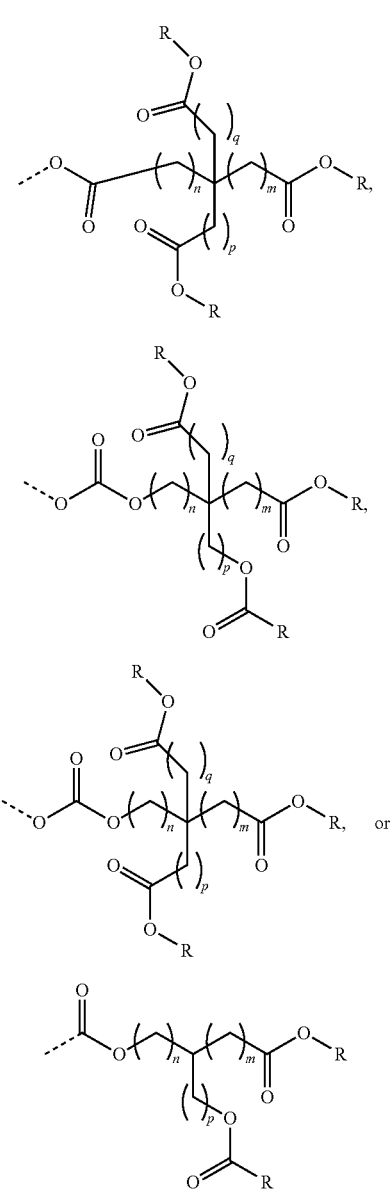

R is $C_{5-22}$ alkyl, $C_{5-22}$ alkenyl, or $C_{5-22}$ alkynyl;
n is 0-12;
m, p, and q are each independently 0, 1, 2, 3 or 4;
provided that chains (a)-(h) have 12-30 carbon atoms and chains (i)-(k) have 12-70 carbon atoms;
X is $CR^6$ or N; and
$R^6$ is H, halo, $C_{1-6}$ alkyl, or $R^4$; or a pharmaceutically acceptable salt thereof.

Embodiment 2

The compound according to embodiment 1 wherein X is $CR^6$; or a pharmaceutically acceptable salt thereof.

Embodiment 3

The compound according to embodiment 2 wherein $R^6$; is H, chloro, bromo, or $C_{1-3}$ alkyl or a pharmaceutically acceptable salt thereof.

Embodiment 4

The compound according to embodiment 3 wherein $R^6$ is H; or a pharmaceutically acceptable salt thereof.

Embodiment 5

The compound according to embodiment 4 wherein L is $C_{1-6}$ alkylene, *—$C_{1-4}$ alkylene-L2-, *—$C_{1-4}$ alkylene-L2-$C_{1-4}$ alkylene-,

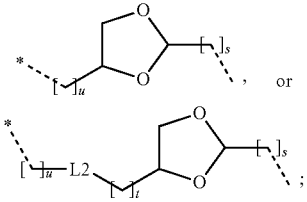

or a pharmaceutically acceptable salt thereof.

Embodiment 6

The compound according to embodiment 5 wherein $R^1$ and $R^2$ are each independently optionally substituted $C_{1-6}$ alkyl or $R^1$ and $R^2$ are joined together forming an optionally substituted 4-7 membered heterocyclic ring; or a pharmaceutically acceptable salt thereof.

Embodiment 7

The compound according to embodiment 6 wherein:
L is methylene, ethylene, or propylene, or
L is *—$C_{1-3}$ alkylene-OC(O)— or
L is *—$C_{1-4}$ alkylene-L2-$C_{1-2}$ alkylene-, wherein L2, attached in either direction, is C(O)O or OC(O)O; or a pharmaceutically acceptable salt thereof.

Embodiment 8

The compound according embodiment 7 wherein $R^1$ and $R^2$ are each independently optionally substituted methyl or optionally substituted ethyl; or a pharmaceutically acceptable salt thereof.

Embodiment 9

The compound according to embodiment 4 wherein L-$NR^1R^2$ group of formula (I) is selected from the group consisting of:

| Structure |
| --- |
| 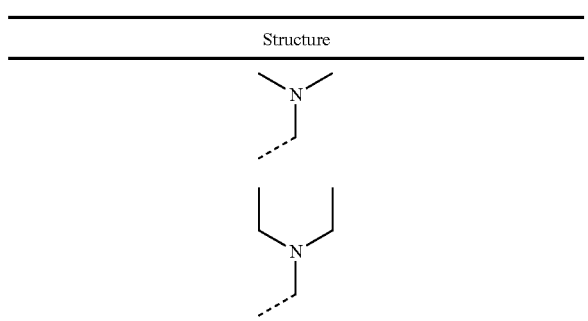 |

| 197 -continued | 198 -continued |
|---|---|
| Structure | Structure |
| 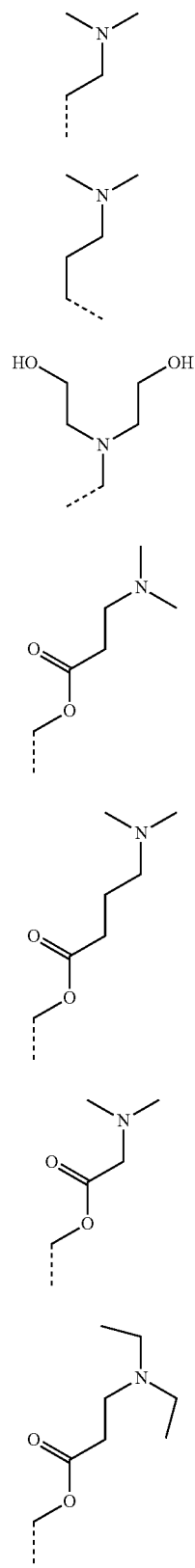 | 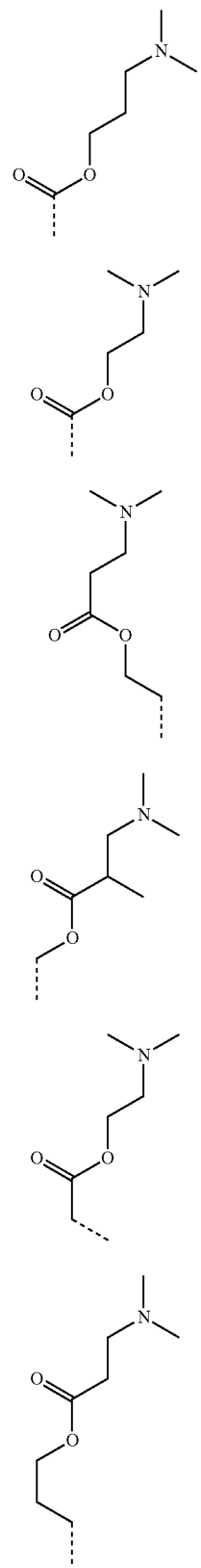 |

| 199 -continued | | 200 -continued |
|---|---|---|
| Structure | | Structure |
| 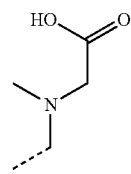 | | 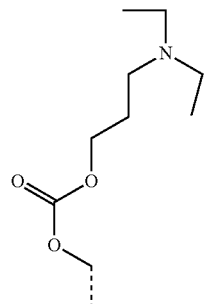 |
| 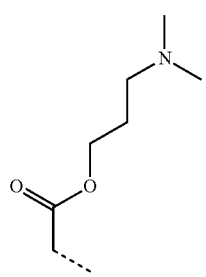 | | 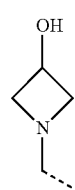 |
| 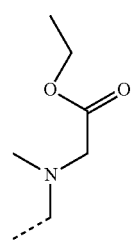 | | 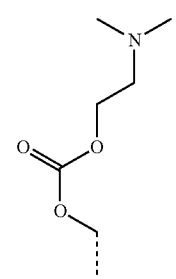 |
| 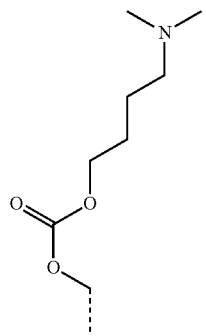 | | 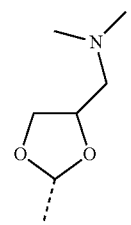 |
| 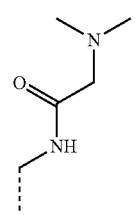 | | 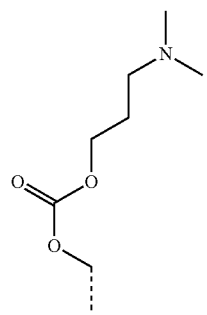 |
| 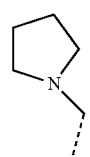 | | |

-continued

Structure

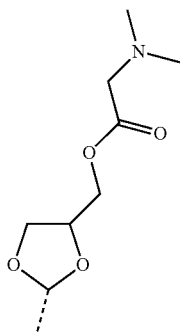

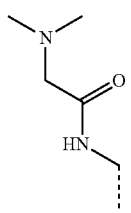

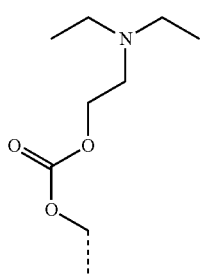

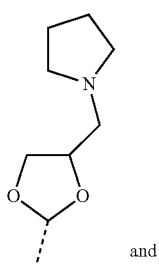

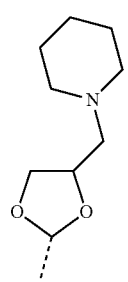

and wherein the dashed line indicate the point of attachment to formula (I); or a pharmaceutically acceptable salt thereof.

Embodiment 10

The compound according to embodiment 9 wherein $R^3$ and $R^4$ are each independently:

(a) $-Z^1-R^a$,
(b) $-Z^1-R^b-Z^2-R^a$,
(c) $-Z^1-R^b-Z^2-R^b-Z^3-R^a$,
(e) $-R^b-Z^1-R^a$,
(f) $-R^b-Z^1-R^b-Z^2-R^a$,
(g) $-R^b-Z^1-R^b-Z^2-R^b-Z^3-R^a$,
(i) $-R^c$, or
(j) $-Z^1-R^b-R^c$; or a pharmaceutically acceptable salt thereof.

Embodiment 11

The compound according to embodiment 10 wherein $R^3$ and $R^4$ are each independently:

(a) $-Z^1-R^a$,
(b) $-Z^1-R^b-Z^2-R^a$, or
(f) $-R^b-Z^1-R^b-Z^2-R^a$; or a pharmaceutically acceptable salt thereof.

Embodiment 12

The compound according to embodiment 11 wherein $R^3$ and $R^4$ are each independently (b) $-Z^1-R^b-Z^2-R^a$; or a pharmaceutically acceptable salt thereof.

Embodiment 13

The compound according to embodiment 12 wherein $Z^1$ is $-O-$; $R^b$ is $C_{1-10}$ alkylene; $Z^2$ is $-OC(O)-$; and $R^a$ is $C_{5-18}$ alkyl or $C_{11-18}$ alkenyl having one to three double bonds; or a pharmaceutically acceptable salt thereof.

Embodiment 14

The compound according to embodiment 10 wherein $R^3$ and $R^4$ are each independently (i) $-R^c$; $R^c$ is c1 or c3; n is 1 or 2; m is 0 or 1; and p is 1; or a pharmaceutically acceptable salt thereof.

Embodiment 15

The compound according to any one of embodiments 1-14 wherein $R^4=R^3$; or a pharmaceutically acceptable salt thereof.

Embodiment 16

The compound according to embodiment 1 having the following formula:

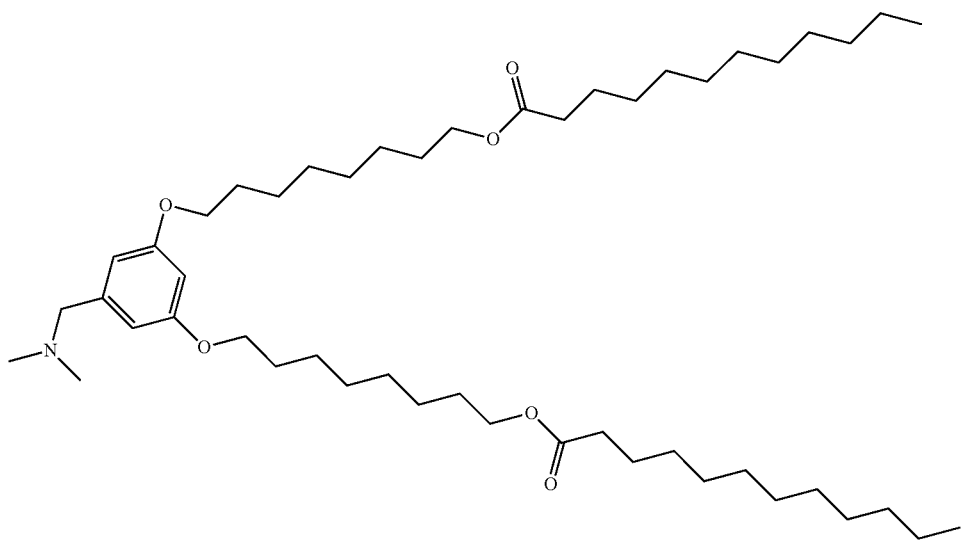 [SMILES: CCCCCCCCCCCC(=O)OCCCCCCCCOc1cc(CN(C)C)cc(OCCCCCCCCOC(=O)CCCCCCCCCCC)c1]

or a pharmaceutically acceptable salt thereof.

Embodiment 17

The compound according to embodiment 1 having the following formula:

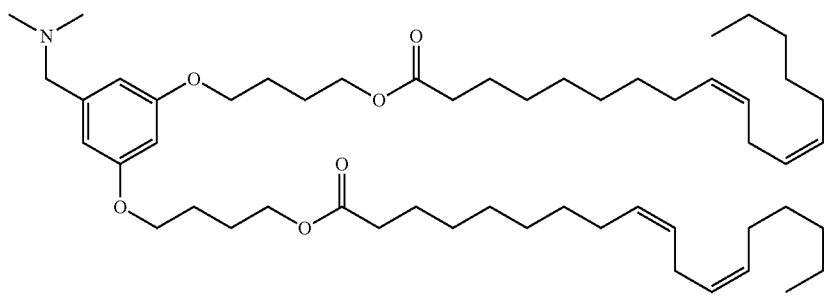 [SMILES: CCCCC/C=C\C/C=C\CCCCCCCC(=O)OCCCCOc1cc(CN(C)C)cc(OCCCCOC(=O)CCCCCCC/C=C\C/C=C\CCCCC)c1]

or a pharmaceutically acceptable salt thereof.

Embodiment 18

A lipid composition comprising a compound according to anyone of embodiments 1-17 or a pharmaceutically acceptable salt thereof.

Embodiment 19

The lipid composition according embodiment 18 further comprising a biologically active agent.

Embodiment 20

The lipid composition according embodiment 19 wherein the biologically active agent is a siRNA.

Embodiment 21

The lipid composition according to embodiment 20 further comprising a helper lipid.

Embodiment 22

The lipid composition according to embodiment 21 further comprising a neutral lipid.

Embodiment 23

The lipid composition according to embodiment 22 further comprising a stealth lipid.

Embodiment 24

The lipid composition according to embodiment 23 wherein the helper lipid is cholesterol, the neutral lipid is DSPC, and the stealth lipid is PEG-DMG, S010 or S011.

Embodiment 25

The lipid composition according to embodiment 24 in the form of a lipid nanoparticle.

Embodiment 26

The lipid composition according to embodiment 25 having a molar ratio of about 44/about 45/about 9/about 2 of a compound of formula (I)/cholesterol/DSPC/S010 or S011.

Embodiment 27

A pharmaceutical composition comprising a lipid composition according to any one of embodiments 19-26 and a pharmaceutically acceptable carrier or excipient.

Embodiment 28

A method for the treatment of a disease or condition comprising the step of administering a therapeutically effective amount of lipid composition according to any one of embodiments 19-27 to a patient in need of treatment thereof.

Embodiment 29

A method for the treatment of a disease or condition comprising the step of administering a therapeutically effective amount of pharmaceutical composition according embodiment 28.

---

What is claimed is:

1. A method for the treatment of a disease or condition in a patient in need thereof, the method comprising immunizing the patient against an immunogen by administering to the patient a therapeutically effective amount of a lipid composition comprising:

a compound of formula (I) or a pharmaceutically acceptable salt thereof, wherein:

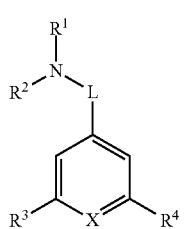

(I)

L is $C_{1-6}$ alkylene, *—$C_{1-4}$ alkylene-L2-, or *—$C_{1-4}$ alkylene-L2-$C_{1-4}$ alkylene-, wherein the * denotes attachment of the moiety to the $NR^1R^2$ group;

L2, attached in either direction, is —C(O)O—;

$R^1$ and $R^2$ are each independently optionally substituted $C_{1-6}$ alkyl; wherein said $C_{1-6}$ alkyl is optionally substituted with one or two substituents each independently selected from the group consisting of: OH, $C_{1-3}$ alkoxy, COOH, and COO—$C_{1-4}$ alkyl, $R^3$ and $R^4$ are each independently $Z^1$—$R^b$—$Z^2$—$R^a$, wherein $Z^1$, attached in either direction, is each independently —O— or —C(O)O—;

$Z^2$, attached in either direction, is —C(O)O—;

$R^a$ is $C_{2-22}$ alkyl, $C_{2-22}$ alkenyl, or $C_{2-22}$ alkynyl;

each $R^b$ is independently $C_{1-20}$ alkylene, $C_{2-20}$ alkenylene, or $C_{2-20}$ alkynylene;

provided that —$Z^1$—$R^b$—$Z^2$—$R^a$ has at least 12 carbon atoms and no more than 30 carbon atoms;

X is $CR^6$; and $R^6$ is H, halo, $C_{1-6}$ alkyl, or $R^4$;

and a biologically active agent that elicits an immune response, thereby treating the patient.

2. The method of claim 1, comprising administering a lipid composition comprising:

a compound of formula (I) of a pharmaceutically acceptable salt thereof, wherein:

209

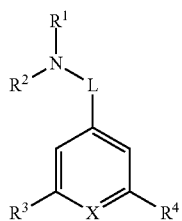

(I)

L is $C_{1-6}$ alkylene, *—$C_{1-4}$ alkylene-L2-, or *—$C_{1-4}$ alkylene-L2-$C_{1-4}$ alkylene-, wherein in the * denotes attachment of the moiety to the $NR^1R^2$ group;

L2, attached in either direction, is —C(O)O—;

$R^1$ and $R^2$ are each independently optionally substituted $C_{1-6}$ alkyl; wherein said $C_{1-6}$ alkyl is optionally substituted with one or two substituents each independently selected from the group consisting of: OH, $C_{1-3}$ alkoxy, COOH, and COO—$C_{1-4}$ alkyl,

210

$R^3$ and $R^4$ are each independently —$Z^1$—$R^b$—$Z^2$—$R^a$, wherein $Z^1$, attached in either direction, is each independently —O— or —C(O)O—;

$Z^2$, attached in either direction, is —C(O)O—;

$R^a$ is $C_{2-22}$ alkyl, $C_{2-22}$ alkenyl, or $C_{2-22}$ alkynyl;

each $R^b$ is independently $C_{1-20}$ alkylene, $C_{2-20}$ alkenylene, or $C_{2-20}$ alkynylene;

provided that —$Z^1$—$R^b$—$Z^2$—$R^a$ has at least 12 carbon atoms and no more than 30 carbon atoms;

X is $CR^6$; and $R^6$ is H, halo, $C_{1-6}$ alkyl, or $R^4$;

a biologically active agent;

and a pharmaceutically acceptable carrier or excipient.

3. A method for the treatment of a disease or condition in a patient in need thereof, the method comprising immunizing the patient against an immunogen by administering to the patient a therapeutically effective amount of a lipid composition comprising:

a compound of formula:

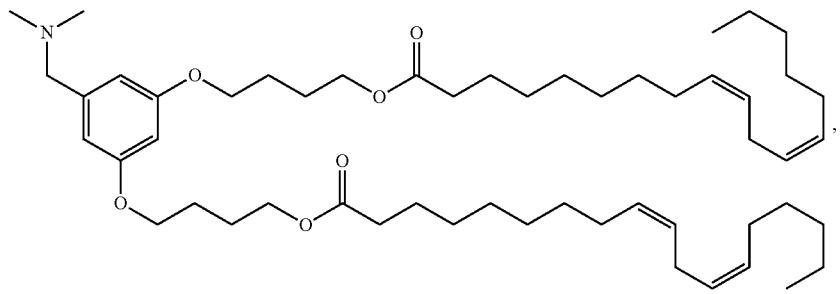 [SMILES: CCCCC/C=C\C/C=C\CCCCCCCC(=O)OCCCCOc1cc(CN(C)C)cc(OCCCCOC(=O)CCCCCCC/C=C\C/C=C\CCCCC)c1]

(9Z, 9'Z, 12Z, 12'Z)-((5-((dimethylamino)methyl)-1,3-phenylene)bis(oxy))bis(butane-4,1-diyl)bis(octadeca-9, 12-dienoate), or a pharmaceutically acceptable salt thereof;

and a biologically active agent that elicits an immune response, thereby treating the patient.

4. The method of claim 3, comprising administering a lipid composition comprising:

a compound of formula:

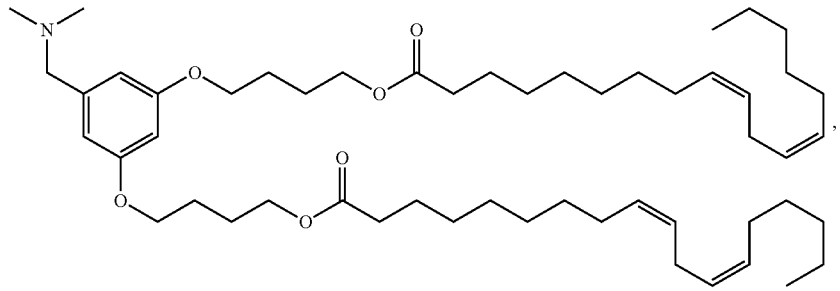 [SMILES: CCCCC/C=C\C/C=C\CCCCCCCC(=O)OCCCCOc1cc(CN(C)C)cc(OCCCCOC(=O)CCCCCCC/C=C\C/C=C\CCCCC)c1]

(9Z, 9'Z, 12Z, 12'Z)-((5-((dimethylamino)methyl)-1,3-phenylene)bis(oxy))bis(butane-4,1-diyl)bis(octadeca-9, 12-dienoate), or a pharmaceutically acceptable salt thereof;

a biologically active agent;

and a pharmaceutically acceptable carrier or excipient.

5. A method for the treatment of a disease or condition in a patient in need thereof, the method comprising immunizing the patient against an immunogen by administering to the patient a therapeutically effective amount of a lipid composition comprising:
a compound of formula:

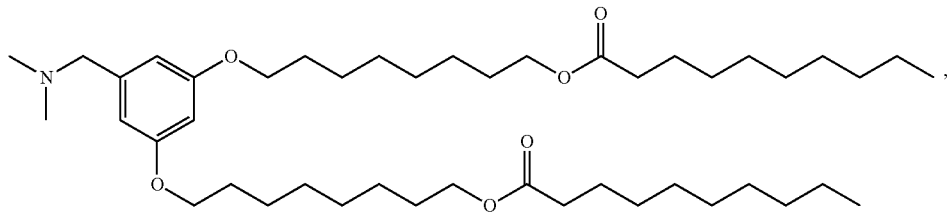 [SMILES: CCCCCCCCCC(=O)OCCCCCCCCOc1cc(CN(C)C)cc(OCCCCCCCCOC(=O)CCCCCCCCC)c1]

((5-((dimethylamino)methyl)-1,3-phenylene)bis(oxy))bis(octane-8,1-diyl)bis(decanoate), or a pharmaceutically acceptable salt thereof;
and
a biologically active agent that elicits an immune response, thereby treating the patient.

6. The method of claim 5, comprising administering a lipid composition comprising:
a compound of formula:

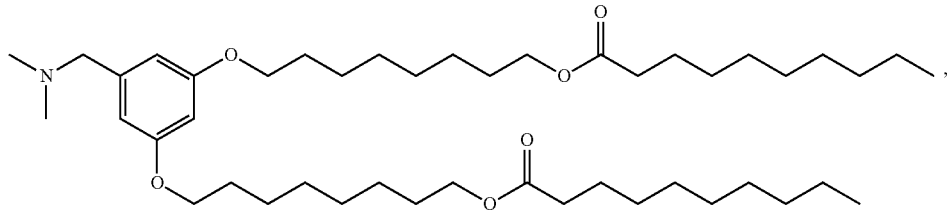 [SMILES: CCCCCCCCCC(=O)OCCCCCCCCOc1cc(CN(C)C)cc(OCCCCCCCCOC(=O)CCCCCCCCC)c1]

((5-((dimethylamino)methyl)-1,3-phenylene)bis(oxy))bis(octane-8,1-diyl)bis(decanoate), or a pharmaceutically acceptable salt thereof;
a biologically active agent;
and
a pharmaceutically acceptable carrier or excipient.

7. The method of claim 1, wherein the composition comprises one or more of a helper lipid, a neutral lipid, and a stealth lipid.

8. The method of claim 7, wherein the helper lipid is cholesterol, the neutral lipid is DSPC, and the stealth lipid is PEG-DMG, S010, or S011.

9. The method of claim 3, wherein the composition comprises one or more of a helper lipid, a neutral lipid, and a stealth lipid.

10. The method of claim 9, wherein the helper lipid is cholesterol, the neutral lipid is DSPC, and the stealth lipid is PEG-DMG, S010, or S011.

11. The method of claim 5, wherein the composition comprises one or more of a helper lipid, a neutral lipid, and a stealth lipid.

12. The method of claim 11, wherein the helper lipid is cholesterol, the neutral lipid is DSPC, and the stealth lipid is PEG-DMG, S010, or S011.

13. The method of claim 1, wherein the composition is in a form of a lipid nanoparticle.

14. The method of claim 3, wherein the composition is in a form of a lipid nanoparticle.

15. The method of claim 5, wherein the composition is in a form of a lipid nanoparticle.

16. The method of claim 8, wherein the stealth lipid is PEG-DMG.

17. The method of claim 10, wherein the stealth lipid is PEG-DMG.

18. The method of claim 12, wherein the stealth lipid is PEG-DMG.

19. The method of claim 8, wherein the lipid composition has a molar ratio of about 40/about 38/about 10/about 2 of the compound of formula (I)/cholesterol/DSPC/PEG-DMG, S010, or S011, respectively.

20. The method of claim 10, wherein the lipid composition has a molar ratio of about 40/about 38/about 10/about 2 of the compound of (9Z, 9'Z, 12Z, 12'Z)-((5-((dimethylamino)methyl)-1,3-phenylene)bis(oxy))bis(butane-4,1-diyl) bis(octadeca-9, 12-dienoate)/cholesterol/DSPC/PEG-DMG, S010, or S011, respectively.

21. The method of claim 12, wherein the lipid composition has a molar ratio of about 40/about 38/about 10/about 2 of a compound of ((5-((dimethylamino)methyl)-1,3-phenylene)bis(oxy))bis(octane-8,1-diyl)bis(decanoate)/cholesterol/DSPC/PEG-DMG, S010, or S011, respectively.

* * * * *